US010729730B2

(12) United States Patent
Zhao

(10) Patent No.: US 10,729,730 B2
(45) Date of Patent: Aug. 4, 2020

(54) COMPOSITIONS AND METHODS FOR REPROGRAMMING ADULT CELLS THROUGH THE STEMNESS OF A PLATELET RICH FRACTION OF BLOOD CONTAINING PLATELET-LIKE CELLS IN HUMANS

(71) Applicant: Hackensack University Medical Center, Hackensack, NJ (US)

(72) Inventor: Yong Zhao, River Edge, NJ (US)

(73) Assignee: HACKENSACK UNIVERSITY MEDICAL CENTER, Hackensack, NJ (US)

( * ) Notice: Subject to any disclaimer, the term of this patent is extended or adjusted under 35 U.S.C. 154(b) by 77 days.

(21) Appl. No.: 15/688,464

(22) Filed: Aug. 28, 2017

(65) Prior Publication Data

US 2018/0055891 A1    Mar. 1, 2018

Related U.S. Application Data

(60) Provisional application No. 62/520,241, filed on Jun. 15, 2017, provisional application No. 62/380,913, filed on Aug. 29, 2016.

(51) Int. Cl.
| A61K 35/51 | (2015.01) |
| A61K 38/18 | (2006.01) |
| A61K 38/30 | (2006.01) |
| C12N 5/00 | (2006.01) |
| A61L 27/36 | (2006.01) |
| C12N 5/071 | (2010.01) |
| A61K 38/28 | (2006.01) |
| A61K 35/17 | (2015.01) |
| A61K 35/39 | (2015.01) |
| G01N 30/88 | (2006.01) |

(52) U.S. Cl.
CPC .............. *A61K 35/51* (2013.01); *A61K 35/17* (2013.01); *A61K 35/39* (2013.01); *A61K 38/18* (2013.01); *A61K 38/28* (2013.01); *A61K 38/30* (2013.01); *A61L 27/3616* (2013.01); *C12N 5/0018* (2013.01); *C12N 5/0676* (2013.01); *C12N 2500/84* (2013.01); *C12N 2502/115* (2013.01); *C12N 2506/115* (2013.01); *C12N 2513/00* (2013.01); *G01N 2030/8813* (2013.01); *G01N 2333/59* (2013.01)

(58) Field of Classification Search
None
See application file for complete search history.

(56) References Cited

U.S. PATENT DOCUMENTS

| 8,835,163 B2 | 9/2014 | Zhao et al. | |
| 2009/0317439 A1* | 12/2009 | Turzi | A61L 24/0005 424/422 |
| 2010/0129440 A1 | 5/2010 | Zhao et al. | |
| 2014/0356893 A1 | 12/2014 | Mishra | |
| 2015/0071886 A1 | 3/2015 | Houze et al. | |

FOREIGN PATENT DOCUMENTS

WO    2004/098646 A1    11/2004

OTHER PUBLICATIONS

Kondo M, et al. Biology of hematopoietic stem cells and progenitors: implications for clinical application. Annu Rev Immunol. 2003;21:759-806.
Kondo M, et al. Cell-fate conversion of lymphoid-committed progenitors by instructive actions of cytokines. Nature. Sep. 21, 2000;407:383-6.
Kondo, M. "Lymphoid and myeloid lineage commitment in multipotent hematopoietic progenitors," Immunol. Rev. Nov. 2010; 238(1): 37-46.
Kopp, JL et al, "Small increases in the level of Sox2 trigger the differentiation of mouse embryonic stem cells," Stem Cells 2008; 26: 903-11.
Kuter DJ., The end is just the beginning: megakaryocyte apoptosis and platelet release. Int J Hematol. 2001;74:365-374.
Kuter, DJ et al, "Recombinant human thrombopoietin: basic biology and evaluation of clinical studies", 2002; Blood; 100: 3457-69.
Lambert, MP et al, "Intramedullary megakaryocytes internalize released platelet factor 4 and store it in alpha granules," J. Thromb. Haemost. 2015; 13(10): 1888-99.
Lansdorp, P. A I. and Dragowaka, W., Long-term erythropoiesis from constant numbers of CD34+ cells in serum-free cultures initiated with highly purified progenitor cells from human marrow bone., (1992) J.Exp. Med. 175:1501-1509.
Lanza, Robert, et al., Principles of Tissue Engineering, 4th Ed., Eds, Elsevier, Inc.: New York, 2014, Chapter 48;1047-1048.

(Continued)

*Primary Examiner* — David W Berke-Schlessel
(74) *Attorney, Agent, or Firm* — McCarter & English, LLP; Beverly W. Lubit

(57) ABSTRACT

The described invention provides a method of functionally reprogramming adult cells to an immature cell type that expresses one or more embryonic biomarkers. The reprogramming is accomplished by contacting the adult cells with a platelet rich fraction comprising platelet-like cells from umbilical cord blood or peripheral blood, and expanding the immature cell type in vitro under culture conditions to generate an insulin-producing cell population that expresses human beta-cell specific transcription factors and is functionally equivalent to human pancreatic beta-cells. Without being limited by theory, platelet-like cells and their released mitochondria display immune tolerance-associated markers that may modulate the function and differentiation of immune cells. The described invention further provides a pharmaceutical composition comprising a cell product containing a therapeutic amount of an insulin-producing cell population derived from functionally reprogrammed adult cells, wherein the insulin-producing cell population expresses human beta-cell specific transcription factors and is functionally equivalent to human pancreatic beta-cells.

20 Claims, 62 Drawing Sheets
(51 of 62 Drawing Sheet(s) Filed in Color)

(56) References Cited

OTHER PUBLICATIONS

Leary, AG et al, "Single cell origin of multi-lineage colonies in culture. Evidence that differentiation of multipotent progenitors and restriction of proliferative potential of monopotent progenitors ar stochastic processes," J. Clin. Invest. (1984); 74: 2193-97.
Lehuen A. et al., "Immune cell crosstalk in type I diabetes", Nat Rev Immunol. vol. 10: 501-513, (2010).
Li, R et al., "A mesenchymal-to-epithelial transition initiates and is required for the nuclear reprogramming of mouse fibroblasts," Cell Stem Cell 2010; 7: 51-63.
Lin, T., et al, "A chemical platform for improved induction of human iPSCs," Nat. Methods 2009; 6: 805-808.
Lindsay, C. et al, 2015; Functionally Distinct Cell Populations Characterize Cord Blood Derived Megakaryocytes. Blood 126(23): 4754.
Liu, X et al, "Sequential introduction of reprogramming factors reveals a time-sensitive requirement for individual factors and a sequential EMT-MET mechanism for optimal reprogramming," Nat. Cell Biol. 2013; 15: 829-38.
Livnah O, et al, Crystallographic evidence for preformed dimers of erythropoietin receptor before ligand activation. Science. 1999;283:987-990.
Loh, YH, et al, "The Oct4 and Nanog transcriptin network regulates pluripotency in mouse embryonic stem cells," Nat. Genet., 2006, 38: 431-440.
Lok S., et al.; Cloning and expression of murine thrombopoietin cDNA and stimulation of platelet production in vivo. Nature. 1994;369:565-568.
Luoh SM, et al. Role of the distal half of the c-Mpl intracellular domain in control of platelet production by thrombopoietin in vivo. Mol Cell Biol. 2000;20:507-515.
Macdonald P.E. et al., "The multiple actions of GLP-1 on the process of glucose-stimulated insulin secretion", Diabetes, vol. 51 (Suppl. 3): S434-S442, (2002).
Macey, Marion G., Flow cytometry: principles and applications, Humana Press, 2007.
Magne S, et al, STAT5 and Oct-1 form a stable complex that modulates cyclin D1 expression. Mol Cell Biol. 2003;23:8934-8945.
Maguer-Satta V, et al., A novel role for fibronectin type I domain in the regulation of human hematopoietic cell adhesiveness through binding to follistatin domains of FLRG and follistatin. Exp Cell Res 2006;312:434-442.
Maguer-Satta V, et al., Regulation of human erythropoiesis by activin A, BMP2, and BMP4, members of the TGFbeta family. Exp Cell Res 2003; 282:110-120.
Maguer-Satta V, Rimokh R., FLRG, member of the follistatin family, a new player in hematopoiesis. Mol Cell Endocrinol 2004; 225:109-118.
Maherali, N et al, "Tgfb signal inhibition cooperates in the induction of iPSCs and replaces Sox2 and cMyc," Curr. Biol. 2009; 19:1718-23.
Majumdar, et al., Phenotypic and functional comparison of cultures of marrow-derived mesenchymal stem cells (MSCs) and stromal cells., J. Cell Physiol. 176: 57-66 (1998).
Manz MG, et al., Dendritic cell potentials of early lymphoid and myeloid progenitors. Blood. Jun. 1, 2001; 97(11):3333-41.
Manz, MG, et al, "Prospective isolation of human clonogenic common myeloid progenitors," Proc. Natl Acad. Sci. U. S. 2002 99(18): 11872-11877.
Martin D.I.K.,et al., Expression of an erythroid transcription factor in megakaryocytic and mast cell lineages. Nature. 1990;344:444-447.
Martinovic, S. et al, "Expression of bone morphogenetic proteins in stromal cells from human bone marrow long-term culture," J. Histochem. Cytochem. 2004; 52: 1159-67.

Martnieau, I., et al, Effects of calcium and thrombin on growth factor release from platelet concentrates: kinetics and regulation of endothelial cell proliferation, Biomaterials 2004; 25: 4489-4502.
Mathieu C. et al., "Arresting type I diabetes after diagnosis: GAD is not enough", Lancet, vol. 378: 291-292, (2011).
Matsumura I, et al. Thrombopoietin-induced differentiation of a human megakaryoblastic leukemia cell line, CMK, involves transcriptional activation of p21(WAF1/Cip1) by STAT5. Mol Cell Biol. 1997;17:2933-2943.
McDonald T.P. and Sullivan P.S.; Megakaryocytic and erythrocytic cell lines share a common precursor cell. Exp Hematol. 1993;21:1316-1320.
McGuckin, CP, et al, "Production of stem cells with embryonic characteristics from human umbilical cord blood," Cell Prolif., 38: 245-55 (2005).
Meier JJ, et al., Direct evidence of attempted beta cell regeneration in an 89-year-old patient with recent-onset type 1 diabetes. Diabetologia 2006, 49: 1838-1844.
Metcalf, D et al, "Anomalous megakaryocytopoiesis in mice with mutations in the c-Myb gene," Blood 2005; 105: 3480-87.
Michelson, A.D. and Furman, M.I., "Markers of Platelet Activation and Granule Secretion," in Contemporary Cardiology: Platelet Function: Assessment, Diagnosis and Treatment, M. Quinn and D. Fitzgerald, Eds, Humana Press, Towaco NJ: Chapter 13: 307-320 (2005).
Mihu, C. et al., Isolation and Characterization of Stem Cells From the Placenta and the Umbilical Cord. 2008, Romanian Journal of Morphology and Embryology, 2008, 49(4):441-446.
Miyakawa Y, et al, Thrombopoietin induces phosphoinositol 3-kinase activation through SHP2, Gab, and insulin receptor substrate proteins in BAF3 cells and primary murine megakaryocytes. J Biol Chem. 2001;276:2494-2502.
Miyakawa Y, et al. Recombinant thrombopoietin induces rapid protein tyrosine phosphorylation of Janus kinase 2 and Shc in human blood platelets. Blood. 1995;86:23-27.
Mojsov S., "Preproglucagon gene expression in pancreas and intestine diversifies at the level of post-translational processing", J. Biol. Chem., vol. 261: 11880-11889 (1986).
Muench, M. and Barcena, A., "Megakaryocyte Growth and Development Factor is a Potent Growth Factor for Primitive Hematopoietic Progenitors in the Human Fetus," Ped. Res. 2004; 55(6): 1050-56.
Munn, D. et al., "Inhibition of T Cell Proliferation by Macrophage Tryptophan Catabolism", J Exp Med, 1999, 189: 1363-1372.
Munn, D. et al., Prevention of Allogeneic Fetal Rejection by Tryptophan Catabolism Science, 1998, 281: 1191-1193.
Najfeld V, et al, Numerical gain and structural rearrangements of JAK2, identified by FISH, characterize both JAK2617V>F-positive and -negative patients with Ph-negative MPD, myelodysplasia, and B-lymphoid neoplasms. Exp Hematol. 2007;35:1668-1676.
Nakahata T. and Okumura N.; Cell surface antigen expression in human erythroid progenitors: erythroid and megakaryocytic markers. Leuk Lymphoma. 1994;13:401-409.
Nakao T, et al, PI3K/Akt/FOXO3a pathway contributes to thrombopoietin-induced proliferation of primary megakaryocytes in vitro and in vivo via modulation of p27(Kip1) Cell Cycle. 2007;7:2, 257-266.
Nakorn T.N., et al., Characterization of mouse clonogenic megakaryocyte progenitors. Proc Natl Acad Sci U S A. 2003;100:205-210.
E. Harlow and D. Lane, Antibodies: A Laboratory Manual, Cold Spring Harbor Laboratory Press, 1988.
Eisbacher, M. et al, "Protein-protein interaction between Fli-1 and GATA-1 mediates synergistic expression of megakaryocyte-specific genes through cooperative DNA binding," Mol. Cell Biol. 2003; 23: 3427-41.
Elzey BD, et al., The emerging role of platelets in adaptive immunity. Cell Immunol. 2005; 238:1-9.
Endo TA, et al. A new protein containing an SH2 domain that inhibits JAK kinases. Nature. 1997;387:921-924.
Fichelson S, et al. Megakaryocyte growth and development factor-induced proliferation and differentiation are regulated by the mitogen-activated protein kinase pathway in primitive cord blood hematopoietic progenitors. Blood. 1999;94:1601-1613.

(56) References Cited

OTHER PUBLICATIONS

Fox N, et al, Thrombopoietin expands hematopoietic stem cells after transplantation. J Clin Invest. 2002;110:389-394.
French, D.L. and Seligsohn, U., "Platelet Glycoprotein IIb/IIIa receptors and Glanzmann's throbasthenia," Arteriosclerosis, Thrombosis and Vascular Biology 2000: 20: 607-610.
Fujihara, S. et al, "Galectin-9 in cancer therapy," Recent Pat. Endocr. Metab. Immune Drug Discov. (2013); 7(2): 130-7.
Funakoshi-Tago M, et al, Receptor specific downregulation of cytokine signaling by autophosphorylation in the FERM domain of Jak2. Embo J. 2006; 25:4763-4772.
Fusaki, N. et al, "Efficient induction of transgene-free human pluripotent stem cells using a vector based on Sendai virus, an RNA virus that does not integrate into the host genome," Proc. Jpn Acad. Ser. B. Phys. Biol. Sci., 85: 348-62 (2009).
Garcia J, et al, Thrombopoietin-mediated sustained activation of extracellular signal-regulated kinase in UT7-Mpl cells requires both Ras-Raf-1- and Rap1-B-Raf-dependent pathways. Mol Cell Biol. 2001;21:2659-2670.
Geddis AE and Kaushansky K., Inherited thrombocytopenias: toward a molecular understanding of disorders of platelet production. Curr Opin Pediatr. 2004;16:15-22.
Geddis AE, et al, Thrombopoietin: a pan-hematopoietic cytokine. Cytokine Growth Factor Rev. 2002;13:61-73.
Geddis AE, et al. Phosphatidylinositol 3-kinase is necessary but not sufficient for thrombopoietin-induced proliferation in engineered Mpl-bearing cell lines as well as in primary megakaryocytic progenitors. J Biol Chem. 2001;276:34473-34479.
Geddis, A.E, "Megakaryopoiesis," Semin. Hematol. 2010; 47(3): 212-219.
Gekas, C. and Graf, T., "CD41 expression marks myeloid-biased adult hematopoietic stem cells and increases with age," Blood. 2013; 121: 4463-62.
Gerli, R et al, Activation of cord T lymphocytes. I. Evidence for a defective T cell mitogenesis induced through the CD2 molecule, J. Immunol. 1989; 142: 2583-89.
Guerriero R, et al. Inhibition of TPO-induced MEK or mTOR activity induces opposite effects on the ploidy of human differentiating megakaryocytes. J Cell Sci. 2006;119:744-752.
Gurney AL, et al. Thrombocytopenia in c-mpl-deficient mice. Science. 1994;265:1445-1447.
Gutensohn, K. "Alteration of platelet-associated membrane glycoproteins during extracorporeal apheresis of peripheral blood progenitor cells," J. Hematother. 1997; 6: 315-21.
Gutensohn, K. et al, "Flow cytometric analysis of platelet membrane antigens during and after continuous flow plateletpheresis," Transfusion 1997: 37: 809-15.
Habener J. F. et al., "Alpha cells come of age", Trends in Endocrinology & Metabolism: TEM vol. 24, 153-163 (2013).
Haley, KM et al, "Neonatal platelets:mediators of primary hemostasis in the developing hemostatic system," Pediatr. Res. 2014; 76(3): 230-37.
Harir N, et al. Constitutive activation of Stat5 promotes its cytoplasmic localization and association with PI3-kinase in myeloid leukemias. Blood. 2007;109:1678-1686.
Hart A, et al., Fli-1 is required for murine vascular and megakaryocytic development and is hemizygously deleted in patients with thrombocytopenia. Immunity. 2000;13:167-177.
Hawkins, K. et al, "Cell signalling pathways underlying iPSc reprogramming," World J. Stem Cells, 6(5): 620-28 (2014).
Heazlewood, SY et al, "Megakaryocytes co-localise with hemopoietic stem cells and release cytokines that up-regulate stem cell proliferation," Stem Cell Res. 2013; 11:782-92.
Hitchcock IS, et al, YRRL motifs in the cytoplasmic domain of the thrombopoietin receptor regulate receptor internalization and degradation. Blood. 2008.
Ho, R, et al, "Stage-specific regulation of reprogramming to induced pluripotent stem cells by Wnt signaling and T cell factor proteins," Cell Rep. 2013; 3: 2113-26.
Hodohara K, et al., Stromal cell-derived factor-1 (SDF-1) acts together with thrombopoietin to enhance the development of megakaryocytic progenitor cells (CFU-MK). Blood 2000;95:769-775.
Hou, P. et al, "Pluripotent stem cells induced from mouse somatic cells by small molecule compounds," Science 2013; 341: 651-54.
Hutton, JF, et al,"Bone morphogenetic protein 4 contributes to the maintenance of primitive cord blood hematopoietic progenitors in an ex vivo stroma-non contact co-culture system," Stem Cell Dev. 2006; 15: 805-13.
International Preliminary Report on Patentability; PCT/US2017/48907; dated Sep. 17, 2018, 5 pages.
International Search Report and Written Opinion; PCT/US2017/48907; dated Dec. 28, 2017, 12 pages.
Italiano JE,et al., Blood platelets are assembled principally at the ends of proplatelet processes produced by differentiated megakaryocytes. J Cell Biol. 1999;147:1299-1312.
Iwasaki, H. and Akashi, K. "Myeloid lineage commitment from the hematopoietic stem cell,", Immunity 26(6) Jun. 2007, 726-40.
Jaatinen, T., Laine, J. "Isolation of Mononuclear Cells from Human Cord Blood by Ficoll-Paque Density Gradient," Unit 2A, Curr. Protocols in Stem Cell Biol., DOI: 10.1002/9780470151808.sc02a01s1.
Jacoby, DR and Oldstone, MBA, "Delineation of suppressor and helper activity within the OKTA4-defined T lymphocyte subset in human newborns," 1983; J. Immunol. 131: 1765-70.
Jagannathan-Bogdan M. et al., "Elevated proinflammatory cytokine production by a skewed T cell compartment requires monocytes and promotes inflammation in type 2 diabetes", J Immunol, vol. 186: 1162-1172, (2011).
Jeanpierre, S. et al, "BMP4 regulation of human megakaryocytic differentiation is involved in thrombopoietin signaling," Blood 2008; 112: 3154-63.
Jenne CN et al., Platelets: bridging hemostasis, inflammation, and immunity. Int J Lab Hematol. 2013;35:254-61.
Jennings, L.K and Phillips, D.R, Purification of glycoproteins IIb and III from human platelet plasma membranes and characterization of a calcium-dependent glycoprotein IIb-III complex. J Biol Chem. 1982;257:10458-10466.
Jiao, J. et al, "Promoting reprogramming by FGF2 reveals that the extracellular matrix is a barrier for reprogramming fibroblasts to pluripotency," Stem Cells 2013; 31: 729-740.
Kaushansky, K. "Thrombopoietin: the primary regulator of platelet production," 1995; Blood 86:2; 419-311.
Kaushansky, K., "Historical Review: megakaryopoiesis and thrombopoiesis," Blood 2008; 111(3): 981-86.
Kauskot, A. et al, "PEAR1 attenuates megakaryopoiesis via control of the P13K/PTEN pathway," Blood. 2013; 121: 5208-17.
Kim, JB, et al, "OCT4-Induced Pluripotency in Adult Neural Stem Cells, " Cell 2009; 136: 411-19.
Kinnaird et al, Local Delivery of Marrow-Derived Stromal Cells Augments Collateral Perfusion Through Paracrine Mechanisms., Circulation 109: 1543-49 (2004).
Kirito K, et al, Thrombopoietin regulates Bcl-xL gene expression through Stat5 and phosphatidylinositol 3-kinase activation pathways. J Biol Chem. 2002;277:8329-8337.
Kodaki T, et al, The activation of phosphatidylinositol 3-kinase by Ras. Curr Biol. 1994;4:798-806.
Zhu, C. et al, "The Tim-3 ligand galectin-9 negatively regulates T helper type 1 immunity," Nat. Immunol. 2005; 6, 1220: 1245-62.
Zhu, S. et al, "Reprogramming of human primary somatic cells by OCT4 and chemical compounds," Cell Stem Cell 2010; 7: 651-55.
Nerlov, C. et al, "GATA-1 interacts with the myeloid PU.1 transcription factor and represses PU.1-dependent transcription," Blood 2000; 95: 2543-51.
Niwa, H. et al, "Quantitative expression of Oct-3/4 defines differentiation, dedifferentiation or self-renewal of ES cells," Nat. Genet. 2000; 24: 372-76.
Norol, F. et al, Effects of cytokines on platelet production from blood and marrow CD34+ cells. Blood 1998; 91(3); 830-43.
Okino, F, "Pre-B cells and B lymphocytes in human cord blood and adult peripheral blood," Acta Paediatr. Jpn (1987): 29: 195-201.

(56) References Cited

OTHER PUBLICATIONS

Olson, TS, et al, "Megakaryocytes promote murine osteoblastic HSC niche expansion and stem cell engraftment after radioablative conditioning," Blood 2013; 121: 5238-49.
Pagliuca FW, et al., Generation of functional human pancreatic b cells in vitro. Cell 2014, 159: 428-439.
Paluru, P. et al, "The negative impact of Wnt signaling on megakaryocyte and primitive erythroid progenitors derived from hyman embryonic stem cells," Stem Cell Res. 2014; 12: 441-51.
Pan, G. et al, "A negative feedback loop of transcription factors that controls stem cell pluripotency and self-renewal," FASEB J. 2006; 20: 1730-32.
Panopoulos, A.D. et al, "The metabolome of induced pluripotent stem cells reveals metabolic changes occurring in somatic cell reprogramming," Cell Res. 2012; 22: 168-77.
Papp, B, et al, "Reprogramming to pluripotency: stepwise resetting of the epigenetic landscape," Cell Res. 2011; 21: 486-501.
Patel SR, et al. Differential roles of microtubule assembly and sliding in proplatelet formation by megakaryocytes. Blood. 2005;106:4076-4085.
Patel SR, et al, The biogenesis of platelets from megakaryocyte proplatelets. J Clin Invest. 2005;115:3348-3354.
PCT/US17/48945 International Search Report and Written Opinion, dated Oct. 18, 2017, 10 pages.
Peichev, M. et al., Expression of VEGFR-2 and AC133 by circulating human CD341 cells identifies a population of functional endothelial precursors, Blood 95: 952-58 (2000).
Peng et al., Comparative Analysis of Mesenchymal Stem Cells from Bone Marrow, Cartilage, and Adipose Tissue, 2008, Stems Cells and Development, 17: 761-774.
Perussia, B et al., "Human natural killer cells analyzed by B73.1, a monoclonal antibody blocking Fc receptor function. I. Characterization of the lymphocyte subset reactive with B73.1," J. Immunol. 1983; 130: 2133-41.
Pevny L., et al., Erythroid differentiation in chimaeric mice blocked by a targeted mutation in the gene for transcription factor GATA-1. Nature. 1991;349:257-260.
Pittenger, M.F. et al., Multilineage Potential of Adult Human Mesenchymal Stem Cells., Science 284: 143-47 (1999).
Poli, A. et al, "CD56bright natural killer (NK) cells: an important NK cell subset," Immunol. Apr. 2009; 126(4): 458-65.
Portha B. et al., "Activation of the GLP-1 receptor signalling pathway: a relevant strategy to repair a deficient beta-cell mass", Exptl Diabetes Res. Article 376509: 1-11, (2011).
Quiskamp N, et al., Differentiation of human pluripotent stem cells into beta-cells: Potential and challenges. Best Pract Res Clin Endocrinol Metab 2015, 29: 833-847.
Radley JM and Haller CJ.; Fate of senescent megakaryocytes in the bone marrow. Br J Haematol. 1983;53:277-287.
Raskin P. et al. Glucagon and diabetes. Medical Clinics of North America, vol. 62, Issue 4, Jul. 1978, pp. 113-722.
Raslova H, et al. Mammalian target of rapamycin (mTOR) regulates both proliferation of megakaryocyte progenitors and late stages of megakaryocyte differentiation. Blood. 2006;107:2303-2310.
Redmer, T et al, "E-cadherin is crucial for embryonic stem cell pluripotency and can replace OCT4 during somatic cell reprogramming," EMBO Rep. 2011; 12:720-26.
Richardson JL, et al., Mechanisms of organelle transport and capture along proplatelets during platelet production. Blood. 2005;106:4066-4075.
Rojnuckarin P, et al, Thrombopoietin-induced activation of the mitogen-activated protein kinase (MAPK) pathway in normal megakaryocytes: role in endomitosis. Blood. 1999;94:1273-1282.
Roth GJ, et al., The platelet glycoprotein Ib-V-IX system: regulation of gene expression. Stem Cells 1996;14 Suppl 1:188-193.
Rouyez MC, et al, Control of thrombopoietin-induced megakaryocytic differentiation by the mitogen-activated protein kinase pathway. Mol Cell Biol. 1997;17:4991-5000.
Ruhnke, M et al, Differentiation of In Vitro-Modified Human Peripheral Blood Monocytes Into Hepatocyte-like and Pancreatic Islet-like Cells. Gastroenterology vol. 128, Issue 7, Jun. 2005, pp. 1774-1786.
Sabath DF, et al. Deletion of the extracellular membrane-distal cytokine receptor homology module of Mpl results in constitutive cell growth and loss of thrombopoietin binding. Blood. 1999;94:365-367.
Saigo, K., et al., "RANTES and p-Selectin in peripheral blood stem," Ther. Apher. Dial. 2001; 5: 517-18.
Saito, T. et al., Myogenic Expression of Mesenchymal Stem Cells within Myotubes of mdx Mice in Vitro and in Vivo, Tissue Eng. 1: 327-43 (1995).
Sakamaki, S. et al, "Transforming growth factor-?1 (TGF-?1) induces thrombopoietin from bone marrow stromal cells, which stimulates the expression of TGF-? receptor on megakaryocytes and, in turn, renders them susceptible to suppression by TGF-? itself with high specificity," Blood 1999; 94: 1961-70.
Salahuddin, SZ, et al, "Long term suspension cultures of human cord blood myeloid cells," 1981; Blood 58: 931-38.
Samavarchi-Tehrani, P. et al, "Functional genomics reveals a BMP-driven mesenchymal-to-epithelial transition in the initiation of somatic cell reprogramming," Cell Stem Cell 2010; 7: 64-77.
Sambrook, J and Russell, D.W., Molecular Cloning: A Laboratory Manual, Cold Spring Harbor Laboratory Press; 3rd ed., 2001.
Sanjuan-Pla, A., et al, "Platelet-biased stem cells reside at the apex of haematopoietic stem-cell hierarchy," Nature 2013; 502: 232-36.
Schulze H, et al., Thrombopoietin induces the generation of distinct Stat1, Stat3, Stat5a and Stat5b homo- and heterodimeric complexes with different kinetics in human platelets. Exp Hematol. 2000;28:294-304.
Seita J, et al. Lnk negatively regulates self-renewal of hematopoietic stem cells by modifying thrombopoietin-mediated signal transduction. Proc Natl Acad Sci U S A. 2007;104:2349-2354.
Shattil S.J., et al., Integrin signaling: The Platelet Paradigm, Blood. 1998; 91:2645-2657.
Shi, Y. et al, "A combined chemical and genetic approach for the generation of induced pluripotent stem cells," Cell Stem Cell 2008; 2: 525-28.
Shivdasani R.A., A lineage-selective knockout establishes the critical role of transcription factor GATA-1 in megakaryocyte growth and platelet development. EMBO J. 1997;16:3965-3973.
Sipe, JB et al, "Localization of bone morphogenetic proteins (BMPs)-2, -4, and -6 within megakaryocytes and platelets," Bone 2004; 35: 1316-22.
Skolnik EY, et al. The function of GRB2 in linking the insulin receptor to Ras signaling pathways. Science. 1993;260:1953-1955.
Smith, BW et al, "The aryl hydrocarbon receptor directs hematopoietic progenitor cell expansion and differenhation," Blood. 2013; 122: 376-85.
Smith, BW, and Murphy, GJ, "Stem cells, megakaryocytes, and platelets," Curr. Opin. Hematol. 2014; 21(5): 430-37.
Smith, S & Broxmeyer, HE; "The influence of oxygen tension on the long-term growth in vitro of hemopoietic progenitor cells from human cord blood," Brit. J. Haematol. (1986): 63: 29-34.
Soda M, et al, Inhibition of GSK-3beta promotes survival and proliferation of megakaryocytic cells through a beta-catenin-independent pathway. Cell Signal. 2008;20:2317-2323.
Spangrude, Gerald J. and Slayton, William B, "Isolation and Characterization of Hematopoietic Stem Cells," Handbook of Stem Cells, , vol. 2, Robert Paul Lanza, Ed. Elsevier Inc. (2004) Chapter 54, pp. 609-614.
Aatonen M., et al., Platelet-Derived Microvesicles: Multitalented Participants in Intercellular Communication, Seminars in Thrombosis and Hemostasis vol. 38, No. 1 (2012).
Aatonen MT et al., Isolation and characterization of platelet-derived extracellular vesicles, J. Extracellular Vesicles, vol. 3 (2014) 24692.
Abdi R. et al., "Immunomodulation by mesenchymal stem cells: a potential therapeutic strategy for type 1 diabetes", Diabetes, vol. 57: 1759-1767, (2008).
Abo, T et al, "Postnatal expansion of the natural killer and killer cell population in humans identified by the monoclonal HNK-1 antibody," J. Exp. Med. 1982; 155: 321-26.

(56) References Cited

OTHER PUBLICATIONS

Aghideh, AN et al, "Platelet growth factors suppress ex vivo expansion and enhance differentiation of umbilical cord blood CD133+ stem cells to megakaryocyte progenitor cells," Growth Factors 2010; 28(6): 409-16.
Aguayo-Mazzucato C. et al., "Stem cell therapy for type I diabetes", Nat Rev Endocrinol., vol. 6: 139-148, (2010).
Akashi K, et al., A clonogenic common myeloid progenitor that gives rise to all myeloid lineages. Nature. 2000; 404:193-197.
Alexander WS, et al, Tyrosine-599 of the c-Mpl receptor is required for Shc phosphorylation and the induction of cellular differentiation. Embo J. 1996;15:6531-6540.
Alexander WS, Hilton DJ. The role of suppressors of cytokine signaling (SOCS) proteins in regulation of the immune response. Annu Rev Immunol. 2004;22:503-529.
Anderson, U et al., Evidence for the ontogenic precedence of suppressor T cell functions in the human neonate, Eur. Immunol. 1983; 13: 6-13.
Athanasiou M, et al., Increased expression of the ETS-related transcription factor FLI-1/ERGB correlates with and can induce the megakaryocytic phenotype. Cell Growth Differ. 1996;7:1525-1534.
Ausubel, Ed., Short Protocols in Molecular Biology, Current Protocols; 5th ed., 2002.
Avruch J, et al. Ras activation of the Raf kinase: tyrosine kinase recruitment of the MAP kinase cascade. Recent Prog Horm Res. 2001;56:127-155.
Baban, B. et al., "Indoleamine 2,3-dioxygenase expression is restricted to fetal trophoblast giant cells during murine gestation and is maternal genome specific", J Reprod Immunol, 2004, 61: 67-77.
Bach J.F., "Anti-CD3 antibodies for type 1 diabetes: beyond expectations", Lancet., vol. 378: 459-460, (2011).
Baj-Krzyworzeka et al., Platelet derived microparticles stimulate proliferation, survival, adhesion, and chemotaxis of hematopoietic cells, Exp. Hematology 30 (2002) 450-459.
Baksh, et al., Adult mesenchymal stem cells: characterization, differentiation, and application in cell and gene therapy., J. Cell. Mol. Med. 8(3): 301-16, 305 (2004).
Bersenev A, et al, Lnk controls mouse hematopoietic stem cell self-renewal and quiescence through direct interactions with JAK2. J Clin Invest. 2008;118:2832-2844.
Bertozzi CC et al., Platelets regulate lymphatic vascular development through CLEC-2-SLP-76 signaling. Blood. 2010;116:661-70.
Bhatia, M. et al, "Bone morphogenetic proteins regulate the developmental program of human hematopoietic stem cells," J. Exp. Med. 1999; 189: 1139-48.
Boyer, LA et al, "Core transcriptional regulatory circuitry in human embryonic stem cells," Cell 2005; 122: 947-56.
Brizzi MF, et al, Discrete protein interactions with the Grb2/c-Cbl complex in SCF- and TPO-mediated myeloid cell proliferation. Oncogene. 1996;13:2067-2076.
Broudy V.C., et al.; Thrombopoietin (c-mpl ligand) acts synergistically with erythropoietin, stem cell factor, and interleukin-11 to enhance murine megakaryocyte colony growth and increases megakaryocyte ploidy in vitro. Blood. 1995;85:1719-1726.
Broxmeyer, HE et al, "Human umbilical cord blood as a potential source of transplantable hemopoietic stem/progenitor cells, " Proc. Natl Acad. Sci. USA (1989) 86: 3828-3719.
Bruno, S. et al, In vitro and in vivo megakaryocyte differentiation of fresh and ex-vivo expanded cord blood cells; rapid and transient megakaryocyte reconstitution., Haematologica 2003; 88(4): 379-87.
Bruserud, O et al, Autologous stem cell transplantation as post-remission therapy in adult acute myelogenous leukemia: Does platelet contamination of peripheral blood mobilized stem cell grafts influence the risk of leukemia relapse?, J. Hematother. Stem cell Res. 2000; 9: 433-43.
Bryant, et al, Nat. Rev. Mol. Cell Biol. "Regulated transport of the glucose transporter GLUT 4", vol. 3(4): 267-277, (2002).
Bunting S, et al. Normal platelets and megakaryocytes are produced in vivo in the absence of thrombopoietin. Blood. 1997;90:3423-3429.
Cabrera O. et al., "The unique cytoarchitecture of human pancreatic islets has implications for islet cell function", Proc. Natl Acad. Sci. U.S., vol. 103: 2334-2339, (2006).
Chambers, I., Tomlinson, S.R,"The transcriptional foundation of pluripotency," Development 2009; 136:(14) 2311-2322.
Chen, M. et al, "Promotion of the induction of cell pluripotency through metabolic remodeling by thyroid hormone triiodothyronine-activated PI3K/AKT signal pathway," Biomaterials 2012; 33: 5514-23.
Choi ES, et al., Platelets generated in vitro from proplatelet-displaying human megakaryocytes are functional. Blood. 1995;85:402-413.
Chou ST et al, "Graded repression of PU.1/Sfpi1 gene transcription by GATA factors regulates hematopoietic cell fate," Blood 2009; 114: 983-94.
Cicuttini, FM and Boyd AW, "Hematopoietic and lymphoid progenitor cells in human umbilical cord blood," Devel. Immunol. 4: 1-11.
Clement, LT et al, "Novel immunoregulatory functions of phenotypically distinct subpopulations of CD4+ cells in the human neonate," J. Immunol. (1990): 145: 102-108.
Coombs, MR. et al, "Apigenin inhibits the inducible expression of programmed death ligand 1 by human and mouse mammary carcinoma cells," Cancer Lett. 2016; 380(2): 424-33.
Craig, W., et al. CD45 isoform expression on human haemopoietic cells at different stages of development. British Journal of Haematology, 88:24-30. 1994.
Da Silva Xavier, G., et al.,"Per-amt-sim (PAS) domain-containing protein kinase is downregulated in human islets in type 2 diabetes and regulates glucagon secretion", Diabetologia, vol. 54: 819-827, (2011).
Dahlen DD, et al., Internalization of the thrombopoietin receptor is regulated by 2 cytoplasmic motifs. Blood. 2003;102:102-108.
David, L, and Polo, JM, "Phases of reprogramming," Stem Cell Res. 2014; 12: 754-61.
De Botton S, et al. Platelet formation is the consequence of caspase activation within megakaryocytes. Blood. 2002;100:1310-1317.
Defronzo R.A., "Pathogenesis of type 2 diabetes mellitus" Med. Clin. N. Am., vol. 88: 787-835 (2004)]; Gerich J.E., "Physiology of glucose homeostasis", Diabetes Obes. Metab. vol. 2: 345-350, (2000).
Delgado E, et al.: Modulation of Autoimmune T-Cell Memory by Stem Cell Educator Therapy: Phase 1/2 Clinical Trial. EBioMedicine 2015, 2: 2024-2036.
Delogu A, et al., Gene repression by Pax5 in B cells is essential for blood cell homeostasis and is reversed in plasma cells. Immunity. Mar. 2006; 24(3):269-81.
Dey A. et al., "Significance of prohormone convertase 2, PC2, mediated initial cleavage at the proglucagon interdomain site, Lys70-Arg71, to generate glucagon", Endocrinol., vol. 146: 713-727, (2005).
Doubeikovski, A., et al., Thrombopoietin-induced expression of the glycoprotein IIb gene involves the transcription factor PU. 1/Spi-1 in UT7-Mpl cells. J Biol Chem. 1997; 272:24300-24307.
Drachman JG, Kaushansky K. Dissecting the thrombopoietin receptor: functional elements of the Mpl cytoplasmic domain. Proc Natl Acad Sci U S A. 1997;94:2350-2355.
Drachman JG, Kaushansky K. Structure and function of the cytokine receptor superfamily. Curr Opin Hematol. 1995; 2:22-28.
Drucker D.J. et al., "The incretin system: glucagon-like peptide-1 receptor agonists and dipeptidyl peptidase-4 inhibitors in type 2 diabetes", Lancet, vol. 368: 1696-1705, (2006).
Drucker D.J., "The biology of incretin hormones", Cell Metab. vol. 3: 153-165, (2006).
Starr R, et al. A family of cytokine-inducible inhibitors of signalling. Nature. 1997;387:917-921.
Stenberg PE and Levin J.; Mechanisms of platelet production. Blood Cells. 1989; 15:23-47.
Stroncek, DF et al, "Collection of two peripheral blood stem cell concentrates from healthy donors", Transfus. Med. 1999; 9: 37-50.
Stroncek, et al., "Composition of peripheral blood progenitor cell components collected from a healthy donors [sic]," Transfusion 1997; 37: 411-17.

(56) References Cited

OTHER PUBLICATIONS

Su,Yu-Chieh, et al,"RAD001-mediated STAT3 upregulation and megakaryocytic differentiation," Thromb. Haemost. 2013; 109: 540-49.
Suarez-Alvarez, B. et al, "Mobilization and homing of hematopoietic stem cells," Adv. Exp. Med. Biol. 2012; 741: 152-70 (2012).
Sumarac-Dumanovic M. et al.,"Increased activity of interleukin-23/interleukin-17 proinflammatory axis in obese women", Int J Obes (Lond), vol. 33: 151-156, (2009).
Sutherland, H. J., et al., Characterization and partial purification of human marrow cells capable of initiating long-term hematopoiesis in vitro., (1989), Blood 74.1563-1570.
Takahashi, K., Yamanaka, S., "Induction of pluripotent stem cells from mouse embryonic and adult fibroblast cultures by defined factors," Cell, 126: 663-76, (2006).
Tang, Y. and Tian, X.C, "JAK-STAT3 and somatic cell reprogramming," JAK-STAT 2013; 2: e24935.
Tarakkanan, J and Saksela, E, "Umbilical cord blood-derived suppressor cells of the human natural killer cell activity are inhibited by interferon," Scand. J. Immunol. 1982; 15: 149-57.
Thierry, J.P, Sleeman, J.P, "Complex networks orchestrate epitheial-mesenchymal transitions," Nat. Rev. Mol. Cell Bio. 2006; 7: 131-42.
Tomita, S. et al., Autologous Transplantation of Bone Marrow Cells Improves Damaged Heart Function, Circulation 100 (Suppl. II): 247-256 (1999); Saito, T. et al., Tissue Eng. 1: 327-43 (1995).
Tong W, Lodish HF. Lnk inhibits Tpo-mpl signaling and Tpo-mediated megakaryocytopoiesis. J Exp Med. 2004;200:569-580.
Tostato, G., et al, "B cell differentiation and immunoregulatory T cell function in human cord blood lymphocytes," 1980; J. Clin. Invest. 66: 383-880.
Traver D, et al. Development of CD8alpha-positive dendritic cells from a common myeloid progenitor. Science (New York, NY. Dec. 15, 2000; 290 (5499):2152-4.
Triplitt C.L., "Examining the mechanisms of glucose regulation", Am. J. Manag. Care, vol. 18 (1 Suppl) S4-S10, (2012).
Uccelli A. et al., "Mesenchymal stem cells in health and disease", Nat Rev Immunol., vol. 8: 726-736, (2008).
Uldry M. et al., "The SLC2 family of facilitated hexose and polyol transporters", Thorens B, Eur. J. Physiol. 2004; vol. 447: 480-489, (2004).
Unger R.H. et al., "Glucagonocentric restructuring of diabetes: a pathophysiologic and therapeutic makeover", J. Clinical Investig. vol. 122(1): 4-12, (2012).
Unger R.H. et al., "Paracrinology of islets and the paracrinopathy of diabetes", Proc. Natl Acad. Sci., U.S., vol. 107 (37): 16009-16012, (2010).
Ungerer, M., et al, Generation of functional culture-derived platelets from CD34+ progenitor cells to study transgenes in the platelet environment; Cir. Res. 2004; 95(5): e36-44.
Vigon I, et al. Molecular cloning and characterization of MPL, the human homolog of the v-mpl oncogene: identification of a member of the hematopoietic growth factor receptor superfamily. Proc Natl Acad Sci U S A. 1992;89:5640-5644.
Voss, et al, "Flow cytometric detection of platelet activation in patients undergoing diagnostic and interventional coronary angiography," Platelets 1996; 7: 237-41 1996.
Vuguin P.M. et al. "Novel insight into glucagon receptor action: lessons from knockout and transgenic mouse models", Diabetes, Obesity & Metabolism, vol. 13(1), 144-150, (2011).
Wagner C.L, et al., Analysis of GPIIb/IIIa receptor number by quantification of 7E3 binding to human platelets. Blood. 1996;88:907-914.
Wahren J. et al., "The clinical potential of C-peptide in replacement in type 1 diabetes", Diabetes, vol. 61(4), 761-772,(2012).
Wang Q, et al. Interferon-a directly represses megakaryopoiesis by inhibiting thrombopoietin-induced signaling through induction of SOCS-1. Blood. 2000;96:2093-2099.

Wang, J. S. et al., The coronary delivery of marrow stromal cells for myocardial regeneration: Pathophysiologic and therapeutic implications, J. Thorac. Cardiovasc. Surg. 122: 699-705 (2001).
Wang, W. et al, "Rapid and efficient reprogramming of somatic cells to induced pluripotent stem cells by retinoic acid receptor gamma and liver receptor homolog 2," Proc. Natl Acad. Sci. USA 2011; 108: 18283-288.
Weissman IL., Translating stem and progenitor cell biology to the clinic: barriers and opportunities. Science (New York, NY. Feb. 25, 2000; 287(5457):1442-6.
Wherrett D.K. et al., "Antigen-based therapy with glutamic acid decarboxylase (GAD) vaccine in patients with recent-onset type 1 diabetes: a randomized double-blind trial", Lancet., vol. 378: 319-327, (2011).
Witthuhn BA, et al. JAK2 associates with the erythropoietin receptor and is tyrosine phosphorylated and activated following stimulation with erythropoietin. Cell. 1993;74:227-236.
Wu H.P. et al., "High interleukin-12 production from stimulated peripheral blood mononuclear cells of type 2 diabetes patients", Cytokine, vol. 51: 298-304, (2010).
Yamamoto, R. et al, "Clonal analysis unveils self-renewing lineage-restricted progenitors generated directly from hematopoietic stem cells," Cell. 2013; 154: 1112-26.
Yeh, et al., Transdifferentiation of Human Peripheral Blood CD34+-Enriched Cell Population Into Cardiomyocytes, Endothelial Cells, and Smooth Muscle Cells In Vivo, Circulation 108: 2070-73 (2003).
Yi, F. et al, "Rejuvenating liver and pancreas through cell transdifferentiation," Cell Res., 22(4): 616-619 (2012).
Yu, J. et al, "Induced pluripotent stem cell lines derived from human somatic cells," Science; 318: 1917-20 (2007).
Zhang J, et al. PTEN maintains haematopoietic stem cells and acts in lineage choice and leukaemia prevention. Nature. 2006;441:518-522.
Zhang, et al, "Identification of the haematopoietic stem cell niche and control of the niche size," Nature 2003; 425: 836-41.
Zhang, X, et al., "Successful immortalization of mesenchymal progenitor cells derived from human placenta and the differenhation abilities of immortalized cells", Biochem Biophys Res Commun, 2006, 351: 853-859.
Zhao Y, et al. Targeting insulin resistance in type 2 diabetes via immune modulation of cord blood-derived multipotent stem cells (CB-SCs) in stem cell educator therapy: phase I/II clinical trial. BMC Med 2013, 11: 160.
Zhao Y, et al., Human cord blood stem cell modulated regulatory T lymphocytes reverse the autoimmune-caused type 1 diabetes in non-obese diabetic (NOD) mice. PLoS ONE 2009, 4: e4226.
Zhao Y. et al., "Human cord blood stem cells and the journey to a cure for type 1 diabetes", Autoimmun Rev., vol. 10: 103-107, (2010).
Zhao Y. et al., "Reversal of type 1 diabetes via islet ?-cell regeneration following immune modulation by cord blood-derived multipotent stem cells", BMC Med. vol. 10(3), 1-11, (2012).
Zhao Y. et al., A unique human blood-derived cell population displays high potential for producing insulin., Biochemical and Biophysical Research Communications 360 (2007) 205-211.
Zhao Y. et al., Identification of stem cells from human umbilical cord blood with embryonic and hematopoietic characteristics. Exp. Cell Res., 312, 2454 (2006).
Zhao Y. et al.,"Immune regulation of T lymphocyte by a newly characterized human umbilical cord blood stem cell", Immunol Lett., vol. 108: 78-87, (2007).
Zhao, Y. et al, A human peripheral blood monocyte-derived subset acts as pluripotent stem cells., Proc. Natl Acad. Sci. USA (2003); 100: 2426-31.
Zhou, H. et al, "Generation of induced pluripotent stem cells using recombinant proteins," Cell Stem Cell 2009; 4: 381-84.
Donghui Zhang et al: "Highly efficient differentiation of human ES cells and iPS cells into mature pancreatic Insulin-producing cells", Cell Research, vol. 19, No. 4, Apr. 1, 2009 (Apr. 1, 2009), pp. 429-438.
Yong Zhao et al., "Platelet-Derived Mitochondria Display Embryonic Stem Cell Markers and Improve Pancreatic Islet [beta]-cell Function in Humans: Platelet Mitochondria Expand Islet [beta]-Cell

(56) References Cited

OTHER PUBLICATIONS

Function", Stem Cells Translational Medicine, vol. 6, No. 8, Jul. 7, 2017 (Jul. 7, 2017), pp. 1684-1697.

Yong Zhao, "Stem Cell Educator Therapy and Induction of Immune Balance", Current Diabetes Reports, Current Science Inc, New York, vol. 12, No. 5, Jul. 26, 2012 (Jul. 26, 2012), pp. 517-523.

Zhao Yong et al: "A human peripheral blood monocyte-derived subset acts as pluripotent stem cells", Proceedings of the National Academy of Sciences, National Academy of Sciences, US, vol. 100, No. 5, Mar. 4, 2003 (Mar. 4, 2003), pp. 2426-2431.

\* cited by examiner

D

H Western blot—PB-derived platelets preparations:

K

4 CB-derived platelets preparations

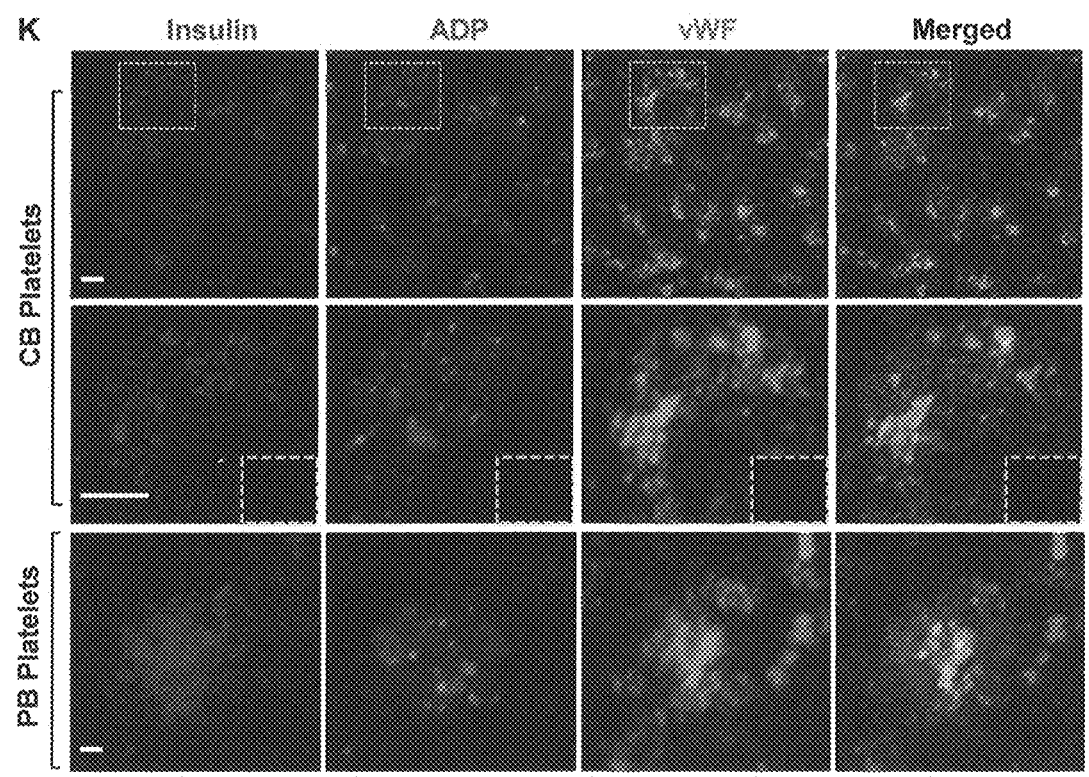

C

D

J

O

COMPOSITIONS AND METHODS FOR REPROGRAMMING ADULT CELLS THROUGH THE STEMNESS OF A PLATELET RICH FRACTION OF BLOOD CONTAINING PLATELET-LIKE CELLS IN HUMANS

CROSS-REFERENCE TO RELATED APPLICATIONS

This application claims benefit of priority to U.S. Provisional Application No. 62/520,241, filed on Jun. 15, 2017, and to U.S. Provisional Application No. 62/380,913 filed on Aug. 29, 2016, the entire contents of which are incorporated by reference herein.

FIELD

The described invention relates generally to methods of generating, isolating, and using functionally modified adult mononuclear cells. The described invention also relates to methods of generating, isolating, and using insulin producing cells derived from adult peripheral blood.

BACKGROUND OF THE INVENTION

Stem Cell Based Therapy

Stem cell manipulation for applications in tissue engineering and regenerative medicine has attracted considerable attention.

Embryonic stem cells (EmSC) are stem cells derived from an embryo that are pluripotent, i.e., they are able to differentiate in vitro into endodermal, mesodermal and ectodermal cell types. Embryonic stem (ES) cells are attractive because of their high potential for self-renewal and their pluripotent differentiation capability, but ethical concerns have limited their availability and practical usefulness.

Adult (somatic) stem cells are undifferentiated cells found among differentiated cells in a tissue or organ. Their primary role in vivo is to maintain and repair the tissue in which they are found. Adult stem cells have been identified in many organs and tissues, including brain, bone marrow, peripheral blood, blood vessels, skeletal muscles, skin, teeth, gastrointestinal tract, liver, ovarian epithelium, and testis. They reside in a specific local microenvironment of each tissue, known as a stem cell niche, where they may remain quiescent (non-dividing) for long periods of time until they are activated by a normal need for more cells to maintain tissue, or by disease or tissue injury. Examples of adult stem cells include, but not limited to, hematopoietic stem cells, mesenchymal stem cells, neural stem cells, epithelial stem cells, and skin stem cells.

Bone marrow consists of a variety of precursor and mature cell types, including hematopoietic cells (the precursors of mature blood cells) and stromal cells (the precursors of a broad spectrum of connective tissue cells), both of which appear to be capable of differentiating into other cell types. Wang, J. S. et al., J. Thorac. Cardiovasc. Surg. 122: 699-705 (2001); Tomita, S. et al., Circulation 100 (Suppl. II): 247-256 (1999); Saito, T. et al., Tissue Eng. 1: 327-43 (1995).

CD34+ cells represent approximately 1% of bone marrow derived nucleated cells. Hematopoietic stem cells (also known as the colony-forming unit of the myeloid and lymphoid cells (CFU-M,L), or CD34+ cells) are rare pluripotent cells within the blood-forming organs that are responsible for the continued production of blood cells during life. CD34 antigen also is expressed by immature endothelial cell precursors; mature endothelial cells do not express CD34+. Peichev, M. et al., Blood 95: 952-58 (2000). In vitro, CD34+ cells derived from adult bone marrow give rise to a majority of the granulocyte/macrophage progenitor cells (CFU-GM), some colony-forming units-mixed (CFU-Mix) and a minor population of primitive erythroid progenitor cells (burst forming units, erythrocytes or BFU-E). Yeh, et al., Circulation 108: 2070-73 (2003).

While there is no single cell surface marker exclusively expressed by hematopoietic stem cells, it generally has been accepted that human HSCs have the following antigenic profile: CD 34+, CD59+, Thy1+(CD90), CD38low/−, C-kit−/low and, lin−. CD45 is also a common marker of HSCs, except platelets and red blood cells, which are CD45−. HSCs can generate a variety of cell types, including erythrocytes, neutrophils, basophils, eosinophils, platelets, mast cells, monocytes, tissue macrophages, osteoclasts, T lymphocytes, and B lymphocytes. The regulation of hematopoietic stem cells is a complex process involving self-renewal, survival and proliferation, lineage commitment and differentiation and is coordinated by diverse mechanisms including intrinsic cellular programming and external stimuli, such as adhesive interactions with the micro-environmental stroma and the actions of cytokines.

Different paracrine factors are important in causing hematopoietic stem cells to differentiate along particular pathways. Paracrine factors involved in blood cell and lymphocyte formation are called cytokines. Cytokines can be made by several cell types, but they are collected and concentrated by the extracellular matrix of the stromal (mesenchymal) cells at the sites of hematopoiesis. For example, granulocyte-macrophage colony-stimulating factor (GM-CSF) and the multilineage growth factor IL-3 both bind to the heparan sulfate glycosaminoglycan of the bone marrow stroma. The extracellular matrix then presents these factors to the stem cells in concentrations high enough to bind to their receptors.

HSCs reside in the bone marrow but can be forced into the blood, a process termed mobilization. Stem cell mobilization is a process whereby stem cells are stimulated out of the bone marrow into the bloodstream, so they are available for collection from the peripheral blood for future reinfusion. Current mobilization strategies used in the clinic, mainly G-CSF cytokine, are well tolerated but often produce suboptimal number of collected HSCs. HSCs in the bone marrow niche generate energy mainly via anaerobic metabolism and have low levels of ROS, which promotes their self-renewal. Once recruited to the peripheral blood, however, their metabolic state changes, leading to the production of higher levels of ROS, which can induce the cells to differentiate, undergo senescence or lead to apoptosis. (Suda, T. et al, "Metabolic regulation of hematopoietic stem cells in the hypoxic niche," Cell Devel. 2007; 134(14): 2541-7).

Mobilization and homing are mirror processes depending on an interplay between chemokines, chemokine receptors, intracellular signaling, adhesion molecules and proteases. Homing to the bone marrow is necessary to optimize cell engraftment. The interaction between SDF-1/CXCL12 and its receptor CXCR4 is critical to retain HSCs within the bone marrow. (Suarez-Alvarez, B. et al, "mobilization and homing of hematopoietic stem cells," Adv. Exp. Med. Biol. 2012; 741: 152-70).

Human umbilical cord blood has long been a focus of attention as an important source of stem cells for transplantation for several reasons, e.g., (1) it contains a higher number of primitive hematopoietic stem cells (HSC) per volume unit, which proliferate more rapidly, than bone marrow; (2) there is a lower risk of rejection after transplantation; (3) transplantation does not require a perfect HLA antigen match (unlike in the case of bone marrow); (4) UC blood has already been successfully used in the treatment of inborn metabolic errors; and (5) there is no need for a new technology for collection and storage of the mononuclear cells from UC blood, since such methods are long established.

Stem cells expressing embryonic molecular markers have been reported from cord blood after removal of hematopoietic cells (including deletion of all leukocyte common antigen CD45 positive cells. (McGuckin, C P, et al, "Production of stem cells with embryonic characteristics from human umbilical cord blood," Cell Prolif. 2005; 38: 245-55). However, the scarcity of this cell population in cord blood significantly restricts its practical application.

Under certain conditions, an adult differentiated cell can switch its phenotype to that of another mature cell type by transdifferentiation. Transdifferentiation is highly facilitated when the cells are from closely related lineages or are derived from the same embryonic layer. For example, since both the pancreas and liver are endoderm-derived organs, using the appropriate sets of lineage-specific reprogramming transcription factors, hepatocytes can be turned into pancreatic beta cells and vice versa. (Yi, F. et al, "Rejuvenating liver and pancreas through cell transdifferentiation," Cell Res. 2012; 22(4): 616-619).

In addition, adult somatic cells can be reprogrammed to enter an embryonic stem cell-like state by being forced to express a set of transcription factors, for example, Oct-3/4 (or Pou5f1, the Octamer transcription factor-3/4), the Sox family of transcription factors (e.g., Sox-1, Sox-2, Sox-3, and Sox-15), the Klf family transcription factors (Klf-1, Klf-2, Klf-4, and Klf-5), and the Myc family of transcription factors (e.g., c-Myc, N-Myc, and L-Myc).

For example, human inducible Pluripotent Stem cells (iPSCs) are cells reprogrammed to express transcription factors that express stem cell markers and are capable of generating cells characteristic of all three germ layers (i.e., ectoderm, mesoderm, and endoderm). As originally published by Takahashi et al (Hawkins, K. et al, "Cell signalling pathways underlying iPSc reprogramming," World J. Stem Cells 2014; 6(5): 620-28, citing Takahashi, K., Yamanaka, S., "Induction of pluripotent stem cells from mouse embryonic and adult fibroblast cultures by defined factors," Cell 2006; 126: 663-76), Oct4, Sox2, Klf4 and cMyc were constitutively expressed using genome integrating retroviruses in both mouse and subsequently human fibroblasts, and under ES cell culture conditions were able to induce pluripotency. iPS cells have been successfully generated using episomal plasmids (Id. Citing Yu, J. et al, "Induced pluripotent stem cell lines derived from human somatic cells," Science 2007; 318: 1917-20), Sendai viruses (Id. Citing Fusaki, N. et al, "Efficient induction of transgene-free human pluripotent stem cells using a vector based on Sendai virus, an RNA virus that does not integrate into the host genome," Proc. Jpn Acad. Ser. B. Phys. Biol. Sci. 2009; 85: 348-62), and transposons (Id. Citing Wang, W. et al, "Rapid and efficient reprogramming of somatic cells to induced pluripotent stem cells by retinoic acid receptor gamma and liver receptor homolog 2," Proc. Natl Acad. Sci. USA 2011; 108: 18283-288) to deliver the reprogramming factors, and even proteins (Id. Citing Zhou, H. et al, "Generation of induced pluripotent stem cells using recombinant proteins," Cell Stem Cell 2009; 4: 381-84) or small molecules (Hou, P. et al, "Pluripotent stem cells induced from mouse somatic cells by small molecule compounds," Science 2013; 341: 651-54) alone. The initial need for viral transfection raised concerns about safety with respect to teratogenicity and immunogenicity, and ex vivo transfection of cells may not be stable in the patient. Reprogramming using episomes raises the same concerns. Likewise, chemical reprogramming may not be stable in the patient.

That being said, many diverse cell types have been successfully reprogrammed to pluripotency (Id.). Often, the minimal factors necessary to reprogram a cell depend on the endogenous "stemness" of the starting cell; for example, neural stem cells can be reprogrammed using Oct4 alone since they express high levels of the other factors (Id. Citing Kim, J B, et al, "Oct4-induced pluripotency in adult neural stem cells, "Cell 2009; 136: 411-19).

A "core circuitry" of homeodomain transcription factors, Oct4, Sox2 and Nanog, governs pluripotency in both mouse and human ES cells (Id. Citing Chambers, I., Tomlinson, S R," The transcriptional foundation of pluripotency," Development 2009; 136: 2311022). These transcription factors are expressed both in vivo in the inner cell mass of the blastocyst and in vitro in pluripotent cells. Their close interaction facilitates the precise regulation of the core circuitry necessary to maintain the pluripotent state; for instance Oct4 overexpression leads to endoderm and mesoderm differentiation, whereas blockade of Oct4 induces trophoblast differentiation (Id. Citing Niwa, H. et al, "Quantitative expression of Oct3/4 defines differentiation, dedifferentiation or self-renewal of ES cells," Nat. Genet. 2000; 24: 372-76). Low levels of Oct4 result in upregulation of Nanog, whereas higher levels of Oct4 result in downregulation of Nanog (Id. Citing Loh, Y H, et al, "The Oct4 and Nanog transcriptin network regulates pluripotency in mouse embryonic stem cells," Nat. Genet. 2006' 38: 431-440). Similarly, small increases in Sox2 expression or ablation of Sox 2 expression both induce multilineage differentiation (Id. Citing Klopp, J L et al, "Small increases in the level of Sox2 trigger the differentiation of mouse embryonic stem cells," Stem Cells 2008; 26: 903-11). All 3 factors have been shown to regulate the expression of each other as well as themselves. (Id. Citing Boyer, L A et al, "Core transcriptional regulatory circuitry in human embryonic stem cells," Cell 2005; 122: 947-56; Loh, Y H, et al, "The Oct4 and Nanog transcription network regulates pluripotency in mouse embryonic stem cells," Nat. Genet. 2006' 38: 431-440; Pan, G. et al, "A negative feedback loop of transcription factors that controls stem cell pluripotency and self-renewal," FASEB J. 2006; 20: 1730-32).

Cell Signalling Pathways Underlying iPSc Reprogramming

Induced pluripotent stem cell reprogramming consists of three phases: initiation, maturation, and stabilization. Hawkins, K. et al, "Cell signalling pathways underlying iPSc reprogramming," World J. Stem Cells 2014; 6(5): 620-28), citing Samavarchi-Tehrani et al (36).

The initiation phase is characterized by somatic genes being switched off by methylation, an increase in cell proliferation, a metabolic switch from oxidative phosphorylation to glycolysis, reactivation of teleomerase activity and a mesenchymal-to-epithelial transition (MET)(Id. Citing David, L, and Polo, J M, "Phases of reprogramming," Stem Cell Res. 2014; 12: 754-61), which involves the loss of mesenchymal characteristics, such as motility, and the acquisition of epithelial characteristics, such as cell polarity and expression of E-Cadherin (Id. Citing Redmer, T et al, "E-cadherin is crucial for embryonic stemcell pluripotency and can replace OCT4 during somatic cell reprogramming,"

EMBO Rep. 2011; 12: 720-26). Mechanistically, Sox2 suppresses expression of Snail, an EMT inducer (Id. Citing Liu, X et al, "Sequential introduction of reprogramming factors reveals a time-sensitive requirement for individual factors and a sequential EMT-MET mechanism for optimal reprogramming," Nat. Cell Biol. 2013; 15: 829-38), and Klf4 induces E-cadherin expression, thus promoting MET (Id. Citing Li, R et al., "A mesenchymal-to-epithelial transition initiates and is required for the nuclear reprogramming of mouse fibroblasts," Cell Stem Cell 2010; 7: 51-63). TGFβ inhibition can enhance the initiation stage of both mouse (Id. Citing Maherali, N et al, "Tgfbeta signal inhibition cooperates in the induction of iPSCs and replaces Sox2 and cMyc," Curr. Biol. 2009; 19: 1718-23; Shi, Y. et al, "A combined chemical and genetic approach for the generation of induced pluripotent stem cells," Cell Stem Cell 2008; 2: 525-28) and human somatic cell reprogramming (Id. Citing Lin, T., et al, "A chemical platform for improved induction of human iPSCs," Nat. Methods 2009; 6: 805-808), showing that addition of recombinant TGFβ abrogates iPS cell formation, likely due to the EMT-inducing action of TGFβ signaling, which then prevents MET. TGFβ inhibitors promote Nanog expression, and mitogen-activated protein kinase (MAPK) signalling, activated by TGFβ, further induces the expression of mesodermal genes. (Id. Citing Thierry, J P, Sleeman, J P, "Complex networks orchestrate epitheial-mesenchymal transitions," Nat. Rev. Mol. Cell Bio. 2006; 7: 131-42). Inhibitors of MAPK signalling have therefore been used in combination with TGFβ inhibitors to promote MET (Id. Citing Lin, T., et al, "A chemical platform for improved induction of human iPSCs," Nat. Methods 2009; 6: 805-808).

Bone morphogenetic protein (BMP) signaling also plays an important role in the initiation stage of mouse iPS cell reprogramming by promoting MET via upregulation of epithelial genes, such as E-cadherin, occludin and epithelial cell adhesion molecule (Id. Citing Samavarchi-Tehrani, P. et al, "Functional genomics reveals a BMP-driven mesenchymal-to-epithelial transition In the initiation of somatic cell reprogramming," Cell Stem Cell 2010; 7: 64-77). However, constitutive BMP activation prevents human somatic cell reprogramming.

Fibroblast growth factor (FGF) signaling has also been implicated at the initiation stage (Id. Citing Jiao, J. et al, "Promoting reprogramming by FGF2 reveals that the extracellular matrix is a barrier for reprogramming fibroblasts to pluripotency," Stem Cells 2013; 31: 729-740). It has been shown that FGF2 promotes the early stages of reprogramming through accelerating cell proliferation, facilitating MET and eliminating extracellular collagens. In addition to an increased proliferation rate, the minority of cells that undergo successful reprogramming also exhibit resistance to apoptosis and senescence by transgene expression (Id. Citing Papp, B, "Reprogramming to pluripotency: stepwise resetting of the epigenetic landscape," Cell Res. 2011; 21: 486-501).

The initiation phase is also characterized by a metabolic switch from oxidative phosphorylation to glycolysis (Id. Citing Panopoulos, A D et al, "The metabolome of induced pluripotent stem cells reveals metabolic changes occurring in somatic cell reprogramming," Cell Res. 2012; 22: 168-77), which involves PI3K/AKT signaling (Id. Citing Zhu, S. et al, "Reprogramming of human primary somatic cells by OCT4 and chemical compounds," Cell Stem Cell 2010; 7: 651-55; Chen, M. et al, "Promotion of the induction of cell pluripotency through metabolic remodeling by thyroid hormone triiodothyronine-activated PI3K/AKT signal pathway," Biomaterials 2012; 33: 5514-23).

During the maturation phase, epigenetic changes occur allowing expression of the first pluripotency-associated genes (Id. Citing David, L, and Polo, J M, "Phases of reprogramming," Stem Cell Res. 2014; 12: 754-61), which include Fbxo15, Sal4, Oct4, Nanog and Esrrb. LIF/STAT3 signaling is required for the maturation phase of mouse iPS cell reprogramming (Id. Citing Tang, Y and Tian, X C, "JAK-STAT3 and somatic cell reprogramming," JAK-STAT 2013; 2: e24935). Wnt signaling also enhances the maturation phase of mouse somatic cell reprogramming, whereby exogenous stimulation of the pathway using Wnt3a after induction of reprogramming enhances formation of Nanog positive colonies (id. Citing Ho, R, et al, "Stage-specific regulation of reprogramming to induced pluripotent stem cells by Wnt signaling and T cell factor proteins," Cell Rep. 2013; 3: 2113-26).

The stabilization phase is characterized by transgene independence; therefore, only cells that have activated endogenous pluripotency gene expression are able to maintain pluripotency at this late stage.

Platelets

Platelets (thrombocytes), anucleate discoid-shaped cell fragments generated from large (50 to 100 μm in diameter) multinucleated (up to 128 N) megakaryocytes (MK), play a central role in hemostasis (meaning the stoppage of blood loss at sites of vascular injury) and vascular repair. Principles of Tissue Engineering, 4$^{th}$ Ed., Robert Lanza, Robert Langer, Joseph Vacanti, Eds, Elsevier, Inc.: New York, 2014 at 1047-1048. They represent about $3 \times 10^{11}$ cells/liter in peripheral blood, i.e., second only to those of RBCs. Platelets have a short life span, lasting only 7-9 days in the circulation.

Platelet Function

Primary hemostasis is achieved through a synergistic network of receptor/ligand interactions that result in platelet adhesion and simultaneous platelet activation, platelet secretion to activate nearby platelets, platelet aggregation, and ultimately formation of a platelet plug and generation of a surface amenable to assembly of coagulation factor complexes. Haley, K M et al, "Neonatal platelets: mediators of primary hemostasis in the developing hemostatic system," Pediatr. Res. 2014; 76(3): 230-37.

Platelet Adhesion.

Following vascular injury and the attendant endothelial damage, platelet adhesion, initiating the process of primary hemostasis, is mediated through receptor/ligand interactions in a step-wise fashion. Id. Extracellular von Willebrand factor (VWF)-platelet glycoprotein (GP) Ib binding mediates initial platelet recruitment to the injured area. Id. Platelet GPVI interacts with fibrillary collagen and platelet β1 integrin interacts with laminin, collagen and fibronectin, allowing for firm adhesion of platelets to the exposed extracellular matrix. Id.

Platelet Activation.

Following platelet adhesion, a series of downstream signaling events results in an increase in intracellular calcium and subsequent platelet activation marked by exposure of negatively-charged phosphatidylserine (PS) on the platelet membrane surface, allowing for the assembly of coagulation factors; platelet alpha and delta granule secretion, resulting in the release of ADP, calcium, serotonin, VWF, coagulation factors V and VIII, and fibrinogen; platelet membrane GPIIb/IIIa integrin conversion to a high affinity state for VWF and fibrinogen binding; thromboxane A2 generation through arachidonic acid metabolism; and cytoskeletal reorganization to increase the surface area of spread platelets. Id.

Platelet Aggregation.

A key step for the development of a stable platelet aggregate is the conversion of the GPIIb/IIIa receptor into its high affinity conformation. Id. This allows for stable interactions between the receptor and fibrinogen, VWF, and fibronectin. Platelets aggregate together, forming a platelet plug, the end product of primary hemostasis.

Platelet Markers

Markers that Appear on the Platelet Surface Before Activation.

Platelet surface markers, which appear on the platelet surface before activation, include CD41 (GP IIb/IIIa), CD42a (GPIX), CD42b (GPIb), and CD61 (avb3, vitronectin receptor).

Integrin alpha chain 2b (CD41) is a heterodimeric integral membrane protein that undergoes post-translational modifications that result in two polypeptide chains linked by a disulfide bond. CD41 is expressed on platelets and megakaryocytes and on early embryonic hematopoietic stem cells. A CD41/CD61 complex formed by the integrin alpha chain associated with a beta 3 chain (CD61) Integrin αIIbβ3 is a receptor for fibronectin, fibrinogen, von Willebrand factor, vitronectin and thrombospondin, and plays an important role in coagulation. The GPIIb/IIIa receptor (integrin αIIbβ3) is one of the most abundant cell surface receptors (≈80 000 per platelet) [Wagner C L, Mascelli M A, Neblock D S, Weisman H F, Coller B S, Jordan R E. Analysis of GPIIb/IIIa receptor number by quantitation of 7E3 binding to human platelets. Blood. 1996; 88:907-914], which represents about 15% of total surface protein. [Jennings, L K, Phillips, D R, "Purification of glycoproteins IIb and III from human platelet plasma membranes and characterization of a calcium-dependent glycoprotein IIb-Ill complex. J Biol Chem. 1982; 257:10458-10466]. On quiescent platelets, this receptor exhibits minimal binding affinity for von Willebrand factor and plasma fibrinogen. [French, D L, Seligsohn, U, "Platelet Glycoprotein IIb/IIIa receptors and Glanzmann's throbasthenia," Arteriosclerosis, thrombosis and Vascular Biology 2000: 20: 607-610].

CD42a-d complex is a receptor for von Willebrand factor and thrombin. CD42a is also called platelet glycoprotein GPIX, GP9a. CD42b is also called platelet GPIb alpha, or glycoprotein 1b-alpha.

Markers which Appear on the Platelet Surface During Activation.

Examples of markers which appear on the platelet surface during activation include activated IIb/IIIa, CD62P (P-selectin), CD31 (PECAM) and CD63.

In an activated state, "inside-out" signal transduction mechanisms [Shattil S J, Kashiwagi H, Pampori N. Integrin signaling: the platelet paradigm. Blood. 1998; 91:2645-2657] trigger a conformational change in the GPIIb/IIIa receptor (integrin αIIbβ33) to a high-affinity ligand-binding state that is competent to bind adhesive glycoproteins and form a platelet plug.

P-selectin mediates the initial adhesion of activated platelets to monocytes and neutrophils via the P-selectin glycoprotein ligand-1 (PSGL-1) counterreceptor on the leukocyte surface. [Michelson, A D and Furman, M I, "Markers of Platelet Activation and Granule Secretion," in Contemporary Cardiology: Platelet Function: Assessment, Diagnosis and Treatment, M. Quinn and D. Fitzgerald, Eds, Humana Press, Towaco N.J.: 2005]. It is a component of the α granule membrane of resting platelets that is only expressed on the platelet surface membrane after a granule secretion. Id. In vivo, circulating degranulated platelets rapidly lose their surface P-selectin but continue to circulate and function. Id. Soluble P-selectin in plasma may be of endothelial cell origin. Id.

Soluble CD40 ligand (sCD40L, CD154) is a plasma marker of in vivo platelet activation. Id. Release of sCD40L by activated platelets is the predominant source of plasma sCD40L; the mechanism of sCD40L release is proteolysis of platelet surface CD40L. Id. Accurate measurement of in vivo circulating sCD40L requires assay in plasma rather than serum. Id.

Lysosomal Activated Membrane Protein (CD63) is a cell surface glycoprotein that is known to complex with integrins. It may function as a blood platelet activation marker.

Platelet surface P-selectin (CD62P) is a component of the α-granule membrane of resting platelets that is only expressed on the platelet surface membrane after a granule secretion.

Megakaryopoiesis and Thrombopoiesis

Megakaryocytes (MK), the precursor of platelets, provide a constant source of platelets to the blood system, and are themselves produced through the process of megakaryopoiesis. As with RBCs MKs are generated through the initial differentiation of hematopoietic stem cells (HSCs) into common myeloid progenitors (CMPs). (Kaushansky, K., "Historical Review: megakaryopoiesis and thrombopoiesis," Blood 2008; 111(3): 981-86). Progressive commitment of CMPs to the megakaryocyte lineage is principally regulated by thrombopoietin (TPO). The committed megakaryocyte progenitor cells, colony forming units-megakaryocyte (CFU-MK), proliferate and differentiate into megakaryocytes. Id. The maturation of a megakaryocyte involves an increase in expression of the cell surface markers GPIIb/IIIa (also known as CD41 or αIIb/βIII integrin receptor) and GPIb/GPIX/GPV receptors, and a substantial increase in cell mass, which results in cytosolic accumulation of a granules, dense bodies, and platelet-associated proteins like von Willebrand factor (vWF) and platelet factor-4. Id. Several rounds of endomitosis lead to polyploidization and cells with up to 128N in DNA content. Id. Once polyploid MKs are produced, cellular processes on the MK body called 'protoplatelets' begin to appear, with their eventual fragmentation and release, resulting in the generation of platelets. Id.

HSCs from peripheral blood (PB), bone marrow (BM) and CB are also capable of producing megakaryocytes and functional platelets. (See Norol, F et al, Effects of cytokines on platelet production from blood and marrow CD34+ cells. Blood 1998; 91(3); 830-43; Bruno, S. et al, In vitro and in vivo megakaryocyte differentiation of fresh and ex-vivo expanded cord blood cells; rapid and transient megakaryocyte reconstitution. Haematologica 2003; 88(4): 379-87; Ungerer, M et al, Generation of functional culture-derived platelets from CD34+ progenitor cells to study transgenes in the platelet environment; Cir. Res. 2004; 95(5): e36-44).

Cellular Origins of Megakaryopoiesis

Two colony morphologies that contain exclusively megakaryocytes have been described in semisolid media. [Kaushansky, K., "Historical review: megakaryopoiesis and thrombopoiesis, Blood 2001; 111(3): 981-86]. The colony-forming unit-megakaryocyte (CFU-MK) is a cell that develops into a simple colony containing from 3 to 50 mature megakaryocytes; larger, more complex colonies that include satellite collections of megakaryocytes and contain up to several hundred cells are derived from the burst-forming unit-megakaryocyte (BFU-MK). Id. Because of the difference in their proliferative potential and by analogy to erythroid progenitors, BFU-MK and CFU-MK are thought to represent the primitive and mature progenitors restricted to the lineage, respectively. Id. Like their erythroid counterparts, the cytokine requirements for CFU-MK are simple; thrombopoietin stimulates the growth of 75% of all CFU-MK, with interleukin (IL)-3 being required along with thrombopoietin for the remainder. IL-3 or steel factor (SF) is required along with thrombopoietin for more complex, larger MK colony formation from primitive progenitor cells.

Megakaryocytes also arise in clonal colonies containing cells of one or more additional hematopoietic lineages. The most primitive in vitro colony-forming cell is termed a colony-forming unit-granuloycte-erythrocyte-monocyte-megakaryocte (CFU-GEMM), mixed progenitor colony (CFU-Mix), or common myeloid progenitor (CMP; Id. Citing Akashi K, Traver D, Miyamoto T, Weissman I L. A clonogenic common myeloid progenitor that gives rise to all myeloid lineages. Nature. 2000; 404:193-19719), and colonies derived from this cell often contain several megakaryocytes. A derivative of the CMP is the mixed MK/erythroid progenitor cell (MEP; Id. Citing Nakorn T N, Miyamoto T, Weissman I L. Characterization of mouse clonogenic megakaryocyte progenitors. Proc Natl Acad Sci USA. 2003; 100:205-210). Before their purification, the existence of an MEP was postulated based on the many common features of cells of the erythroid and megakaryocytic lineage, including the expression of several common transcription factors (SCL, GATA1, GATA2, NF-E2), cell surface molecules (TER119), and cytokine receptors (for IL-3, SF, erythropoietin, and thrombopoietin), and the finding that most erythroid and MK leukemia cell lines display, or can be induced to display, features of the alternate lineage. (Id. Citing McDonald T P, Sullivan P S. Megakaryocytic and erythrocytic cell lines share a common precursor cell. Exp Hematol. 1993; 21:1316-1320; Nakahata T, Okumura N. Cell surface antigen expression in human erythroid progenitors: erythroid and megakaryocytic markers. Leuk Lymphoma. 1994; 13:401-409) Moreover, the cytokines most responsible for development of these two lineages, erythropoietin and thrombopoietin, the two most closely related proteins in the hematopoietic cytokine family (Id. Citing Lok S, Kaushansky K, Holly R D, et al. Cloning and expression of murine thrombopoietin cDNA and stimulation of platelet production in vivo. Nature. 1994; 369:565-568), display synergy in stimulating the growth of progenitors of both lineages. (Id. Citing Broudy V C, Lin N L, Kaushansky K. Thrombopoietin (c-mpl ligand) acts synergistically with erythropoietin, stem cell factor, and interleukin-11 to enhance murine megakaryocyte colony growth and increases megakaryocyte ploidy in vitro. Blood. 1995; 85:1719-1726).

The transcription factors expressed by megakaryocytic progenitors that allow for their commitment to the lineage include GATA1, and FOG29. GATA1 is an X-linked gene encoding a 50 kDa zinc finger DNA binding protein. (Id. Citing Martin D I, Zon L I, Mutter G, Orkin S H. Expression of an erythroid transcription factor in megakaryocytic and mast cell lineages. Nature. 1990; 344:444-447). Genetic elimination of the transcription factor established the critical role of this transcription factor in hematopoiesis; the GATA1−/− condition is embryonic lethal due to failure of erythropoiesis (Id. Citing Pevny L, Simon M C, Robertson E, et al. Erythroid differentiation in chimaeric mice blocked by a targeted mutation in the gene for transcription factor GATA-1. Nature. 1991; 349:257-260), and megakaryocyte-specific elimination of GATA1 leads to severe thrombocytopenia due to dysmegakaryopoiesis. (Id. Citing Shivdasani R A, Fujiwara Y, McDevitt M A, Orkin S H. A lineage-selective knockout establishes the critical role of transcription factor GATA-1 in megakaryocyte growth and platelet development. EMBO J. 1997; 16:3965-3973). GATA1 acts in concert with friend of GATA (FOG29), another protein that affects transcription without binding to DNA, The ets family of transcription factors includes approximately 30 members that bind to a purine box sequence, and consists of proteins that interact in both positive and antagonistic ways. For example, PU.1, initially termed Spi-1 based on its association with spleen focus-forming virus products, blocks erythroid differentiation, although it supports megakaryocyte development. (Id. Citing Doubeikovski A, Uzan G, Doubeikovski Z, et al. Thrombopoietin-induced expression of the glycoprotein IIb gene involves the transcription factor PU. 1/Spi-1 in UT7-Mpl cells. J Biol Chem. 1997; 272:24300-24307). Moreover, the ets factor Fli-1 is essential for megakaryopoiesis (Id. Citing Athanasiou M, Clausen P A, Mavrothalassitis G J, Zhang X K, Watson D K, Blair D G. Increased expression of the ETS-related transcription factor FLI-1/ERGB correlates with and can induce the megakaryocytic phenotype. Cell Growth Differ. 1996; 7:1525-1534), and mutations in the genetic region of the transcription factor are associated with congenital thrombocytopenia in humans. (Id. Citing Hart A, Melet F, Grossfeld P, et al. Fli-1 is required for murine vascular and megakaryocytic development and is hemizygously deleted in patients with thrombocytopenia. Immunity. 2000; 13:167-177).

Thrombopoiesis

Thrombopoiesis is the process of formation of thrombocytes (platelets). On a molecular level, thrombopoiesis is a highly coordinate process, with sophisticated reorganization of membrane and microtubules and precise distribution of granules and organelles. Platelets form by fragmentation of mature megakaryocyte membrane pseudopodial projections termed proplatelets (Kaushansky citing Patel S R, Hartwig J H, Italiano J E., Jr The biogenesis of platelets from megakaryocyte proplatelets. J Clin Invest. 2005; 115:3348-3354), in a process that consumes nearly the entire cytoplasmic complement of membranes, organelles, granules, and soluble macromolecules. It has been estimated that each megakaryocyte gives rise to 1000 to 3000 platelets (Id. Citing Stenberg P E, Levin J. Mechanisms of platelet production. Blood Cells. 1989; 15:23-47) before the residual nuclear material is eliminated by macrophage-mediated phagocytosis. (Id. Citing Radley J M, Haller C J. Fate of senescent megakaryocytes in the bone marrow. Br J Haematol. 1983; 53:277-287). This process involves massive reorganization of megakaryocyte membranes and cytoskeletal components, including actin and tubulin, during a highly active, motile process in which the termini of the process branch and issue platelets. (Id. Citing Italiano J E, Jr, Lecine P, Shivdasani R A, Hartwig J H. Blood platelets are assembled principally at the ends of proplatelet processes produced by differentiated megakaryocytes. J Cell Biol. 1999; 147:1299-1312) Localized apoptosis may play a role in initiating the final stages of platelet formation, (Id. Citing Li J, Kuter D J. The end is just the beginning: megakaryocyte apoptosis and platelet release. Int J Hematol. 2001; 74:365-374; De Botton S, Sabri S, Daugas E, et al. Platelet formation is the consequence of caspase activation within megakaryocytes. Blood. 2002; 100:1310-1317) potentially by allowing the issuing of proplatelet processes from the constraints of the actin cytoskeleton. During the final stages of proplatelet maturation, cytoplasmic organelles and secretory granules traffic to the distal tips of proplatelet processes and are trapped there. (Id. Citing Richardson J L, Shivdasani R A, Boers C, Hartwig J H, Italiano J E., Jr Mechanisms of organelle transport and capture along proplatelets during platelet production. Blood. 2005; 106:4066-4075) Microtubules sliding over one another are the engine that drives the elongation of proplatelet processes and organelle transportation. (Id. Citing Patel S R, Richardson J L, Schulze H, et al. Differential roles of microtubule assembly and sliding in proplatelet formation by megakaryocytes. Blood. 2005; 106: 4076-4085). While thrombopoietin is the primary regulator of thrombopoiesis, little is known about what determines the size of mature platelets or how the mechanism of platelet formation is affected by the transcription factor GATA1, the glycoprotein Ib/IX complex, the Wiskott Aldrich syndrome protein (WASP), and platelet myosin, as defects in each of these genes leads to unusually large or small platelets. (Id. Citing Geddis A E, Kaushansky K. Inherited thrombocytopenias: toward a molecular understanding of disorders of platelet production. Curr Opin Pediatr. 2004; 16:15-22). Despite the importance of thrombopoietin for the generation of fully mature megakaryocytes from which platelets arise, elimination of the cytokine during the final stages of platelet formation is not detrimental (Id. Citing Choi E S, Nichol J L, Hokom M M, Hornkohl A C, Hunt P. Platelets generated in vitro from proplatelet-displaying human megakaryocytes are functional. Blood. 1995; 85:402-413).

Umbilical Cord

Two types of umbilical stem cells can be found, namely hematopoietic stem cells (UC-HS) and mesenchymal stem cells, which in turn can be found in umbilical cord blood (UC-MS) or in Wharton's jelly (UC-MM).

Umbilical cord (UC) vessels and the surrounding mesenchyma (including the connective tissue known as Wharton's jelly) derive from the embryonic and/or extraembryonic mesodermis. Thus, these tissues, as well as the primitive germ cells, are differentiated from the proximal epiblast, at the time of formation of the primitive line of the embryo, containing MSC and even some cells with pluripotent potential. The UC matrix material is speculated to be derived from a primitive mesenchyma, which is in a transition state towards the adult bone marrow mesenchyma (Mihu, C. et al., 2008, Romanian Journal of Morphology and Embryology, 2008, 49(4):441-446).

The blood from the placenta and the umbilical cord, which contains all the normal elements of blood—red blood cells, white blood cells, platelets and plasma—is relatively easy to collect in usual blood donation bags, which contain anticoagulant substances. Mononuclear cells then are separated by density gradient centrifugation. In Ficoll-Paque density gradient centrifugation, anticoagulant-treated and diluted cord blood is layered on the Ficoll-Paque solution and centrifuged. During centrifugation, erythrocytes and granulocytes sediment to the bottom layer. Cord blood mononuclear cells and other slowly sedimenting particles with low density (e.g., platelets) are retained at the interface between the plasma and Ficoll-Paque, where they can be collected. (Jaatinen, T., Laine, J. "Isolation of Mononuclear Cells from Human Cord Blood by Ficoll-Paque Density Gradient," Unit 2A, Curr. Protocols in Stem Cell Biol., DOI: 10.1002/9780470151808.sc02a01 s1). Exposure of the cells at the interface to platelet growth factors has the potential to affect the functional properties of such cells (Aghideh, A N et al, "Platelet growth factors suppress ex vivo expansion and enhance differentiation of umbilical cord blood CD133+ stem cells to megakaryocyte progenitor cells," Growth Factors 2010; 28(6): 409-16, Citing Voss, et al, "Flow cytometric detection of platelet activation in patients undergoing diagnostic and interventional coronary angiography, "Platelets 1996; 7: 237-41 1996; Gutensohn, K. et al, "Flow cytometric analysis of platelet membrane antigens during and after continuous flow plateletpheresis," Transfusion 1997: 37: 809-15; Gutensohn, K. "Alteration of platelet-associated membrane glycoproteins during extracorporeal apheresis of peripheral blood progenitor cells," J. Hematother. 1997; 6: 315-21; Stroncek, et al., "/composition of peripheral blood progenitor cell components collected from a healthy donors [sic]," Transfusion 1997; 37: 411-17; Stroncek, D F et al, "Collection of two peripheral blood stem cell concentrates from healthy donors," Transfus. Med. 1999; 9: 37-50; Bruserud, O et al, "Autologous stem cell transplantation as post-remission therapy in adult acute myelogenous leukemia: Does platelet contamination of peripheral blood mobilized stem cell grafts influence the risk of leukemia relapse?, J. Hematother. Stem cell Res. 2000; 9: 433-43; Saigo, K., et al., "RANTES and p-Selectin in peripheral blood stem," Ther. Apher. Dial. 2001; 5: 517-18).

The mononuclear cell fraction includes two stem cell populations: (1) hematopoietic stem cells (HSC), which express certain characteristic markers (CD34, CD133); and (2) mesenchymal stem cells (MSC) that are capable of adhering to a culture surface under certain conditions (e.g., modified McCoy medium and lining of vessels with Fetal Bovine Serum (FBS) or Fetal Calf Serum (FCS)). (Munn, D. et al., Science, 1998, 281: 1191-1193; Munn, D. et al., J Exp Med, 1999, 189: 1363-1372). Umbilical cord blood MSCs (UC-MS) can produce cytokines, which facilitate grafting in the donor and in vitro HSC survival compared to bone marrow MSC. (Zhang, X et al., Biochem Biophys Res Commun, 2006, 351: 853-859).

MSCs from the umbilical cord matrix (UC-MM) are obtained by different culture methods depending on the source of cells, e.g., MSCs from the connective matrix, from subendothelial cells from the umbilical vein or even from whole umbilical cord explant. They are generally well cultured in DMEM medium, supplemented with various nutritional and growth factors; in certain cases prior treatment of vessels with hyaluronic acid has proved beneficial (Baban, B. et al., J Reprod Immunol, 2004, 61: 67-77).

Human umbilical cord blood (HUCB) is rich in hematopoietic progenitor cells, as measured in standard clonogenic assays for burst-forming units and granulocyte-macrophage colony-forming units. (Cicuttini, F M and Boyd A W, "Hematopoietic and lymphoid progenitor cells in human umbilical cord blood," Devel. Immunol. 4: 1-11 (1994), citing Broxmeyer, H E et al, "Human umbilical cord blood as a potential source of transplantable hemopoietic stem/progenitor cells," Proc. Natl Acad. Sci. USA (1989) 86: 3828-3719).

In vitro culture of human umbilical cord blood has demonstrated multipotential (CFU-GEMM), erythroid (BFU-E), and granulocyte-macrophage (CFU-GM) progenitor cells (Id. citing Leary, A G et al, "Single cell origin of multi-lineage colonies in culture. Evidence that differentiation of multipotent progenitors and restriction of proliferative potential of monopotent progenitors ar stochastic processes," J. Clin. Invest. (1984); 74: 2193-97). A proportion of colonies also contains progenitors that form secondary colonies when replated in a secondary agar culture, suggesting that the colony arises from a single cell with limited self-renewal properties. The frequency of cord blood progenitors (number of colonies formed/number of cells plated) equals or exceeds that of marrow and greatly surpasses that of adult blood. Progenitor cells from HUCB can be maintained for several weeks in long-term liquid culture systems, suggesting their production from more primitive cells (Id.

citing Salahuddin, S Z et al, "Long term suspension cultures of human cord blood myeloid cells," 1981; Blood 58: 931-38; Smith, S & Broxmeyer, H E; "The influence of oxygen tension on the long-term growth in vitro of hemopoietic progenitor cells from human cord blood," Brit. J. Haematol. (1986): 63: 29-34).

Purification of highly purified CD34+ progenitor cells from HUCB by immunodepletion followed by positive FACS sorting resulted in >100 fold enrichment of colony-forming cells (CFC). Id. Cord blood progenitor cells were shown to be skewed to very early cells in that cord blood CD34+ cells grown in the presence of stem cell factor (SCF) and optimal growth factors resulted in 50-80% of mixed colonies (CFU-GEMM), suggesting that the stem/progenitor cell pool in cord blood is weighted toward very early progenitor cells. Id.

Cord Blood B Cells

Human umbilical cord blood has been shown to be enriched for pre-B and B cells compared to adult peripheral blood. Id. The mean frequency of pre-B cells has been shown to be 0.7% of total lymphocytes in cord blood compared to 0.2% in adult blood (Id. citing Okino, F, "Pre-B cells and B lymphocytes in human cord blood and adult peripheral blood," Acta Paediatr. Jpn (1987): 29: 195-201). The mean relative frequency of B lymphocytes in cord blood is also higher, being 11.4% of total lymphocytes compared to 5.4% in adult blood (Id). In terms of absolute numbers of preB cells, cord blood contains 10 times the number in adult blood. Id.

The antigens CD1C, CD38, CD5 and CD23 are highly expressed on cord blood B cells, but are normally expressed on only a small percentage of circulating B cells in normal adults. Id. It has been suggested that whereas neonatal B cells are probably functionally naïve, their inherent potential for stimulation, which approaches that of adult B cells, can be realized as long as sufficiently strong T-cell help is available. Id.

Cord Blood T Cells

Generally cord blood T cells have a relative absence of helper activity (Id. citing Anderson, U et al., Evidence for the ontogenic precedence of suppressor T cell functions in the human neonate," Eur. Immunol. 1983; 13: 6-13). The percentage of lymphocytes expressing CD2 (a surface antigen of the human T-lymphocyte lineage that is expressed on all peripheral blood T cells), CD3 (T lymphocyte marker) and CD8 (marker for T cells with suppressor and cytotoxic activity) is lower in cord blood than in adult blood. Id. However, due to the increased white cell count in cord blood, the absolute numbers of CD2+ and CD8+ cells are comparable (Id. citing Gerli, R et al, Activation of cord T lymphocytes. I. Evidence for a defective T cell mitogens through the CD molecule," J. Immunol. 1989; 142: 2583-89). In contrast, the percentages of CD4+ cells (helper/inducer T cells) in cord blood and adult peripheral blood are similar, although the absolute numbers of CD4+ cells are higher in cord blood. Id. Nevertheless, cord blood CD4+ cells are deficient in their ability to provide help for antibody production. Id.

Greater than 90% of cord blood CD4+ cells express high levels of CD45RA and L-selectin (Leu-8) (Id. citing Clement, L T et al, "Novel immunoregulatory functions of phenotypically distinct subpopulations of CD4+ cells in the human neonate," J. Immunol. (1990): 145: 102-108)) and have low levels of CD45RO (citing Sanders et al 1988). Their cytokine profiles suggest that they are naïve THp cells. The dominant immunoregulatory phenotype of cord blood CD4+ cells has been shown to be largely immunosuppressive, consistent with the preponderance of CD4+CD45RA+ (and CD38+) cells (Id. citing Tostato, G I et al, "B cell differentiation and immunoregulatory T cell function in human cord blood lymphocytes," 1980; J. Clin. Invest. 66: 383-880; Jacoby, D R and Oldstone, MBA, "Delineation of suppressor and helper activity within the OKTA4-defined T lymphocyte subset in human newborns," 1983; J. Immunol. 131: 1765-70; Clement, L T et al, "Novel immunoregulatory functions of phenotypically distinct subpopulations of CD4+ cells in the human neonate," J. Immunol. (1990): 145: 102-108)). Cord blood CD4+ cells cultured with adult B cells and pokeweed mitogen (PWM), or anti CD4+ mAb, demonstrated no helper function (Clement, L T et al, "Novel immunoregulatory functions of phenotypically distinct subpopulations of CD4+ cells in the human neonate," J. Immunol. (1990): 145: 102-108)). However, after activation with phytohemagglutinin (PHA) and culture in IL-2, cord blood CD4++CD45RA+ cells acquired the ability to provide help for B cell differentiation. This functional maturation was accompanied by conversion to the CD4+CD45RA-CD45RO+ phenotype. When the small number of CD4+CD45RA-CD45RO+ cells in cord blood were purified and similarly analyzed, helper activity comparable to that of adult CD4+CD45RA- was found. Id. This helper function was blocked by the presence of even small numbers of cord blood (but not adult) CD4+CD45RA+ cells. Irradiation or mitomycin C treatment of cord blood CD4+CD45RA+ cells abrogated their suppressive activity, but did not induce helper capability. It has been proposed that uncommitted "naïve" CD4+CD45RA+ cells undergo age-related maturational changes that are unrelated to their postulated activation-dependent post-thymic differentiation into CD4+CD45RA- "memory" cells capable of helper functions (Id)

Natural Killer (NK) Cells

Human natural killer (NK) cells can be subdivided into different populations based on the relative expression of the surface markers CD16 and CD56. (Poli, A. et al, "CD56bright natural killer (NK) cells: an important NK cell subset," Immunol. 2009 April; 126(4): 458-65. Cord blood NK cells are heterogeneous. Although cells bearing the NK marker CD57+ are negligible in cord blood (Cicuttini, F M and Boyd A W, "Hematopoietic and lymphoid progenitor cells in human umbilical cord blood," Devel. Immunol. 4: 1-11 (1994), citing Abo, T et al, "Post natal expansion of the natural killer and killer cell population in humans identified by the monoclonal HNK-1 antibody," J. Exp. Med. 1982; 155: 321-26), the proportions of CD16+ lymphocytes are equal to those of adult peripheral blood (Id. citing Tarakkanan, J and Saksela, E, "Umbilical cord blood-derived suppressor cells of the human natural killer cell activity are inhibited by interferon," Scand. J. Immunol. 1982; 15: 149-57; Perussia, B et al., "Human natural killer cells analyzed by B73.1, a monoclonal antibody blocking Fcreceptor function. I. Characterization of the lymphocyte subset reactive with B73.1," J. Immunol. 1983; 130: 2133-41). Spontaneous NK activity of cord blood cells is profoundly reduced compared to the adult. Id. It is thought that CD7+NK+ and CD7+NK- populations may represent a developmental sequence amongst NK cell precursors in human umbilical cord blood, with CD7+NK- cells as candidates for the most immature NK precursor cells in cord blood. Id.

Hematopoietic Stem Cells.

The hematopoietic stem cell is the common ancestor of all blood cells. Hematopoietic stem cell maturation involves the diversification of the lymphoid and myeloid cell lineages, the two major branches of hematopoietic cells. (Kondo, M. "Lymphoid and myeloid lineage commitment in multipotent hematopoietic progenitors," Immunol. Rev. 2010 November; 238(1): 37-46). Lymphoid lineage cells include T, B, and natural killer (NK) cells. The myeloid lineage includes megakaryocytes and erythrocytes (MegE) as well as different subsets of granulocytes (neutrophils, eosinophils and basophils), monocytes, macrophages, and mast cells (GM), which belong to the myeloid lineage (Id. citing Kondo M, et al. Biology of hematopoietic stem cells and progenitors: implications for clinical application. Annu Rev Immunol. 2003; 21:759-806, Weissman I L. Translating stem and progenitor cell biology to the clinic: barriers and opportunities. Science (New York, N.Y. 2000 Feb. 25; 287(5457): 1442-6; see also Iwaskaki, H. and Akashi, K. "Myeloid lineage commitment from the hematopoietic stem cell,", Immunity 26(6) June 2007, 726-40).

The lymphoid and myeloid lineages are separable at the progenitor level. Common lymphoid progenitors (CLPs) can differentiate into all types of lymphocytes without noticeable myeloid potential under physiological conditions (Kondo M, Scherer D C, Miyamoto T, King A G, Akashi K, Sugamura K, et al. Cell-fate conversion of lymphoid-committed progenitors by instructive actions of cytokines. Nature. 2000 Sep. 21; 407(6802):383-6), although some myeloid related genes might be detected in CLPs, depending on the experimental conditions (Delogu A, Schebesta A, Sun Q, Aschenbrenner K, Perlot T, Busslinger M. Gene repression by Pax5 in B cells is essential for blood cell homeostasis and is reversed in plasma cells. Immunity. 2006 March; 24(3):269-81).

Similarly, common myeloid progenitors (CMPs) can give rise to all classes of myeloid cells with no or extensively low levels of B-cell potential (Akashi K, Traver D, Miyamoto T, Weissman I L. A clonogenic common myeloid progenitor that gives rise to all myeloid lineages. Nature. 2000 Mar. 9; 404(6774):193-7). Another cell type, dendritic cells (DCs), is not clearly grouped either in lymphoid or myeloid lineage, because DC can arise from either CLPs or CMPs (Manz M G, Traver D, Miyamoto T, Weissman I L, Akashi K. Dendritic cell potentials of early lymphoid and myeloid progenitors. Blood. 2001 Jun. 1; 97(11):3333-41, Traver D, Akashi K, Manz M, Merad M, Miyamoto T, Engleman E G, et al. Development of CD8alpha-positive dendritic cells from a common myeloid progenitor. Science (New York, N.Y. 2000 Dec. 15; 290(5499):2152-4).

CMPs can proliferate and differentiate into megakaryocyte-erythrocyte (MegE) progenitors and granulocyte-monocyte (GM) progenitors, which further give rise to megakaryocytes, erythrocytes, granulocytes, monocytes and others. (Iwasaki H, Akashi K. Myeloid lineage commitment from the hematopoietic stem cell. Immunity. 2007; 26:726-740).

The monopotent megakaryocyte lineage-committed progenitor (MKPs) has been isolated downstream of MEPs by CD9, a megakaryocyte-associated surface protein. MKPs have the phenotype CD9+IL-7Rα– Lin– Sca-1– c-Kit+ Thy1.1– and represent only 0.01% of the total bone-marrow cells. (Iwasaki H, Akashi K. Myeloid lineage commitment from the hematopoietic stem cell. Immunity. 2007; 26:726-740). MKPs give rise exclusively to various sizes of megakaryocyte colonies. (Id. Citing T. N. Nakorn, T. et al, Characterization of mouse clonogenic megakaryocyte progenitors, Proc. Natl. Acad. Sci. USA, 100 (2003), pp. 205-210). MEPs represent the majority of day 8 CFU-S activity; MKPs do not have CFU-S activity, and generate only megakaryocytes in vitro. Id.

Like other primitive hematopoietic cells, bipotent MEPs resemble small lymphocytes but can be distinguished by a specific pattern of cell surface protein display, IL-7Rα–/Lin–/c-Kit+/Sca-1–/CD34–/FcRγlo. (Kaushansky, K., "Historical review: megakaryopoiesis and thrombopoiesis," Blood 2008; 111(3): 981-86). Cells committed to the megakaryocytic lineage then begin to express CD41 and CD61 (integrin αIIbβ3), CD42 (glycoprotein Ib) and glycoprotein V. (Id. Citing Hodohara K, et al., Stromal cell-derived factor-1 (SDF-1) acts together with thrombopoietin to enhance the development of megakaryocytic progenitor cells (CFU-MK). Blood 2000; 95:769-775; Roth G J, et al., The platelet glycoprotein Ib-V-IX system: regulation of gene expression. Stem Cells 1996; 14 Suppl 1:188-193). Those that are committed to the erythroid lineage begin to express the transferrin receptor (CD71), and as they mature they lose CD41 expression but express the thrombospondin receptor (CD36), glycophorin, and ultimately globin. Id.

The human clonogenic common myeloid progenitors (CMPs) and their downstream progeny, the granulocyte/macrophage (GMPs) and megakaryocyte/erythrocyte progenitors (MEPs), reside in the lineage-negative (lin–) CD34+CD38+ fraction of adult bone marrow as well as in cord blood. They are distinguishable by the expression of the IL-3Rα chain, the receptor of an early-acting hematopoietic cytokine, and CD45RA, an isoform of a phosphotyrosine phosphatase involved in negative regulation of cytokine signaling. (Manz, M G, et al, "Prospective isolation of human clonogenic common myeloid progenitors," Proc. Natl Acad. Sci. U.S. 2002 99(18): 11872-11877).

75% of lin–CD34+CD38+IL-3Rα$^{lo}$CD45RA+ cells isolated from adult human bone marrow gave rise exclusively to CFU-granulocyte, CFU-macrophage, and CFU-granulocyte/macrophage, whereas 87% of lin–CD34+CD38+IL-3Rα–CD45RA– cells isolated from adult human bone marrow produced burst-forming units erythroid, CFU-megakaryocyte, CFU-megakaryocyte/erythroid, and two CFU-granulocyte (0.5%). In analogy to the defined mouse progenitors the IL-3RαloCD45RA+ cells were termed GMPs and the IL-3Rα–CD45RA– cells termed MEPs. Upon culture on Sys-1 stromal cells with different cytokine combinations, development of both GMPs and MEPs was achieved with SCF, IL-11, FL, Epo, and Tpo after 72 h of culture. IL-3RαloCD45RA– cells gave rise to all types of colonies (but CFU-GEMM), GMPs exclusively gave rise to granulocyte/macrophage colonies, and MEPs gave rise to megakaryocyte/erythrocyte colonies and four (1.6%) granulocyte and macrophage colonies. Therefore, the IL-3Rα$^{lo}$CD45RA– cells, which represent the CMP population, can give rise to functional GMPs and MEPs. (Manz, M G, et al, "Prospective isolation of human clonogenic common myeloid progenitors," Proc. Natl Acad. Sci. U.S. 2002 99(18): 11872-11877).

Gene Expression Profiles.

Whereas granulocyte colony-stimulating factor receptor, C/EBPs, and MPO were expressed by GMPs and not by MEPs, GATA-1, EpoR, c-mpl, β-globin, and von Willebrand factor were detected in MEPs but not in GMPs. None of the myeloid progenitors expressed detectable levels of genes relevant in lymphoid development as TdT, GATA-3, preTα, IL-7Rα, and Pax-5, which were expressed in the lymphoid-committed lin–CD34+CD38+CD10+ progenitors. (Manz, M G, et al, "Prospective isolation of human clonogenic common myeloid progenitors," Proc. Natl Acad. Sci. U.S. 2002 99(18): 11872-11877).

Myeloid progenitor cells with similar lineage restrictions can be found in cord blood. Although the distinct surface-marker expression profile was similar to adult bone marrow, percentages of the myeloid progenitor populations were slightly different in cord blood: IL-3Rα$^{lo}$CD45RA− CMPs account for about 0.4%, IL-3Rα$^{lo}$CD45RA+ GMPs for about 0.3%, and IL-3Rα−CD45RA+ MEPs for about 0.05% of the mononuclear cell fraction of umbilical cord blood. HSC-enriched lin−CD34+CD38− cells and CMPs formed all types of colonies with cloning efficiencies of 68 and 83%, respectively. GMPs formed exclusively granulocyte/macrophage colonies (cloning efficiency 41%), and MEPs formed megakaryocyte/erythrocyte colonies (cloning efficiency 88%) with only 4% granulocyte/macrophage colony readout. (Manz, M G, et al, "Prospective isolation of human clonogenic common myeloid progenitors," Proc. Natl Acad. Sci. U.S. 2002 99(18): 11872-11877).

A subset of HSCs has been shown to express the gene for von Willebrand's factor, a platelet-associated peptide once thought to be restricted to the megakaryocyte lineage. (Smith, B W, and Murphy, G J, "Stem cells, megakaryocytes, and platelets," Curr. Opin. Hematol. 2014; 21(5): 430-37). These cells produce greater transcript levels of C-mpl, and are primed for megakaryocyte lineage commitment (Id. Citing Sanjuan-Pla, A., et al, "Platelet-biased stem cells reside at the apex of haematopoietic stem-cell hierarchy," Nature 2013; 502: 232-36). Studies show that transplanted HSCs preferentially home to adjacent megakaryocytes within the endosteal bone marrow niche, in which TPO promotes niche expansion (Id. Citing Olson, T S, et al, "Megakaryocytes promote murine osteoblastic HSC niche expansion and stem cell engraftment after radio-ablative conditioning," Blood 2013; 121: 5238-49) and mature megakaryocytes release cytokines to promote HSC proliferation (Heazlewood, S Y et al, "Megakaryocytes co-localise with hemopoietic stem cells and release cytokines that up-regulate stem cell proliferation," Stem Cell Res. 2013; 11:782-92)). There is also evidence for a myeloid-restricted progenitor that may be a direct descendant of the HSC, completely bypassing the oligopotent progenitor thought to be a crucial intermediary of normal hematopoiesis (Yamamoto, R. et I al, "Clonal analysis unveils self-renewing lineage-restricted progenitors generated directly from hematopoietic stem cells," Cell. 2013; 154: 1112-26). This population may descend from CD41+ HSCs, which are more entrenched and less transient than once thought (Gekas, C. and Graf, T., "CD41 expression marks myeloid-biased adult hematopoietic stem cells and increases with age," Blood. 2013; 121: 4463-62)).

Transcription Factors

Multiple transcription factors, including Runx1, Gata1, Fli1 and cMyb, form complex networks that regulate the differentiation of megakaryocytes both positively and negatively. (Geddis, A. E., "Megakaryopoiesis," Semin. Hematol. 2010; 47(3): 212-219). Runx1 interacts with additional megakaryocytic factors including Gata1 and Fli1. Gata1 and its cofactor, Friend of Gata1 (Fog1) are critical in promoting megakaryocyte-erythroid differentiation, while at the same time inhibiting expression of Pu.1 and myeloid differentiation. (Id. Citing Nerlov, C. et al, "GATA-1 interacts with the myeloid PU.1 transcription factor and represses PU.1-dependent transcription," Blood 2000; 95: 2543-51; Chou S T et al, "Graded repression of PU.1/Sfpil gene transcription by GATA factors regulates hematopoietic cell fate," Blood 2009; 114: 983-94). Binding sites for Gata1 and Flli1 can be found in the enhancers of many megakaryocyte-specific genes (Id. Citing Eisbacher, M. et al, "Protein-protein interaction between Fli-1 and GATA-1 mediates synergistic expression of megakaryocyte-specific genes through cooperative DNA binding," Mol. Cell Biol. 2003; 23: 3427-41) and Fli1 enhances the activity of Gata1 at megakaryocytic promoters, and represses the activity of erythroid factors at erythroid promoters. Thus, Fli1 expression may act to restrict the MEP to the megakaryocytic lineage. In contrast, expression of the proto-oncogene c-Myb in the MEM favors erythropoiesis, and c-Myb expression is down regulated during megakaryopoiesis (Metcalf, D et al, "Anamaloous megakaryocytopoiesis in mice with mutations in the c-Myb gene," Blood 2005; 105: 3480-87).

Megakaryocytes.

Multiple distinct cell population of cord blood-derived megakaryocytes have been observed by flow cytometry, and similar populations were also observed in the megakaryocytic Meg-01 cell line. (Lindsay, C. et al, 2015; Blood 126(23): 4754). The largest cells (called P1), were the most abundant, making up nearly 100% of cells at day 3 in culture. P2 cells, which are smaller and more granular than P1, appeared at day 6 and by day 13 were about 50% of the total. P3 appeared at day 6 and are the smallest, with size and granularity roughly similar to platelets; by day 13 these were about 30% of the total. P1, but not P2 or P3, became CD61/CD41/CD42 positive and CD34 negative over 13 days in culture. 97% and 93% of P2 and P3 cells, respectively, were phosphatidylserine (PS) positive, whereas 93% of P1 cells were PS negative. The PS negative (P1) cells showed many typical features of bone marrow megakaryocytes by electron microscopy, including large size, polypoid nucleus, mitochondria and immature granules, although the demarcation membrane system was poorly developed. Virtually all of the PS positive P2 cells were apoptotic, lacked granules, and had no discernable nuclei. It was found that P1 gives rise to both the P2 and P3 populations, whereas P2 gave rise to no other population. Stimulation of P1, P2 and P3 populations with collagen related peptide, thrombin, protease activated receptor 1-activating peptide (PAR1-AP) and PAR4-AP showed strong integrin activation in P1 cells, but not in P2 or P3 cells. Thus, only a portion of cord blood-derived megakaryocytes are functional.

Growth Factors

Growth factors are extracellular polypeptide molecules that bind to a cell-surface receptor triggering an intracellular signaling pathway, leading to proliferation, differentiation, or other cellular response. These pathways stimulate the accumulation of proteins and other macromolecules, and they do so by both increasing their rate of synthesis and decreasing their rate of degradation.

Platelet α granules contain several different growth factors, including platelet-derived growth factors (PDGF-AA, PDGF-BB, BDGF-AB), transforming growth factor-β (TGF-β1 and TGF-β2), fibroblast growth factor (FGF), vascular endothelial growth factor (VEGF), epithelial growth factor (EGF), and insulin-like growth factor-1 (IGF-1), which are actively secreted by platelets (Aghideh, A N et al, "Platelet growth factors suppress ex vivo expansion and enhance differentiation of umbilical cord blood CD133+ stem cells to megakaryocyte progenitor cells," Growth Factors 2010; 28(6): 409-16, citing Martieau, I., et al, "Effects of calcium and thrombin on growth factor release from platelet concentrates: kinetics and regulation of endothelial cell proliferation," Biomaterials 2004; 25: 4489-4502). Megakaryocytes express and store platelet factor 4 (PF4), a negative regulator of megakaryopoiesis and hematopoietic stem cell regulation, in alpha granules (Lambert, M P et al, "Intramedullary megakaryocytes internalize released platelet factor 4 and store it in alpha granules," J. Thromb. Haemost. 2015; 13(10): 1888-99).

Thrombopoietin

Multiple growth factors support megakaryopoesis, the most important of which is megakaryocyte growth and development factor (MGDF), also known as thrombopoietin (TPO). Thrombopoietin, the major regulator of megakaryocyte development and platelet production and a potent stimulator of thrombopoiesis, is a ligand for the Mpl receptor. (Muench, M. and Barcena, A., "Megakaryocyte Growth and Development Factor is a Potent Growth Factor for Primitive Hematopoietic Progenitors in the Human Fetus," Ped. Res. 2004; 55(6): 1050-56). It can stimulate, both in vitro and in vivo, an increase in megakaryocyte production and megakaryocyte ploidy, and has a broad spectrum of activity on hematopoiesis (Id. Citing Kaushansky, K. "Thrombopoietin: the primary regulator of platelet production," 1995; Blood 86: 419-311, 2); Kuter, D J et al, 2002 Blood; 100: 3457-69)), and supports the growth of multipotent hematopoietic progenitors and stem cells. (Id.)

TPO belongs to the four-helix bundle family of cytokines, which includes erythropoietin, G-CSF, growth hormone and leukemia inhibitory factor among others. (Geddis, A. E., "Megakaryyopoiesis," Semin. Hematol. 2010; 47(3): 212-219). The TPO receptor c-Mpl was identified based on its homology to the oncogne v-Mpl, already known at the time as the transforming factor of the murine myeloproliferative leukemia virus (Id. Citing Vigon I, et al. Molecular cloning and characterization of MPL, the human homolog of the v-mpl oncogene: identification of a member of the hematopoietic growth factor receptor superfamily. Proc Natl Acad Sci USA. 1992; 89:5640-5644). TPO and c-Mpl are critical for megakaryocyte growth and development, and in mouse models where one or the other is absent, platelets and megakaryocytes are reduced to approximately 10% of normal values (Gurney A L, et al. Thrombocytopenia in c-mpl-deficient mice. Science. 1994; 265:1445-1447; Bunting S, et al. Normal platelets and megakaryocytes are produced in vivo in the absence of thrombopoietin. Blood. 1997; 90:3423-3429). In addition to megakaryocytic cells, HSCs also express c-Mpl and depend on TPO signaling for their maintenance and expansion (Id. Citing Fox N, et al, Thrombopoietin expands hematopoietic stem cells after transplantation. J Clin Invest. 2002; 110:389-394).

The c-Mpl gene encodes a 635 amino acid protein consisting of a 25 amino acid signal peptide (1-25), a 465 amino acid extracellular domain (26-491), a 22 residue transmembrane domain (492-513) and an intracellular domain containing two conserved motifs termed box 1 (528-536) and box 2 (565-574). The extracellular domain is composed of two repeating modules; the membrane distal module appears to have an inhibitory effect on signaling, as its deletion results in constitutive activation of the receptor (Id. Citing Sabath D F, Kaushansky K, Broudy V C. Deletion of the extracellular membrane-distal cytokine receptor homology module of Mpl results in constitutive cell growth and loss of thrombopoietin binding. Blood. 1999; 94:365-367). c-Mpl does not have intrinsic kinase activity, but instead associates with the cytoplasmic tyrosine kinase Janus kinase 2 (Jak2) through its box 1 domain (Id. Citing Drachman J G, Kaushansky K. Structure and function of the cytokine receptor superfamily. Curr Opin Hematol. 1995; 2:22-28). Additional elements regulate receptor internalization and subsequent degradation following TPO binding. These include dileucine repeats located within box 2, Tyr591 and Tyr625 (Id. Citing Dahlen D D, et al., Internalization of the thrombopoietin receptor is regulated by 2 cytoplasmic motifs. Blood. 2003; 102:102-108; Hitchcock I S, et al, YRRL motifs in the cytoplasmic domain of the thrombopoietin receptor regulate receptor internalization and degradation. Blood. 2008).

TPO signaling depends on the activation of Jak2. Jak2 associates with box 1 of c-Mpl through its FERM (band 4.1/ezrin/radixin/moesin) domain. Based on X-ray crystal studies of the erythropoietin receptor (Id. Citing Livnah O, et al, Crystallographic evidence for preformed dimers of erythropoietin receptor before ligand activation. Science. 1999; 283:987-990), it is believed that in the unliganded state c-Mpl exists as a homodimer, and that TPO binding results in a conformational change that brings the cytoplasmic tails of the receptor into closer proximity. Consequently, the Jak2 molecules associated with the receptor are brought close enough to each other to become activated through trans-autophosphorylation (Id. Citing Witthuhn B A, Quelle F W, Silvennoinen O, Yi T, Tang B, Miura O, et al. JAK2 associates with the erythropoietin receptor and is tyrosine phosphorylated and activated following stimulation with erythropoietin. Cell. 1993; 74:227-236). Active Jak2 then phosphorylates itself on multiple residues and phosphorylates c-Mpl on at least Tyr625 and Tyr630 (Id. Citing Drachman J G, Kaushansky K. Dissecting the thrombopoietin receptor: functional elements of the Mpl cytoplasmic domain. Proc Natl Acad Sci USA. 1997; 94:2350-2355). These phosphotyrosine residues provide docking sites for src homology 2 (SH2)-domain-containing signaling proteins that modulate receptor signaling.

Following the activation of Jak2, multiple signaling molecules are activated and mediate the cellular response to TPO. These include members of the signal transducer and activator of transcription (STAT), mitogen-activated protein kinase (MAPK) and phosphoinositol-3 kinase (PI3K) pathways (Id. Citing Geddis A E, et al, Thrombopoietin: a pan-hematopoietic cytokine. Cytokine Growth Factor Rev. 2002; 13:61-73). Jak2 directly phosphorylates STAT family members including STAT1, 3, 5a and 5b (Id. Citing Schulze H, et al., Thrombopoietin induces the generation of distinct Stat1, Stat3, Stat5a and Stat5b homo- and heterodimeric complexes with different kinetics in human platelets. Exp Hematol. 2000; 28:294-304). Once phosphorylated, these STAT proteins dimerize and translocate to the nucleus of the cell where they can bind to STAT-responsive transcriptional elements within genes such as p21 (Id. Citing Matsumura I, et al. Thrombopoietin-induced differentiation of a human megakaryoblastic leukemia cell line, CMK, involves transcriptional activation of p21(WAF1/Cip1) by STAT5. Mol Cell Biol. 1997; 17:2933-2943), Bcl-xL (Id. Citing Kirito K, et al, Thrombopoietin regulates Bcl-xL gene expression through Stat5 and phosphatidylinositol 3-kinase activation pathways. J Biol Chem. 2002; 277:8329-8337) and cyclin D1 (Id. Citing Magne S, et al, STAT5 and Oct-1 form a stable complex that modulates cyclin D1 expression. Mol Cell Biol. 2003; 23:8934-8945). Constitutive activation of the Jak2/STAT pathway can lead to cytokine-independent growth and contribute to transformation, as demonstrated by the finding of mutant Jak2 in myeloproliferative disorders, translocations involving Jak2 in lymphoid leukemias, and constitutively active STAT5 in leukemic cell lines (Id. Citing Harir N, et al. Constitutive activation of Stat5 promotes its cytoplasmic localization and association with PI3-kinase in myeloid leukemias. Blood. 2007; 109:1678-1686; Najfeld V, et al, Numerical gain and structural rearrangements of JAK2, identified by FISH, characterize both JAK2617V>F-positive and -negative patients with Ph-negative MPD, myelodysplasia, and B-lymphoid neoplasms. Exp Hematol. 2007; 35:1668-1676).

Jak2 also activates the small GTPase Ras and the MAPK cascade, culminating in the activation of extracellular signal-related kinase (ERK)1/2. Multiple studies have demonstrated the importance of TPO-induced MAPK signaling in megakaryocytic differentiation (Id. Citing Rouyez M C, et al, Control of thrombopoietin-induced megakaryocytic differentiation by the mitogen-activated protein kinase pathway. Mol Cell Biol. 1997; 17:4991-5000; Rojnuckarin P, et al, Thrombopoietin-induced activation of the mitogen-activated protein kinase (MAPK) pathway in normal megakaryocytes: role in endomitosis. Blood. 1999; 94:1273-1282; Fichelson S, et al. Megakaryocyte growth and development factor-induced proliferation and differentiation are regulated by the mitogen-activated protein kinase pathway in primitive cord blood hematopoietic progenitors. Blood. 1999; 94:1601-1613). The classical pathway by which TPO signaling is thought to activate Ras depends on the binding of the adaptor protein Shc to phosphorylated c-Mpl Tyr625 (Id. Citing Drachman J G, Kaushansky K. Dissecting the thrombopoietin receptor: functional elements of the Mpl cytoplasmic domain. Proc Natl Acad Sci USA. 1997; 94:2350-2355; Miyakawa Y, et al. Recombinant thrombopoietin induces rapid protein tyrosine phosphorylation of Janus kinase 2 and Shc in human blood platelets. Blood. 1995; 86:23-27) and the assembly of a complex containing the adaptor protein Grb2 and the guanine nucleotide exchange factor SOS (Id. Citing Alexander W S, et al, Tyrosine-599 of the c-Mpl receptor is required for Shc phosphorylation and the induction of cellular differentiation. Embo J. 1996; 15:6531-6540; Skolnik E Y, et al. The function of GRB2 in linking the insulin receptor to Ras signaling pathways. Science. 1993; 260:1953-1955). Ras then activates Raf-1, mitogen-induced extracellular kinase (MEK) and finally Erk 1/2 (Id. Citing Avruch J, et al. Ras activation of the Raf kinase: tyrosine kinase recruitment of the MAP kinase cascade. Recent Prog Horm Res. 2001; 56:127-155). Although activation of MAPK is significantly reduced in the absence of c-Mpl Tyr625 and Tyr630, it is not eliminated (Id. Citing Luoh S M, et al. Role of the distal half of the c-Mpl intracellular domain in control of platelet production by thrombopoietin in vivo. Mol Cell Biol. 2000; 20:507-515), suggesting that activation of Erk1/2 can be mediated either through a Shc-independent mechanism, possibly through Grb2/Sos complexes recruited to Jak2 (Id. Citing Brizzi M F, et al, Discrete protein interactions with the Grb2/c-Cbl complex in SCF- and TPO-mediated myeloid cell proliferation. Oncogene. 1996; 13:2067-2076). Alternatively, the small GTPase Rap1 can activate Erk1/2 via B-Raf independent of Ras (Id. Citing Garcia J, et al, Thrombopoietin-mediated sustained activation of extracellular signal-regulated kinase in UT7-Mpl cells requires both Ras-Raf-1- and Rap1-B-Raf-dependent pathways. Mol Cell Biol. 2001; 21:2659-2670).

The PI3K pathway is also essential for megakaryopoiesis (Id. Citing Geddis A E, Fox N E, Kaushansky K. Phosphatidylinositol 3-kinase is necessary but not sufficient for thrombopoietin-induced proliferation in engineered Mpl-bearing cell lines as well as in primary megakaryocytic progenitors. J Biol Chem. 2001; 276:34473-34479). PI3K is composed of a kinase (p110) and a regulatory subunit (p85). TPO induces formation of a complex between phosphorylated p85 and the adaptor Gab, although this complex has not been found to bind directly to c-Mpl (Id. Citing Miyakawa Y, et al, Thrombopoietin induces phosphoinositol 3-kinase activation through SHP2, Gab, and insulin receptor substrate proteins in BAF3 cells and primary murine megakaryocytes. J Biol Chem. 2001; 276:2494-2502); alternatively, PI3K may become activated indirectly through Ras (Id. Citing Kodaki T, et al, The activation of phosphatidylinositol 3-kinase by Ras. Curr Biol. 1994; 4:798-806). TPO-induced PI3K phosphorylates and activates the serine/threonine kinase Akt whose substrates include Forkhead, glycogen synthase kinase 3 beta (GSK-3β) and Bad (Id. Citing Geddis A E, Fox N E, Kaushansky K. Phosphatidylinositol 3-kinase is necessary but not sufficient for thrombopoietin-induced proliferation in engineered Mpl-bearing cell lines as well as in primary megakaryocytic progenitors. J Biol Chem. 2001; 276:34473-34479; Nakao T, et al, PI3K/Akt/FOXO3a pathway contributes to thrombopoietin-induced proliferation of primary megakaryocytes in vitro and in vivo via modulation of p27(Kip1) Cell Cycle. 2007; 7; Soda M, et al, Inhibition of GSK-3beta promotes survival and proliferation of megakaryocytic cells through a beta-catenin-independent pathway. Cell Signal. 2008; 20:2317-2323), collectively promoting survival and proliferation of megakaryocytic cells. PI3K also activates mammalian target of rapamycin (mTOR), whose targets SK6 and 4E-BP1 increase proliferation and maturation of megakaryocytic progenitors (Id. Citing Raslova H, et al. Mammalian target of rapamycin (mTOR) regulates both proliferation of megakaryocyte progenitors and late stages of megakaryocyte differentiation. Blood. 2006; 107:2303-2310; Guerriero R, et al. Inhibition of TPO-induced MEK or mTOR activity induces opposite effects on the ploidy of human differentiating megakaryocytes. J Cell Sci. 2006; 119:744-752). PI3K is itself negatively regulated by phosphatase and tensin homolog (PTEN), a tumor suppressor that promotes quiescence in hematopoietic stem cells (HSC) (Id. Citing Zhang J, et al. PTEN maintains haematopoietic stem cells and acts in lineage choice and leukaemia prevention. Nature. 2006; 441:518-522). Although PTEN regulates the activity of Akt and mTOR, its role in TPO signaling and megakaryopoiesis has not yet been defined.

Checks on TPO signaling and megakaryopoiesis are required to maintain homeostatic balance. To ensure that signals are appropriately terminated, many positive regulators also induce their own inhibitors. For example, activation of Jak/STAT pathway induces the transcription of members of the suppressor of cytokine signaling (SOCS) family (Id. Citing Starr R, et al. A family of cytokine-inducible inhibitors of signalling. Nature. 1997; 387:917-921; Endo T A, et al. A new protein containing an SH2 domain that inhibits JAK kinases. Nature. 1997; 387:921-924). This family includes at least 8 members that can inhibit Jak signaling in a variety of ways, including binding to the activation loop of Jak and targeting it for degradation, acting as a pseudosubstrate for Jak, or binding to phosphorylated tyrosines within the cytokine receptor itself (Id. Citing Alexander W S, Hilton D J. The role of suppressors of cytokine signaling (SOCS) proteins in regulation of the immune response. Annu Rev Immunol. 2004; 22:503-529). Induction of a SOCS response from one receptor can negatively regulate another, thereby providing a mechanism for cytokine cross-talk; this is illustrated by the finding that treatment of megakaryocytes with interferon-α induces SOCS1, which then down-regulates TPO signaling through inhibition of Jak2 (Id. Citing Wang Q, Miyakawa Y, Fox N, Kaushansky K. Interferon-alpha directly represses megakaryopoiesis by inhibiting thrombopoietin-induced signaling through induction of SOCS-1. Blood. 2000; 96:2093-2099).

Jak2 has other binding partners that regulate its activity. For example, Lnk is an adaptor protein that inhibits growth in HSCs, erythroid and megakaryocytic cells (Id. Citing Tong W, Lodish H F. Lnk inhibits Tpo-mpl signaling and Tpo-mediated megakaryocytopoiesis. J Exp Med. 2004; 200:569-580; Seita J, et al. Lnk negatively regulates self-renewal of hematopoietic stem cells by modifying thrombopoietin-mediated signal transduction. Proc Natl Acad Sci USA. 2007; 104:2349-2354). Lnk binds to phosphorylated tyrosines within Jak2 through its SH2-domain (Id. Citing Bersenev A, et al, Lnk controls mouse hematopoietic stem cell self-renewal and quiescence through direct interactions with JAK2. J Clin Invest. 2008; 118:2832-2844); however, the exact mechanism by which it inhibits TPO signaling is not understood. In addition to binding negative regulators, Jak2 may be phosphorylated within the FERM domain, inducing its dissociation from c-Mpl and thus providing another mechanism to 'turn off' signaling (Id. Citing Funakoshi-Tago M, et al, Receptor specific downregulation of cytokine signaling by autophosphorylation in the FERM domain of Jak2. Embo J. 2006; 25:4763-4772).

Some extracellular signal proteins, including platelet-derived growth factor (PDGF), can act as both growth factors and mitogens, stimulating both cell growth and cell-cycle progression. This functional overlap is achieved in part by overlaps in the intracellular signaling pathways that control these two processes. The signaling protein Ras, for example, is activated by both growth factors and mitogens. It can stimulate the PI3-kinase pathway to promote cell growth and the MAP-kinase pathway to trigger cell-cycle progression. Similarly, Myc stimulates both cell growth and cell-cycle progression. Extracellular factors that act as both growth factors and mitogens help ensure that cells maintain their appropriate size as they proliferate.

Since many mitogens, growth factors, and survival factors are positive regulators of cell-cycle progression, cell growth, and cell survival, they tend to increase the size of organs and organisms. In some tissues, however, cell and tissue size also is influenced by inhibitory extracellular signal proteins that oppose the positive regulators and thereby inhibit organ growth. The best-understood inhibitory signal proteins are TGF-β and its relatives. TGF-β inhibits the proliferation of several cell types, either by blocking cell-cycle progression in G1 or by stimulating apoptosis. TGF-β binds to cell-surface receptors and initiates an intracellular signaling pathway that leads to changes in the activities of gene regulatory proteins called Smads. This results in complex changes in the transcription of genes encoding regulators of cell division and cell death.

Bone morphogenetic protein (BMP), a TGF-β family member, helps trigger the apoptosis that removes the tissue between the developing digits in the mouse paw. Like TGF-β, BMP stimulates changes in the transcription of genes that regulate cell death.

Fibroblast Growth Factor (FGF)

The fibroblast growth factor (FGF) family currently has over a dozen structurally related members. FGF1 is also known as acidic FGF; FGF2 is sometimes called basic FGF (bFGF); and FGF7 sometimes goes by the name keratinocyte growth factor. Over a dozen distinct FGF genes are known in vertebrates; they can generate hundreds of protein isoforms by varying their RNA splicing or initiation codons in different tissues. FGFs can activate a set of receptor tyrosine kinases called the fibroblast growth factor receptors (FGFRs). Receptor tyrosine kinases are proteins that extend through the cell membrane. The portion of the protein that binds the paracrine factor is on the extracellular side, while a dormant tyrosine kinase (i.e., a protein that can phosphorylate another protein by splitting ATP) is on the intracellular side. When the FGF receptor binds an FGF (and only when it binds an FGF), the dormant kinase is activated, and phosphorylates certain proteins within the responding cell, activating those proteins.

FGFs are associated with several developmental functions, including angiogenesis (blood vessel formation), mesoderm formation, and axon extension. While FGFs often can substitute for one another, their expression patterns give them separate functions. FGF2 is especially important in angiogenesis, whereas FGF8 is involved in the development of the midbrain and limbs.

The expression levels of angiogenic factors, such as VEGF, IGF, PDGF, HGF, FGF, TGFm Angiopoeitin-1, and stem cell factor (SCF) have been found to differ amongst bone-derived-, cartilage-derived-, and adipose-derived MSCs. (Peng et al., 2008, Stems Cells and Development, 17: 761-774).

Insulin-Like Growth Factor (IGF-1)

IGF-1, a hormone similar in molecular structure to insulin, has growth-promoting effects on almost every cell in the body, especially skeletal muscle, cartilage, bone, liver, kidney, nerves, skin, hematopoietic cells, and lungs. It plays an important role in childhood growth and continues to have anabolic effects in adults. IGF-1 is produced primarily by the liver as an endocrine hormone as well as in target tissues in a paracrine/autocrine fashion. Production is stimulated by growth hormone (GH) and can be retarded by undernutrition, growth hormone insensitivity, lack of growth hormone receptors, or failures of the downstream signaling molecules, including SHP2 and STAT5B. Its primary action is mediated by binding to its specific receptor, the Insulin-like growth factor 1 receptor (IGF1R), present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the pituitary gland, released into the blood stream, and then stimulates the liver to produce IGF-1. IGF-1 then stimulates systemic body growth. In addition to its insulin-like effects, IGF-1 also can regulate cell growth and development, especially in nerve cells, as well as cellular DNA synthesis.

Transforming Growth Factor Beta (TGF-β)

There are over 30 structurally related members of the TGF-β superfamily, and they regulate some of the most important interactions in development. The proteins encoded by TGF-β superfamily genes are processed such that the carboxy-terminal region contains the mature peptide. These peptides are dimerized into homodimers (with themselves) or heterodimers (with other TGF-β peptides) and are secreted from the cell. The TGF-β superfamily includes the TGF-β family, the activin family, the bone morphogenetic proteins (BMPs), the Vg-1 family, and other proteins, including glial-derived neurotrophic factor (GDNF, necessary for kidney and enteric neuron differentiation) and Millerian inhibitory factor, which is involved in mammalian sex determination. TGF-β family members TGF-β1, 2, 3, and 5 are important in regulating the formation of the extracellular matrix between cells and for regulating cell division (both positively and negatively). TGF-β1 increases the amount of extracellular matrix epithelial cells make both by stimulating collagen and fibronectin synthesis and by inhibiting matrix degradation. TGF-βs may be critical in controlling where and when epithelia can branch to form the ducts of kidneys, lungs, and salivary glands.

Among various hematoregulatory cytokines examined, TGF-β1 was by far the most potent enhancer of mRNA expression of bone marrow stromal TPO, a commitment of lineage specificity. The TPO, in turn, induced TGB-β receptors I and II on megakaryoblasts at the midmegakaryopoietic stage. At this stage, TGF-β1 was able to arrest the maturation of megakaryocyte colony forming units (CFU-Meg) in a dose-dependent manner. This effect was relatively specific when compard with its effect on burst-forming unit-erythroid (BFU-E) or CFU-GM. (Sakamaki, S. et al, "Transforming growth factor-31 (TGF-β1) induces thrombopoietin from bone marrow stromal cells, which stimulates the expression of TGF-β receptor on megakaryocytes and, in turn, renders them susceptible to suppression by TGF-β itself with high specificity," Blood 1999; 94: 1961-70).

Activin A and BMP 2 induce cell commitment and differentiation toward erythropoiesis, even in the absence of erythropoietin (EPO). Their biological activities are antagonized by binding with follistatin or FLRG (follistatin-related gene), 2 secreted glycoproteins expressed by human bone marrow and regulated by TGF-β and activin A ((Jeanpierre, S. et al, "BMP4 regulation of human megakaryocytic differentiation is involved in thrombopoietin signaling," Blood 2008; 112: 3154-63) citing Maguer-Satta V, et al., Regulation of human erythropoiesis by activin A, BMP2, and BMP4, members of the TGFbeta family. Exp Cell Res 2003; 282:110-120; Maguer-Satta V, Rimokh R., FLRG, member of the follistatin family, a new player in hematopoiesis. Mol Cell Endocrinol 2004; 225:109-118). FLRG and follistatin are involved in the regulation of human hematopoietic cell dhesiveness in immature hematopoietic progenitors and stem cells through direct interactions between the type I motifs of fibronectin and follistatin domains. (Id. Citing Maguer-Satta V, et al., A novel role for fibronectin type I domain in the regulation of human hematopoietic cell adhesiveness through binding to follistatin domains of FLRG and follistatin. Exp Cell Res 2006; 312:434-442 10).

Bone Morphogenetic Proteins (BMPs)

The members of the BMP family were originally discovered by their ability to induce bone formation. Bone formation, however, is only one of their many functions, and they have been found to regulate cell division, apoptosis (programmed cell death), cell migration, and differentiation. BMPs can be distinguished from other members of the TGF-β superfamily by their having seven, rather than nine, conserved cysteines in the mature polypeptide. The BMPs include proteins such as Nodal (responsible for left-right axis formation) and BMP4 (important in neural tube polarity, eye development, and cell death).

In humans, BMP2, BMP4 and BMP7 regulate the proliferation, maintenance (Jeanpierre, S. et al, "BMP4 regulation of human megakaryocytic differentiation is involved in thrombopoietin signaling," Blood 2008; 112: 3154-63) citing Hutton, J F, et al, "Bone morphogenetic protein 4 contributes to the maintenance of primitive cord blood hematopoietic progenitors in an ex vivo stroma-non contact co-culture system," Stem Cell Dev. 2006; 15: 805-13), clonogenicity, and repopulating capacity of CD34+CD38− primitive hematopoietic populations (Id. Citing Bhatia, M. et al, "Bone morphogenetic proteins regulate the developmental program of human hematopoietic stem cells," J. Exp. Med. 1999; 189: 1139-48). BMP2 and BMP4, either alone or in combination with activin A, have been shown to regulate erythropoiesis in various models (Id. Citing Maguer-Satta, V, and Rimokh, R, "FLRG, member of the follistatin family, a new player in hematopoiesis," Mol. Cell Endocrinol. 2004; 225: 109-11).

It has been shown that BMP4 cooperates with SCF to modulate the primitive hematopoietic stem cell compartment in the absence of any other cytokine. Id.

Of the TGFβ family, only BMP4 has the same capacity as TPO to induce early and late MK markers, and similar terminal differentiation properties, such as polyploidization, secretion of PF4, and platelet production. (Id). It has been demonstrated that BMP4, an element of a key signaling pathway involved in the regulation of the hematopoietic "niche" (Id. Citing Zhang, et al, "Identification of the haematopoietic stem cell niche and control of the niche size," Nature 2003; 425: 836-41), which is mainly produced by the bone marrow stroma (Id. Citing Martinovic, S. et al, "Expression of bone morphogenetic proteins in stromal cells from human bone marrow long-term culture," J. Histochem. Cytochem. 2004; 52: 1159-67), localized in human megakaryocytes and platelets (Id. Citing Sipe, J B et al, "Localization of bone morphogenetic proteins (BMPs)-2, -4, and -6 within megakaryocytes and platelets," Bone 2004; 35: 1316-22) and autologously produced by MK progenitors, efficiently regulates all stages of human megakaryopoiesis, from maintenance of primitive uncommitted progenitors to late stages of MK differentiation. Furthermore, data suggest that the JAK/STAT and mTOR signaling pathways are involved in the regulation of MK maturation by BMP4, as confirmed for TPO (Id. Citing Guerriero, R. et. Al., "Inhibition of TPO-induced MEK or mTOR activity induces opposite effects on the ploidy of human differentiating megakaryocytes," J. Cell Sci. 2006; 119: 744-52, Raslova, H et al, "Mammalian target of rapamycin (mTOR) regulates both proliferation of megakaryocyte progenitors and late stages of megakaryocyte differentiation," Blood 2006; 107: 2303-10). The reported results thus indicate that BMP4 and TPO use similar signaling pathways to regulate human MK differentiation. Id. Moreover, using specific extracellular inhibitors of TPO or BMP4, it was shown that whereas either inhibitor of the BMP4 signaling pathway efficiently inhibited the effects of TPO, anti-TPO-R antibodies were not able to block the effects of BMP4 on MK differentiation. Id. Moreover, TPO induced BMP4 synthesis and BMP receptor expression in MK progenitors, suggesting that whereas TPO uses the BMP4 signaling pathway to regulate human MK, the reverse does not seem to be true. Id.

PEAR-1, RAD001, Wnt3a, and AHR

Other factors implicated as regulators of megakaryopoiesis include platelet endothelial aggregation receptor-1 (PEAR-1), a stimulator of PI3K/PTEN signaling (Smith, B W, and Murphy, G J, "Stem cells, megakaryocytes, and platelets," Curr. Opin. Hematol. 2014; 21(5): 430-37); citing Kauskot, A. et al, "PEAR1 attenuates megakaryopoiesis via control of the PI3K/PTEN pathway," Blood. 2013; 121: 5208-17) and RAD001, an mTOR inhibitor (Id. Citing Su-Y-C et al, "RAD001-mediated STAT3 upregulation and megakaryocytic differentiation," Thromb. Haemost. 2013; 109: 540-49)). Wnt3a has been implicated as a repressor of human megakaryocyte progenitor expansion in an in-vitro iPSC derivation system that causes production of CD41/CD235 dual positive progenitors (Id. Citing Paluru, P. et al, "The negative impact of Wnt signaling on megakaryocyte and primitive erythroid progenitors derived from hyman embryonic stem cells," Stem Cell Res. 2014; 12: 441-51). A role for the aryl hydrocarbon receptor (AHR) in the regulation of iPSC-based in vitro megakaryopoiesis (Id. Citing Smith, B W et al, "The aryl hydrocarbon receptor directs hematopoietic progenitor cell expansion and differentiation," Blood. 2013; 122: 376-85) has been described.

Platelet Derived Microparticles and Exosomes

Platelets have a well-described physiological role in hemostasis and coagulation, but recently, they have also been shown to participate in immunity, tissue repair and development (Elzey B D, et al., The emerging role of platelets in adaptive immunity. Cell Immunol. 2005; 238:1-9; Jenne C N et al., Platelets: bridging hemostasis, inflammation, and immunity. Int J Lab Hematol. 2013; 35:254-61; Bertozzi C C et al., Platelets regulate lymphatic vascular development through CLEC-2-SLP-76 signaling. Blood. 2010; 116:661-70). Platelet-derived extracellular vesicles (EVs) can provide the molecules necessary to orchestrate these diverse functions. Platelets can generate microvesicles or microparticles (MPs), which are derived from the plasma membrane, and exosomes (EXOs), which are derived from endosomal pathways (Aatonen M T et al., Isolation and characterization of platelet-derived extracellular vesicles, J. Extracellular Vesicles, vol. 3 (2014) 24692).

Platelet plasma membrane derived microparticles (PMPs) are generally known to be 100 to 1000 nm in size. Platelets are also known to produce exosomes, which are 40 to 100 nm in size, from multivesicular bodies. In contrast to the heterogenous PMPs, exosomes in general form a more homogenous population, both by size and molecular content, but in platelets, the normally distinct formation processes of the two are jumbled because of α-granules. Multivesicular bodies, the source of exosomes, are also considered to be pre stages of α-granules, which may then liberate exosomes on fusion with the plasma membrane, and several α-granule-derived molecules are also present on PMPs. The molecular markers present on or in platelet-derived microvesicles, plasma membrane-derived microparticles, and platelet-derived exosomes include, without limitation, the following: Growth factors such as VEGF, bFGF, PDGF, TGF-beta1; Immune response factors such as CD40L (CD154); Chemokines/cytokines such as Rantes(CCL5), CCL23, CXCL7, CXCR4, PF-4(CXCL4), TNF-RI-II, IL-1 beta, CX3CR1, and beta-thromboglobulin; Complement proteins such as CD55, CD59, C5b-9, C1q, C3B, C1-INH, Factor H; Apoptosis markers such as Caspace-3, Caspace-9, FasR(CD95); Coagulation factors such as Fva, FVIII, TFPI, TF, PAR-1, FXIIIA; Active Enzymes such as PDI, 12-LO, NADPH oxidase, iNOS2, Heparnase; Adhesion proteins such as alpha-IIb/beta3 (CD41/CD61), GPIb (CD42b), GPIX (CD42a), P-selectin (CD62P), PECAM-1 (CD31), GPIIIb (CD36), CD49, CD29, CD47, CD9, JAM-A, vWF, fibrinogen, thrombospondin, vitronectin; Bioactive lipids such as PS, AA, LPA, TXA2; among other miscellaneous markers such as Peta-3 (CD151), CD63, PPAR-gamma, TIMP3, Lactadherin, PAI-1, PrPC, beta2GPI (Aatonen et al., Seminars in Thrombosis and Hemostasis Vol. 38, No. 1 (2012)). The common exosomal marker, CD63, is not only enriched in the platelet-derived exosomes but is also present on PMPs and, vice versa, many common PMP proteins are detected on subsets of exosomes.

Platelet-derived microvesicles (PMVs) seem to participate in diverse and sometimes paradoxal activities such as coagulation, adhesion, inflammation, immunity, and apoptosis. In many of these homeostatic activities, several cell types work in concert and may provide microvesicles (MVs) for intercellular communication. This dialogue depends on the formation of functionally variable MVs tailored for the purpose. The effect of PMVs can be either direct, that is, mediated by the PMV itself, such as acting as a catalytic surface, or indirect, that is, mediated by the recipient cells, which change their phenotype on PMV fusion. However, the presence of a molecule is not a guarantee for its function, as demonstrated by the unexpected anti-inflammatory response induced by CD40L(CD154)-containing PMPs (Aatonen et al., Seminars in Thrombosis and Hemostasis Vol. 38, No. 1 (2012)). The ultimate effect of PMVs is likely to depend on the cellular milieu (both temporally and spatially), which may explain, for example, the apparently contradictory pro- and anticoagulant capacity of the same PMVs.

PMVs can transfer fully operational surface receptors (CXC4R, CD41) onto the recipient cells. Receptor transfer by PMVs may confound the origin of cells: PMP-mediated transfer of CD31 and von Willebrand factor into monocytes falsely implied a presence of endothelial progenitor cells. PMVs also contain and transfer active enzymes, for example protein disulfide isomerase for platelet aggregation, inducible nitric oxide synthase II and nicotinamide adenine dinucleotide phosphate oxidase during endothelial dysfunction, and 12-lipo-oxygenase in lipoxin A4 production from mast cells. The participation of PMVs in innate and adaptive immunity is further inferred by the presence of several molecule groups such as cytokines and chemokines and their receptors, CD40L, and PF4 (Aatonen et al., Seminars in Thrombosis and Hemostasis Vol. 38, No. 1 (2012)).

Platelets harbor RNA molecules which are translated into proteins in an activation-dependent manner, for example CD41, CD61, and IL-1$\beta^{33}$ which are all members of the PMP proteome. It has been suggested that agonist-dependent changes in the platelet translatome may underlie the molecular, or even the functional, differences of PMP species (Aatonen et al., Seminars in Thrombosis and Hemostasis Vol. 38, No. 1 (2012)).

Previous Work Using Adult Peripheral Blood Platelets

In our previous work, we identified embryonic-like stem cells isolated from adult human peripheral blood, designated as peripheral blood-stem cells (PB-SC), which display characteristics of pluripotent cells. These cells were shown to have the capability of proliferation and differentiation into other cell types making them suitable for use in stem cell based therapies. These cells, which display embryonic stem cell characteristics and hematopoietic cell characteristics, are phenotypically distinct from lymphocytes, macrophages, monocytes, and hematopoietic stem cells.

The described invention provides umbilical cord blood derived platelet-like cells that can be used to generate induced pluripotent stem cells from adult mononuclear cells without the safety concerns involved in the generation of induced pluripotent stem cells by viral- or drug-induced transduction that may be stable when transferred to the patient.

SUMMARY OF THE INVENTION

According to one aspect, the described invention provides a method for functionally reprogramming adult cells to insulin-producing cells comprising: (a) isolating a population of peripheral blood mononuclear cells (PBMCs) from a human subject; (b) isolating a platelet rich fraction comprising platelet-like cells from umbilical cord blood or peripheral blood; (c) contacting the population of PBMCs of step (a) with the platelet rich fraction of step (b) in vitro, wherein the contacting is effective to reprogram the PBMCs to an immature cell type that expresses one or more embryonic biomarkers; and (d) expanding the immature cell type in vitro under culture conditions effective to generate an insulin-producing cell population, wherein the insulin-producing cell population expresses human beta-cell specific transcription factors and is functionally equivalent to human pancreatic beta-cells. According to one embodiment, the method further comprises isolating the adult PBMCs of step (a) from a Ficoll-Paque gradient fraction. According to another embodiment, the method further comprises isolating the platelet rich fraction comprising platelet-like cells from a Ficoll-Paque gradient fraction. According to another embodiment, the platelet rich fraction comprising platelet-like cells comprises one or more of whole cells, mitochondria, microparticles, exosomes, lysed cells, and alpha granules. According to another embodiment, the platelet-rich fraction comprising platelet-like cells comprising one or more of whole cells, mitochondria, microparticles, exosomes, lysed cells, and alpha granules contains transcription factors, growth factors, or both. According to another embodiment, the whole cells comprise one or more of hematopoietic stem cells, hematopoietic progenitor cells, common lymphoid progenitors, common myeloid progenitors, megakaryocyte-erythrocyte progenitors; granulocyte-monocyte progenitors, megakaryocyte lineage-committed progenitors, megakaryocytes, and platelet-like cells. According to another embodiment, the platelet-like cells that express one or more embryonic biomarkers from step (c) comprises one or more of OCT3/4, NANOG, NKX6.1, MAFA, Sur1, Kir6.2, PD-L1, CD270, Galectin 9, TGF-□1, AIRE, CCR3, CXCR4, and CCL2. According to another embodiment, the reprogrammed adult cells comprise one or more cell types selected from the group consisting of neuronal cells, endothelial cells, myocardiocytes, muscle cells, epithelial cells, corneal endothelial cells, retinal pigment cells, osteoblast cells, keratinocytes, hair follicle cells, and gland cells.

According to another aspect, the described invention provides a method for treating a recipient subject suffering from a disease characterized by hyperglycemia comprising: (a) isolating a population of peripheral blood mononuclear cells (PBMCs) from a human donor; (b) isolating a platelet rich fraction comprising platelet-like cells from umbilical cord blood or peripheral blood of the donor; (c) contacting the population of PBMCs of step (a) with the platelet rich fraction of step (b) in vitro, wherein the contacting is effective to reprogram the PBMCs to an immature cell type that expresses one or more embryonic biomarkers; (d) expanding the immature cell type in vitro under culture conditions effective to generate a cell product containing a therapeutic amount of an insulin-producing cell population, wherein the insulin-producing cell population expresses human beta-cell specific transcription factors and is functionally equivalent to human pancreatic beta-cells; and (e) administering the cell product from step (d) to the recipient subject; wherein the cell product containing the therapeutically effective amount of the insulin-producing cell population from step (d) is effective to reduce symptoms of the hyperglycemia disease. According to one embodiment, the donor and the recipient subject are the same individual. According to another embodiment, the autoimmune disease is diabetes. According to another embodiment, the autoimmune disease is type 1 diabetes. According to another embodiment, the donor is allogeneic to the recipient subject. According to another embodiment, in step (b) the platelet rich fraction comprising platelet-like cells comprises one or more of whole cells, mitochondria, microparticles, exosomes, lysed cells, and alpha granules.

According to another aspect of the descried invention, a pharmaceutical composition comprising a cell product containing a therapeutic amount of an insulin-producing cell population derived from adult PBMCs that have been functionally reprogrammed to an immature cell type that expresses one or more embryonic biomarkers by contact with a platelet rich fraction comprising platelet-like cells from umbilical cord blood or peripheral blood of a donor and expanded and redifferentiated in vitro, wherein the insulin-producing cell population expresses human beta-cell specific transcription factors and is functionally equivalent to human pancreatic beta-cells, wherein the platelet-rich fraction that expresses one or more embryonic biomarkers of step (c) comprises a population of cells positive for one or more of OCT3/4, NANOG, NKX6.1, MAFA, Sur1, Kir6.2, PD-L1, CD270, Galectin 9, TGF-β1, AIRE, CCR3, CXCR4, and CCL2; and negative for CXCL10, CCR4, CCR5, CCR7, CXCR1, CXCR2, CXCR3, CD62L, and CXCL1. According to one embodiment, the cell product is produced by a process comprising: (a) isolating a population of peripheral blood mononuclear cells (PBMCs) from a human donor; (b) isolating a platelet rich fraction comprising platelet-like cells from umbilical cord blood or peripheral blood of the donor; (c) contacting the population of PBMCs of step (a) with the platelet rich fraction of step (b) in vitro, wherein the contacting is effective to reprogram the PBMCs to an immature cell type that expresses one or more embryonic biomarkers; (d) expanding the immature cell type in vitro under culture conditions effective to generate a cell product containing a therapeutically effective amount of an insulin-producing cell population, wherein the insulin-producing cell population expresses human beta-cell specific transcription factors and is functionally equivalent to human pancreatic beta-cells; and e) formulating the cell product with a pharmaceutically acceptable carrier to form the pharmaceutical composition, wherein the cell product containing the therapeutically effective amount of the insulin-producing cell population from step (d) when administered to a subject with a disease characterized by hyperglycemia is effective to reduce symptoms of the hyperglycemia. According to another embodiment, in step (b) of the process, the platelet rich fraction comprising platelet-like cells comprises one or more of whole cells, mitochondria, microparticles, exosomes, lysed cells, and alpha granules. According to another embodiment, the population of functionally reprogrammed adult cells that present one or more of OCT3/4, NANOG, NKX6.1, MAFA, Sur1, Kir6.2, PD-L1, CD270, Galectin 9, TGF-1, AIRE, CCR3, CXCR4, and CCL2 that are negative for CXCL10, CCR4, CCR5, CCR7, CXCR1, CXCR2, CXCR3, CD62L, and CXCL1. According to another embodiment, the functionally reprogrammed cells are capable of producing insulin.

According to another aspect, the described invention provides for use of a pharmaceutical composition comprising a cell product containing a therapeutic amount of an insulin-producing cell population derived from adult PBMCs that have been reprogrammed to an immature cell type that expresses one or more embryonic biomarkers by contact with a platelet rich fraction comprising platelet-like cells from umbilical cord blood or peripheral blood of a donor and expanded and redifferentiated in vitro for the preparation of a medicament formulated for delivery to a hyperglycemic subject, wherein the insulin-producing cell population expresses human beta-cell specific transcription factors and is functionally equivalent to human pancreatic beta-cells. According to one embodiment, the hyperglycemia results from an autoimmune disease and the therapeutic amount is effective to ameliorate symptoms of the autoimmune disease. According to another embodiment, the autoimmune disease is type 1 diabetes.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 1A) Data showing platelet count (y-axis). (FIG. 1B) Data showing platelet distribution width (PDW, y-axis). (FIG. 1C) Data showing mean platelet volume (MPV, y-axis) (y-axis). (FIG. 1D) Data showing platelet count before and after treatment of Caucasian T1D subjects with CB-SCs (N=8).

(FIG. 2A) Co-expression of CD270 and CD41 and CD270 and CD61on cord blood platelet like cells. (FIG. 2B) Co-expression of CD41 and TGF-β1 and CD42 and TGF-β1 in cord blood platelet like cells. (FIG. 2C) Western blot showing expression of AIRE in seven cord blood preparations. (FIG. 2D) Double staining showing expression of AIRE in CD41+ cord blood platelet-like cells. Isotypematched IgGs served as controls. (FIG. 2E) Expression of co-inhibitory surface markers CD270, and Galectin 9 on CD41+CD42+ adult blood platelet like cells. Isotypematched IgGs served as controls. (FIG. 2F) Double immunostaining showing high expression of PD-L1 and CD270, low expression of Galectin 9, and no expression of ICOS on adult blood-derived platelet like cells. Representative data were from eight individual preparations. (FIG. 2G) expression of TGF-β1 in CD41+ adult blood platelet like cells. (FIG. 2H) Western blot showing expression of AIRE in nine adult blood preparations. (FIG. 2I) Double staining show the expression of AIRE in CD41+ adult blood platelet like cells. Isotype-matched IgGs served as controls.

FIG. 2L shows real time PCR Array analysis of mitochondrial DNA from CB-platelets and PB-platelets showing expression of T cell anergy and immune tolerance-related genes. Mitochondria were purified from CB-platelets and PB-platelets for gene transcription of mitochondria DNA (MitoDNA) to identify the origin of immune marker-related genes, Mitochondria were isolated from PB-platelets using the Qproteome Mitochondria Isolation kit (Qiagen, Hidden, Germany) according to the manufacturer's recommended protocol. Flow cytometry analysis showing that platelets releasing mitochondria displayed immune tolerance-related markers CD270 and CD274 (PD-L1) (FIG. 2M).

Peripheral blood-derived mononuclear cells (PBMCs) were treated with allogeneic PB-platelet-derived mitochondria in the presence of Dynabeads coupled with anti-CD3+ anti-CD28 antibodies+recombinant human IL-2 (rIL-2). After ex-vivo expansion for 4 days, large numbers of cell clusters were seen, with different sizes floating in the supernatant (FIG. 2N, bottom middle panel), suggestive of significant T cell proliferation. In the presence of mitochondria, this phenomenon was not evident (FIG. 2N, right panels). FIG. 2O shows that after the combination treatment with mitochondria, cell number was markedly declined.

FIG. 2P shows that the percentage of CD4+PD1+ T cells was increased to 15%±0.64% following treatment with mitochondria (FIG. 2P) (P=0.001).

FIG. 2Q shows by flow cytometry that the percentage of CD8+PD1+ T cells also was improved, from 2.43%±1.18% to 6.46%±0.28% in the presence of mitochondria (FIG. 2Q) (P=0.034).

FIG. 3A to FIG. 3P provide flow cytometry data (FIG. 3A-FIG. 3C, FIG. 3E, FIG. 3F), bar graphs (FIG. 3D and FIG. 3M), tissue sections (FIG. 3G-FIG. 3L), and micrographs of cells (FIG. 3N, FIG. 3O and FIG. 3P) showing interaction of platelet-like cells with immune cells in blood.

FIG. 3A is an ungated dot plot of CBMCs. Four major populations are shown: lymphocytes (Ly, purple circle), monocytes (Mo, black circle), granulocytes (Gr, yellow circle), and platelet-like cells (PI, blue circle). The panel on the extreme right is a gated dot plot showing a broad distribution (green color) among the different regions of four populations;

FIG. 3B is a histogram showing the distribution of the gated CD42+ platelet like cells in dot plot of CBMCs.

FIG. 3C shows flow cytometry data illustrating the co-distribution of platelet-like cells and other immune cells from freshly-isolated CBMCs. The data show that platelets adhere to CD14+ monocytes and to CD66b+ granulocytes as well as to some CD4+ T cells, CD8+ T cells, CD19+ B cells and CD56+NK cells.

FIG. 3D is a bar graph quantifying cells positive for platelet marker CD41+ and lineage markers. Representative data were from three experiments.

FIG. 3E shows flow cytometry data. Representative data were from three experiments. CBMCs were treated with EDTA/trypsin for 5 minutes at room temperature, and washed with PBS at 1000 rpm for 5 minutes. Controls (left panel) were CBMCs without treatment with EDTA/trypsin. The center panel shows that expression of CD41 on granulocytes was markedly declined after the treatment with EDTA/trypsin. Significant numbers of CD41+ platelet like cells that adhere to monocytes (CD14+) were observed. The right panel is a dot plot showing the gated CD14+CD41+ cells (blue).

FIG. 3F to FIG. 3M shows data illustrating the interaction of platelets with monocytes/macrophages (Mo/Mφ) (CD14+). Platelets were purified from adult blood units of healthy donors (New York Blood Bank).

FIG. 3F shows flow cytometry data. The percentage of CD14+CD41 b+ and CD14+CD42a+ cells was increased after permeabilization. Isotype-matched IgGs served as controls. Representative data were from three experiments.

FIG. 3G to FIG. 3L are transmission electron micrographs documenting interaction of platelets with Mφ.

FIG. 3G is an electron micrograph showing the ultrastructure of platelets (top panel) and Mφ.

FIG. 3H is an electron micrograph showing a pseudopod from M (yellow arrow) extended into a platelet.

FIG. 3I, FIG. 3J, and FIG. 3K are electron micrographs showing fusion of platelet and M membranes. Red arrow identifies fusion of platelet with Mφ. FIG. 3I Top panel, dotted line shows area of higher magnification shown in lower panel. FIG. 3J Box in top panel left is shown magnified in panel right and in bottom panel left. FIG. 3K box in left panel is magnified in right panel.

FIG. 3L Left panel shows phagocytosis of platelets by a M. The right panel is at high magnification.

FIG. 3M, FIG. 3N, FIG. 3O and FIG. 3P show purified Mo/Mφ from cord blood were treated with trypsin/EDTA to detach attached platelets from Mo/Mφ. Trypsin/EDTA-treated Mo/Mφ then were cultured in the presence of 50 ng/ml macrophage colony-stimulating factor (M-CSF). Trypsin/EDTA-untreated Mo/Mφ served as control. Panel M is a bar graph comparing the percentage of fibroblast-like macrophages (f-Mφ) in EDTA-trypsin treated and EDTA-trypsin untreated cells. The percentage of f-Mφ was markedly declined after treatment with trypsin/EDTA.

Figure 1:
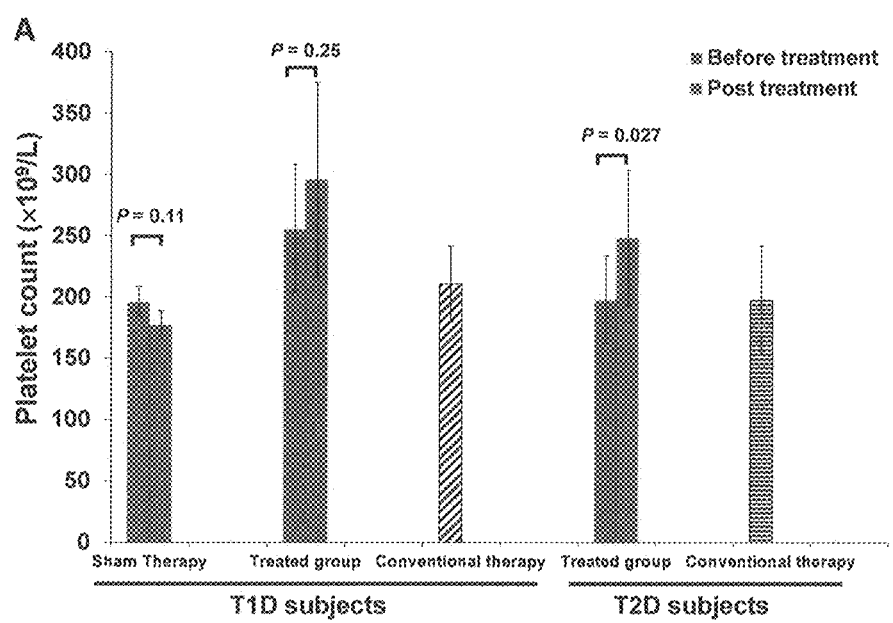
FIG. 1A, FIG. 1B, FIG. 1C and FIG. 1D are bar graphs of data showing modulation of platelets by circulating a patient's blood through a bioreactor that briefly co-cultures the lymphocytes in the presence of adherent cord blood stem cells (CB-SCs) and then returns the "educated" lymphocytes to the patient's circulation ("Stem Cell Education Therapy") in type 1 diabetes and type 2 diabetes subjects (y-axis) after sham therapy (no CB-SC education), CB-SC education, and conventional therapy.
Figure 1:
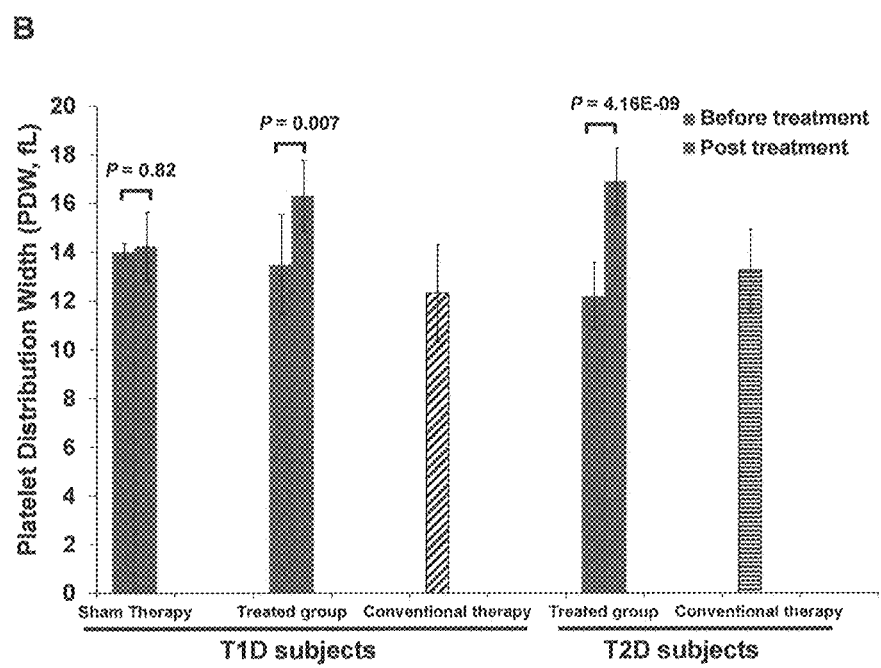
Figure 1:
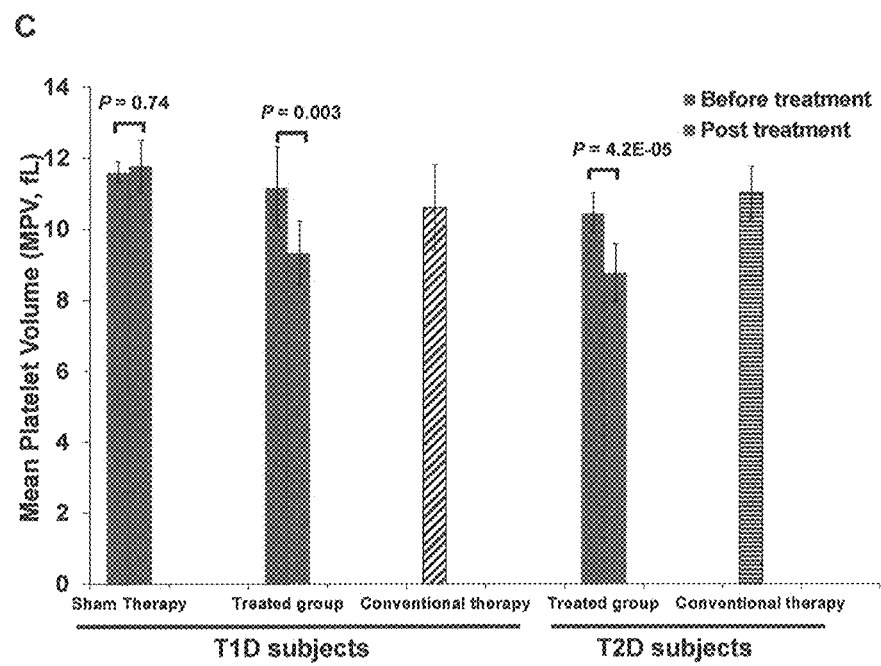
Figure 1:
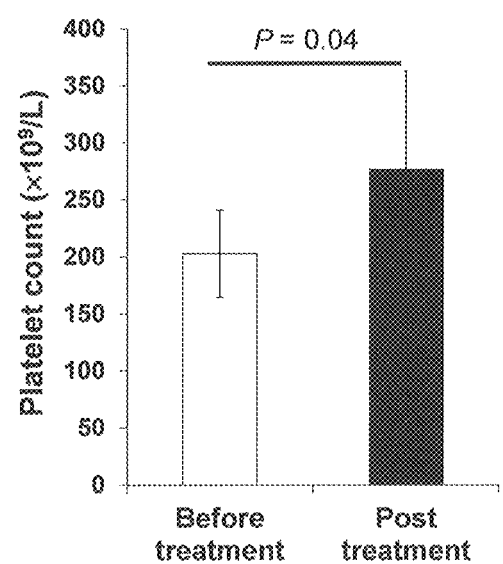

The percentage of f-Mφ formation was quantified after culture for 2 days in 8-well chamber slides. Representative data were from four experiments.

FIG. 3N is a phase contrast micrograph of EDTA/trypsin-treated MoMφ (left panel) and of EDTA/trypsin-untreated Mo/Mφ (control) after culture for 7 days in 24-well tissue-culture-treated plates. Representative data were from five experiments. Cell number was visibly reduced after treatment with trypsin/EDTA.

FIG. 3O f-Mφ were treated with 100 ng/ml epithelial growth factor (EGF) in the trypsin/EDTA-treated Mo/Mφ group (left panel). Cells were examined after the differentiation for 10 days in 24-well tissue-culture-treated plates, and then immunostained with mouse anti-Pan-Cadherin Ab at 1:100 dilution, magnification, ×100. Representative data were from four experiments. Differentiation of trypsin/EDTA-treated Mo/Mφ into the epithelial-like cells was reduced after EGF treatment.

FIG. 3P contains cells visualized by confocal microscopy showing expression of platelet marker CD42a and transcription factor OCT4 in Mφ after triple immunostaining. Representative data were from four experiments.

FIG. 4A to FIG. 4H show cell markers expressed by platelet like cells purified from human cord blood FIG. 4A, FIG. 4B, FIG. 4D, and FIG. 4E and adult peripheral blood FIG. 4C, FIG. 4F, FIG. 4G. Representative images were from four experiments.

FIG. 4A is an analysis of purified platelet like cells by flow cytometry. The gated platelet like cells in the dot plot shown (top left panel, blue) were analyzed by using platelets' markers CD41 and CD42, along with ES marker OCT4 as shown.

FIG. 4B shows flow cytometry analysis after double staining with CD41 and ES markers SOX2 (center panel) and NANOG (right panel) in CB platelet like cells. Isotype-matched IgGs served as controls (left panel).

FIG. 4C shows flow cytometry analysis after double staining with CD41 and ES markers OCT4 (top right panel), SOX2 (bottom left panel) and NANOG (bottom right panel) in PB platelet like cells. Isotypematched IgGs served as controls (top left panel).

FIG. 4D shows expression of ES markers in platelet like cells derived from cord blood after electrophoresis of real time PCR products.

FIG. 4E shows Western blots showing expression of ES markers in platelet like cells derived from cord blood.

FIG. 4F shows expression of ES markers in platelet like cells derived from peripheral blood after electrophoresis of real time PCR products.

FIG. 4G shows Western blots showing expression of ES markers in platelet like cells derived from peripheral blood.

FIG. 4H and FIG. 4I show PCR array analysis of mitochondrial DNA purified from cord blood and peripheral blood-derived platelet like cells Gene transcripts were analyzed by RT$^2$ Profiler PCR Array. Expression values were normalized over β-actin. Colors represent the levels of gene expression, as shown in the key. Genes with high expressions are depicted in red, genes with lower expression are depicted in green, and genes with no expression are depicted in black with a cross. FIG. 4H PCR array data for human stem cell transcription factors. FIG. 4I PCR Array data for human stem cell genes. Represented data from one of five preparations.

FIG. 5A to FIG. 5K depict data showing expression of pancreatic islet β cell-related markers in platelet preparations derived from cord blood (FIG. 5A, to FIG. 5F and FIG. 5K, top and middle row) and peripheral blood (FIG. 5G to FIG. 5J and FIG. 5K, bottom row). n=6;

FIG. 5A shows data from real time PCR analysis of pancreatic islet-related hormone products and β-cell-related functional markers in CB-derived platelet like cells, followed by electrophoresis.

FIG. 5B shows data from real time PCR analysis of pancreatic islet β-cell-related transcription factors in CB-derived platelet like cells, followed by electrophoresis.

FIG. 5C is a Western blot for an islet β cell-specific transcription factor MAFA in CB-derived platelet like cells.

FIG. 5D shows flow cytometry data for human pancreatic islet-related hormone products in freshly-isolated human pancreatic islet cells. Isotype-matched IgGs (grey histograms) served as negative controls.

FIG. 5E shows flow cytometry data for pancreatic islet-related hormone products double stained for platelet markers CD41 or CD42 in CB-derived platelet like cells.

FIG. 5F shows flow cytometry data for pancreatic islet β-cell-related transcription factors double stained for platelet marker CD41 or CD42 in CB-derived platelet like cells.

FIG. 5G shows data from real time PCR analysis of pancreatic islet-related hormone products and β-cell-related functional markers in PB-derived platelet like cells, followed by electrophoresis.

FIG. 5H shows flow cytometry data for pancreatic islet-related hormone products double stained for platelet marker CD41 or CD42 in PB derived platelet like cells.

FIG. 5I shows data from real time PCR analysis of pancreatic islet β-cell-related transcription factors in PB-derived platelet like cells, followed by electrophoresis.

FIG. 5J shows flow cytometry data of pancreatic islet β-cell-related transcription factors in PB-derived platelet like cells.

FIG. 5K shows data from confocal microscopy of human CB- and PB-derived platelet like cells after triple immunostaining with insulin (blue), dense granule marker ADP (red), and a granule marker vWF (green). Immunostaining with isotype-matched IgGs served as a negative control (inserted yellow dashed rectangle). Scale bars, 5 μm. Representative data were from six experiments.

Figure 6:
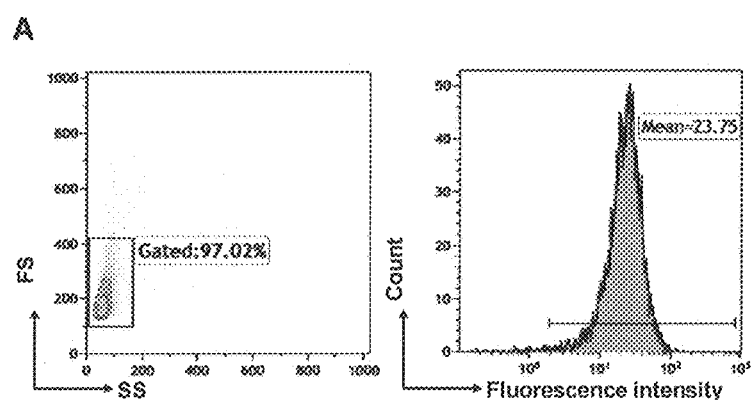
Figure 6:
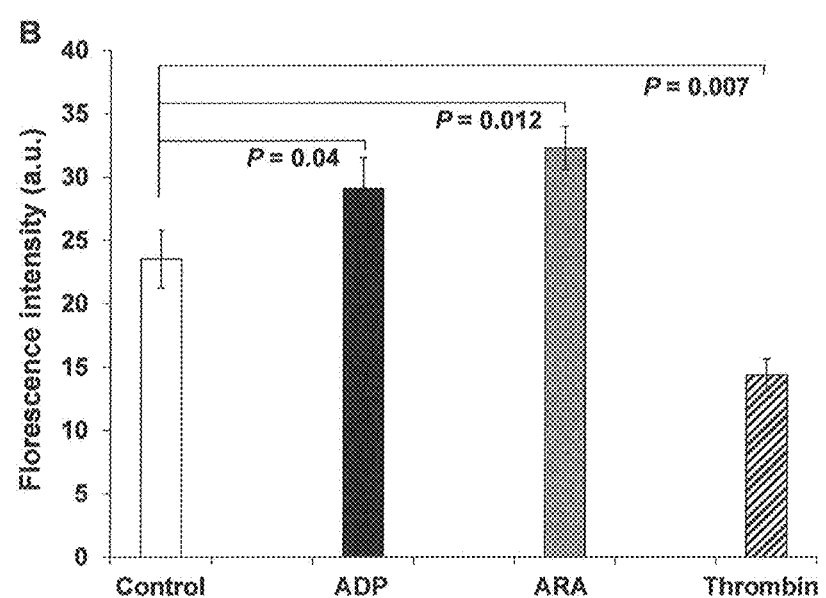
Figure 6:
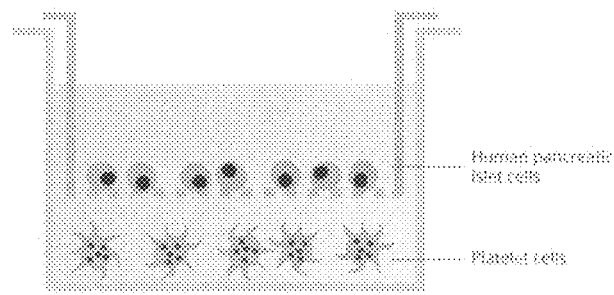
Figure 6:
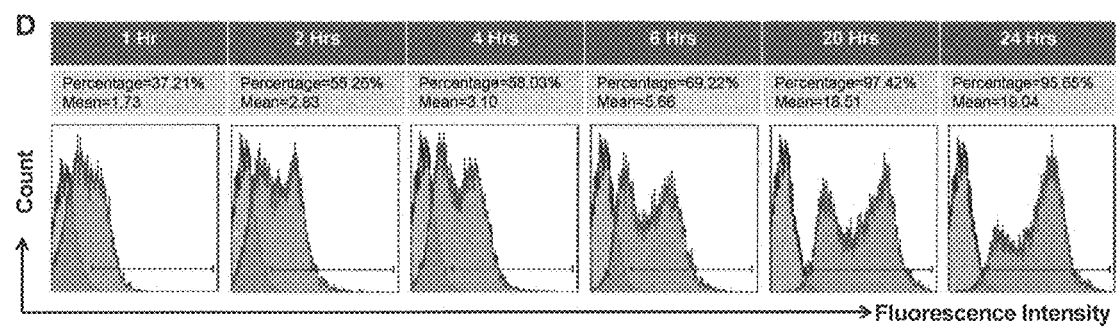
Figure 6:
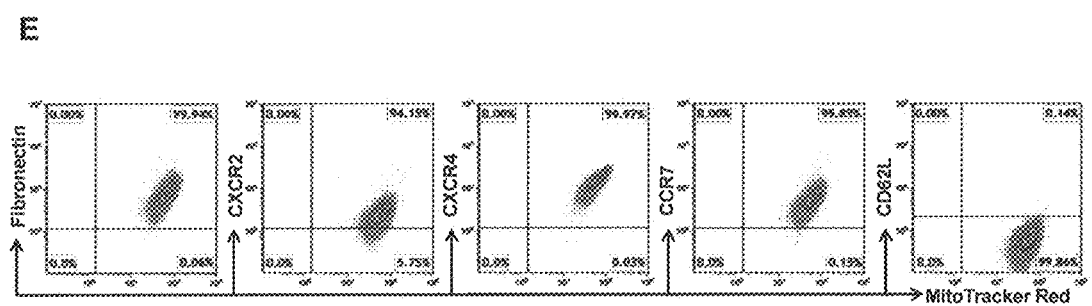
Figure 6:
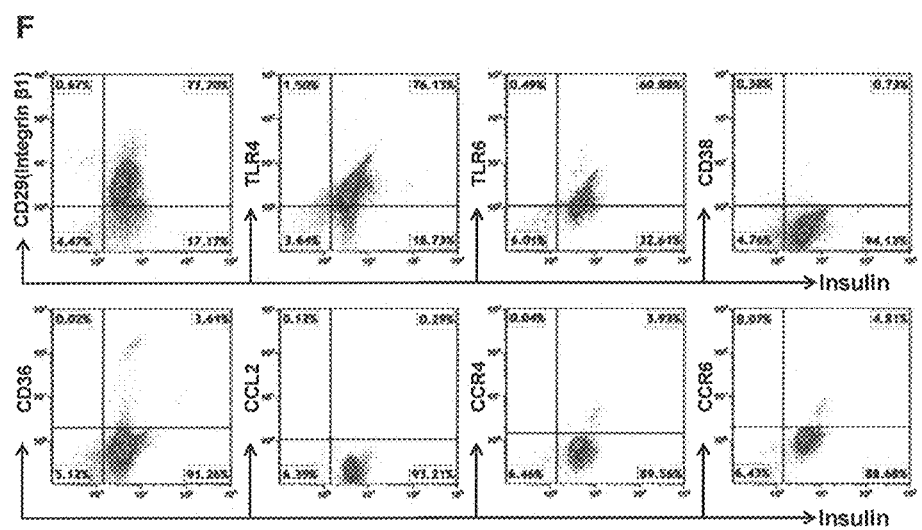
Figure 6:
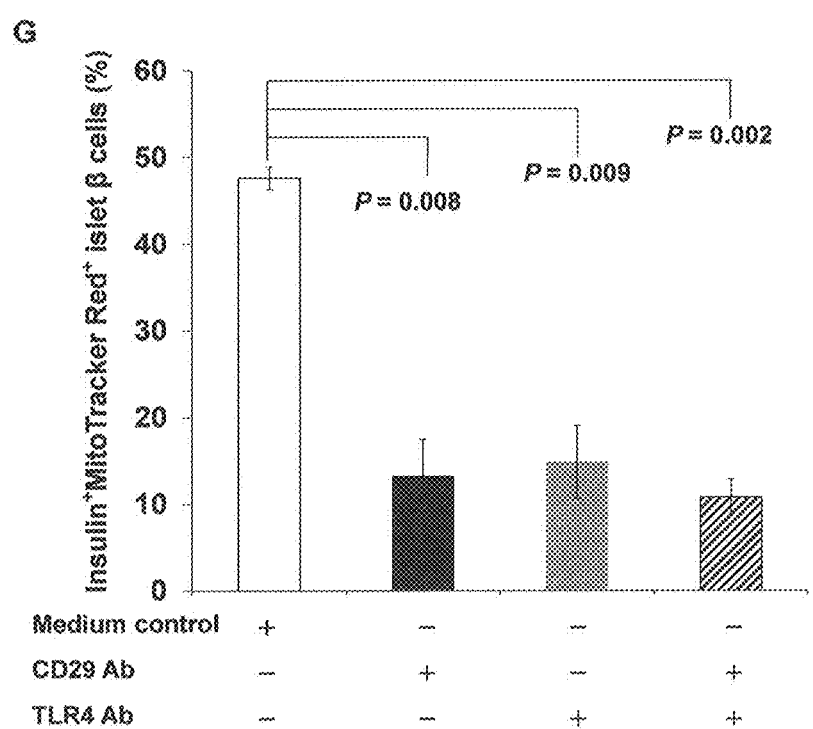
Figure 6:
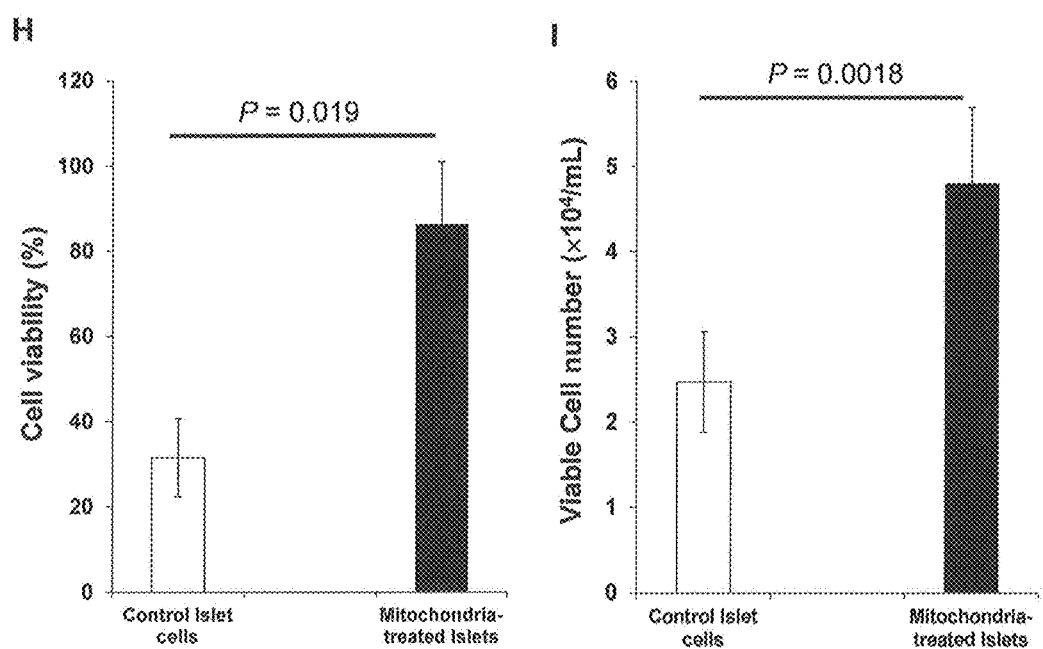
Figure 6:
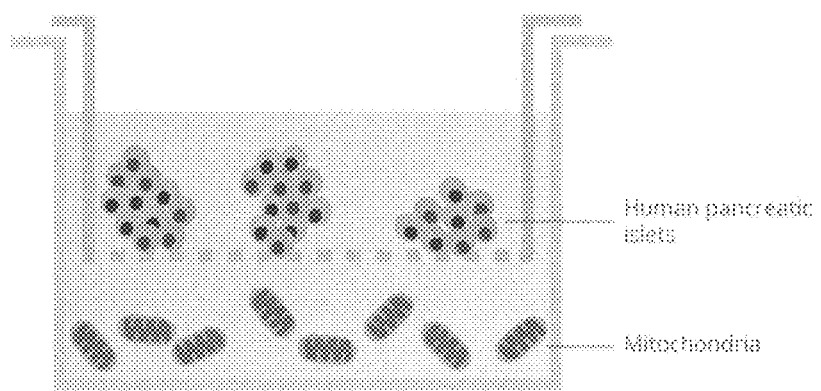
Figure 6:
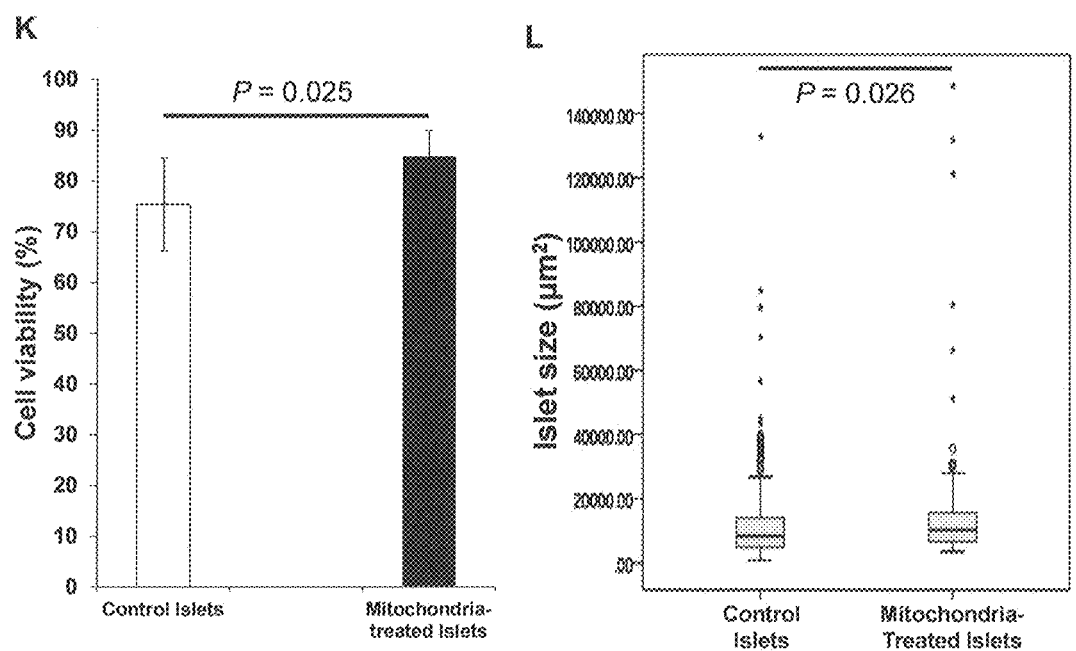
Figure 6:
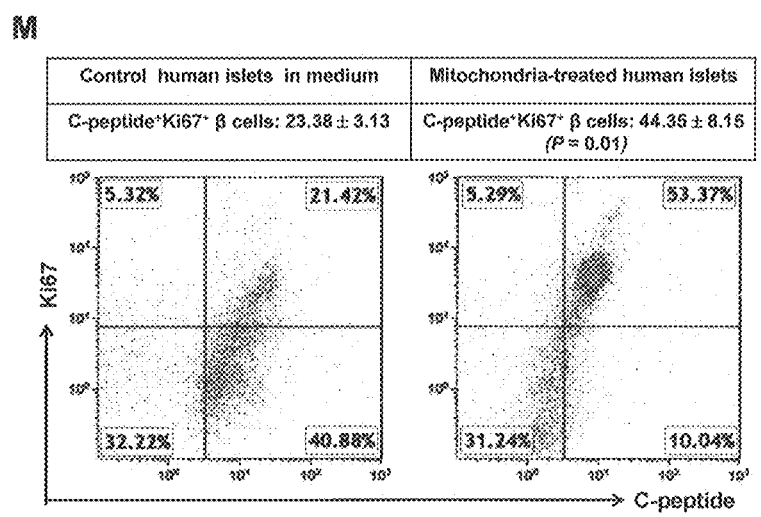
Figure 6:
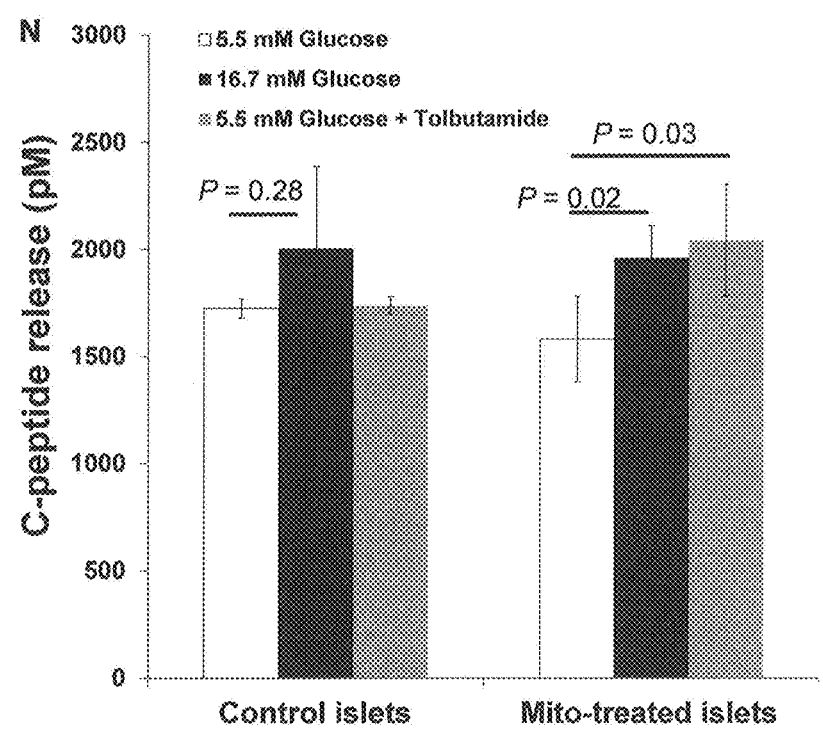
Figure 6:
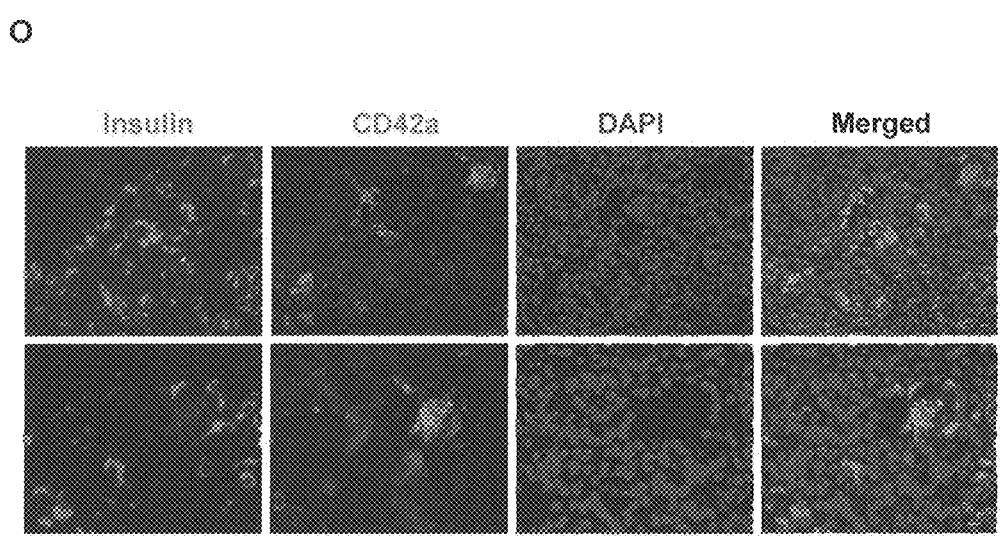

FIG. 6A to FIG. 6O depict data demonstrating improved pancreatic islet β-cell function by mitochondria released by platelet like cells.

FIG. 6A shows flow cytometry data showing the basal release of mitochondria from platelet like cells in dot plot (left panel) and histogram (right panel) format.

FIG. 6B shows bar graph plots representing the level of release of release of mitochondria after stimulation with different platelet aggregators in the presence of agonists ADP, ARA and Thrombin, compared to a control FIG. 6C depicts the experimental setup of a transwell culture system for co-culture of freshly-isolated human pancreatic islet cells (top) with platelet like cells labeled with MitoTracker Deep Red (bottom) in the transwells.

FIG. 6D shows kinetic measurements by flow cytometry from the experiment depicted in FIG. 6C. The data show that human pancreatic islet cells uptake MitoTracker Deep Red-labeled mitochondria released from the platelet like cells (bottom) in the transwell co-culture.

FIG. 6E shows flow cytometry data for expression of chemokine and chemokine receptors (from left to right, fibronectin, CXCR2, CXCR4, CCR7) and CD62L (L-selectin, which mediates adhesion) on mitochondria derived from platelet-like cells.

FIG. 6F shows flow cytometry data for expression of adhesion molecules (CD29, CD38, CD36), chemokine CCL2, and chemokine receptors (TLR4, TLR6, CCR4 and CCR6) on human islet β cells.

FIG. 6G data obtained by coculturing platelet-derived mitochondria with platelet islets in the presence of blocking antibodies to CD29 or to TLR4. Migration and uptake of mitochondria by human islet β cells were markedly declined in the presence of the anti-CD29, anti-TLR4, or both.

FIG. 6H shows bar graphs representing cell viability for trypsin/EDTA-dissociated single pancreatic islet β cells cocultured with platelet-like cells and control islet cells in transwells as depicted in FIG. 6C. Cell viability was increased after single islet β cells co-cultured with platelet like cells in the transwells.

FIG. 6I shows bar graphs representing viable cell number for trypsin/EDTA-dissociated single pancreatic islet β cells cocultured with platelet-like cells and control islet cells in transwells as depicted in FIG. 6C. The number of islet β cells was increased after co-culture with platelet like cells in the transwells.

FIG. 6J Schematic depicting co-culture of freshly isolated whole human pancreatic islets (top) with platelet like cells labeled with mitochondria (bottom) in the transwells.

FIG. 6K shows bar graphs representing cell viability (%) for control islets and for whole islets co-cultured with platelet-like cell derived mitochondria in the transwells as depicted in FIG. 6J. Cell viability was increased when whole islets were co-cultured with platelet like cell derived mitochondria in the transwells.

FIG. 6L shows data quantifying average islet size for control islets and for whole islets co-cultured with platelet-like cell derived mitochondria in the transwells as depicted in FIG. 6J. The average islet size was increased after whole islets were co-cultured with platelet like cell derived mitochondria (bottom) in the transwells as depicted in FIG. 6J.

FIG. 6M is a flow cytometry plot of Ki67 vs. C-peptide for control islets and for mitochondria-treated human islets. The data show that the percentage of Insulin+Ki67+ islet β cells increased after whole islets were co-cultured with platelet like cell derived mitochondria (bottom) in the transwells as depicted in FIG. 6J.

FIG. 6N shows bar graphs of C-peptide release for control islets and mitochondria-treated islets in the presence of the insulin secretogogues 5.5 mM glucose (white), 16.7 mM glucose (gray), and 5.5 mM glucose+tolbutamide (black), The functional analysis shows that pancreatic islet β cell function, as measured by C-peptide release from islet β cells, was improved in cells treated with 5 mM glucose+tolbutamide after whole islets were co-cultured with platelet-derived mitochondria (bottom) in the transwells compared to control islets as depicted in FIG. 6J.

FIG. 6O depicts immunohistochemical colocalization of islet β-cell marker insulin (red) and platelet marker CD42a (green) of human pancreatic tissues from diabetic patients. Scale bar, 10 μm.

DETAILED DESCRIPTION OF THE INVENTION

Glossary

The terms "alpha cell" or "α-cell" are used interchangeably herein to refer to a type of cell in the pancreas that makes and releases the hormone glucagon when blood glucose level falls too low. Glucagon stimulates the liver to release glucose into the blood for energy.

The term "Beta cells" or "β-cells" as used herein refers to a pancreatic cell that makes insulin.

The term "bipotent" as used herein refers to a cell that can differentiate into two cell lineages.

CD3 (TCR complex) is a protein complex composed of four distinct chains. In mammals, the complex contains a CD3γ chain, a CD3δ chain, and two CD3ε chains, which associate with the T cell receptor (TCR) and the ξ-chain to generate an activation signal in T lymphocytes. Together, the TCR, the ξ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

Integrins are receptors that mediate attachment between a cell and the tissues surrounding it and are involved in cell-cell and cell-matrix interactions. In mammals, 18 α and 8 β subunits have been characterized. Both α and β subunits contain two separate tails, both of which penetrate the plasma membrane and possess small cytoplasmic domains.

Integrin αM (ITGAM; CD11 b; macrophage-1 antigen (Mac-1); complement receptor 3 (CR3)) is a protein subunit of the heterodimeric integrin αMβ2 molecule. The second chain of αMβ2 is the common integrin β2 subunit (CD18). αMβ2 is expressed on the surface of many leukocytes including monocytes, granulocytes, macrophages and natural killer cells. It generally is believed that αMβ2 mediates inflammation by regulating leukocyte adhesion and migration. Further, αMβ2 is thought to have a role in phagocytosis, cell-mediated cytotoxicity, chemotaxis and cellular activation, as well as being involved in the complement system due to its capacity to bind inactivated complement component 3b (iC3b). The ITGAM subunit of integrin αMβ2 is involved directly in causing the adhesion and spreading of cells, but cannot mediate cellular migration without the presence of the β2 (CD18) subunit.

CD14 is a cell surface protein expressed mainly by macrophages and, to a lesser extent, neutrophil granulocytes. CD14+ cells are monocytes that can differentiate into a host of different cells; for example, differentiation to dendritic cells is promoted by cytokines such as GM-CSF and IL-4. CD14 acts as a co-receptor (along with toll-like receptor (TLR) 4 and lymphocyte antigen 96 (MD-2)) for the detection of bacterial lipopolysaccharide (LPS). CD14 only can bind LPS in the presence of lipopolysaccharide binding protein (LBP).

CD15 (3-fucosyl-N-acetyl-lactosamine; stage specific embryonic antigen 1 (SSEA-1)) is a carbohydrate adhesion molecule that can be expressed on glycoproteins, glycolipids and proteoglycans. CD15 commonly is found on neutrophils and mediates phagocytosis and chemotaxis.

CD16 is an Fc receptor (FcγRIIa and FcγRIIIb) found on the surface of natural killer cells, neutrophil polymorphonuclear leukocytes, monocytes and macrophages. Fc receptors bind to the Fc portion of IgG antibodies.

CD19 is a human protein expressed on follicular dendritic cells and B cells. This cell surface molecule assembles with the antigen receptor of B lymphocytes in order to decrease the threshold for antigen receptor-dependent stimulation. It generally is believed that, upon activation, the cytoplasmic tail of CD19 becomes phosphorylated, which allows binding by Src-family kinases and recruitment of phosphoinositide 3 (PI-3) kinases.

CD20 is a non-glycosylated phosphoprotein expressed on the surface of all mature B-cells. Studies suggest that CD20 plays a role in the development and differentiation of B-cells into plasma cells. CD20 is encoded by a member of the membrane-spanning 4A gene family (MS4A). Members of this protein family are characterized by common structural features and display unique expression patterns among hematopoietic cells and nonlymphoid tissues.

CD31 (platelet/endothelial cell adhesion molecule; PECAM1) normally is found on endothelial cells, platelets, macrophages and Kupffer cells, granulocytes, T cells, natural killer cells, lymphocytes, megakaryocytes, osteoclasts and neutrophils. CD31 has a key role in tissue regeneration and in safely removing neutrophils from the body. Upon contact, the CD31 molecules of macrophages and neutrophils are used to communicate the health status of the neutrophil to the macrophage.

CD34 is a monomeric cell surface glycoprotein normally found on hematopoietic cells, endothelial progenitor cells, endothelial cells of blood vessels, and mast cells. The CD34 protein is a member of a family of single-pass transmembrane sialomucin proteins and functions as a cell-cell adhesion factor. Studies suggest that CD34 also may mediate the attachment of stem cells to bone marrow extracellular matrix or directly to stromal cells.

CD44 (the "hyaluronan receptor"), a cell-surface glycoprotein involved in cell-cell interactions, cell adhesion and migration, is used to identify specific types of mesenchymal cells.

CD45 (protein tyrosine phosphatase, receptor type, C; PTPRC) cell surface molecule is expressed specifically in hematopoietic cells. CD45 is a protein tyrosine phosphatase (PTP) with an extracellular domain, a single transmembrane segment, and two tandem intracytoplasmic catalytic domains, and thus belongs to receptor type PTP. Studies suggest it is an essential regulator of T-cell and B-cell antigen receptor signaling that functions by direct interaction with components of the antigen receptor complexes, or by activating various Src family kinases required for antigen receptor signaling. CD45 also suppresses JAK kinases, and thus functions as a regulator of cytokine receptor signaling. The CD45 family consists of multiple members that are all products of a single complex gene. Various known isoforms of CD45 include: CD45RA, CD45RB, CD45RC, CD45RAB, CD45RAC, CD45RBC, CD45RO, and CD45R (ABC). Different isoforms may be found on different cells. For example, CD45RA is found on naïve T cells and CD45RO is found on memory T cells.

CD56 (neural cell adhesion molecule, NCAM) is a homophilic binding glycoprotein expressed on the surface of neurons, glia, skeletal muscle and natural killer cells. It generally is believed that NCAM has a role in cell-cell adhesion, neurite outgrowth, and synaptic plasticity. There are three known main isoforms of NCAM, each varying only in their cytoplasmic domains: NCAM-120 kDA (glycosylphopharidylinositol (GPI) anchored); NCAM-140 kDa (short cytoplasmic domain); and NCAM (long cytoplasmic domain). The different domains of NCAM have different roles, with the Ig domains being involved in homophilic binding to NCAM, and the fibronectin type III (FNIII) domains being involved in signaling leading to neurite outgrowth.

CD59 refers to a glycosylphosphatidylinositol (GPI)-linked membrane glycoprotein which protects human cells from complement-mediated lysis.

The CD66 antigen family identifies a neutrophil-specific epitope within the hematopoietic system that is expressed by members of the carcinoembryonic antigen family of adhesion molecules, which belong within the immunoglobulin gene superfamily. The extracellular portions of all CD66 (a-f) molecules possess a N-terminal V-set IgSF domain which, lacks the canonical inter-b-sheet disulfide of the CD-2 family. CD66a is heavily glycosylated type 1 glycoprotein with more than 60% of the mass contributed by N-linked glycans, which bear sialylated Lex (sLe x, CD15s) structures. In CD66a they are spaced further apart, VxYxxLx21 IxYxxV, and resemble motifs which bind tyrosine phosphatases such as SHIP-1 and -2. Activation of neutrophils leads to phosphorylation of tyrosine residues in the CD66a cytoplasmic domain. CD66a is expressed on granulocytes and epithelial cells. Products of 4 of the 7 functional carcinoembryonic antigen (CEA) family genes, CD66a-d, are known to be expressed on hematopoietic cells. The expression of these molecules on hematopoietic cells is generally restricted to the myeloid lineage. These molecules are present at low levels on resting mature granulocytes but expression increases rapidly following activation with inflammatory agonists, probably as a result of exocytosis from storage granules. CD66a is detected on some macrophages in tissue sections and has been reported on T cells and a subpopulation of activated NK cells.

CD66b ((CGM1); CD67, CGM6, NCA-95) is a glycosyl-phosphatidylinositol (GPI)-linked protein that is a member of the immunoglobulin superfamily and carcinoembryonic antigen (CEA)-like subfamily. CD66b, expressed on granulocytes, generally is believed to be involved in regulating adhesion and activation of human eosinophils.

CD90 or Thy-1 is a 25-37 kDa heavily N-glycosylated, glycophosphatidylinositol (GPI) anchored conserved cell surface protein with a single V-like immunoglobulin domain, originally discovered as a thymocyte antigen. It belongs to the immunoglobulin gene superfamily. The complex carbohydrate side chains vary in composition between tissues and species. Generally, CD90 is expressed on hematopoietic stem cells and neurons. CD90 is highly expressed in connective tissue, on various fibroblast and stromal cell lines and is expressed on all thymocytes and peripheral T cells in mice. In humans, CD90 is expressed only on a small number of fetal thymocytes, 10%-40% of blood CD34+ cells in bone marrow, and <1% of CD3+CD4+ lymphocytes in peripheral circulation. CD90 also is expressed in the human lymph node HEV endothelium but not on other endothelia and lastly, is expressed on a limited number of lymphoblastoid and leukemic cell lines.

CD105 (endoglin) is a homodimeric integral membrane glycoprotein composed of disulfide-linked subunits of 90-95 kDa. In humans, it is expressed at high levels on vascular endothelial cells and on syncytiotrophoblast of term placenta. During human heart development, it is expressed at high levels on endocardial cushion tissue mesenchyme during heart septation and valve formation; subsequently expression drops as the valves mature. It also is expressed by a population of pre-erythroblasts, leukemic cells of lymphoid and myeloid lineages, and bone marrow stromal fibroblasts. Endoglin is an accessory protein of multiple kinase receptor complexes of the TGF-β superfamily. The TGF-β1 superfamily of structurally related peptides includes the TGF-β isoforms, β1, β2, β3, and β5, the activins and the bone morphogenetic proteins (BMPs). TGF-β-like factors are a multifunctional set of conserved growth and differentiation factors that control biological processes such as embryogenesis, organogenesis, morphogenesis of tissues like bone and cartilage, vasculogenesis, wound repair and angiogenesis, hematopoiesis, and immune regulation. Signaling by ligands of the TGF-β superfamily is mediated by a high affinity, ligand-induced, heteromeric complex consisting of related Ser/Thr kinase receptors divided into two subfamilies, type I and type II. The type II receptor transphosphorylates and activates the type I receptor in a Gly/Ser-rich region. The type I receptor in turn phosphorylates and transduces signals to a novel family of recently identified downstream targets, termed Smads. Endoglin binds transforming growth factor (TGF) TGF-β1 and -β3 by associating with the TGF-β type II receptor, interacts with activin-A, interacts with bone morphogenic protein (BMP)-7 via activin type II receptors, ActRII and ActRIIB, and binds BMP-2 by interacting with the ligand binding type I receptors ALK3 and ALK6.

CD166 antigen (ALCAM), a 556 amino acid glycoprotein belonging to the immunoglobulin gene superfamily, is encoded by the activated leukocyte-cell adhesion molecule (ALCAM) gene in humans. It contains a secretory signal sequence, an extracellular domain which contains 3 Ig-like C2-type domains, 2 Ig-like V-type domains and 9 potential N-linked glycosylation sites, a hydrophobic transmembrane spanning domain and a 32 amino acid cytoplasmic domain with no known motifs. The N-terminal Ig domain is the binding site for both homophilic and CD166-CD6 interactions. CD166 is anchored to the actin cytoskeleton via the cytoplasmic domain but the receptors involved in this interaction are unknown. The soluble CD166 is produced by proteolytic cleavage of extracellular domains or by alternative splicing. It is expressed on mesenchymal stem cells and progenitor cells and on cortical thymic epithelial cells and medullary thymic epithelial cells, neurons, activated T cells, B cells, monocytes, fibroblasts, endothelium, epithelium, primitive subsets of hematopoietic cells including pluripotent stem cells, blastocysts and endometrium.

CD270, also known as TR2, Herpesvirus entry mediator A (HVEMA), Tumor necrosis factor receptor superfamily, member 14, TNFRSF14, Tumor necrosis factor receptor like 2, is a type I transmembrane protein containing 2 TNF receptor domains with a predicted molecular weight of approximately 30 kD. HVEM is widely expressed in blood vessels, brain, heart, kidney, liver, lung, prostate, spleen, thymus and other organs. Resting T cells and naïve and memory B cells express high levels of HVEM as well. In humans, HVEM is not expressed in germinal center B cells. Immature dendritic cells express high levels of HVEM that is downregulated upon maturation. In vitro it has been shown to directly interact with TRAF1, TRAF2, TRAF3, TRAF5, B and T lymphocyte associated protein (BTLA), and estrogen receptor alpha. [http://www.biolegend.com/pe-anti-human-cd270-hvem-tr2-anti body-3873.html]

The term "CXCR-4" as used herein refers to a G-protein-linked chemokine receptor. Stromal-derived factor-1 (SDF-1), an alpha-chemokine that binds to G-protein-coupled CXCR4, plays an important role in the regulation of stem/progenitor cell trafficking.

The term "cell" is used herein to refer to the structural and functional unit of living organisms and is the smallest unit of an organism classified as living.

The term "chemokine" as used herein refers to a class of chemotactic cytokines that signal leukocytes to move in a specific direction.

The terms "chemotaxis" or "chemotactic" refer to the directed motion of a motile cell or part along a chemical concentration gradient towards environmental conditions it deems attractive and/or away from surroundings it finds repellent.

The term "clonogenicity" and its other grammatical forms as used herein refers to the property of a single stem cell to produce a colony of cells through self-renewal.

The term "component" as used herein refers to a constituent part, element or ingredient.

The term "connecting peptide" or "C-peptide" as used herein refers to a short 31-amino-acid polypeptide that connects insulin's A-chain to its B-chain in the proinsulin molecule. It is used as a marker in autoimmune diseases like diabetes. Increased levels are an indication for insulin release as they are released at equimolar quantities and a better outcome for a patient. A very low C-peptide confirms type 1 diabetes and insulin dependence and is associated with high glucose variability, lack of glucose homeostasis and increased complications with poor outcome. Measurement of C-peptide levels is clinically validated by assessment of proper β-cell function [Wahren J. et al., "The clinical potential of C-peptide in replacement in type 1 diabetes", Diabetes, Vol. 61(4), 761-772, (2012)].

The term "contact" and its various grammatical forms as used herein refers to a state or condition of touching or of immediate or local proximity. Contacting a composition to a target destination may occur by any means of administration known to the skilled artisan.

The terms "cord blood-derived stem cells (CB-SCs)" and "cord blood mononuclear cells" (CBMCs) are used interchangeably with the term "cord blood mononuclear stem cell".

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Nonlimiting examples of cytokines include e.g., IL-1.alpha., IL-.beta., IL-2, IL-3, IL-4, IL-5, IL-6, IL-7, IL-8, IL-9, IL-10, IL-11, IL-12/IL-23 P40, IL3, IL-17, IL-18, TGF-beta., IFN-gamma., GM-CSF, Gro.alpha., MCP-1 and TNF-alpha.

The term "derived from" as used herein encompasses any method for receiving, obtaining, or modifying something from a source of origin. For example, the platelet-like cells from the platelet-like fraction may be derived from cord blood, meaning the platelet-like cells, directly or indirectly, came from the cord blood. As another example, whole platelet-like cells, lysed platelet-like cells, components of platelet-like cells including exosomes, microparticles, nucleic acids, growth factors, etc. may be derived from cord blood, meaning each of those components, directly or indirectly, came from the cord blood. As another example, lysed platelet-like cells may be derived from whole platelet-like cells, meaning that the lysed platelet-like cells, directly or indirectly, came from whole platelet-like cells.

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "differential label" as used herein generally refers to a stain, dye, marker, or antibody used to characterize or contrast structures, components or proteins of a single cell or organism.

The term "differentiation" as used herein refers to the process of development with an increase in the level of organization or complexity of a cell or tissue, accompanied with a more specialized function. The term "differentiation inducer" as used herein refers to a compound that is a direct, or indirect, causative agent of the process of cell differentiation. A "differentiation inducer" while sufficient to cause differentiation is not essential to differentiation.

The term "enrich" as used herein refers to increasing the proportion of a desired substance, for example, to increase the relative frequency of a subtype of cell compared to its natural frequency in a cell population. Positive selection, negative selection, or both are generally considered necessary to any enrichment scheme. Selection methods include, without limitation, magnetic separation and FACS. Regardless of the specific technology used for enrichment, the specific markers used in the selection process are critical, since developmental stages and activation-specific responses can change a cell's antigenic profile. According to some embodiments, negative magnetic selection can be accomplished by mixing a cell population marked by antibodies with a suspension of paramagnetic particles that bind to the antibody tag. Application of a magnetic field will then separate bead-cell aggregates from the unmarked cells, which can be collected by aspiration. According to some embodiments, positive magnetic selection can be accomplished by labeling the cells of interest with antibody-labeled-magnetic particles directed to known cell markers; generally, small particles (e.g., 50 nm) are used to minimize potential effects of the antibody-particle complexes on the biology of the selected cells. (Spangrude, Gerald J. and Slayton, William B, "Isolation and Characterization of Hematopoietic Stem Cells," Handbook of Stem Cells, Vol. 2, Robert Paul Lanza, Ed. Elsevier Inc. (2004) Chapter 54, pages 610-11). Commercial magnetic positive selection systems, for example, use a flow column packed with a fibrous metal, into which the magnetic field is introduced by induction, which creates a high-flux magnetic field with short distances between the labeled cells and the magnetized column matrix. This results in retention of the labeled cells in the column. Once the unlabeled cells are passed through the column and washed out, the column is removed from the magnetic field and the selected cells collected. According to some embodiments, FACS separation allows the simultaneous application of positive and negative selection for a variety of surface markers. According to some embodiments, positive and negative selection by FACS can be modified by substituting magnetic selections using the same combinations of antibodies. According to some such embodiments, unconjugated primary antibodies are used in combination with magnetic beads conjugated to secondary immunoglobulins for negative selection; for positive selection, an avidin-biotin system using biotinylated antibodies followed by avidin-conjugated microbeads can be used. According to some embodiments, negative selection can be used before FACS sorting to reduce cellularity of the sample. According to some embodiments, samples subjected to positive selection can subsequently be processed to isolate specific cellular subsets by FACS. Pre-enrichment of a target population before FACS can have a significant impact on the final purity of the isolated cell populations.

The term "factors" as used herein refers to nonliving components that have a chemical or physical effect. For example, a "paracrine factor" is a diffusible signaling molecule that is secreted from one cell type that acts on another cell type in a tissue. A "transcription factor" is a protein that binds to specific DNA sequences and thereby controls the transfer of genetic information from DNA to mRNA.

The term "fragment" as used herein refers to a small part, derived from, cut off, or broken from a larger unit which retains the desired biological activity of the larger unit.

The term "flow cytometry" as used herein refers to a tool for interrogating the phenotype and characteristics of cells. It senses cells or particles as they move in a liquid stream through a laser (light amplification by stimulated emission of radiation)/light beam past a sensing area. The relative light-scattering and color-discriminated fluorescence of the microscopic particles is measured. Flow Analysis and differentiation of the cells is based on size, granularity, and whether the cells is carrying fluorescent molecules in the form of either antibodies or dyes. As the cell passes through the laser beam, light is scattered in all directions, and the light scattered in the forward direction at low angles (0.5-10°) from the axis is proportional to the square of the radius of a sphere and so to the size of the cell or particle. Light may enter the cell; thus, the 90° light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogeneous population [Marion G. Macey, Flow cytometry: principles and applications, Humana Press, 2007]. Fluorescence-activated cell sorting (FACS), which allows isolation of distinct cell populations too similar in physical characteristics to be separated by size or density, uses fluorescent tags to detect surface proteins that are differentially expressed, allowing fine distinctions to be made among physically homogeneous populations of cells.

The term "functional equivalent" or "functionally equivalent" are used interchangeably herein to refer to substances, molecules, polynucleotides, proteins, peptides, or polypeptides having similar or identical effects or use.

The term "growth factor" as used herein refers to extracellular polypeptide molecules that bind to a cell-surface receptor triggering an intracellular signaling pathway, leading to proliferation, differentiation, or other cellular response. Growth factors include, but are not limited to, cytokines and hormones.

The term "hematopoietic stem cell" (HSC) refers to a cell isolated from the blood or from the bone marrow that can renew itself, differentiate to a variety of specialized cells, mobilize out of the bone marrow into the circulating blood, and undergo programmed cell death (apoptosis). In some embodiments of the described invention, hematopoietic stem cells derived from human subjects express at least one type of cell surface marker, including, but not limited to, CD34, CD38, HLA-DR, c-kit, CD59, Sca-1, Thy-1, and/or CXCR-4, or a combination thereof.

The term "isolated" as used herein refers to the separation of cells from a population through one or more isolation methods such as, but not limited to, mechanical separation or selective culturing. An "isolated" population of cells does not have to be pure. Other cell types may be present. According to some embodiments, and isolated population of a particular cell type refers to greater than 10% pure, greater than 20% pure, greater than 30% pure, greater than 40% pure, greater than 50% pure, greater than 60% pure, greater than 70% pure, greater than 80% pure, greater than 90% pure, or greater than 95% pure.

The term "labeling" as used herein refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The term "labile" as used herein refers to subject to increased degradation.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The term "matrix" refers to a surrounding substance within which something is contained or embedded.

The term "mechanical agitation" as used herein refers to a process whereby tissue is physically shaken or churned via mechanical means. Such mechanical means include, but are not limited to, a mixer or other mechanical device.

The term "mesenchymal stem cells (MSCs)" as used herein refers to non-blood adult stem cells found in a variety of tissues. They are characterized by their spindle-shape morphologically; by the expression of specific markers on their cell surface; and by their ability under appropriate conditions, to differentiates along a minimum of three lineages (osteogenic, chondrogenic and adipogenic). When referring to bone or cartilage, MSCs commonly are known as osteochondrogenic, osteogenic, or chondrogenic, since a single MSC has shown the ability to differentiate into chondrocytes or osteoblasts, depending on the medium.

MSCs secrete many biologically important molecules, including interleukins 6, 7, 8, 11, 12, 14, and 15, M-CSF, Flt-3 ligand, SCF, LIF, bFGF, VEGF, PIGF and MCP1 (Majumdar, et al., J. Cell Physiol. 176: 57-66 (1998), Kinnaird et al, Circulation 109: 1543-49 (2004)). In 2004, it was reported that no single marker that definitively identifies MSCs in vivo had yet been identified, due to the lack of consensus from diverse documentations of the MSC phenotype. Baksh, et al., J. Cell. Mol. Med. 8(3): 301-16, 305 (2004). There is general agreement that MSCs lack typical hematopoietic antigens, namely CD14, CD34, and CD45. (Id.; citing Pittenger, M. F. et al., Science 284: 143-47 (1999)).

The term "multilineage differentiation capability" as used herein refer to the property of a single stem cell to generate different types of mature progenies.

The term "multipotent" as used herein refers to a cell, such as mesenchymal stem cells and several other adult stem cells, which can differentiate into multiple cell lineages, but not all the lineages derived from the three germ layers.

The term "nonexpanded" as used herein refers to a cell population that has not been grown in culture (in vitro) to increase the number of cells in the cell population.

The term "Platelet Derived Growth Factor" (PDGF) as used herein refers to a major mitogen for connective tissue cells and certain other cell types. It is a dimeric molecule consisting of disulfide-bonded, structurally similar A and B-polypeptide chains, which combine to homo- and heterodimers. The PDGF isoforms exert their cellular effects by binding to and activating two structurally related protein tyrosine kinase receptors, the α-receptor and the β-receptor. Activation of PDGF receptors leads to stimulation of cell growth, but also to changes in cell shape and motility; PDGF induces reorganization of the actin filament system and stimulates chemotaxis, i.e., a directed cell movement toward a gradient of PDGF. In vivo, PDGF plays a role in embryonic development and during wound healing.

The term "platelet rich fraction of blood" or "platelet rich blood fraction" or "platelet rich fraction" as used herein refers to a fraction of human or animal blood obtained via a fractionation method that separates one or more components of blood wherein platelets account for at least 1%, at least 5%, at least 10%, at least 20%, at least 30%, at least 40%, at least 50%, at least 60%, at least 70%, at least 80%, or at least 90% of the total number of cells in the fraction. The platelet rich fraction of blood may comprise other components of blood, including, without limitation, serum, mononuclear cells including progenitor cells, granulocytes, erythrocytes, microparticles, exosomes, proteins (e.g., growth factors, transcription factors), lipids, and nucleic acids. The platelet rich fraction of blood may be further processed to isolate or remove one or more components of blood that are present in the platelet rich fraction. By way of non-limiting example, according to some embodiments a platelet rich fraction of blood may be obtained via Ficoll-Paque gradient separation. According to some embodiments, the Ficoll-Paque separated fractions of blood can comprise (from top to bottom), the plasma fraction, the mononuclear cell fraction, the Ficoll-Paque media fraction, and the granulocyte/erythrocyte fraction. According to some embodiments, the Ficoll-Paque separated platelet rich fraction of blood comprises one or more of the plasma fraction and the mononuclear cell fraction. According to some embodiments, the platelet-rich fraction from cord blood comprises cord blood platelet-like cells.

The term "platelet-like cell" as used herein refers to a cell in the platelet-rich fraction of a Ficoll-Paque gradient capable of platelet function (e.g., adhesion, activation, aggregation), or that comprises one or more platelet markers, platelet growth factors, or platelet nucleic acids. For purposes of this definition, a platelet-like cell includes cell precursors and one or more exosomes or microparticles.

The term "pluripotent" as used herein refers to the ability to develop into all the cells of the three embryonic germ layers, forming the body organs, nervous system, skin, muscle and skeleton. Examples include the inner cell mass of the eblastocyst, embryonic stem cells, and reprogrammed cells, such as iPS cells.

The term "progenitor cell" as used herein refers to an early descendant of a stem cell that can only differentiate, but can no longer renew itself. Progenitor cells mature into precursor cells that mature into mature phenotypes. Hematopoietic progenitor cells are referred to as colony-forming units (CFU) or colony-forming cells (CFC). The specific lineage of a progenitor cell is indicated by a suffix, such as, but not limited to, CFU-E (erythrocytic), CFU-F (fibroblastic), CFU-GM (granulocytic/macrophage), and CFU-GEMM (pluripotent hematopoietic progenitor). Examples in the platelet lineage include, without limitation, common myeloid progenitors (CMPs), megakaryocyte/erythrocyte progenitors (MEPs), megakaryocyte-erythrocyte progenitors (MegE), and megakaryocyte lineage-committed progenitors (MKPs), The term "propagate" as used herein refers to reproduce, multiply, or to increase in number, amount or extent by any process.

The term "purification" as used herein refers to the process of isolating or freeing from foreign, extraneous, or objectionable elements.

The term "self-renewal" as used herein refers to the capacity for extensive proliferation and generation of stem cells with the same properties as the parent cell.

The term "stem cells" refers to undifferentiated cells having high proliferative potential with self-renewal and clonogenic properties capable of multi-lineage differentiation. Stem cells are distinguished from other cell types by two characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

The term "totipotent" as used herein refers to a stem cell that can form the embryo and the trophoblast of the placenta.

The term "transforming growth factor beta (TGFβ) signaling pathway" is used herein to refer to the signaling pathway is involved in many cellular processes in both the adult organism and the developing embryo including cell growth, cell differentiation, apoptosis, cellular homeostasis and other cellular functions. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression.

The term "unipotent" as used herein refers to a cell that can differentiate into only one mature cell lineage.

Method for Reprogramming Adult Mononuclear Cells

According to one aspect, a method for reprogramming adult mononuclear cells comprises:

1. Providing UC blood cells or adult peripheral blood cells to isolate a platelet-rich fraction.
2. Collecting a platelet rich fraction from the UC blood cells or adult peripheral blood cells, the platelet rich fraction comprising platelet-like cells.
3. Providing peripheral blood from a subject and collecting a mononuclear cell fraction from the subject's peripheral blood.
4. Contacting the subject's mononuclear cell fraction of cells suitable for reprogramming with the platelet-rich fraction.
5. The contacting is effective to reprogram cells, which can be identified by biomarkers.
6. Optionally expanding the reprogrammed adult mononuclear cells.

According to some embodiments, the mononcuclear fraction of cells suitable for reprogramming contains adult mononuclear cells. According to some embodiments, the adult mononuclear cells are isolated from peripheral blood, bone marrow, liver, spleen, pancreas, kidney, brain, spinal cord, thyroid, lung, stomach intestines, or any other body part that can be affected by autoimmune diseases.

According to some embodiments, the collecting of the UC blood cells or adult peripheral blood cells step is performed by Ficoll-Paque gradient. According to some embodiments, the platelet rich fraction of cord blood or adult peripheral blood is obtained from a fraction of the Ficoll-Paque gradient.

According to some embodiments, the contacting of the adult mononuclear cells with the platelet rich fraction of cord blood is effective to transfer one or more components of the platelet rich fraction of cord blood to the adult mononuclear cells.

According to some embodiments, the contacting of the isolated mononuclear cells with the platelet rich fraction is in the presence of 2 mM $CaCl_2$ at 37° C. for between 10 minutes and 2 hours (Baj-Krzyworzeka et al., Platelet derived microparticles stimulate proliferation, survival, adhesion, and chemotaxis of hematopoietic cells, Exp. Hematology 30 (2002) 450-459). According to some embodiments, the contacting of the isolated mononuclear cells with the platelet rich fraction is for at least 10 minutes. According to some embodiments, the contacting of the isolated mononuclear cells with the platelet rich fraction is for at least 20 minutes. According to some embodiments, the contacting of the isolated mononuclear cells with the platelet rich fraction is for at least 30 minutes. According to some embodiments, the contacting of the isolated mononuclear cells with the platelet rich fraction is for at least 40 minutes.

According to some embodiments, the contacting of the isolated mononuclear cells with the platelet rich fraction is for at least 50 minutes. According to some embodiments, the contacting of the isolated mononuclear cells with the platelet rich fraction is for at least 60 minutes. According to some embodiments, the contacting of the isolated mononuclear cells with the platelet rich fraction is for at least 70 minutes. According to some embodiments, the contacting of the isolated mononuclear cells with the platelet rich fraction is for at least 80 minutes. According to some embodiments, the contacting of the isolated mononuclear cells with the platelet rich fraction is for at least 90 minutes. According to some embodiments, the contacting of the isolated mononuclear cells with the platelet rich fraction is for at least 100 minutes. According to some embodiments, the contacting of the isolated mononuclear cells with the platelet rich fraction is for at least 110 minutes. According to some embodiments, the contacting of the isolated mononuclear cells with the platelet rich fraction is for at least 120 minutes.

According to some embodiments, the contacting occurs in a cell suspension at 37° C. without agitation. According to some embodiment, the platelet rich fraction comprising platelet-like cells is activated prior to contacting. According to some embodiments, the contacting occurs in a cell suspension at 37° C. without agitation for a time that is sufficient for phagocytosis of platelets; e.g. at least 10 minutes, at least 20 minutes, at least 30 minutes, at least 40 minutes, at least 50 minutes, at least 60 minutes.

According to some embodiments, the contacting of the isolated mononuclear cells is with a lysed platelet rich fraction. According to some embodiments, the platelet rich fraction of blood is lysed with a whole cell lysis buffer. According to some embodiments, the lysed platelet rich fraction of blood is cleared by centrifugation.

According to some embodiments, the contacting of the isolated mononuclear cells with the lysed platelet rich fraction is for at least 10 minutes. According to some embodiments, the contacting of the isolated mononuclear cells with the lysed platelet rich fraction is for at least 20 minutes. According to some embodiments, the contacting of the isolated mononuclear cells with the lysed platelet rich fraction is for at least 30 minutes. According to some embodiments, the contacting of the isolated mononuclear cells with the lysed platelet rich fraction is for at least 40 minutes. According to some embodiments, the contacting of the isolated mononuclear cells with the lysed platelet rich fraction is for at least 50 minutes. According to some embodiments, the contacting of the isolated mononuclear cells with the lysed platelet rich fraction is for at least 60 minutes. According to some embodiments, the contacting of the isolated mononuclear cells with the lysed platelet rich fraction is for at least 70 minutes. According to some embodiments, the contacting of the isolated mononuclear cells with the lysed platelet rich fraction is for at least 80 minutes. According to some embodiments, the contacting of the isolated mononuclear cells with the lysed platelet rich fraction is for at least 90 minutes. According to some embodiments, the contacting of the isolated mononuclear cells with the lysed platelet rich fraction is for at least 100 minutes. According to some embodiments, the contacting of the isolated mononuclear cells with the lysed platelet rich fraction is for at least 110 minutes. According to some embodiments, the contacting of the isolated mononuclear cells with the lysed platelet rich fraction is for at least 120 minutes.

According to some embodiments, after the contacting step, the isolated mononuclear cells are washed in buffer and then cultured to expand the total number of reprogrammed cells.

According to some embodiments, the adult mononuclear cells are peripheral blood mononuclear cells (PBMCs). According to some embodiments, the method comprises contacting isolated adult PBMCs in vitro, with a platelet rich fraction of cord blood. According to some embodiments, the PBMCs and a platelet rich fraction of cord blood are derived from genetically distinct individuals. According to some embodiments, the PBMCs and platelet rich fraction of cord blood are derived from the same individual.

According to some embodiments, the method comprises contacting the isolated adult peripheral blood mononuclear cells (PBMCs) in vitro, with an enriched population of platelet-like cells derived from cord blood. According to some embodiments, the PBMCs are treated with trypsin/EDTA prior to the contacting to remove mature or adult platelets from the surface of the PBMCs.

According to some embodiments, the method comprises contacting in the adult peripheral blood mononuclear cells (PBMCs) in vitro with a lysate of a platelet rich fraction of blood. According to some embodiments, the peripheral blood mononuclear cells are contacted with a whole cell lysate derived from the platelet rich fraction of blood. According to some embodiments, the lysate of the platelet rich fraction of blood comprises mitochondria and alpha granule contents. According to some embodiments, the contacting comprises fusing the PBMCs with one or more of the components of the lysate of the platelet rich fraction of blood.

According to some embodiments, the method comprises contacting the adult peripheral blood mononuclear cells (PBMCs) with one or more of microparticles and exosomes derived from the platelet-rich fraction. According to some embodiments, the microparticles and exosomes are derived from a platelet rich fraction of cord blood. According to some embodiments, the microparticles and exosomes comprise one or more of embryonic stem cell like mRNA and protein. According to some embodiments, the microparticles and/or exosomes comprise one or more of growth factors such as VEGF, bFGF, PDGF, TGF-beta1; Immune response factors such as CD40L(CD154); Chemokines/cytokines such as Rantes(CCL5), CCL23, CXCL7, CXCR4, PF-4 (CXCL4), TNF-RI-II, IL-1 beta, CX3CR1, and beta-thromboglobulin; Complement proteins such as CD55, CD59, C5b-9, C1q, C3B, C1-INH, Factor H; Apoptosis markers such as Caspace-3, Caspace-9, FasR(CD95); Coagulation factors such as Fva, FVIII, TFPI, TF, PAR-1, FXIIIA; Active Enzymes such as PDI, 12-LO, NADPH oxidase, iNOS2, Heparnase; Adhesion proteins such as alpha-IIb/beta3 (CD41/CD61), GPIb (CD42b), GPIX (CD42a), P-selectin (CD62P), PECAM-1 (CD31), GPIIIb (CD36), CD49, CD29, CD47, CD9, JAM-A, vWF, fibrinogen, thrombospondin, vitronectin; Bioactive lipids such as PS, AA, LPA, TXA2; among other miscellaneous markers such as Peta-3 (CD151), CD63, PPAR-gamma, TIMP3, Lactadherin, PAI-1, PrPC, beta2GPI.

According to some embodiments, the method comprises contacting the adult peripheral blood mononuclear cells (PBMCs) with alpha granules of the platelet-like cells. According to some embodiments, the alpha granules are acquired from a platelet rich fraction of cord blood.

According to some embodiments, the platelet rich fraction of human blood comprises platelets, platelet like cells or other components associated with stem cells. According to some embodiments, the platelet rich fraction of human blood comprises cell signaling molecules associated with signaling pathways underlying induced pluripotent stem cell reprogramming. According to some embodiments, the platelet rich fraction of human blood comprises platelet-like cells comprising embryonic stem cell markers. According to some embodiments, the platelet rich fraction of human blood comprises the transcription factors OCT3/4 and SOX2 (See FIGS. 1A and 1B). According to some embodiments, the platelet rich fraction of human blood comprises one or more of the proteins OCT3/4, SOX2, NANOG, CRIPTO, GATA-4, and C-myc (See FIG. 1C). According to some embodiments, the platelet fraction of human blood comprises one or more of proteins OCT3/4, SOX2, NANOG, and C-myc (See FIGS. 1D, 1E, and 1F).

According to some embodiments the PBMCs comprise one or more of the markers CD14, CD66, CD4, CD8, CD19, CD56, CD41b, and CD42a.

According to some embodiments, the method comprises contacting peripheral blood mononuclear cells (PBMCs) with a platelet rich fraction of blood to reprogram monocytes and macrophages into a more stem-like state. According to some embodiments, PBMCs are contacted with a platelet rich fraction of blood to reprogram monocytes and macrophages into peripheral blood insulin producing cells (PB-IPC). According to some embodiments, the method comprises contacting the PBMCs with a platelet rich fraction of blood wherein one or more of transcription factors and nucleic acids are transferred from the platelet rich fraction to the mononuclear cells. According to some embodiments, platelet-like cells from the platelet rich fraction fuse with PBMCs, thereby transferring the transcription factors and nucleic acids from the platelet to the PBMCs. According to some embodiments, microparticles from the platelet rich fraction fuse with mononuclear cells, thereby transferring one or more of transcription factors and nucleic acids to the PBMCs. According to some embodiments, exosomes from the platelet rich fraction fuse with PBMCs, thereby transferring one or more of transcription factors or nucleic acids.

According to some embodiments, PBMCs are reprogrammed by contacting with a platelet rich fraction of blood to display one or more of tetraspanin CD9, leukocyte common antigen CD45, and stem cell factor receptor CD117.

PB-IPCs Contacted with Platelet Rich Fraction

According to some embodiments, the method comprises contacting peripheral blood insulin-producing cells (PB-IPCs) with the platelet-rich cell fraction. According to some embodiments, the isolated PB-IPCs are derived by culturing PBMCs within a vessel with a hydrophobic surface. According to some embodiments, the PB-IPCs may be obtained by providing a sample of adult human peripheral blood; removing red cells from the sample to obtain mononuclear cells; culturing the mononuclear cells on a hydrophobic surface with a net positive charge and obtaining a cell population which is attached to the surface (Zhou Y. et al., U.S. Pat. No. 8,835,163, the entirety of which is herein incorporated by reference).

According to some embodiments, the method comprises contacting PB-IPCs isolated from PBMCs with a platelet rich fraction of cord blood. According to some embodiments, the method comprises contacting PB-IPCs isolated from PBMCs with one or more of microparticles and exosomes acquired from a platelet rich fraction of cord blood. According to some embodiments, the method comprises contacting the PB-IPCs isolated from PBMCs with one or more of microparticles and exosomes acquired from adult peripheral blood.

According to some embodiments, the method comprises contacting peripheral blood insulin producing cells (PB-IPCs) with a platelet rich fraction of blood to enhance potential for insulin production. According to some embodiments, PB-IPCs display embryonic stem cell-associated transcription factors including OCT-4 and NANOG, along with the hematopoetic markers CD9, CD45, and CD117. According to some embodiments, the PB-IPCs lack expression of hematopoetic stem cell marker CD34 as well as lymphocyte and monocyte/macrophage markers. According to some embodiments, the PB-IPCs demonstrate characteristics of islet beta-cell progenitors including the expression of beta-cell specific insulin gene transcription factors and prohormone convertases, production of insulin, and formation of insulin granules. According to some embodiments, PB-IPCs have the ability to reduce hyperglycemia and migrate into pancreatic islets after transplantation into diabetic mice.

According to some embodiments, the instant invention discloses a method of enhancing the insulin-producing characteristics of PB-IPCs, and improving the capacity to reduce hyperglycemia and migrate into pancreatic islets by contacting PB-IPCs from adult blood with a platelet rich fraction of cord blood or platelet rich fraction of adult blood. According to some embodiments, the PB-IPCs are obtained directly from whole cord blood or whole adult blood. According to some embodiments, the PB-IPCs are isolated from whole blood by culturing mononuclear cells on a hydrophobic tissue culture surface. According to some embodiments, the PB-IPCs are contacted with a platelet rich fraction of blood wherein one or more of transcription factors and nucleic acids are transferred from the platelet rich fraction to the PB-IPCs. According to some embodiments, platelet-like cells from the platelet rich fraction fuse with PB-IPCs, thereby transferring the transcription factor and nucleic acids from the platelet-like cell to the PB-IPC. According to some embodiments, microparticles from the platelet rich fraction fuse with PB-IPCs, thereby transferring one or more of transcription factors or nucleic acids to the PB-IPCs. According to some embodiments, exosomes from the platelet rich fraction fuse with PB-IPCs, thereby transferring one or more of transcription factors or nucleic acids.

According to some embodiments, the PB-IPCs contacted with platelet rich fraction have an enhanced ability to migrate into pancreatic islets and become functional producers of insulin. According to some embodiments, the PB-IPCs contacted with platelet rich fraction differentiate into beta-cells.

The Result of the Contacting:

According to some embodiments, the contacting of PBMCs with the platelet rich fraction of human blood produces fibroblast-like macrophages.

According to some embodiments, the contacting of PBMCs with the platelet rich fraction of blood produces a population of cells comprising a proportion of cells for particular markers of undifferentiated cells and/or differentiated cells. For example, relative ratios of transcription products for markers of undifferentiated cells such as Oct4, neuroprogenitor markers such as nestin and Ngn-3, and markers of mature neuron markers such as beta-tubulin and TPH2 can be assessed by quantitative RT-PCR. Also, production and localization of markers of undifferentiated cells can be assessed by immunocytochemistry.

Markers of undifferentiated and differentiated cells are assayed by any of various methods such as antibody-based detection techniques using an antibody specific for a particular marker. Antibody-based techniques include immunofluorescence and immunoblotting. Further assays include assays for detection of mRNAs encoding a particular marker. Such assays include polymerase chain reaction, blot hybridization (also known as Northern blots) and in situ hybridization. Details of these and other such assays are described herein and in standard references including J. Sambrook and D. W. Russell, Molecular Cloning: A Laboratory Manual, Cold Spring Harbor Laboratory Press; 3rd ed., 2001; F. M. Ausubel, Ed., Short Protocols in Molecular Biology, Current Protocols; 5th ed., 2002; and E. Harlow and D. Lane, Antibodies: A Laboratory Manual, Cold Spring Harbor Laboratory Press, 1988.

According to some embodiments, the contacting of PBMCs with a platelet rich fraction of blood results in a reprogramming of one or more of the following cell types comprising the PBMCs: monocytes, macrophages, and lymphocytes. According to some embodiments, the contacting of PBMCs with a platelet rich fraction of blood results in the reprogramming of one or more cell types comprising the PBMCs into a functional insulin producing cell. According to some embodiments, the contacting of PBMCs with a platelet rich fraction of blood results in the reprogramming of one or more cell types comprising the PBMCs into a functional islet beta-cell.

According to some embodiments, the contacting of PBMCs with a platelet rich fraction of blood results in a reprogramming of one or more of the cell types comprising the PBMCs to minimize or eliminate an immune response against the reprogrammed cell when administered to a subject.

According to some embodiments, the functionally modulated adult blood mononuclear cells display stem-like, hematopoietic, or differentiated phenotypic characteristics. According to some embodiments, the functionally modulated adult blood mononuclear cells display one or more of the following pancreatic markers: MafA, Nkx6.1, Pdx-1, Onecut1, NeuroD1, Nkx2.2, insulin, glucagon, pancreatic polypeptide, somatostatin, ghrelin, Sur-1 and Kir6.2. According to some embodiments, the functionally modulated adult blood mononuclear cells display one or more of the following embryonic/hematopoietic markers: tetra-spanin CD9, leukocyte common antigen CD45, stem cell factor receptor CD117. According to some embodiments, the functionally modulated adult blood mononuclear cells display small amounts of or the absence of one or more of the following: hematopoietic stem cell marker CD34, lymphocyte markers CD3 (T cells) and CD20 (B cells). According to some embodiments, the functionally modulated adult blood mononuclear cells are derived from a hematopoietic lineage, and not a mesenchymal lineage, from peripheral blood. According to some embodiments, the functionally modulated adult mononuclear cells display small amounts of, or the absence of, monocyte/macrophage specific antigens CD14 and CD11b/Mac-1. According to some embodiments, the functionally modulated adult mononuclear cells display small amounts of, or the absence of, HLA-DR, CD40, and CD80. According to some embodiments, the functionally modulated adult mononuclear cells display embryonic stem cell related transcription factors Oct-4 and NANOG.

According to some embodiments, the functionally modulated adult blood mononuclear cells display one or more of the following molecules: OCT3/4, NANOG, NKX6.1, MAFA, Sur1, Sur2, PDL-1, CD270, Galectin 9.

According to some embodiments, the functionally modulated adult blood cells display embryonic stem characteristics, including one or more of stem cell markers Oct-4, Nanog, and Sox-2, together with other embryonic stem (ES) cell-related genes, e.g., Zinc finger and SCAN domain containing 10 (ZNF206, also named ZSCAN10), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PTPRZ1), Podocalyxin-like (PODXL), Polyhomeotic homolog 1 (PHC1), and Zinc finger protein 589 (ZNF589). The sequences for Oct-4, Nanog, and Sox-2 can be found under GenBank Accession Nos. NM_002701, Z11898 and Q01860; GenBank Accession Nos. NM_024865 and NP_079141; and GenBank Accession Nos. Z31560 and CAA83435, respectively.

According to some embodiments, the functionally modulated adult blood mononuclear cells are CD45+. According to some embodiments, the functionally modulated adult blood mononuclear cells are phenotypically distinct from lymphocytes, dendritic cells, macrophages and monocytes, in that they are negative for one or more of the following antigenic markers: CD3, CD20 (B-lymphocyte cell-surface antigen B1, Accession No. M27394), CD11c (integrin, alpha X, Accession No. NM_000887), CD11b/Mac-1 (complement component 3 receptor 3 subunit, Accession No. NM_000632) and CD14 (Accession Nos. NM_001040021 and P08571) markers. According to some embodiments, the functionally modulated adult blood mononuclear cells are phenotypically distinct from hematopoietic stem cells in that they are CD34 negative (Hematopoietic progenitor cell antigen CD34, Accession No. P28906) (Craig et al. 1994, British Journal of Haematology, 88:24-30; Lansdorp, P. A I. and Dragowaka, W. (1992) J. Exp. Med. 175:1501-1509; Sutherland, H. J., et al. (1989), Blood 74.1563-1570).

According to some embodiments, the functionally modulated adult blood mononuclear cells are capable of differentiating into other cell types including, but not limited to, insulin producing cells. According to some embodiments, the functionally modulated adult blood mononuclear cells that are insulin-producing cells display glucagon-like peptide 1 (GLP-1) receptor. According to some embodiments, administration of a long acting agonist of GLP-1, exendin-4, increases insulin production and cell differentiation of the functionally modulated adult blood mononuclear cells.

According to some embodiments, the reprogrammed functionally modulated adult blood mononuclear cells can be expanded in culture. According to some embodiments, the expanded reprogrammed adult peripheral blood mononuclear cells comprise cells having the characteristics of pluripotent stem cells that may differentiate into functional pancreatic islet beta-cells.

According to some embodiments, the reprogrammed functionally modulated adult blood mononuclear cells comprise one or more embryonic stem cell markers, human islet beta-cell specific transcription factors or both derived from the cord platelet-like cells. According to some embodiments, the reprogrammed functionally modulated adult blood mononuclear cells express immune tolerance-related markers.

Cord Blood Mononuclear Cells

According to one aspect, a method for reprogramming adult mononuclear cells comprises:

1. Providing UC blood to isolate a platelet-rich fraction.
2. Collecting a platelet rich fraction from the UC blood cells, the platelet rich fraction comprising one or more of platelet-like cells and mononuclear cells.
3. Selecting reprogrammed mononuclear cells, which can be identified by biomarkers.
4. Optionally expanding the reprogrammed adult mononuclear cells.

According to some embodiments, the functionally modulated cord blood mononuclear cells display stem-like, hematopoietic, or differentiated phenotypic characteristics. According to some embodiments, the functionally modulated cord blood mononuclear cells display one or more of the following pancreatic markers: MafA, Nkx6.1, Pdx-1, Onecut1, NeuroD1, Nkx2.2, insulin, glucagon, pancreatic polypeptide, somatostatin, ghrelin, Sur-1 and Kir6.2. According to some embodiments, the functionally modulated cord blood mononuclear cells display one or more of the following embryonic/hematopoietic markers: tetra-spanin CD9, leukocyte common antigen CD45, stem cell factor receptor CD117. According to some embodiments, the functionally modulated cord blood mononuclear cells display small amounts of or the absence of one or more of the following: hematopoietic stem cell marker CD34, lymphocyte markers CD3 (T cells) and CD20 (B cells). According to some embodiments, the functionally modulated cord blood mononuclear cells are derived from a hematopoietic lineage, and not a mesenchymal lineage, from peripheral blood. According to some embodiments, the functionally modulated cord mononuclear cells display small amounts of, or the absence of, monocyte/macrophage specific antigens CD14 and CD11b/Mac-1. According to some embodiments, the functionally modulated cord blood mononuclear cells display small amounts of, or the absence of, HLA-DR, CD40, and CD80. According to some embodiments, the functionally modulated cord blood mononuclear cells display embryonic stem cell related transcription factors Oct-4 and NANOG.

According to some embodiments, the functionally modulated cord blood mononuclear cells display one or more of the following molecules: OCT3/4, NANOG, NKX6.1, MAFA, Sur1, Sur2, PDL-1, CD270, Galectin 9.

According to some embodiments, the functionally modulated cord blood cells display embryonic stem characteristics, including one or more of stem cell markers Oct-4, Nanog, and Sox-2, together with other embryonic stem (ES) cell-related genes, e.g., Zinc finger and SCAN domain containing 10 (ZNF206, also named ZSCAN10), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PTPRZ1), Podocalyxin-like (PODXL), Polyhomeotic homolog 1 (PHC1), and Zinc finger protein 589 (ZNF589). The sequences for Oct-4, Nanog, and Sox-2 can be found under GenBank Accession Nos. NM_002701, Z11898 and 001860; GenBank Accession Nos. NM_024865 and NP_079141; and GenBank Accession Nos. Z31560 and CAA83435, respectively.

According to some embodiments, the functionally modulated cord blood mononuclear cells are CD45+. According to some embodiments, the functionally modulated cord blood mononuclear cells are phenotypically distinct from lymphocytes, dendritic cells, macrophages and monocytes, in that they are negative for one or more of the following antigenic markers: CD3, CD20 (B-lymphocyte cell-surface antigen B1, Accession No. M27394), CD11c (integrin, alpha X, Accession No. NM_000887), CD11b/Mac-1 (complement component 3 receptor 3 subunit, Accession No. NM_000632) and CD14 (Accession Nos. NM_001040021 and P08571) markers. According to some embodiments, the functionally modulated cord blood mononuclear cells are phenotypically distinct from hematopoietic stem cells in that they are CD34 negative (Hematopoietic progenitor cell antigen CD34, Accession No. P28906)

According to some embodiments, the platelet rich fraction of cord blood comprises platelets, platelet like cells or other components associated with stem cells. According to some embodiments, the platelet rich fraction of cord blood comprises cell signaling molecules associated with signaling pathways underlying induced pluripotent stem cell reprogramming. According to some embodiments, the platelet rich fraction of cord blood comprises platelet-like cells comprising embryonic stem cell markers. According to some embodiments, the platelet rich fraction of cord blood comprises the transcription factors OCT3/4 and SOX2 (See FIGS. 1A and 1B). According to some embodiments, the platelet rich fraction of cord blood comprises one or more of the proteins OCT3/4, SOX2, NANOG, CRIPTO, GATA-4, and C-myc (See FIG. 1C). According to some embodiments, the platelet fraction of cord blood comprises one or more of proteins OCT3/4, SOX2, NANOG, and C-myc (See FIGS. 1D, 1E, and 1F).

According to some embodiments the cord blood mononuclear cells comprise one or more of the markers CD14, CD66, CD4, CD8, CD19, CD56, CD41 b, and CD42a.

Cell Product

According to another aspect, the described invention discloses a cell product comprising a pharmaceutical composition containing the functionally modulated adult blood mononuclear cells of the described invention.

According to some embodiments, a method for treating a subject in need thereof comprises administering the cell product to a diabetic mammalian subject, wherein the cell product may be effective to increase a population of functional cells in the pancreas of the subject. According to some embodiments, the cell product may be effective to increase the population of functional p cells in the pancreas of the subject. According to some embodiments, the cell product may be effective to migrate to the pancreas of the subject following administration.

According to some embodiments, the pharmaceutical composition containing the functionally modulated adult blood mononuclear cells may be formulated with an excipient, carrier or vehicle including, but not limited to, a solvent. The terms "excipient", "carrier", or "vehicle" as used herein refers to carrier materials suitable for formulation and administration of the functionally modulate adult blood mononuclear cell product described herein. Carriers and vehicles useful herein include any such materials known in the art which are nontoxic and do not interact with other components. As used herein the phrase "pharmaceutically acceptable carrier" refers to any substantially-non-toxic carrier useable for formulation and administration of the composition of the described invention in which the functionally modulated adult blood mononuclear cell product of the described invention will remain stable and bioavailable.

The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition. For example, the pharmaceutically acceptable carrier may be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions of the described invention include, but are not limited to, water, salt solutions, alcohols, polyethylene glycols, gelatins, amyloses, magnesium stearates, talcs, silicic acids, viscous paraffins, hydroxymethyleelluloses, polyvinylpyrrolidones and the like. Such carrier solutions also can contain buffers, diluents and other suitable additives. The term "buffer" as used herein refers to a solution or liquid whose chemical makeup neutralizes acids or bases without a significant change in pH. Examples of buffers envisioned by the described invention include, but are not limited to, Dulbecco's phosphate buffered saline (PBS), Ringer's solution, 5% dextrose in water (D5W), and normal/physiologic saline (0.9% NaCl). According to some embodiments, the infusion solution is isotonic to subject tissues. According to some embodiments, the infusion solution is hypertonic to subject tissues. Compositions of the described invention that are for parenteral administration may include pharmaceutically acceptable carriers such as sterile aqueous solutions, non-aqueous solutions in common solvents such as alcohols, or solutions in a liquid oil base.

The functionally modulated adult blood mononuclear cell product of the described invention may be administered parenterally in the form of a sterile injectable aqueous or oleaginous suspension. The term "parenteral" or "parenterally" as used herein refers to introduction into the body by way of an injection (i.e., administration by injection), including, but not limited to, infusion techniques.

The functionally modulated adult blood mononuclear cell product of the described invention may be a sterile solution or suspension in a nontoxic parenterally acceptable diluent or solvent. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it does not rapidly settle out. In everyday life, the most common suspensions are those of solids in liquid water. Among the acceptable vehicles and solvents that may be employed are water, Ringer's solution, and isotonic sodium chloride (saline) solution. According to some embodiments, hypertonic solutions are employed. In addition, sterile, fixed oils conventionally are employed as a solvent or suspending medium. For parenteral application, suitable vehicles consist of solutions, e.g., oily or aqueous solutions, as well as suspensions, emulsions, or implants. Aqueous suspensions may contain substances, which increase the viscosity of the suspension and include, for example, sodium carboxymethyl cellulose, sorbitol and/or dextran.

Additional functionally modulated adult blood mononuclear cell product of the described invention readily may be prepared using technology, which is known in the art, such as described in Remington's Pharmaceutical Sciences, 18th or 19th editions, published by the Mack Publishing Company of Easton, Pa., which is incorporated herein by reference.

As used herein the terms "therapeutically effective" or "pharmaceutically effective amount" refer to the amount of the compositions of the invention that result in a therapeutic or beneficial effect following its administration to a subject. The effective amount of the composition may vary with the age and physical condition of the biological subject being treated, the severity of the condition, the duration of the treatment, the nature of concurrent therapy, the timing of the infusion, the specific compound, composition or other active ingredient employed, the particular carrier utilized, and like factors.

A skilled artisan may determine a pharmaceutically effective amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual ED50. The use of the term "individual" distinguishes the ED50 based on the intensity of effect as used herein from the median effective dose, also abbreviated ED50, determined from frequency of response data in a population. "Efficacy" as used herein refers to the property of the compositions of the described invention to achieve the desired response, and "maximum efficacy" refers to the maximum achievable effect. The amount of the chemotactic hematopoietic stem cell product in the pharmaceutical compositions of the described invention that will be effective in the treatment of a particular disorder or condition will depend on the nature of the disorder or condition, and may be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, New York, 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993), each of which is incorporated by reference herein. The precise dose to be employed in the formulations of the described invention also will depend on the route of administration and the seriousness of the disease or disorder, and should be decided according to the judgment of the practitioner and each subject's circumstances.

According to some embodiments, the functionally modulated adult blood mononuclear cell product of the described invention may be administered initially, and thereafter maintained by further administrations. For example, according to some embodiments, the functionally modulated adult blood mononuclear cell product of the described invention may be administered by one method of injection, and thereafter further administered by the same or by different method.

According to some embodiments, the functionally modulated adult blood mononuclear cell product of the described invention can be administered to a subject by direct injection to a desired site, systemically, or in combination with a pharmaceutically acceptable carrier. According to some embodiments, the growth and/or differentiation of the functionally modulated adult blood mononuclear cell product of the described invention, and the therapeutic effect of the functionally modulated adult blood mononuclear cell product of the described invention may be monitored. For example, the functionally modulated adult blood mononuclear cell product of the described invention administered to treat diabetes may be monitored by testing blood glucose and/or insulin levels in a subject. According to some embodiments, the immunological tolerance of the subject to the functionally modulated adult blood mononuclear cell product of the described invention after administration may be tested by various methods known in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Protocols

Isolation of Blood Fractions

Briefly, anticoagulant-treated adult blood or umbilical cord blood is diluted in the range of 1:2 to 1:4 with PBS/EDTA to reduce aggregation of erythrocytes. The diluted blood is then layered above a Ficoll-Paque solution in a centrifuge tube, without mixing. The layered blood/Ficoll-Paque is centrifuged for 40 minutes at 400×g between 18° and 20° C., without the use of the centrifuge brake. This results in the formation of blood fractions comprising, from top to bottom: a first fraction comprising blood plasma and platelet-like cells; a second fraction comprising mononuclear cells and platelet-like cells; a third fraction comprising Ficoll-Paque media; and a fourth fraction comprising granulocytes and erythrocytes.

According to some embodiments, the fractions are further processed to isolate specific fraction components. Briefly, to further process mononuclear cells, the second fraction comprising mononuclear cells and platelet-like cells is carefully removed from the Ficoll-Paque gradient using a Pasteur pipet. The second fraction is then washed and centrifuged at 300×g, 18° and 20° C., three times with PBS/EDTA, discarding the supernatant after each round.

According to some embodiments, the fractions are further processed to isolate platelet-like cells. Briefly, the first fraction comprising blood plasma and platelet-like cells is removed from the Ficoll-Paque gradient. Equal volume of HEP buffer with 1 µM prostaglandin E1 (PGE1) is then added to the platelet rich fraction and mixed gently. The fraction is then centrifuged at 100×g for 15-20 at room temperature with no brake to pellet any contaminating red or white blood cells. The supernatant is then transferred to a new container and centrifuged at 800×g for 15-20 minutes at room temperature. The pelleted platelet-like cells are then washed twice without resuspension to avoid platelet activation.

Flow Cytometry

Flow Cytomtery analysis was performed as previously described (Zhao Y. et al., Exp. Cell Res., 312, 2454 (2006)). Briefly, cells that were either treated with trypsin/EDTA or left untreated were collected by centrifugation and re-suspended in PBS. The cells were fixed in 4% formaldehyde for 10 minutes at 37° C. For extracellular staining with antibodies cells were not permeabilized. For intracellular staining, cells were permeabilized by adding ice-cold 100% methanol to pre-chilled cells to a final concentration of 90% methanol and incubated on ice for 30 minutes. Cells were immunostained by first resuspending cells in incubation buffer and adding primary antibody according to the manufacturer's recommended dilution. Cells were incubated with primary antibody for 1 hour at room temperature, followed by three washes with incubation buffer. Cells were then resuspended in incubation buffer with conjugated secondary antibody at the manufacturer's recommended dilution for 30 minutes at room temperature, followed by three washes in incubation buffer. Stained cells were then analyzed by flow cytometry.

Flow cytometric analysis of surface and intra-cellular markers were performed as previously described in Zhao Y, et al., Human cord blood stem cell modulated regulatory T lymphocytes reverse the autoimmune-caused type 1 diabetes in non-obese diabetic (NOD) mice. PLoS ONE 2009, 4: e4226. Briefly, platelets were washed with PBS at 3000 rpm for 15 min. Human islets were dissociated with 0.25% trypsin/EDTA for 5 min at room temperature with repeated pipetting, followed by a wash in PBS. Cells were incubated with mouse anti-human monoclonal antibodies (mAb; Beckman Coulter, Brea, Calif.), including: FITC-conjugated anti-CD42a, anti-CD61, phycoerythrin (PE)-conjugated anti-CD83, anti-CXCR4, anti-CCR7 and phycoerythrin-Cy7 (PE-Cy7)-conjugated anti-CD41, anti-CD56 and anti-CCR7, APC-conjugated anti-ICOS, APC-Alexa Fluor 750-conjugated anti-CD4 and anti-CD66b, pacific blue (PB)- conjugated anti-CD38, Krome Orange-conjugated anti-CD8a, anti-CD14, and anti-CD19. Other antibodies, such as AF647-conjugated anti-Foxp3, PerCP-Cy5.5-conjugated mouse anti-human PDX-1, Alexa Fluor 488-conjugated mouse anti-human somatostatin and anti-PDX-1, PE-conjugated mouse anti-NEUROD1 and anti-Glucagon, and anti-FOXA2, and anti-NKX6.1, BV421-conjugated mouse anti-human glucagon, Alexa Fluor 647-conjugated mouse anti-human insulin, anti-human C-peptide, anti-NKX6.1, anti-SOX9, anti-PTFA1, and anti-NANOG, and PerCP-Cy5.5-conjugated mouse antihuman SOX17 mAb, were purchased from BD Biosciences (San Jose, Calif.). The FITC conjugated mouse anti-human integrin β1 (CD29), PE-conjugated mouse anti-human CD270 (HVEM) mAb, anti-TLR4, anti-TLR6 and anti-CXCL10, APC-conjugated anti-TGF-β1, and APC/Fire 750-conjugated anti-CD36 mAbs were purchased from Biolegend (San Diego, Calif.). Rabbit anti-AIRE polyclonal antibody was purchased from Abcam (Cambridge, Mass.). FITC conjugated anti-CXCR1 and anti-SOX2, PE-conjugated anti-CD274 (PD-L1), anti-CXCR2, anti-CCR3, anti-CCR5, and anti-fibronectin, APC-conjugated anti-CCL2, eFluor660-conjugated anti-Galectin 9, CXCR3, and anti-CXCL1, PerCP-eFluor710-conjugated anti-CCR4, Alexa Fluor 647-conjugated rat anti-human Oct 3/4 mAb and unconjugated mouse anti-human NANOG were purchased from eBioscience (San Diego, Calif.). FITC-conjugated anti-human MAFA ab was from United States Biological (Salem, Mass.). DyLight 405-conjugated anti-ki67 was purchased from Novus Biologicals (Littleton, Colo.).

Cells were stained for 30 min at room temperature and then washed with PBS prior to flow analysis. Isotype-matched mouse anti-human IgG antibodies (Beckman Coulter) served as a negative control for all fluorescein-conjugated IgG mAb. For intra-cellular staining, cells were fixed and permeablized using a PerFix-nc kit (Beckman Coulter). After staining, cells were collected and analyzed using a Gallios Flow Cytometer (Beckman Coulter), equipped with 3 lasers (488 nm blue, 638 red, and 405 violet lasers) for the concurrent reading of up to 10 colors. The final data were analyzed using the Kaluza Flow Cytometry Analysis Software (Beckman Coulter).

For mitochondrial staining of platelets with fluorescent dyes, platelet-fractions were labeled with MitoTracker Deep Red FM (100 nM) or MitoTracker Green FM (100 nM) (Thermo Fisher Scientific, Waltham, Mass.) at 37° C. for 15 min, followed by two washes with PBS at 3000 rpm×15 min. To determine the release of mitochondria by platelets, MitoTracker Deep Red-labeled platelets were treated with a platelet aggregator, such as 20 μM ADP, 0.5 mM arachidonic acid (ARA), and 1 Unit/ml thrombin, in 0.5 ml serum-free X-VIVO 15 culture medium (Lonza) at 37° C. for 15 min. After such treatment, platelets were removed by centrifugation at 2.7 g for 15 min, 4° C. Supernatants were collected and re-centrifuged at 14 g for 15 min at 4° C. to harvest the released mitochondria for flow analysis.

Immunofluorescence

A standard immunofluorescence protocol was used. Briefly, adherent cells were fixed with 4% formaldehyde diluted in warm PBS for 15 minutes at room temperature. The fixative was aspirated and the cells washed three times with PBS for 5 minutes each. Cells were blocked with blocking buffer for 60 minutes at room temperature. Blocking buffer was then aspirated and a solution of primary antibody diluted according to the manufacturer's instructions was incubated with the cells overnight at 4° C. Cells were then rinsed three times with PBS for 5 minutes each, and subsequently incubated with fluorochrome conjugated secondary antibody diluted according to the manufactures instructions for 1-2 hours at room temperature. Cells were then washed three times with PBS for 5 minutes each and visualized by fluorescence microscopy.

Immunocytochemistry and Histology

Paraffin slides of pancreatic tissue from diabetic patients were purchased from BioChain (Newark, Calif.). Immunostaining was performed as previously described in Zhao Y, et al., Identification of stem cells from human umbilical cord blood with embryonic and hematopoietic characteristics. Exp Cell Res 2006, 312: 2454-2464. To block non-specific staining, sections were incubated in a buffer containing 2.5% horse serum (Vector Laboratories) for 20 min at room temperature. Primary antibodies included guinea pig polyclonal anti-insulin Ab (DakoCytomation, Carpinteria, Calif.), platelet marker FITC-conjugated CD42a (Beckman Coulter), platelet α granule marker von Willebrand factor (vWf) Ab (Sigma), and platelet dense granule marker ADP Ab (GenScript, Piscataway, N.J.), Secondary Ab included Cy3– conjugated AffiniPure donkey anti-guinea pig IgG (Jackson ImmunoResearch Laboratories, West Grove, Pa.). For isotype-matched controls, mouse $IgG_{1\kappa}$ was purchased from BD Biosciences, guinea pig serum from Santa Cruz Biotechnology. For every experiment, isotype-matched antibodies were used as negative controls. Cells were photographed with a ZEISS Imager M1 equipped with AxioCam MRc camera and AxioCam MR Rev 3 software or photographed by Nikon A1R confocal microscope.

To compare the size of pancreatic islets after treatment with mitochondria in transwells, islets were photographed with a Nikon Diaphot equipped with a EC500 digital camera. The size of pancreatic islets was measured and calculated by point-counting morphometric analysis (Meier J J, et al., Direct evidence of attempted beta cell regeneration in an 89-year-old patient with recent-onset type 1 diabetes. *Diabetologia* 2006, 49: 1838-1844) using Image J software, download from the NIH website (http://rsbweb.nih.gov/ij/).

Electron Microscopy

Cell suspensions were pelleted and then fixed by resuspending the cells in an excess volume of 2.5% glutaraldehyde in phosphate buffer at pH 7.0, and incubating for ten minutes at room temperature. Cells were then pelleted and fresh fixative added. Cells were incubated in fresh fixative at 4° C. for 2-3 hours, followed by washing in phosphate buffer adjusted to the osmolarity of the sample to prevent cell damage. After fixation and washes, a 4% low melting agarose was added to the cells and immediately centrifuged to pellet the cells. The cell pellet was then transferred to ice for 20 minutes to solidify the agarose, followed by gentle washing in buffer. Cells were then treated with 1% osmium tetroxide in phosphate buffer for 1-2 hours at 4° C., and then washed a least 5 times in distilled water. Cells were then stained with 2% aqueous uranyl acetate for 2 hours at 4° C. in the dark. Cells were then dehydrated through the following series of acetone washes: 30% acetone for 15 minutes; 50% acetone for 15 minutes; 70% acetone for 15 minutes; 90 acetone for 15 minutes; 100% acetone for 30 minutes three times. Cells were then embedded with resin through the following series of propylene oxide and resin mixtures: 2:1 propylene oxide:resin for 1 hour; 1:1 propylene oxide:resin for 1 hour; 1:2 propylene oxide:resin for 1 hour; 100% resin overnight; fresh 100% resin for 1 hour. Resin was then allowed to polymerize for 12-24 hours at 60°-70° C. The cell pellet was then cut into slices and imaged by electron microscopy.

Western Blotting

A Standard Western blotting protocol was employed. Briefly, cells were lysed with cold lysis buffer and centrifuged to pellet cellular debris. Protein concentration of the supernatant was determined by a protein quantification assay (e.g., Bradford Protein Assay, Bio-Rad Laboratories). The lysate supernatant was then combined with an equal volume of 2×SDS sample buffer and boiled at 100° C. for 5 minutes. Equal amounts of protein in sample buffer were loaded into the wells of an SDS-PAGE gel along with a molecular weight marker, and electrophoresed for 1-2 hours at 100 V. Proteins were then transferred to a nitrocellulose or PVDF membrane. The membrane was then blocked for 1 hour at room temperature using blocking buffer. The membrane was then incubated with appropriate dilutions of primary antibody in blocking buffer according to the manufacturer's instructions, followed by three washes in 20 Mn Tris, Ph 7.5; 150 mM NaCl, 0.1% Tween 20 (TBST) for 5 minutes. The membrane was then incubated with conjugated secondary antibody at manufacturer recommended dilutions in blocking buffer for 1 hour at room temperature, followed by three washes in TBST for 5 minutes each. Images of the blot were obtained using dark room development techniques for chemiluminesence detection, or using image scanning techniques for colorimetric or fluorescent detection.

Fractions containing platelet-like cells were collected from human cord blood units (Cord:Use Cord Blood Bank, Orlando, Fla.) and adult peripheral blood samples (New York Blood Bank, New York). Platelet-like cells were solubilized with Cell Extraction buffer (Invitrogen), with a cocktail of protease inhibitors (Sigma). Samples (20 µg protein each) were mixed with a Laemmli sample buffer (Bio-Rad) in a volume ratio of 1:1, boiled, loaded, and separated by electrophoresis on 10% Tris-HCl Criterion Precast Gel (Bio-Rad). The separated proteins were then transferred to a nitrocellulose membrane, blocked with 5% non-fat dry milk in TBST for 1 hr and incubated with different antibodies: including rabbit anti-AIRE polyclonal Ab, anti-CRIPTO pAb, and anti-GATA4 pAb (Abcam), rat anti-human OCT4 Ab, rat anti-human SOX2 Ab, mouse anti-human NANOG Ab, mouse anti-human C-myc Ab (eBiosciences), and rabbit anti-MAFA pAb (Novus Biologicals) at 1:1,000 dilution in 5% milk-TBS for 2 hr at room temperature. After washing, the blot was exposed to a horseradish peroxidase-conjugated secondary antibody (1:2,000; Pierce) in 5% milk-TBS. Bound immunocomplexes were visualized by the enhanced chemiluminescence (ECL, GE healthcare) method. The β-actin served as an internal loading control.

Real Time PCR

Real-time PCR was performed as described previously to analyze expression level of mRNAs (Zhao Y. et al., Biochemical and Biophysical Research Communications 360 (2007) 205-211). Briefly, total RNA was extracted from cells using the Quiagen kit (Valencia Calif.), followed by first strand cDNA synthesis using random hexamer primers (Fermentas, Hanover Md.). Real-time PCR was performed on each sample using the Mx3000p Quantitative PCR system (Stratagene, La Jolla, Calif.), for 40 cycles using validated gene specific RT-PCR primer sets for each gene of interest. Relative expression level of each transcript was corrected for that of the house keeping gene beta-actin as an internal control.

Expression of different mRNAs in platelet-like cells was analyzed by quantitative real-time PCR. Total RNA from each sample was extracted using a Qiagen kit (Valencia, Calif.). First-strand cDNAs were synthesized from total RNA using iScript gDNA Clear cDNA Synthesis Kit (Bio-Rad, Hercules, Calif.). Real-time PCR was performed on each sample in triplicate using the StepOnePlus Real-Time PCR System (Applied Biosystems, CA), under the following conditions: 95° C. for 10 min, then 40 cycles of 95° C. for 15 s, and 60° C. for 60 s, using the validated gene-specific RT2 PCR Primer sets for each gene including ES cell related markers (e.g., OCT4, NANOG, SOX2, KLF4, and C-myc) and pancreatic islet cell related markers (e.g., insulin, glucagon, somatostatin, PPY, Ghrelin, GCK, Sur1, Kir6.2, MAFA, NKX6.1, PDX-1, NEUROD1, and NGN3) (Qiagen Valencia, Calif.). Expression level of each gene, relative to β-actin as an internal control, was determined. To confirm gene expression, the real time PCR products were examined by 1.5% agarose gel electrophoresis.

For $RT^2$ Profiler real time PCR Arrays, human Stem Cell kit (Qiagen, Cat. No. PAHS-405Z, product 330231) (Gene list: Stem Cell Specific Markers: Regulation of the Cell Cycle: APC, AXIN1, CCNA2, CCND1, CCND2, CCNE1, CDK1 (CDC2), CDC42, EP300, FGF1, FGF2 (BFGF), FGF3, FGF4, MYC, NOTCH2, PARD6A, RB1; Chromatin Modification Enzymes & Remodeling Factors: KAT2A (GCN5L2), HDAC2, KAT8 (MYST1), KAT7 (MYST2), RB1, TERT; Symmetric & Asymmetric Cell Division: DHH, NOTCH1, NOTCH2, NUMB, PARD6A; Self-Renewal Markers: HSPA9, KAT8 (MYST1), KAT7 (MYST2), NEUROG2, SOX1, SOX2; Cytokines & Growth Factors: BMP1, BMP2, BMP3, CXCL12 (SDF1), FGF1, FGF2 (BFGF), FGF3, FGF4, GDF2 (BMP9), GDF3 (VGR-2), IGF1, JAG1; Cell-Cell Communication: DHH, DLL1 (DELTA1), GJA1 (CX43), GJB1 (CX32), GJB2 (CX26), JAG1; Cell Adhesion Molecules: APC, BGLAP, CD4, CD44, CDH1 (E-Cadherin), CDH2 (N-Cadherin), COL9A1, CTNNA1, CXCL12 (SDF1), NCAM1; Metabolic Markers: ABCG2 (BCRP), ALDH1A1 (RALDH1), ALDH2, FGFR1. Stem Cell Differentiation Markers: Embryonic Cell Lineage Markers: ACTC1, ASCL2, FOXA2 (HNF3B), PDX1 (IPF1), ISL1, KRT15, MSX1, MYOD1, T (Brachyury); Hematopoietic Cell Lineage Markers: CD3D, CD4, CD8A, CD8B, MME; Mesenchymal Cell Lineage Markers: ACAN (AGC1), ALPI, BGLAP, COL1A1, COL2A1, COL9A1, PPARG; Neural Cell Lineage Markers: CD44, NCAM1, SIGMAR1, S100B, TUBB3; Signaling Pathways Important for Stem Cell Maintenance: Notch Signaling: DLL1 (DELTA1), DLL3, DTX1, DTX2, DVL1, EP300, KAT2A (GCN5L2), HDAC2, JAG1, NOTCH1, NOTCH2, NUMB; WNT Signaling: ADAR, APC, AXIN1, BTRC (bTrCP), CCND1, FRAT1, FZD1, MYC, PPARD, WNT1). and human stem cell transcription factors kit (Qiagen, Cat. No. PAHS-501Z, Product No. 330231)(96-well format) (Gene List: Somatic Stem Cell Maintenance: CDX2, NANOG, POU5F1 (Oct4), SOX2; Placental Development: CDX2; Placental Development: HAND1, PPARG, SP1, VDR; Induced Pluripotent & Embryonic Stem Cells: NANOG, POU5F1 (Oct4), SOX2, STAT3; Axis/Symmetry/Segmentation: CDX2, DLX1, DLX2, FOXA2 (HNF3B), HOXA11, HOXA2, HOXA3, HOXA7, HOXA9, HOXA10, HOXB1, HOXB3, HOXB5, HOXB8, HOXC10, HOXC4, HOXC5, HOXC6, HOXC9, HOXD10, HOXD4, LMX1B, NEUROD1, NOTCH2, NR2F2, PAX1, PITX2, SMAD2 (MADH2), TBX5, TDGF1, ZIC1; Embryonic Development: CDX2, DLX1, DLX2, FOXA2 (HNF3B), GATA6, GLI2, HAND1, HOXA11, HOXA2, HOXA3, HOXA7, HOXA9, HOXA10, HOXB1, HOXB3, HOXB5, HOXB8, HOXC10, HOXC4, HOXC5, HOXC6, HOXC9, HOXD1, HOXD10, HOXD4, KLF4, LMX1B, MSX2, NANOG, NEUROD1, NOTCH2, PAX1, SIX2, SMAD2 (MADH2), SOX2, SP1, TBX5, TDGF1, ZFPM2, ZIC1; Ectoderm, Endoderm & Mesoderm Formation & Differentiation: FOXA2 (HNF3B), GATA6, HAND1, HOXA7, HOXB13, ISL1, KLF4, SMAD2 (MADH2), SOX9; Organ Morphogenesis: CDX2, DLX1, DLX2, GLI2, HAND1, HOXA11, HOXA2, HOXA3, HOXA7, HOXB1, HOXB13, HOXB3, HOXB5, HOXB8, HOXC4, HOXC9, HOXD10, HOXD4, ISL1, JUN, KLF4, MSX2, MYC, NEUROD1, NOTCH2, NR2F2, PAX1, PAX5, PAX6, PITX2, PITX3, PPARG, RUNX1 (AML1), SIX2, SMAD2 (MADH2), SOX2, SOX9, SP1, STAT3, TBX5, TDGF1, VDR, WT1, ZFPM2, ZIC1; Angiogenesis: CDX2, HAND1, JUN, NR2F2, RUNX1 (AML1), WT1; Neurogenesis: DLX1, DLX2, DNMT3B, FOXA1, FOXA2 (HNF3B), FOXP3, GLI2, HOXA2, HOXC10, HOXD10, ISL1, LMX1B, NEUROD1, NKX2-2, NR2F2, OLIG2, PAX6, PITX3, POU4F1, POU4F2, PPARG, SOX2, STAT3, TLX3; Hematopoiesis: RB1, RUNX1 (AML1), SOX6, SP1, STAT1; Osteogenesis: GLI2, HOXA2, SOX2, SP1; Other Stem Cell Transcription Factors: DACH1, EGR3, ESR1 (ERα), EZH2, FOXP1, FOXP2, GATA1, HOXC12, HTR7, IRX4, KLF2, LIN28B, NFATC1, PAX9, PCNA, TERT, WRN). were used according to the manufacturer's instructions. The data were analyzed using the web-based PCR array data analysis software provided by the manufacturer.

f-Macrophage Culture and Differentiation f-Mφ culture was performed as previously described in Zhao Y, et al., A human peripheral blood monocyte-derived subset acts as pluripotent stem cells. Proc Natl Acad Sci USA 2003, 100: 2426-2431. Briefly, purified monocytes were seeded into the 8-Well Lab-Tek II Chamber Slide (Fisher Scientific) at $1 \times 10^5$ cells/ml, 0.5 ml/well in a serum-free X-VIVO15 medium (Lonza) with 50 ng/ml M-CSF. To explore the interaction between platelets and monocytes/macrophages, purified monocytes were pretreated with 0.25% trypsin/EDTA, and then treated with serum-free X-VIVO15 medium in the presence of 50 ng/ml M-CSF. To determine phagocytosis of platelets-like cells by monocytes/macrophages, purified monocytes/macrophages were planted onto the 27 mm Nunc Glass Base Dish (Thermo Scientific, Rochester, N.Y.), and followed by immunostaining with platelet marker CD42a and ES cell-related marker OCT4. The samples were viewed and photographed by Nikon A1R confocal microscope. To further determine the interaction between platelets and monocytes/macrophages by transmission electron microscope (TEM), purified platelets and monocytes (without treatment with trypsin/EDTA) were fixed with TEM buffer (2% formaldehyde and 2.5% glutaraldehyde in 0.1 M Sodium Cacodylate buffer, pH 7.4). Cell samples were provided for embedding and sectioning. The samples were viewed with JEOL 1200EX transmission electron microscope with AMT-XR41 digital camera.

"Education" of Lymphocytes Obtained from Whole Blood by Co-Culture of the Lymphocytes in the Presence of Adherent Cord Blood-Stem Cells ("Stem Cell Educator Therapy")

Zhao et al developed a procedure in which a patient's blood is circulated through a continuous closed loop system termed a bioreactor device that separates lymphocytes from the whole blood, briefly co-cultures the lymphocytes in the presence of adherent CB-SCs, and then returns the "educated" lymphocytes to the patient's circulation [Zhao Y. et al., "Reversal of type 1 diabetes via islet beta cell regeneration following immune modulation by cord blood-derived multipotent stem cells", BMC Med, Vol. 10:3, (2012]. In an open-label phase 1/2 study, twelve (12) patients of Asian descent with T1D received a single treatment with the bioreactor device, and three patients of Asian descent received a single treatment with the bioreactor device without adherent CB-SCs (i.e., process only control). A 16-gauge IV needle was placed in the left (or right) median cubital vein, and the patient' blood was passed through a Blood Cell Separator MCS+ (Haemonetics®, Braintree, Mass.) at 35 mL/min for 6 to 7 hours to isolate lymphocytes in accordance with the manufacturer's recommended protocol. The collected lymphocytes were transferred into the device for exposure to allogeneic CB-SCs (or process control without CB-SCs), and other blood components were returned to the patient. After 2 to 3 hours in the device, lymphocytes were returned to the patient's circulation via a dorsal vein in the hand under gravity flow control (2 to 3 mL/min) with physiological saline. Approximately 10,000 mL of blood was processed during the procedure resulting in approximately two repeated educations for the lymphocyte fraction. Patients were hospitalized for two days to monitor temperature and to conduct routine laboratory blood tests for adverse reactions following treatments one such treatment.

Patients were selected if they met the diagnosis standards of the American Diabetes Association and a blood test confirmed the presence of at least one autoantibody to pancreatic islet 1-cells for T1 D subjects. Exclusion criteria included clinically significant liver, kidney, or heart disease; pregnancy; immunosuppressive medication; viral diseases; or diseases associated with immunodeficiency. The primary study end points on feasibility and safety of the Stem Cell Educator (SCE) therapy have been published elsewhere (Zhao Y, et al.: Reversal of type 1 diabetes via islet beta cell regeneration following immune modulation by cord blood-derived multipotent stem cells. BMC Med 2012, 10: 3; Zhao Y, et al.: Targeting insulin resistance in type 2 diabetes via immune modulation of cord blood-derived multipotent stem cells (CB-SCs) in stem cell educator therapy: phase I/II clinical trial. BMC Med 2013, 11: 160; Delgado E, et al.: Modulation of Autoimmune T-Cell Memory by Stem Cell Educator Therapy: Phase 1/2 Clinical Trial. EBioMedicine 2015, 2: 2024-2036). Current study end points were preliminary evidence of the effect of SCE therapy on platelets in T1D and T2D subjects. Baseline blood samples were collected prior to SCE therapy.

Stem cell educator therapy and treatment of human patients was performed as described previously in Zhao et al., BMC Medicine 2013, 11:160. Briefly, a needle was placed in a patient's vein, and the patient's blood was passed through a blood cell separator MCS®+(Haemonetics, Braintree, Mass., USA) for six to seven hours to isolate mononuclear cells. The collected mononuclear cells were transferred to a stem cell educator device for exposure to an educator cell type, such as human cord blood derived stem cells (CB-SC). The educated mononuclear cells were then returned to the patient's circulation in physiological saline via the patient's vein.

CB-SCs were obtained and cultured in serum-free culture media at 37° C. in 8% $CO_2$ in a stem cell educator apparatus. According to some embodiments, the stem cell educator apparatus comprises a closed system of stacked tissue culture plates, wherein the chambers formed by the stacked plates are continuous through each adjacent chamber. Peripheral blood mononuclear cells separated from the patient's blood are introduced into one end of the stem cell educator apparatus, passed through the stacked plates covered in strongly adherent CB-SCs, and collected at the other end of the educator apparatus. Educated peripheral blood mononuclear cells were then re-introduced into the vein of a patient.

Example 1. Modulation of Platelets by Stem Cell Educator Therapy

Modulation of platelets was analyzed in nineteen Type 1 Diabetes (T1 D) and twenty Type 2 Diabetes (T2D) patients in comparison with the subjects that received sham therapy (n=3). Age- and gender-matched T1 D (n=8) and T2D (n=10) subjects that received conventional therapies served as additional controls respectively. Clinical results demonstrated that platelet counts were markedly increased in T2D subjects after receiving Stem Cell Educator therapy (P=0.027), however 5/8 of subjects were improved in T1D treatments (FIG. 1A). The values of platelet distribution width (PDW) were significantly increased in both T1D and T2D subjects after the treatment with Stem Cell Educator therapy (FIG. 1B); while their mean platelet volume (MPV) was decreased in both T1D and T2D subjects (FIG. 1C). There were no marked changes for the plateletcrit (PCT) in both T1D and T2D subjects after treatment. Clinical data from Caucasian T1 D subjects (N=8) also showed the increase in the platelet count after receiving the SCE therapy (P=0.04, FIG. 1D). The data suggest that modulation of platelets may contribute to the clinical efficacy of Stem Cell Educator therapy in the autoimmune and metabolic control of diabetic patients (Zhao Y, et al., Reversal of type 1 diabetes via islet beta cell regeneration following immune modulation by cord blood-derived multipotent stem cells. BMC Med 2012, 10: 3; Zhao Y, et al., Targeting insulin resistance in type 2 diabetes via immune modulation of cord blood-derived multipotent stem cells (CB-SCs) in stem cell educator therapy: phase I/II clinical trial. BMC Med 2013, 11: 160.)

Example 2. Expression of Immune Tolerance-Related Markers in Platelet-Like Cells To explore whether cellular components of cord blood are capable of modulating the immune response, expression of immune tolerance-related markers in platelet-like cells was investigated.

A platelet-rich fraction from human cord blood comprising platelet like cells (FIG. 2 A-D) or adult peripheral blood (FIG. 2 E-I) was prepared as described above. Platelet-like cells then were examined for various immune-relevant markers.

Flow cytometry showed that both cord blood derived (FIG. 2A) and adult blood derived (FIG. 2E) platelet-like cells display co-inhibitory immunomodulation surface molecules. As shown in FIG. 2A, flow cytometry shows that platelet-like cells express CD270/CD41 and CD270/CD61. As shown in FIG. 2B, intra-cellular staining of permeabilized cord blood platelet-like cells showed the expression of TGF-β1/CD41, TGF-β1/CD42, Foxp3/CD41, and Foxp3/CD42.

Figure 2:
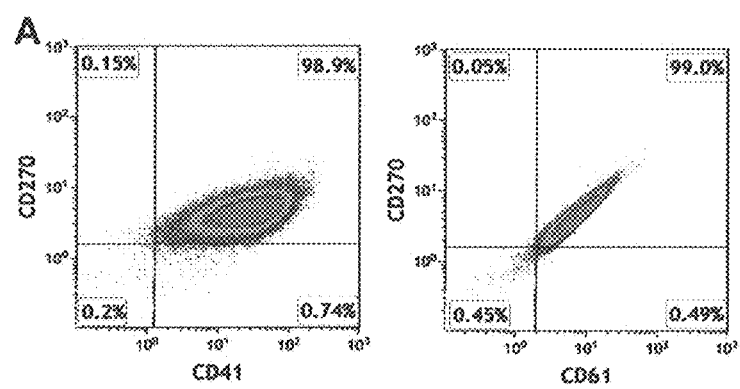
FIG. 2A to FIG. 2I are flow cytometry data showing expression of immune modulation-related markers in platelet like cells. Platelet-like cells were purified from human cord blood (FIG. 2A-FIG. 2D) and from adult peripheral blood units (E-I).
(FIG. 2J) expression (from left to right) of chemokine receptors CCR3, CCR4, and CCR5 (bottom) and ligands CCL2, CXCL1 and CXCL10 (top) at varied levels on adult blood platelet like cells.
(FIG. 2K) expression (from left to right) of chemokine receptors (top) CCR7, CXCR1, CXCR2, (bottom) CXCR3, and CXCR4) and CD62L ligand (bottom right) on adult blood platelet cells.
FIG. 2L to FIG. 2Q depict experimental evidence that platelet-derived mitochondria display immune modulatory properties.
Figure 2:
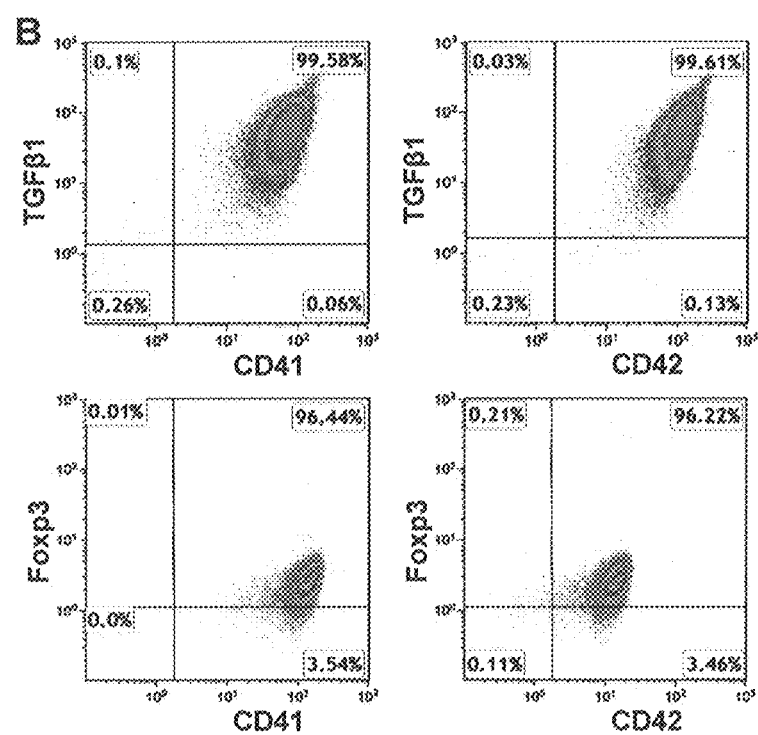
Figure 2:
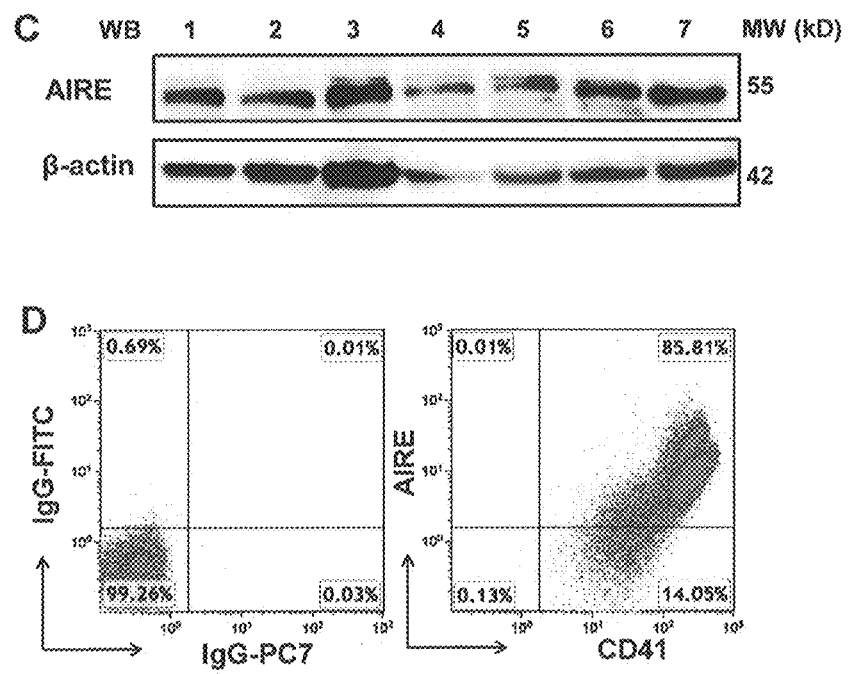
Figure 2:
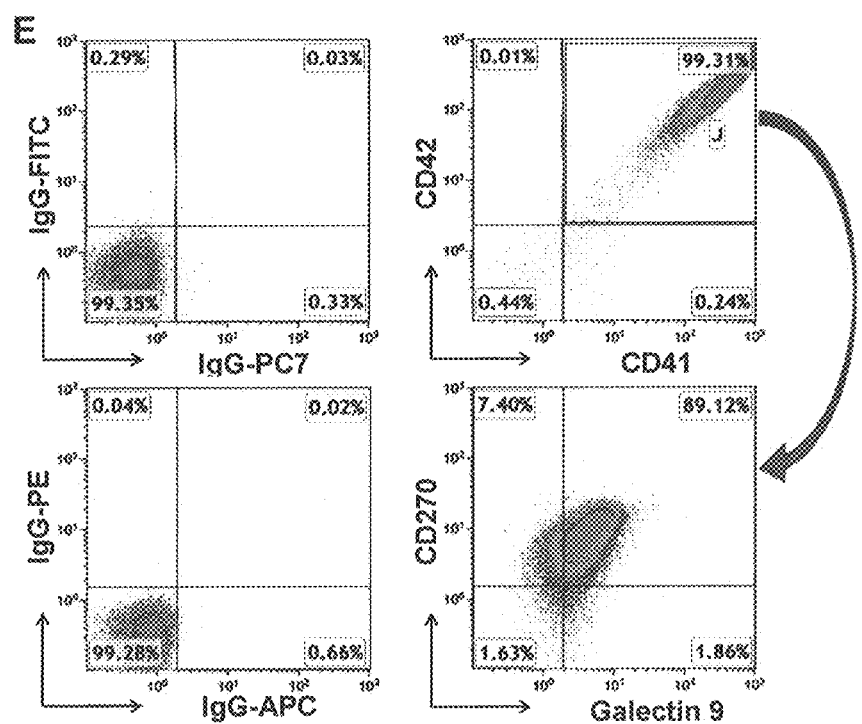
Figure 2:
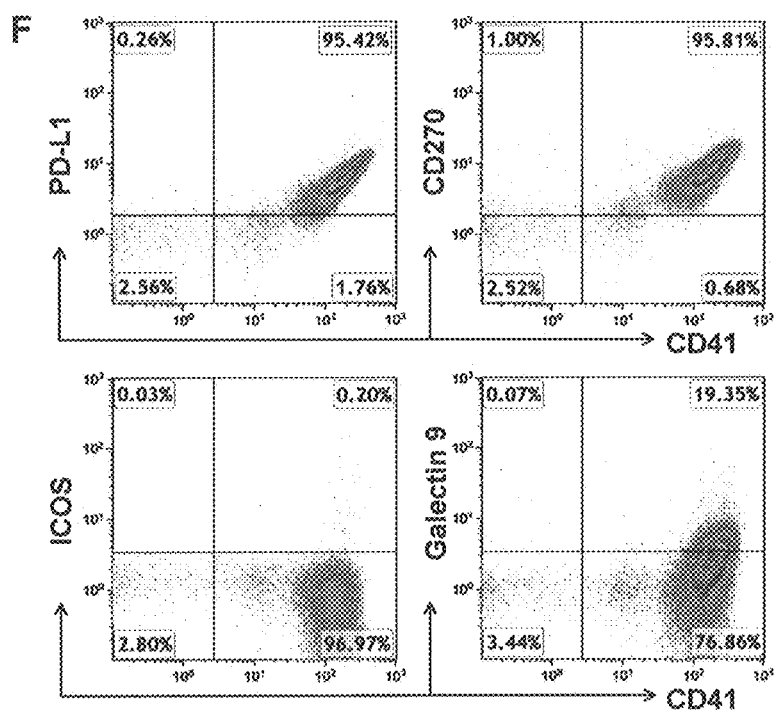
Figure 2:
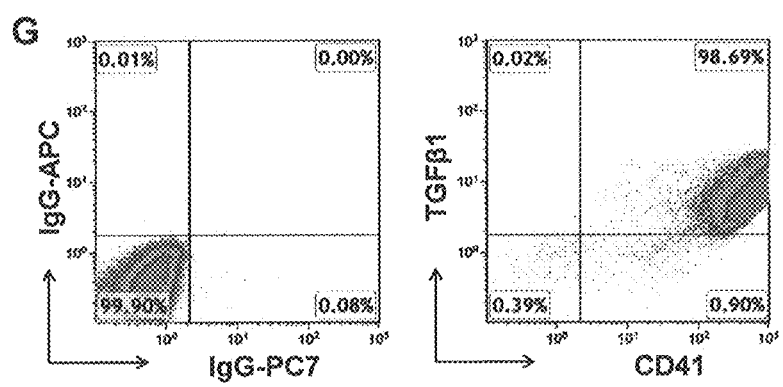
Figure 2:
Figure 2:
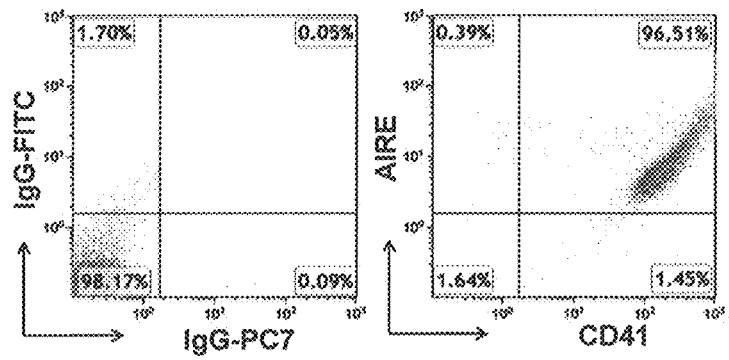
Figure 2:
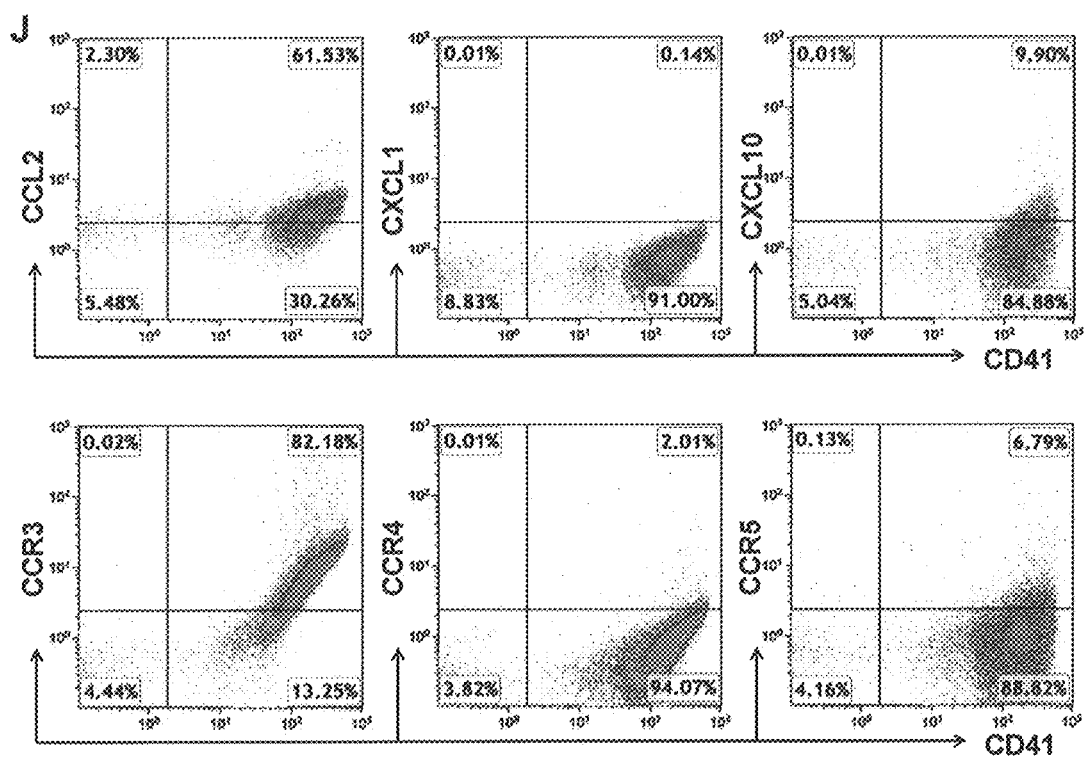

Human cord blood derived platelet-like cells express the autoimmune regulator, AIRE (FIGS. 2 C and D). As shown in FIG. 2C, Western blot analysis revealed that each of seven different samples of cord blood platelet-like cells comprised the AIRE protein. Numbers to the right of each blot in FIG. 2C represent the average quantified amount of protein in arbitrary relative intensity units. As shown in FIG. 2D, over 85% of cord blood platelet-like cells positive for platelet marker CD41 were also positive for AIRE protein (right panel). Isotypematched IgGs, IgG-FITC/IgG-PC7, served as negative controls (left panel).

As shown in FIG. 2E, over 99% of adult peripheral blood platelet-like cells express both CD42 and CD41 (upper right panel), and of those cells over 89% also express the co-inhibitory molecules CD270 and Galectin 9 (lower right panel). Isotype-matched IgGs served as controls (left panels). Furthermore, as shown in FIG. 2F, greater than 95% of adult peripheral blood platelet-like cells express both CD41 with PD-L1 or CD270 (upper panels). In contrast, less than 0.2% of CD41 expressing platelet-like cells also express ICOS (lower left panel), and about 20% of CD41 expressing platelet-like cells also express Galectin 9 (lower right panel). IgG-FITC/IgG-PC7 (upper left panel) and IgG-PE/IgG-APC (lower left panel) served as negative controls.

Thus, flow cytometry showed high expression of PD-L1 and CD270, low expression of Galectin 9, and no expression of ICOS on adult blood-derived platelet-like cells. Representative data were from eight individual preparations.

Galectin 9 is a tandem-repeat type galectin with two carbohydrate-recognition domains, which was first identified as an eosinophil chemoattractant and activation factor; it modulates a variety of biological functions, including cell aggregation and adhesion, as well as apoptosis of tumor cells. (Fujihara, S. et al, "Galectin-9 in cancer therapy," Recent Pat. Endocr. Metab. Immune Drug Discov. (2013); 7(2): 130-7). Galectin 9 has an immunomodulatory role towards lymphocytes, where it shows specific interactions with TIM-3, and can negatively regulate Th1 immunity. (Zhu, C. et al, "The Tim-3 ligand galectin-9 negatively regulates T helper type 1 immunity," Nat. Immunol. 2005; 6(1220: 1245-62).

As shown in FIG. 2G, intra-cellular staining and flow cytometry also revealed that over 98% of human adult peripheral blood platelet-like cells co-expressed CD41 with TGFβ1 (right panel). IgG-APC/IgG-PC7 served as negative controls (left panel).

Human adult peripheral blood platelets were also shown to express the autoimmune regulator AIRE (FIGS. 2 H and I). As shown in FIG. 2H, western blot analysis revealed that each of 9 different samples of human adult peripheral blood platelets comprised the AIRE protein. Numbers on the right outside of each blot represent the average quantified amount of protein in arbitrary relative intensity units. Furthermore, as shown in FIG. 2I, over 96% of human adult peripheral blood platelets are positive for CD41 and AIRE protein (right panel). IgG-FITC/IgG-PC7 served as negative controls.

Additional flow cytometry data demonstrated that platelet-rich cell fractions comprising platelet-like cells derived from both cord blood and adult blood displayed the co-inhibitory surface molecules programmed death ligand 1 (PD-L1) (Data not shown). Programmed death ligand 1 (PD-L1) is expressed by many cancer cell types, as well as by activated T cells and antigen-presenting cells. (Coombs, M R. et al, "Apigenin inhibits the inducible expression of programmed death ligand 1 by human and mouse mammary carcinoma cells," Cancer Lett. 2016; 380(2): 424-33).

Figure 2K:
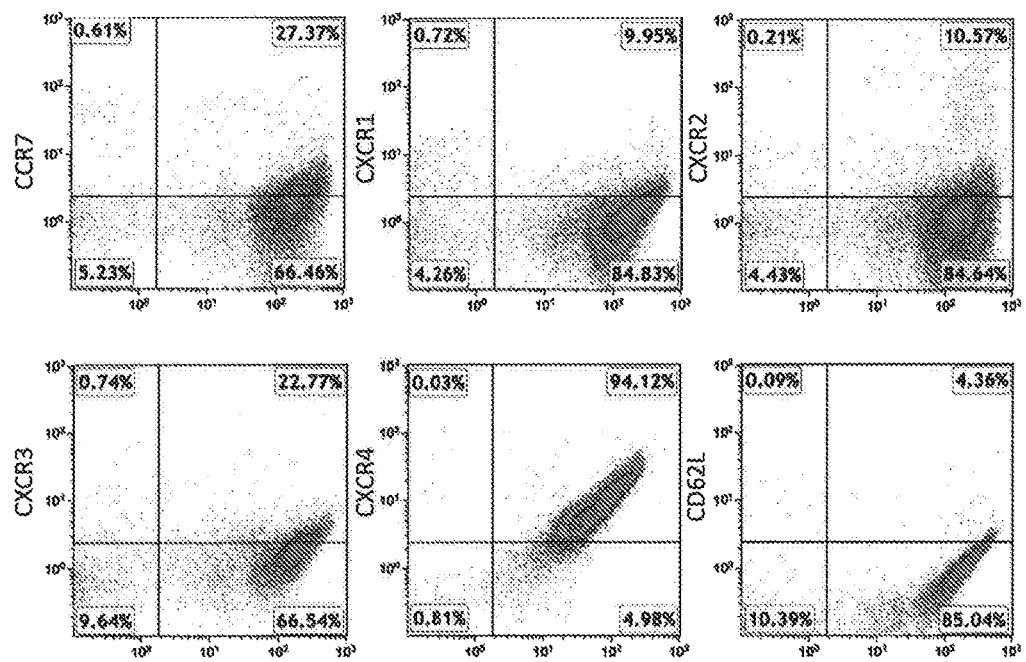

Human adult peripheral blood platelets were shown to express to varying degrees an array of chemokine receptors. As shown in FIG. 2J-K, flow cytometry data showed that a high percentage of human adult peripheral blood-derived platelets express high levels of CCR3 (over 82%) and CXCR4 (over 94%) (FIG. 2J, lower left; FIG. 2K lower middle). It was also shown that over 61% human adult platelets express high levels of CCL2 (FIG. 2J, upper left panel). The percentage of human adult platelets identified as expressing high levels of CXCL10 (9.9%), CCR4 (2.01%), CCR5 (6.79%), CCR7 (27.37%), CXCR1 (9.95%), CXCR2 (10.57%), CXCR3 (22.77%), and CD62L (4.36%) is indicated in parentheses. Virtually none of the adult platelets expressed high levels of CXCL1 (less than 1%). The x-axis for each of the flow cytometry charts in FIGS. 2 J and K. represents the marker CD41 Thus, flow cytometry show the expressions of chemokine receptors and ligands at varied levels on adult blood platelet-like cells.

Without being limited by theory, it is conceivable that adult mononuclear cells that contact the plasma rich fraction of cord blood comprising platelet-like cells can induce immune tolerance via transfer of, or induction of, immune regulatory molecules.

Flow cytometry showed that both cord blood (CB)- and adult peripheral blood PB)-platelet like cells displayed one or more of the co-inhibitory surface molecules such as the programmed death ligand 1 (PD-L1), CD270 (a herpes virus entry mediator, HVEM) and Galectin 9. As shown in FIG. 2F, expression of PD-L1 (95.42%) and CD270 (95.81%) was much higher than expression of ICOS (0.20%) on the adult blood-derived platelets (FIGS. 2 E and F).

The expression of Galectin 9 was positive in the platelet like cells of four individuals (4/8 donors, 54.07%+/−27.59) (Data not shown). Intra-cellular staining showed that platelet-like cells also express the cytokine transforming growth factor β1 (TGF-β1) (FIGS. 2 B and G). We also found that 96.22% of CD42+Foxp3+ platelets and 96.44% of CD41+ Foxp3+ platelets respectively display the immune modulation-associated transcription factor Foxp3 (FIG. 2B). Notably, Western Blotting and flow cytometry revealed the expression of autoimmune regulator (AIRE) in cord blood platelet like cells (FIGS. 2 C and D) and adult blood platelet like cells (FIGS. 2 H and I). Additional flow cytometry showed that platelets displayed high levels of chemokine receptors CCR3 and CXCR4, medium level of CCL2, low levels of CXCL10, CCR4, CCR5, CCR7, CXCR1, CXCR2, CXCR3, and CD62L, and negative for the expression of CXCL1 (FIG. 2 J-K). Without being limited by theory, these data lend support, on the basis of marker expression, to the conclusion that platelet-like cells may act as immune modulators and induce immune tolerance.

Platelet-Derived Mitochondria Display Immune Modulation

Figure 2L:
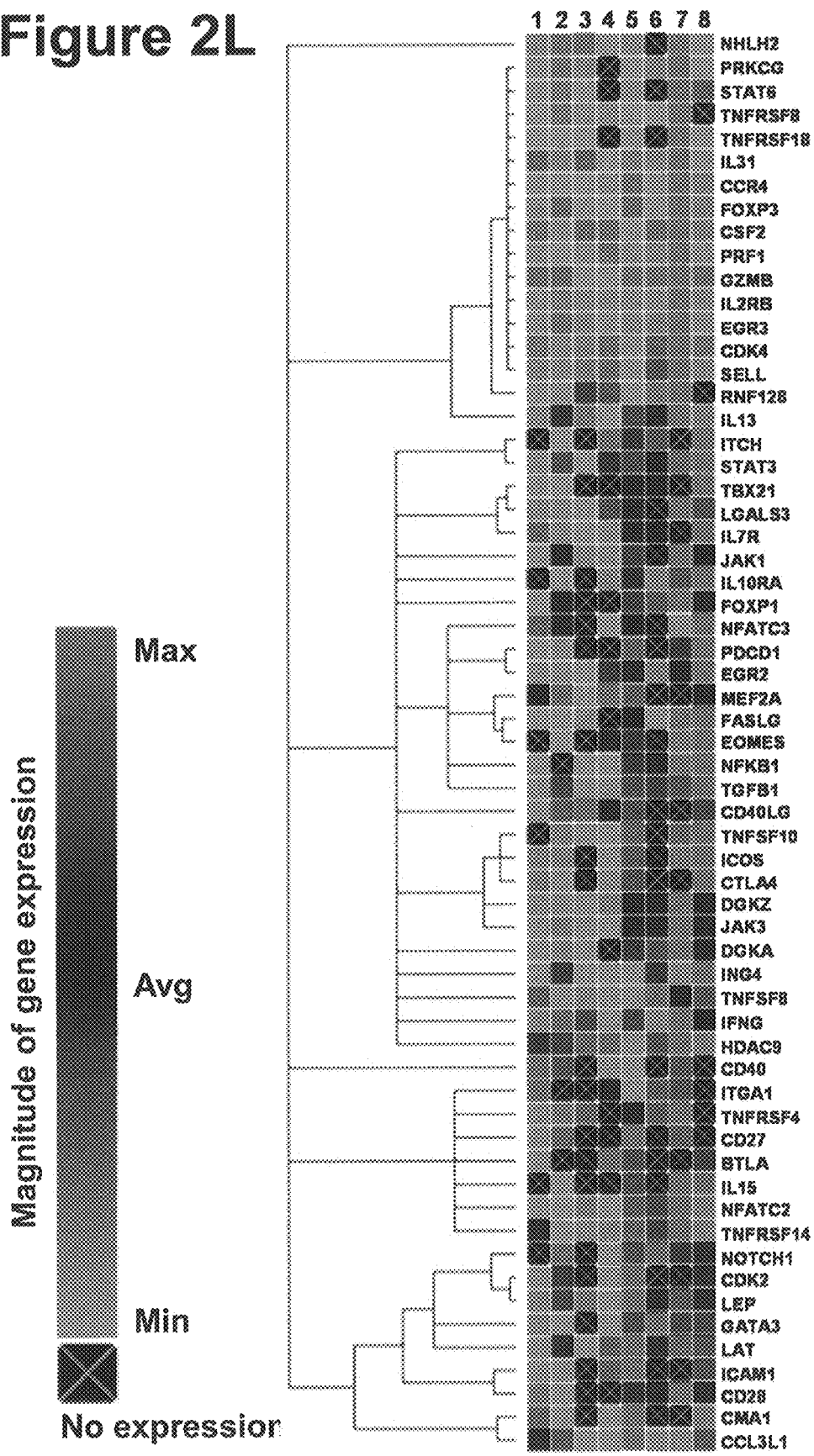
Figure 2:
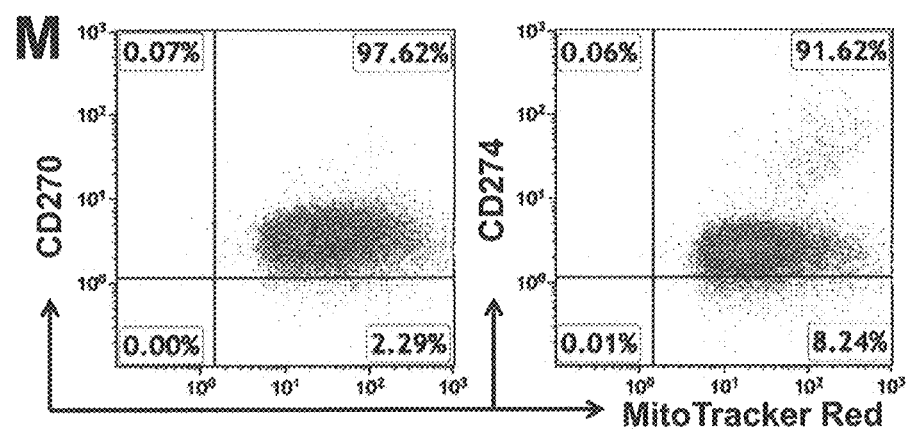
Figure 2:
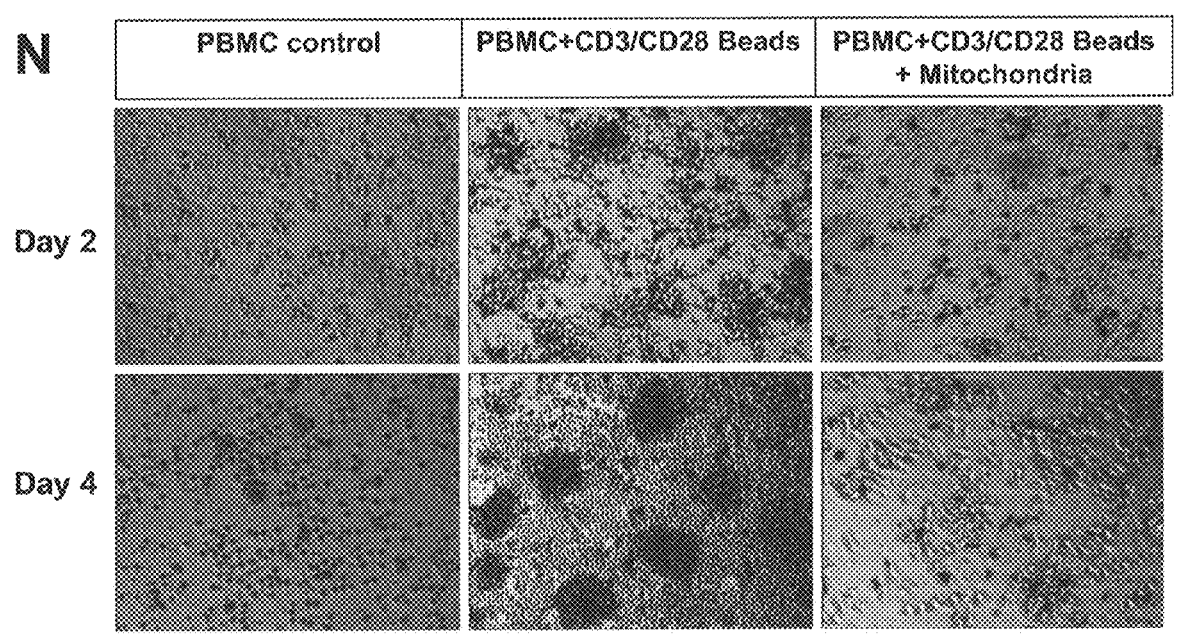
Figure 2:
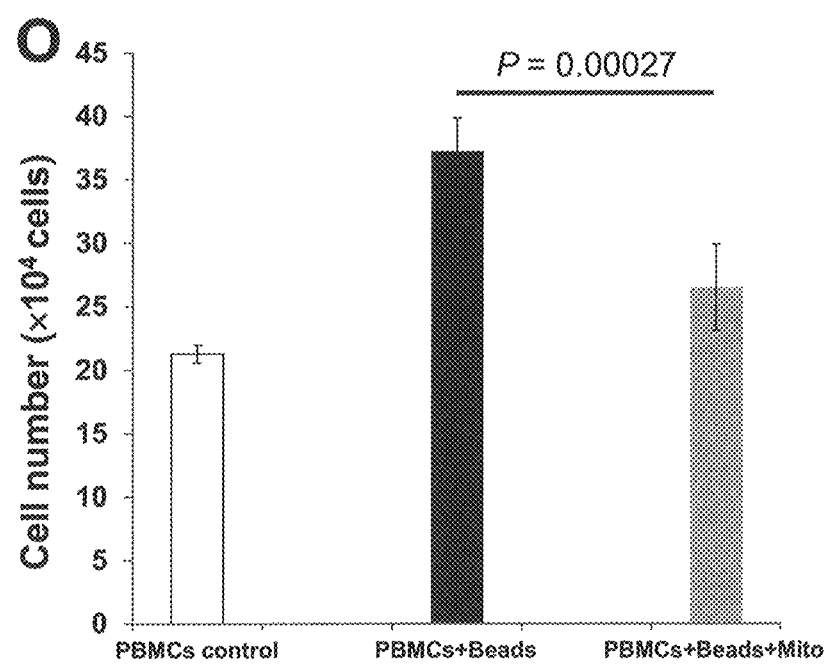
Figure 2:
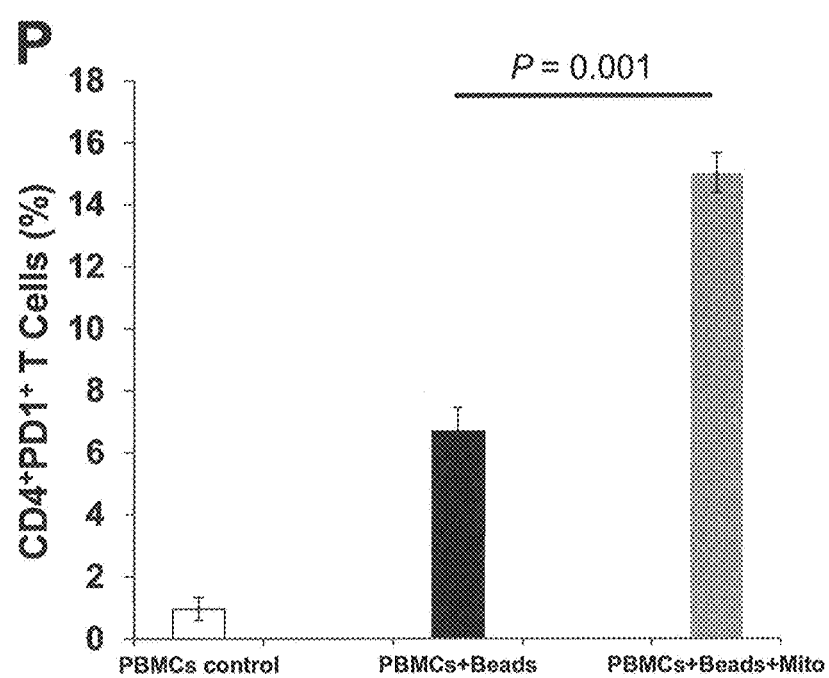
Figure 2:
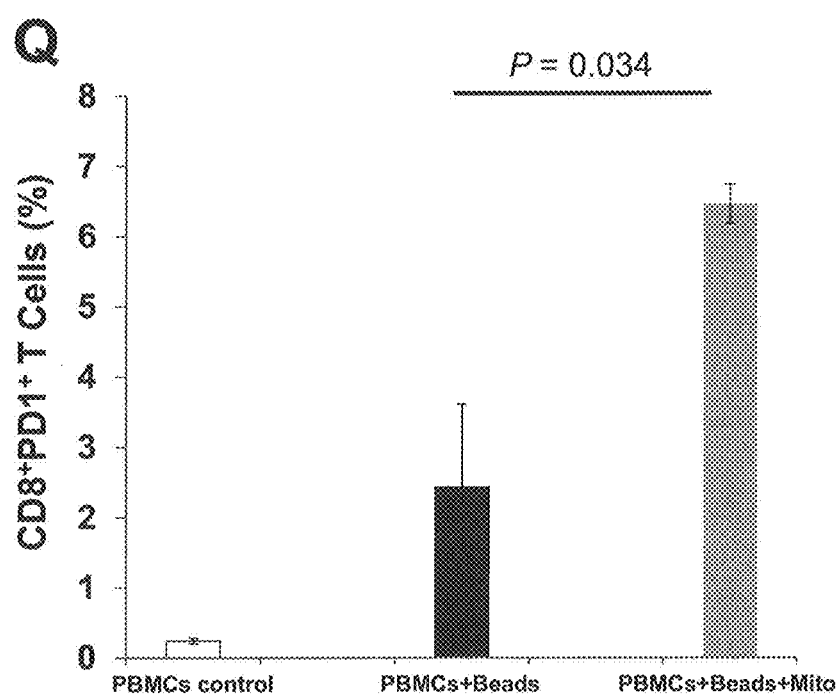

Mitochondria were purified from CB-platelets and PB-platelets for gene transcription of mitochondria DNA (MitoDNA) to identify the origin of immune marker-related genes, Mitochondria were isolated from PB-platelets using the Qproteome Mitochondria Isolation kit (Qiagen, Hidden, Germany) according to the manufacturer's recommended protocol. Real time PCR Array analysis revealed expression of T cell anergy and immune tolerance-related genes (FIG. 2L). Flow cytometry further showed that platelet releasing mitochondria displayed immune tolerance-related markers CD270 and CD274 (PD-L1) (FIG. 2M).

To determine immune modulation activity of mitochondria on T cells, peripheral blood-derived mononuclear cells (PBMCs) were treated with allogeneic PB-platelet-derived mitochondria in the presence of Dynabeads coupled with anti-CD3+anti-CD28 antibodies+recombinant human IL-2 (rIL-2). After ex-vivo expansion of T cells with this monoclonal antibody (mAb) combination for 4 days, large numbers of cell clusters were seen, with different sizes floating in the supernatant (FIG. 2N, bottom middle panel), suggestive of significant T cell proliferation. In the presence of mitochondria, this phenomenon was not evident (FIG. 2N, right panels. Instead, after the combination treatment with mitochondria, cell number was markedly declined. (FIG. 2O).

Next, expression of an immune checkpoint receptor PD-1 (programmed death receptor-1) on cells was examined on T cells. PD-1 is the ligand of PD-L1 (CD274). The percentage of CD4+PD1+ T cells was increased to 15%±0.64% following treatment with mitochondria (FIG. 2P) (P=0.001). Further flow cytometry indicated that the percentage of CD8+ PD1+ T cells also was improved, from 2.43%±1.18% to 6.46%±0.28% in the presence of mitochondria (FIG. 2Q) (P=0.034).

Without being limited by theory, these findings provide further evidence that the molecular content of platelets and their mitochondria is capable of acting as immune modulators and of inducing immune tolerance.

Example 3. Modulation of Monocyte Differentiation by Platelets

To characterize the interaction of platelet-like cells with other blood immune cells, cord blood mononuclear cells (CBMCs) were immunostained with different lineage-specific markers in combination with markers CD41 b and CD42a. CD41 b is a β chain of glycoprotein IIb (known as CD41) which is associated with glycoprotein IIIa (or integrin β3, CD6I) and forms the heterodimeric gpIIb/gpIIIa complex present on human megakaryocytes and platelets; CD42a GP-IX (CD42a), also called platelet glycoprotein GPIX, GP9, is a small membrane protein glycoprotein that forms a non-covalent complex with GP-Ib (CD42b). CD42a-d complex, the receptor for von Willebrand factor and thrombin, mediates adhesion of platelets to subendothelial matrices that are exposed in damaged endothelium and amplifies platelet response to thrombin.

Figure 3:
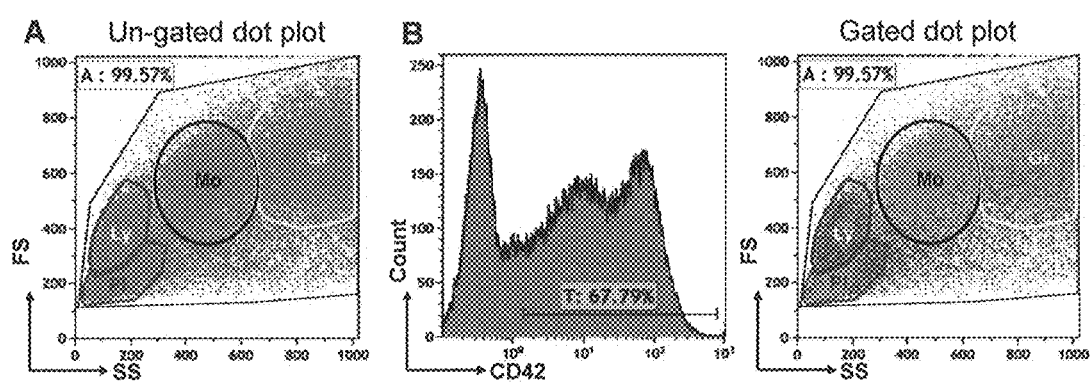
Figure 3:
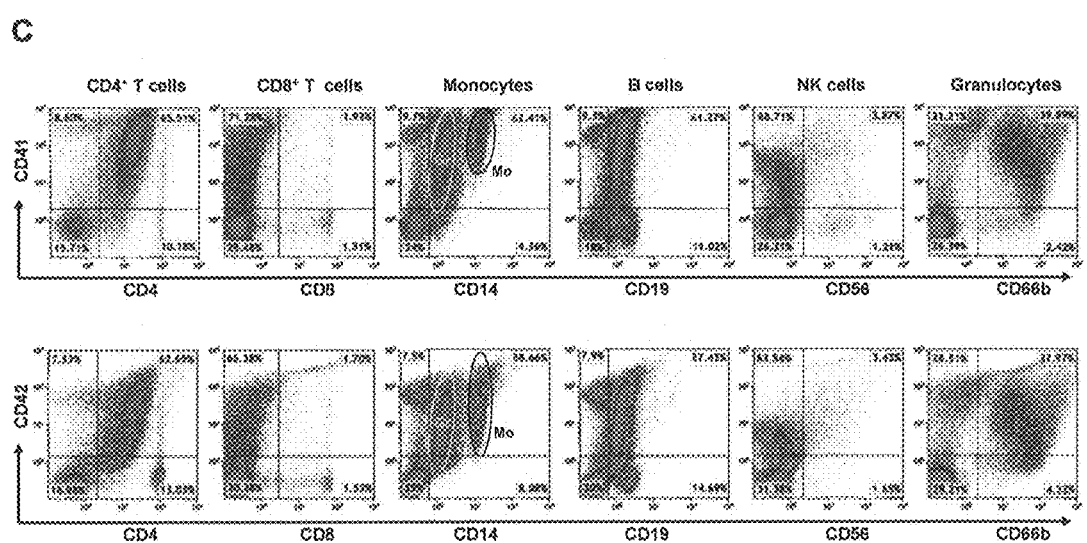
Figure 3:
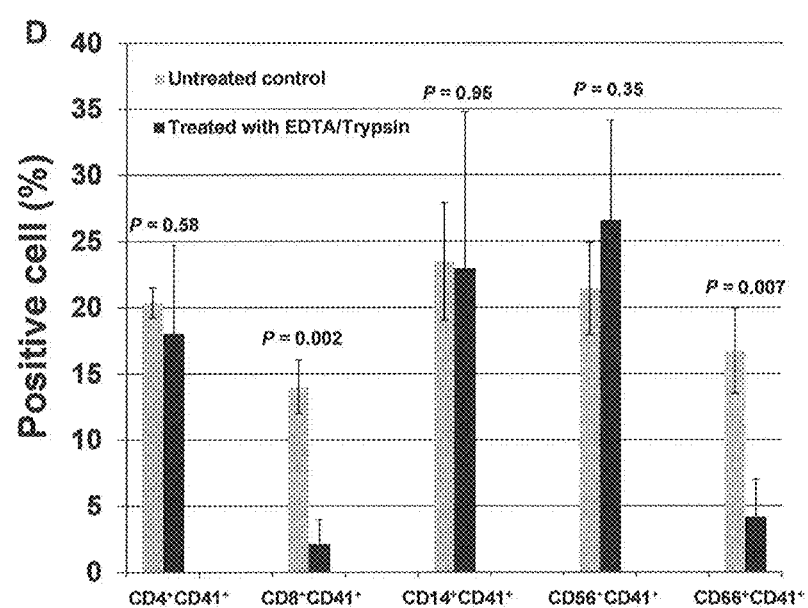
Figure 3:
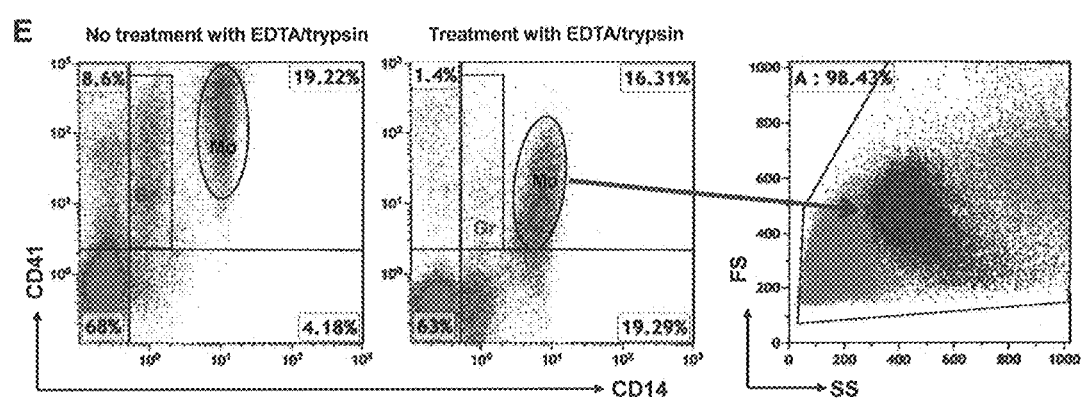
Figure 3:
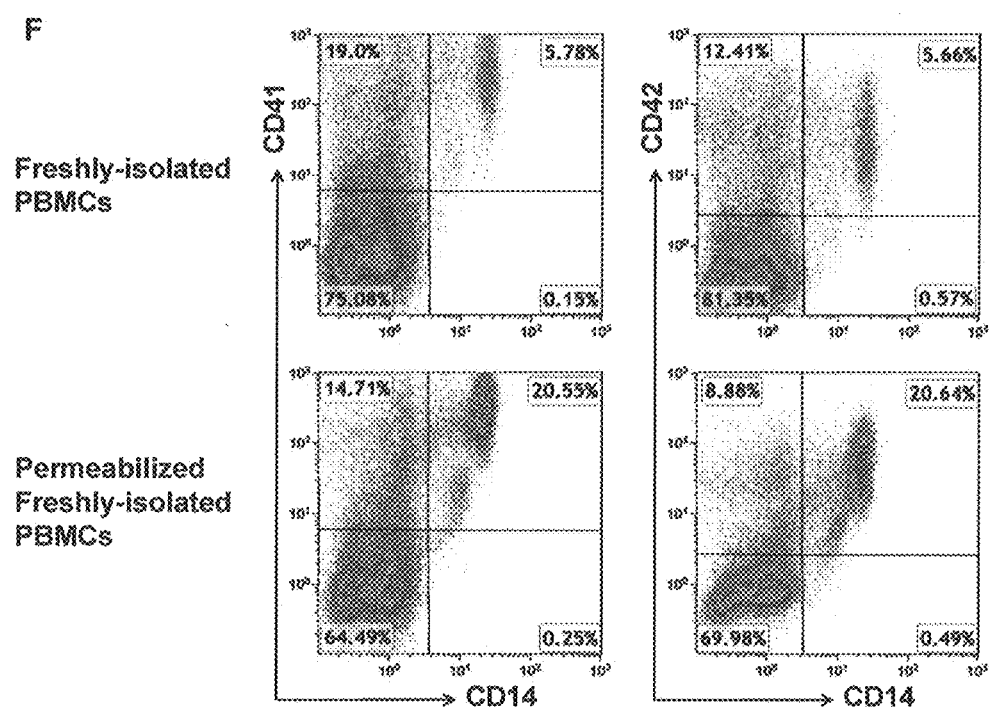
Figure 3:
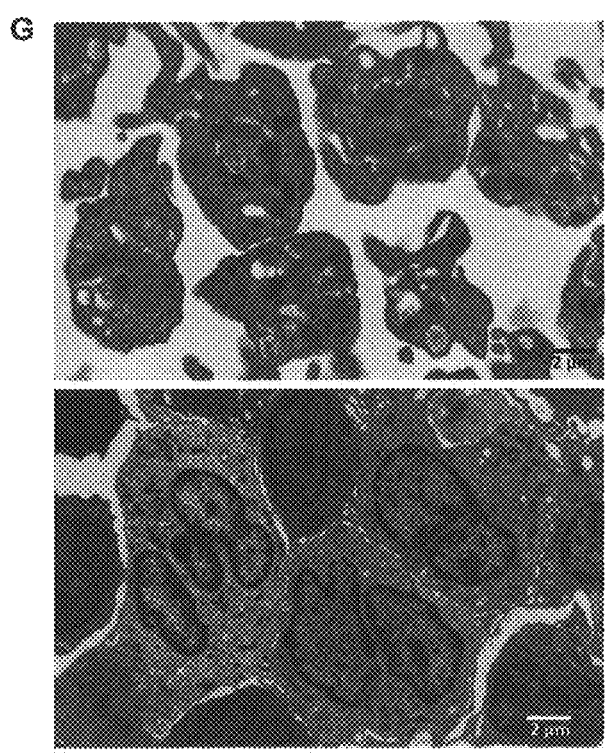
Figure 3:
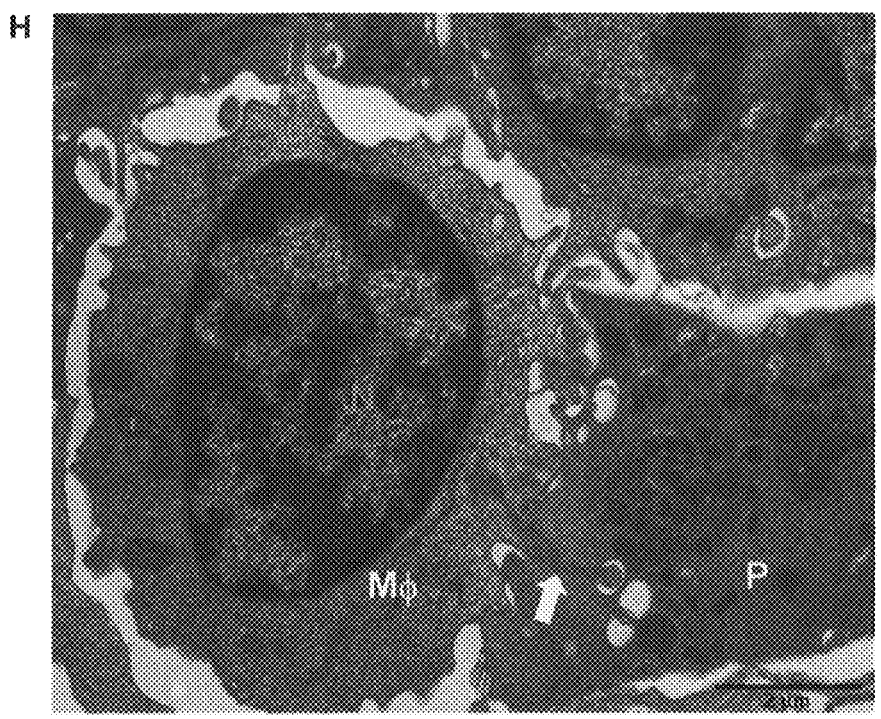
Figure 3:
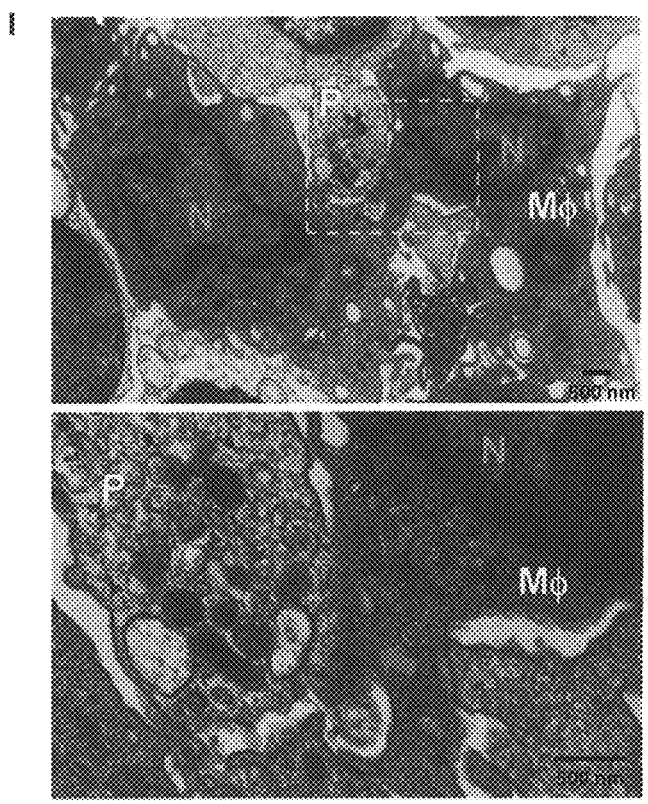
Figure 3:
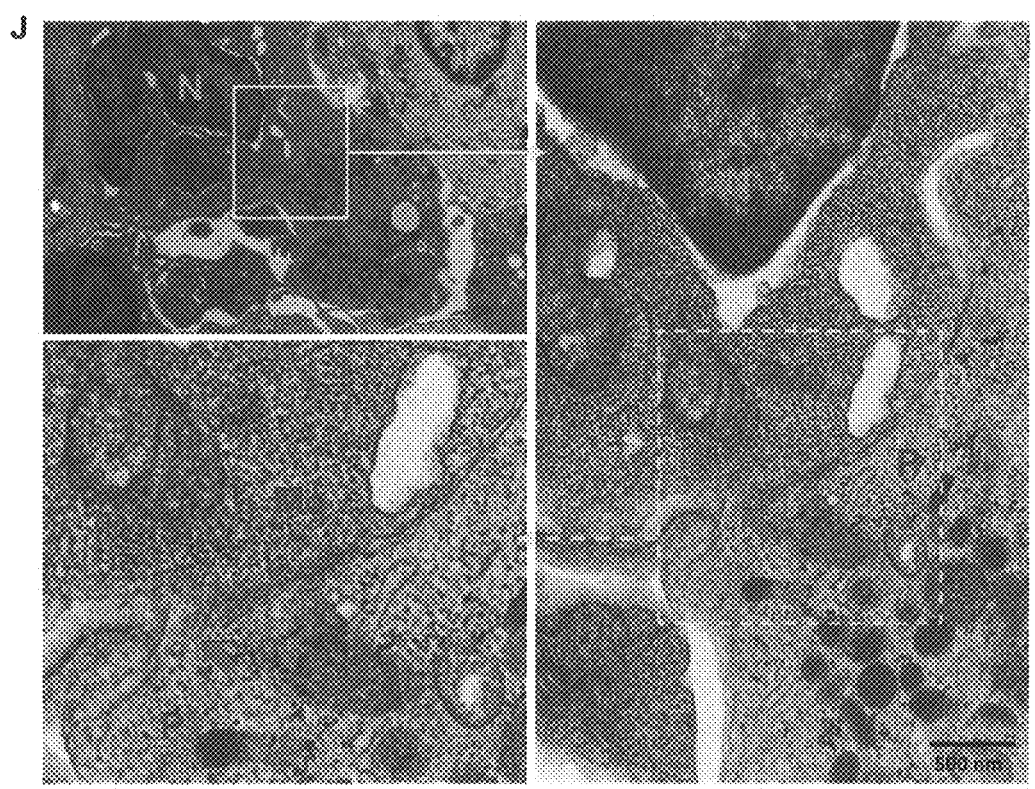
Figure 3:
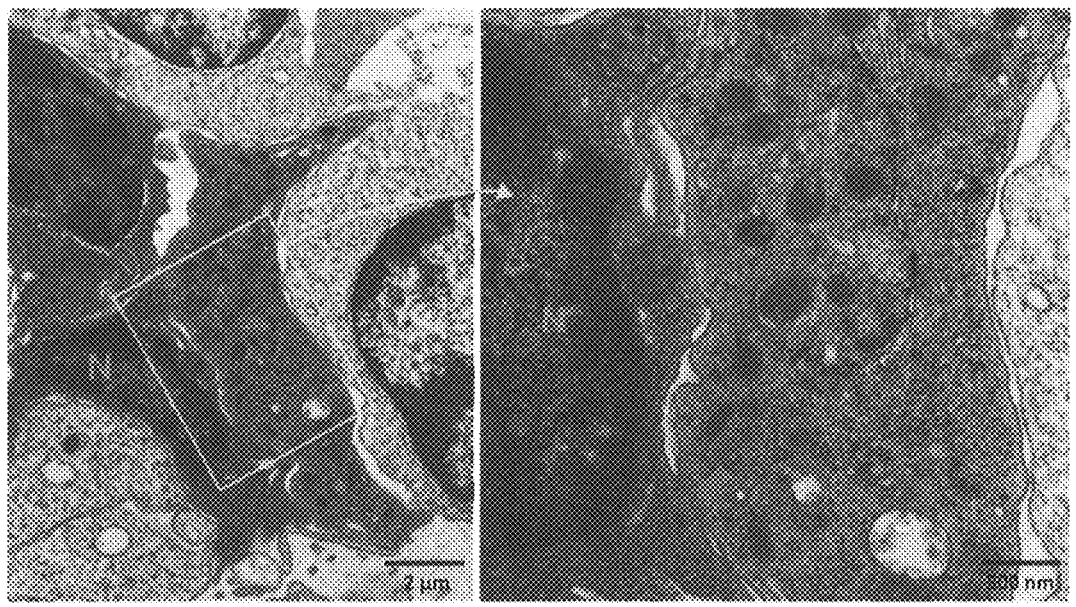
Figure 3:
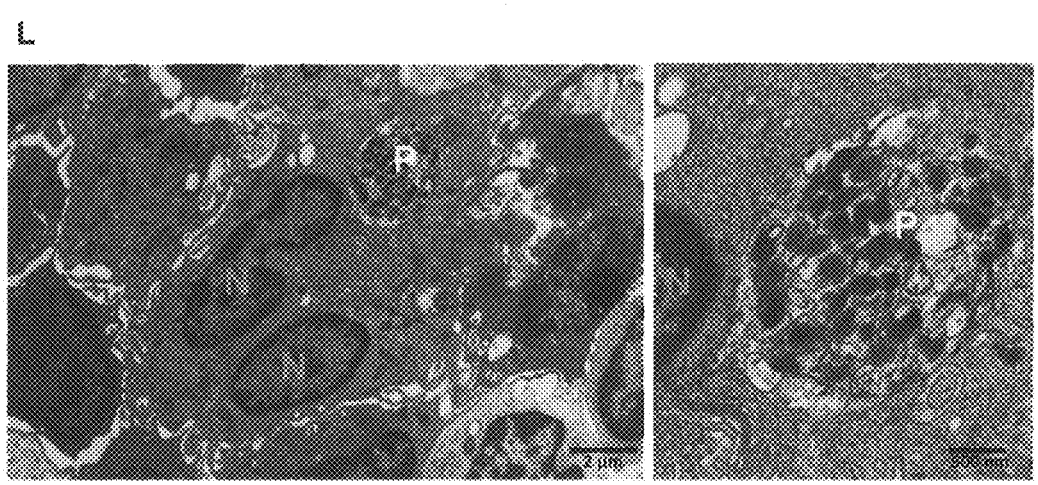
Figure 3:
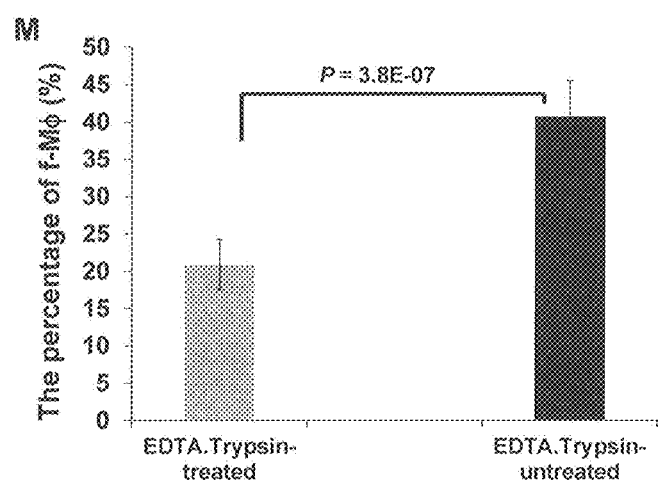
Figure 3:
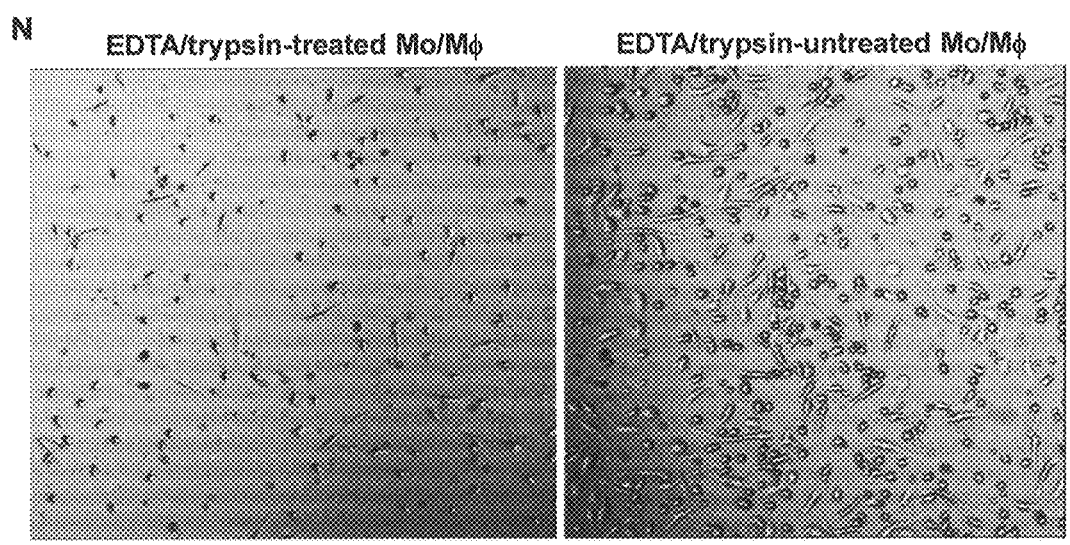
Figure 3:
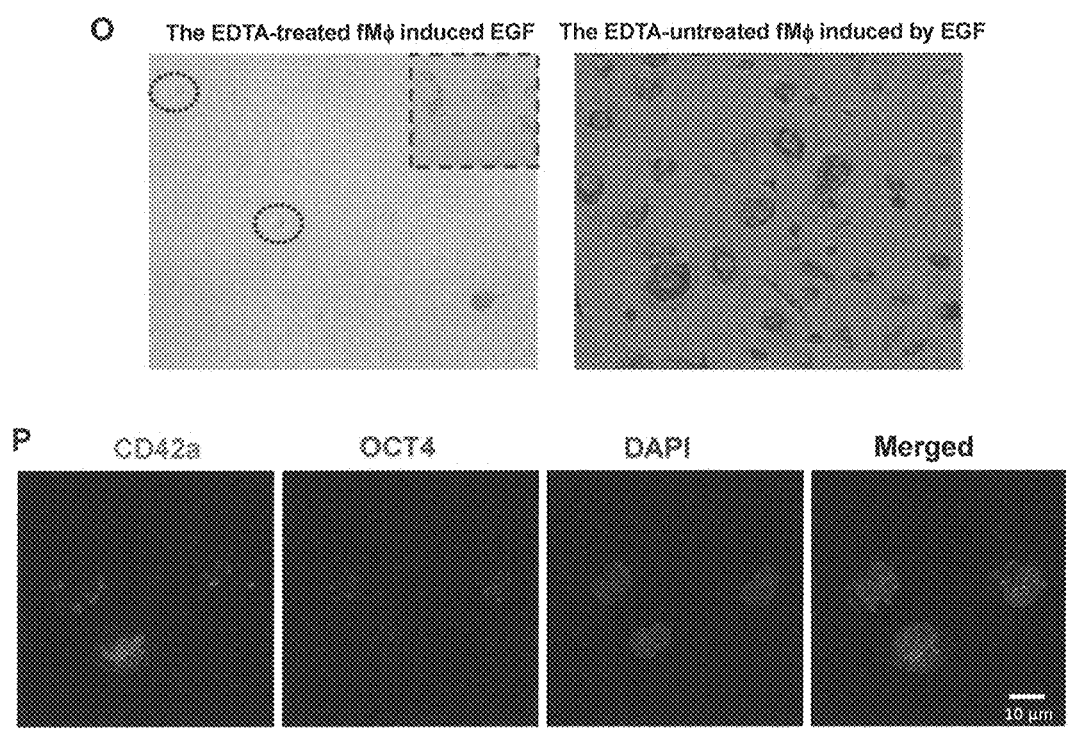

By flow cytometry, platelet-like cells adhere to most CD14+ monocytes and CD66b+ granulocytes, as well as to some CD4+ T cells, CD8+ T cells, CD19+ B cells, and CD56+NK cells (FIG. 3A-C). FIG. 3A is an ungated dot plot of CBMCs, where there are four major cell populations: lymphocytes (Ly, purple circle), monocytes (Mo, black circle), granulocytes (Gr, yellow circle), and platelets (Pl, blue circle). After being treated with the cell dissociation reagents trypsin-EDTA (0.25%), the percentage of CD66b+ CD41+ granulocytes in CBMCs was markedly reduced relative to that of untreated CBMCs (P=0.007, FIG. 3D); however, the percentage of CD14+CD41+ monocytes in CBMCs failed to show significant changes (P=0.95, FIGS. 3 D and E). The data suggest that the platelet-like cells adhere more strongly to monocytes than to granulocytes and other immune cells.

Previous work demonstrated that adult human monocytes/ macrophages (Mo/Mφ) could de-differentiate into pluripotent stem cells (designated as fibroblast-like M s, f-Mφ) after ex vivo treatment with inducers (Zhao Y, Glesne D, Huberman E: A human peripheral blood monocyte-derived subset acts as pluripotent stem cells. *Proc Natl Acad Sci USA* 2003, 100: 2426-2431). To determine whether interaction between platelets and Mo/Mφ contribute to this dedifferentiation, human peripheral blood mononuclear cells (PBMCs) were analyzed by flow cytometry after cell fixation and permeabilization. The percentages of CD14+CD41+ and CD14+CD42+Mo/Mφ in the permeabilized PBMCs were increased four-fold compared to those in the freshly-isolated PBMCs (FIG. 3F).

Purified Mφs were examined by transmission electronic microscopy (FIGS. 3 G-L) and confocal microscopy (FIG. 3P). Electron microscopy revealed close interactions between platelet-like cells and Mφs, including cell fusion (FIGS. 3 I-K) and the phagocytosis of platelet-like cells by Mφs (FIG. 3L).

FIG. 3I shows a zoomed out (upper panel) and zoomed in (lower panel) image of the close association of macrophages (Ms) with platelet-like cells (P) by electron microscopy. The lower panel represents the image outlined by the dashed box in the upper panel. The letter "N" indicates the nuclei of the Mϕs. As shown in FIG. 3I, the membrane boundary of the macrophage (Mϕ) appears to have merged with the membrane boundary of the platelet-like cell (P) (See junction of apparent fusion indicated by arrow, lower panel). Similarly, FIG. 3J shows a series of zoomed images of increasing magnification from upper left, to right, to lower left, showing the interaction of a Mϕ and a platelet-like cell. As shown in FIG. 3J, the membranes of the Mϕ and platelet-like cell appear fused (See apparent fused membrane indicated by arrows, right panel, lower left panel). In some places, the cell membrane boundaries have disappeared (See FIG. 3J, right and lower left panels, indicated by triangular arrow). FIG. 3K also shows a zoomed out (left panel) and zoomed in (right panel) image of the close association between a Mϕ and a platelet-like cell. As shown in FIG. 3K, the membrane of the M and platelet-like cell are closely associated or appear to be fused (See e.g. arrow, right panel).

FIG. 3L shows a zoomed out (left panel) and zoomed in (right panel) image of a macrophage that is in close contact with/appears to have engulfed a platelet-like cell (P). The undulating nucleus of the macrophage is indicated (N). As shown in FIG. 3L, the platelet-like cell is completely surrounded by the boundary of the Me membrane.

Since previous work demonstrated that adult human monocytes/macrophages (Mo/Mϕ) could de-differentiate into pluripotent stem cells, designated as fibroblast-like Mϕs (f-Mϕ), after ex vivo treatment with inducers (Zhao Y, Glesne D, Huberman E: A human peripheral blood monocyte-derived subset acts as pluripotent stem cells. *Proc Natl Acad Sci USA* 2003, 100: 2426-2431), the pluripotency of f-Mϕ derived from the stemness of platelet-like cells was investigated. Macrophages (Mϕs) contacted with a platelet rich fraction of cord blood were treated with trypsin/EDTA or left untreated. Trypsinized and untreated Mϕs were cultured in the presence of 50 ng/nm macrophage colony stimulating factor (M-CSF) for two days and then visually evaluated for the presence or absence of f-Mϕ morphology. As shown in FIG. 3M, the percentage of f-Mϕs significantly decreased in the group of macrophages treated with trypsin/EDTA. Without being limited by theory, this data suggests that the pluripotency of f-Mϕ is derived from contact with, and the stemness of, components within the platelet rich fraction of blood that confer stemness characteristics on the f-Mϕ.

As shown in FIG. 3N, the total cell number of macrophages was also reduced after the treatment with trypsin/EDTA and culturing for 7 days (1.75±0.35×10$^4$ cells/ml vs. 5.13±0.75×10$^4$ cells/ml in untreated group, P=0.0044). Representative phase contrast microscopy images showing the difference in the total cell population of trypsin/EDTA treated (left panel) and untreated (right panel) cells are shown in FIG. 3N. Without being limited by theory, the data indicates that the formation of f-Mϕ was reduced after the (at least partial) removal of attached components in the platelet rich fraction of blood from contact with the Mϕs.

Additionally, the data show that the potential for differentiation of f-Mϕ into epithelial-like cells was decreased after removal of platelet rich blood fraction components via treatments with trypsin/EDTA. Ms were obtained from cord blood and treated with trypsin/EDTA or left untreated. The treated and untreated Mϕs were cultured in 100 ng/ml epithelial growth factor (EGF) for 10 days, immunostained with mouse anti-Pan-Cadherin antibodies (1:100 dilution), and examined by phase contrast microscopy. As shown in FIG. 3O, representative cells treated with trypsin/EDTA (left panel) show decreased staining for cadherins when compared to representative cells of the untreated group (right panel).

Confocal microscopy data confirmed the presence of CD41b, CD42 markers and stemness markers within Mϕ cells. Specifically, confocal data confirmed the distribution of CD42a+OCT3/4+ and CD42a+NANOG+ inside of Mϕs and the translation of OCT3/4 and NANOG into the nucleus of Mϕ (FIG. 3P). As shown in FIG. 3P, Ms were immunoflourescently stained for CD42a and OCT4. The nucleus was stained with DAPI for each group. FIG. 3P, left panels show strong peri-nuclear staining of CD42a, while the middle panels show strong nuclear staining for OCT4. Without being limited by theory, these results suggest that Mϕs are capable of incorporating the protein and/or mRNA present in platelet-like cells via phagocytosis, membrane fusion with platelets, or by receiving platelet microparticles and/or exosomes, and that the transfer of OCT3/4 and NANOG mRNA and protein could reprogram the Ms to a more stem-like state.

In total, without being limited by theory, the data suggests that the platelet rich fraction of cord blood comprising platelet-like cells may provide ES-related transcription factors that, by contacting Mo/Mϕ, leads to the reprogramming of Mo/Mϕ and the proliferation and differentiation of f-Mϕ.

Example 4. Platelet-Like Cells Express Human ES Cell Markers

Figure 4:
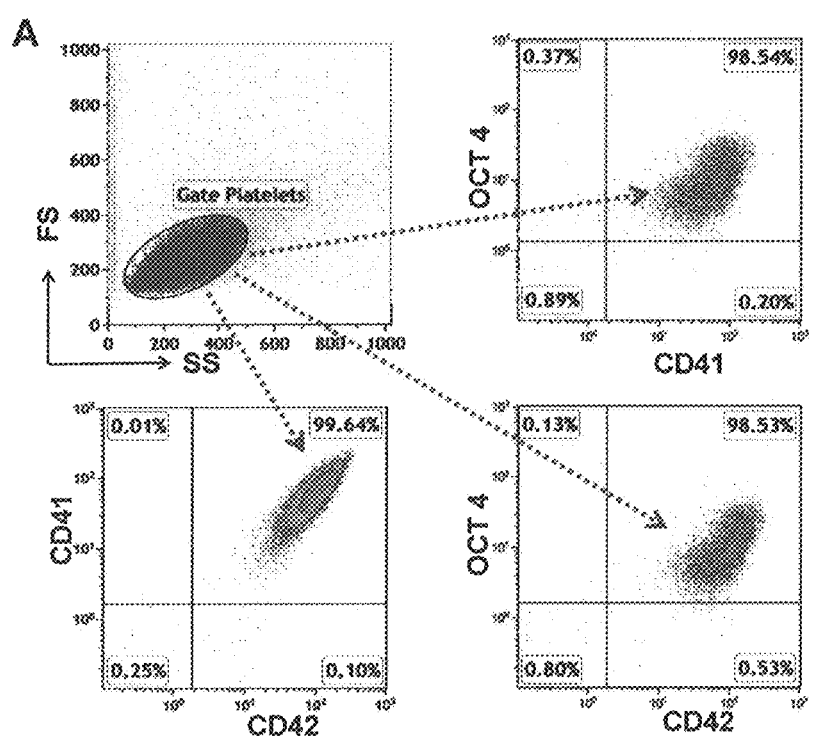
Figure 4:
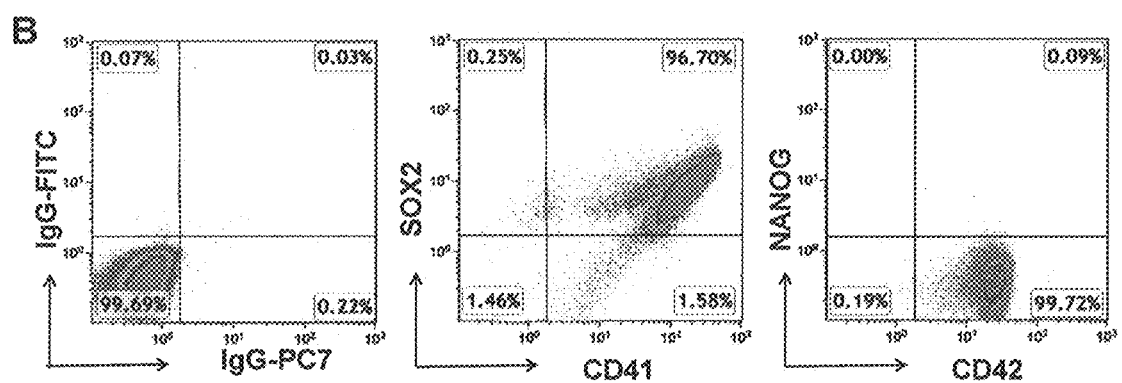
Figure 4:
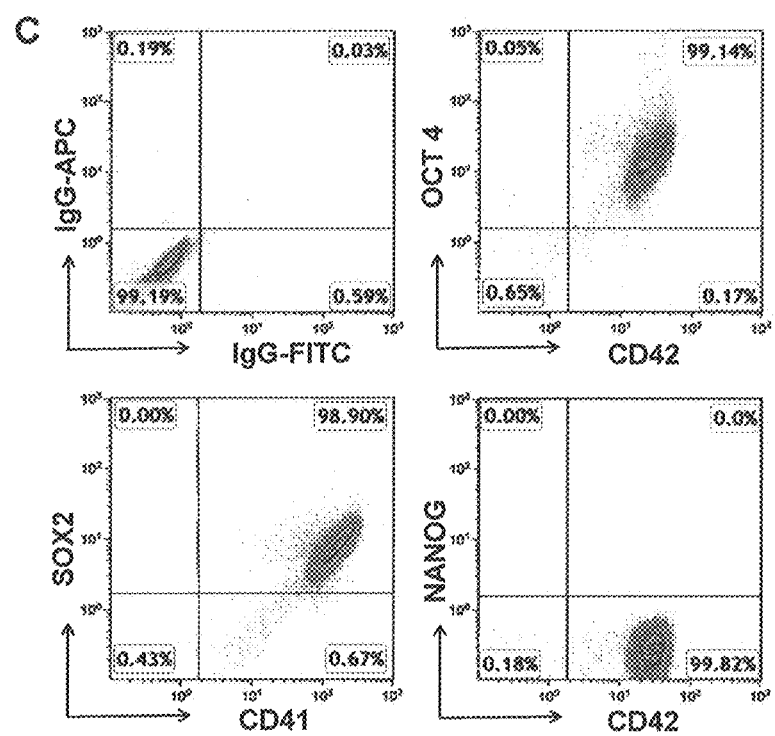
Figure 4:
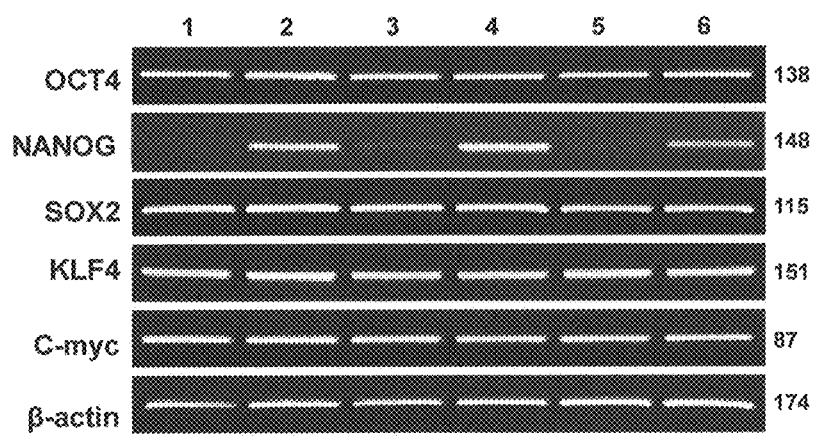
Figure 4:
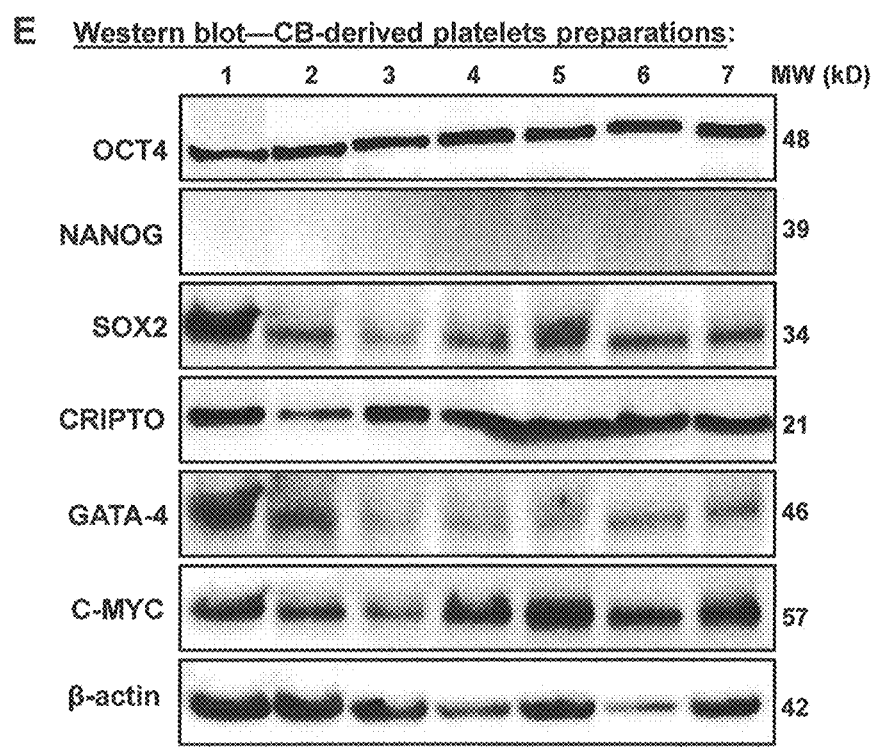
Figure 4:
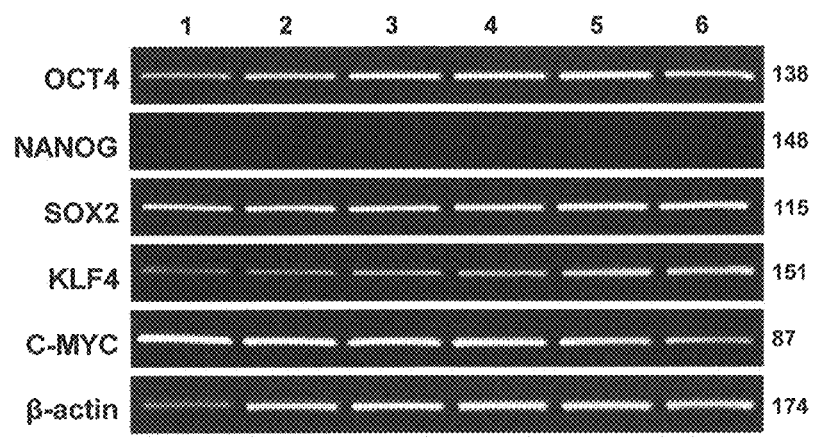
Figure 4:
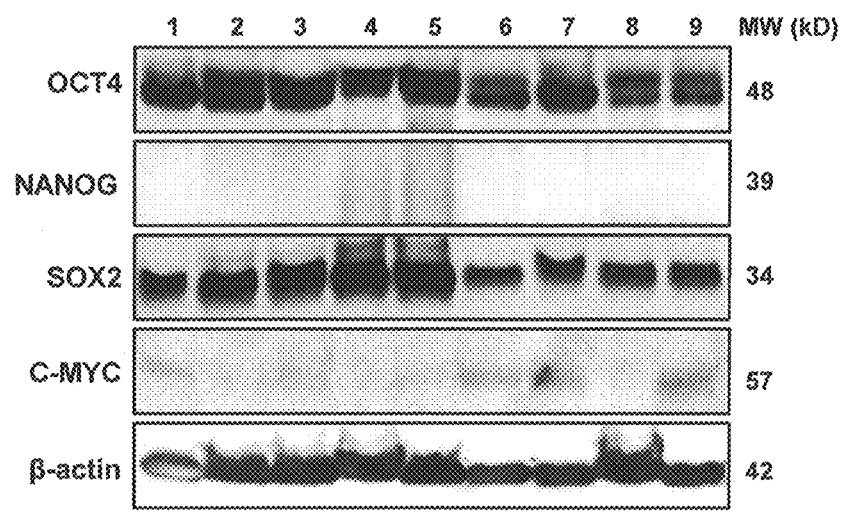
Figure 4:
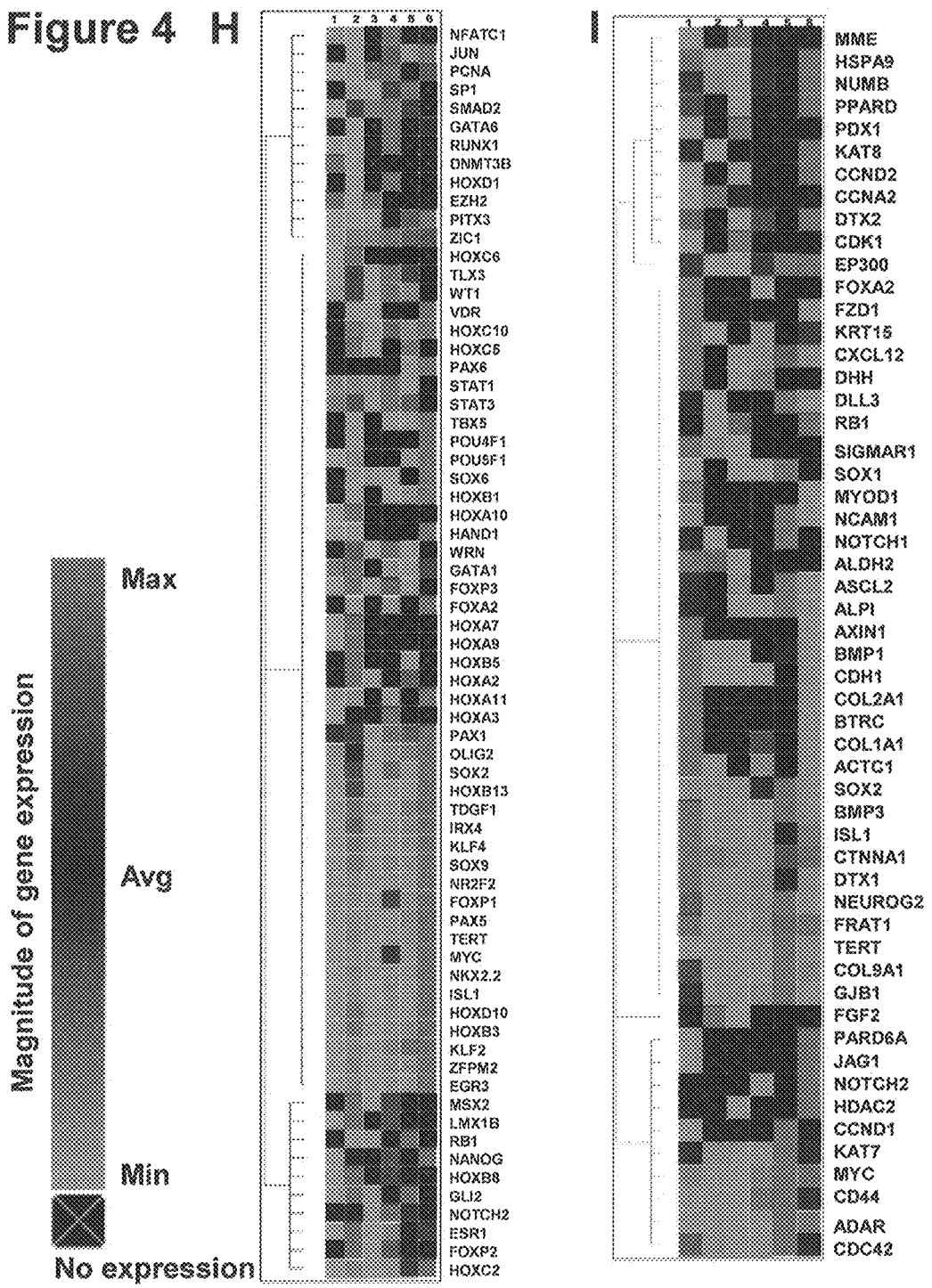

Using human platelets' markers CD41 and CD42, flow cytometry showed that the highly-purified platelets (>98% purity) from human cord blood highly display ES-associated pluripotent gene markers. For example, the transcription factor octamer-binding protein 4 (OCT4) was found to be expressed in over 98% of cells and SRY-box containing gene 2 (SOX2) was found to be expressed in over 96% of cells (FIGS. 4 A and B). Few if any cells (less than 0.1%) expressed NANOG (FIG. 4 B). Similar data was obtained from adult human peripheral blood-derived platelets (FIG. 4C).

The presence of mRNA from OCT4, SOX2, Kruppel-like factor 4 (KLF4), and c-myelocytomatosis oncogene (C-MYC) in cord blood (FIG. 4D) and peripheral blood platelet like cells (FIG. 4F) respectively was demonstrated by real time PCR and gel electrophoresis analysis. Values outside and to the right of each gel panel indicate an averaged quantification of band intensity among the six representative samples in relative intensity units. Western blotting further confirmed the expression of OCT4, SOX2, CRIPTO, GATA-4, and C-MYC at protein levels in cord blood platelet like cells (FIG. 4 E). Similar data were obtained from peripheral blood platelet like cells (FIG. 4G). Values to the right and outside each western blot panel represent relative intensity units averaged from each sample band. The expression of NANOG mRNA was positive in 5/20 CB-platelets (FIG. 4 D); however, its protein expression was very low or negative (FIG. 4 E). Both mRNA and protein levels were negative in PB-platelets (FIGS. 4 F and G). The data shows that platelet like cells hold the "stemness" markers that may contribute to modulating and reprogramming the proliferation and differentiation of adult human cells.

Platelets are anucleate cells without human genomic DNA. To further characterize genes expressed in a platelet like cell fraction, mitochondria were purified from cord blood and peripheral blood derived platelet like for analysis of gene transcriptions of mitochondria DNA (MitoDNA). The RT$^2$ Profiler PCR Array analysis demonstrated expression of human stem cell-related transcription factors (FIG. 4H) including somatic stem cell maintenance (POU5F1 (OCT4) and SOX2), placenta development (HAND1, SP1, and VDR), induced pluripotent & embryonic stem cells (POU5F1, SOX2, and STAT3), axis/symmetry/segmentation (FOXA2, GATA6, GLI2, HAND1, HOXA11, HOXA2, HOXA3, HOXA7, HOXA9, HOXB1, HOXB3, HOXB5, HOXB8, HOXC10, HOXC5, HOXC6, HOXD10, LMX1B, NOTCH2, NR2F2, PAX1, SMAD2, TBX5, TDGF1, and ZIC1), embryonic development (FOXA2, GATA6, GLI2, HAND1, HOXA11, HOXA2, HOXA3, HOXA7, HOXA9, HOXA10, HOXB1, HOXB3, HOXB5, HOXB8, HOXC10, HOXC5, HOXC6, HOXD1, HOXD10, KLF4, LMX1B, MSX2, NOTCH2, PAX1, SMAD2, SOX2, SP1, TBX5, TDGF1, ZFPM2, and ZIC1), ectoderm, endoderm & mesoderm formation & differentiation (FOXA2, GATA6, HAND1, HOXA7, HOXB13, ISL1, KLF4, SMAD2, and SOX9), organ morphogenesis (GL2, HAND1, HOXA11, HOXA2, HOXA3, HOXA7, HOXB1, HOXB13, HOXB3, HOXB5, HOXB8, HOXD10, ISL1, JUN, KLF4, MSX2, MYC, NOTCH2, NR2F2, PAX1, PAX5, PAX6, PITX3, RUNX1, SMAD2, SOX2, SOX9, SP1, STAT3, TBX5, TDGF1, VDR, WT1, ZFPM2, and ZIC1), angiogenesis (HAND1, JUN, NR2F2, RUNX1, and WT1), neurogenesis (DNMT3B, FOXA2, FOXP3, GLI2, HOXA2, HOXC10, HOXD10, ISL1, LMX1B, NKX2.2, NR2F2, OLIG2, PAX6, PITX3, POU4F1, SOX2, STAT3, and TLX3), hematopoiesis (RB1, RUNX1, SOX6, SP1, and STAT1), osteogenesis (GL12, HOXA2, SOX2, and SP1), and others (EGR3, ESR1, EZH2, FOXP1, FOXP2, GATA1, IRX4, KLF2, NFATC1, PCNA, TERT, and WRN).

Additional RT$^2$ Profiler PCR Array analysis demonstrated the expression of multiple genes related to human stem cell-associated markers in the mitochondria of human platelets (FIG. 4I), such as cell cycle regulators (AXIN1, CCNA2, CCND1, CCND2, CDK1, CDC42, EP300, FGF2, MYC, NOTCH2, PARD6A, and RB1), chromosome and chromatin modulators (KAT8, KAT7, RB1, and TERT), genes regulating symmetric/asymmetric cell division (DHH, NOTCH1, NOTCH2, NUMB, PARD6A), self-renewal markers (HSPA9, KAT8, KAT7, NEUROG2, SOX1, and SOX2), cytokines and growth factors (BMP1, BMP3, CXCL12, FGF2, and JAG1), genes regulating cell-cell communication (DHH, GJB1, and JAG1), cell adhesion molecules (CD44, CDH1, COL9A1, CTNNA1, CXCL12, and NCAM1), metabolic markers (ALDH2), embryonic cell lineage markers (ACTC1, ASCL2, FOXA2, ISL1, and KRT15), mesenchymal cell lineage markers (ALPI, COL1A1, COL2A1, and COL9A1), neural cell lineage markers (CD44, NCAM1, and SIGMAR1), as well as the signaling pathways contributing to the maintenance of stem cells such as notch pathway (DLL3, DTX1, DTX2, EP300, HDAC2, JAG1, NOTCH1, NOTCH2, and NUMB) and Wnt pathway (ADAR, AXIN1, BTRC, CCND1, FRAT1, FZD1, MYC, and PPARD).

Each of lanes 1 through 6 of FIGS. 4H and 4I represent gene expression profiles from six separate platelet like cell samples. Each of the genes represented in the Clustergram was found to be highly expressed in at least one of the six platelet like cell samples.

Example 5. Platelet Like Cells Display Human Pancreatic Islet β Cell-Related Markers Type 1 diabetes (T1D) is a T cell-mediated autoimmune disease that causes a deficit of pancreatic islet cells. Millions of individuals worldwide have T1 D, and the incidence is increasing annually among different populations. Islet transplantation, drug-mediated promotion of -cell regeneration, and transplantation of functional islet cells differentiated from human induced pluripotent stem cell (hiPSC) or embryonic stem (ES) cell lines have been proposed and tested as likely approaches for treating T1D (Pagliuca F W, et al., Generation of functional human pancreatic beta cells in vitro. Cell 2014, 159: 428-439; Quiskamp N, et al., Differentiation of human pluripotent stem cells into beta-cells: Potential and challenges. *Best Pract Res Clin Endocrinol Metab* 2015, 29: 833-847). However, the shortage of donors, immune rejections, and the continued presence of autoreactive effector T cells and B cells in the circulation may destroy insulin-producing cells generated through these approaches, thereby minimizing their therapeutic potential. To circumvent these barriers, several approaches are being investigated, including immunosuppressive drugs, manipulation of host immune responses, and the constitution of immune chimerism.

Our working hypothesis is that adult cells reprogrammed with a platelet rich fraction of cord blood via cell contact may be capable of generating platelet-induced pluripotent stem cells (PiPS) that can subsequently differentiate into functional islet cells. Due to safety concerns involved in the generation of iPS cells by viral- or drug-induced transduction, platelet rich fractions of cord blood would be an attractive alternative for protein and mRNA delivery and transduction, leading to cell reprogramming and immune modulation with a much improved safety profile.

Glucose Homeostasis

Normally, following glucose ingestion, the increase in plasma glucose concentration triggers insulin release, which stimulates splanchnic (liver and gastrointestinal tissue) and peripheral glucose uptake and suppresses endogenous (primarily hepatic) glucose production. In healthy adults, blood glucose levels are tightly regulated within a range of 70 to 99 mg/dL, and maintained by specific hormones (e.g., insulin, glucagon, incretins) as well as the central and peripheral nervous system, to meet metabolic requirements. Various cells and tissues within the brain, muscle, gastrointestinal tract, liver, kidney and adipose tissue also are involved in blood glucose regulation by means of uptake, metabolism, storage and secretion [DeFronzo R. A., "Pathogenesis of type 2 diabetes mellitus" Med. Clin. N. Am., Vol. 88: 787-835 (2004)]; Gerich J. E., "Physiology of glucose homeostasis", Diabetes Obes. Metab. Vol. 2: 345-350, (2000)]. Under normal physiologic circumstances, glucose levels rarely rise beyond 140 mg/dL, even after consumption of a high-carbohydrate meal.

Insulin, a potent antilipolytic (inhibiting fat breakdown) hormone, is known to reduce blood glucose levels by accelerating transport of glucose into insulin-sensitive cells and facilitating its conversion to storage compounds via glycogenesis (conversion of glucose to glycogen) and lipogenesis (fat formation) within the islets of Langerhans of the pancreas, β-cells produce insulin.

Glucagon, a hormone that also plays a role in glucose homeostasis, is produced by α-cells within the islets of Langerhans in response to low normal glucose levels or hypoglycemia, and acts to increase glucose levels by accelerating glycogenolysis and promoting gluconeogenesis. After a glucose-containing meal, glucagon secretion is inhibited by hyperinsulinemia, which contributes to suppression of hepatic glucose production and maintenance of normal postprandial glucose tolerance.

Incretins, which include glucose-dependent insulinotropic polypeptide (GIP) and glucagon-like peptide 1 (GLP-1), are also involved in regulation of blood glucose, in part by their effects on insulin and glucagon [Drucker D. J. et al., "The incretin system: glucagon-like peptide-1 receptor agonists and dipeptidyl peptidase-4 inhibitors in type 2 diabetes", Lancet, Vol. 368: 1696-1705, (2006)]. Both GLP-1 and GIP are considered glucose-dependent hormones, meaning they are secreted only when glucose levels increase above normal fasting plasma glucose levels. Normally, these hormones are released in response to meals and, by activating certain receptors on pancreatic β-cells, they aid in stimulation of insulin secretion. When glucose levels are low, however, GLP-1 and GIP levels (and their stimulating effects on insulin secretion) are diminished [Drucker D. J., "The biology of incretin hormones", Cell Metab. Vol. 3: 153-165, (2006)].

The preproglucagon-derived peptides glucagon, GLP1 and GLP2, are encoded by the preproglucagon gene, which is expressed in the central nervous system, intestinal L-cells, and pancreatic and gastric α-cells. A post-translational cleavage by prohormone convertases (PC) is responsible for the maturation of the preglucagon hormone that generates all these peptides. The expression of different PC subtypes in each tissue mediates the production of each different peptide. In α-cells, the predominance of proprotein convertase subtilisin/kexin type 2 (PCSK2) leads to production of glucagon together with the products glicentin, glicentin-repeated pancreatic polypeptide, intervening peptide 1 and the major proglucagon fragment [Dey A. et al., "Significance of prohormone convertase 2, PC2, mediated initial cleavage at the proglucagon interdomain site, Lys70-Arg71, to generate glucagon", Endocrinol., Vol. 146: 713-727, (2005)]. In enteroendocrine cells, PCSK1/3 enzymes cleave the preproglucagon hormone to generate GLP1 and GLP2 along with glicentin, intervening peptide 1 and oxyntomodulin [Mojsov S., "Preproglucagon gene expression in pancreas and intestine diversifies at the level of post-translational processing", J. Biol. Chem., Vol. 261: 11880-11889 (1986)]. Under certain conditions, islet α cells are an extraintestinal site for GLP-1 production [Portha B. et al., "Activation of the GLP-1 receptor signalling pathway: a relevant strategy to repair a deficient beta-cell mass", Exptl Diabetes Res. Article 376509: 1-11, (2011)]. One of the many observed cellular effects of GLP-1 is the inhibition of β-cell KATP channels, which initiates Ca2+ influx through voltage-dependent calcium channels and triggers the exocytotic release of insulin [MacDonald P. E. et al., "The multiple actions of GLP-1 on the process of glucose-stimulated insulin secretion", Diabetes, Vol. 51 (Suppl. 3): S434-S442, (2002)].

Transport of Glucose into Cells

Since glucose cannot readily diffuse through all cell membranes, it requires assistance from both insulin and a family of transport proteins (facilitated glucose transporter [GLUT] molecules) in order to gain entry into most cells [Bryant, et al, Nat. Rev. Mol. Cell Biol. "Regulated transport of the glucose transporter GLUT 4", Vol. 3(4): 267-277, (2002)]. GLUTs act as shuttles, forming an aqueous pore across otherwise hydrophobic cellular membranes, through which glucose can move more easily. Of the 12 known GLUT molecules, GLUT4 is considered the major transporter for adipose, muscle, and cardiac tissue, whereas GLUTs 1, 2, 3, and 8 facilitate glucose entry into other organs (eg, brain, liver). Activation of GLUT4 and, in turn, facilitated glucose diffusion into muscle and adipose tissue, is dependent on the presence of insulin, whereas the function of other GLUTs is more independent of insulin [Uldry M. et al., "The SLC2 family of facilitated hexose and polyol transporters", Thorens B, Eur. J. Physiol. 2004; Vol. 447: 480-489, (2004)].

The majority of glucose uptake (>80%) in peripheral tissue occurs in muscle, where glucose may either be used immediately for energy or stored as glycogen. Skeletal muscle is insulin-dependent, and thus requires insulin for activation of glycogen synthase, the major enzyme that regulates production of glycogen. While adipose tissue is responsible for a much smaller amount of peripheral glucose uptake (2%-5%), it plays an important role in the maintenance of total body glucose homeostasis by regulating the release of free fatty acids (which increase gluconeogenesis) from stored triglycerides, influencing insulin sensitivity in the muscle and liver.

While the liver does not require insulin to facilitate glucose uptake, it does need insulin to regulate glucose output. Thus, for example, when insulin concentrations are low, hepatic glucose output rises. Additionally, insulin helps the liver store most of the absorbed glucose in the form of glycogen.

The kidneys play a role in glucose homeostasis via release of glucose into the circulation (gluconeogenesis), uptake of glucose from the circulation to meet renal energy needs, and reabsorption of glucose at the proximal tubule. The kidneys also aid in elimination of excess glucose (when levels exceed approximately 180 mg/dL, though this threshold may rise during chronic hyperglycemia) by facilitating its excretion in the urine.

Cytoarchitecture of Human Islets

In human islets, insulin-containing β-cells intermingle with other cell types within the islet, i.e., insulin-, glucagon-, and somatostatin-containing cells are found distributed throughout the human islet [Cabrera O. et al., "The unique cytoarchitecture of human pancreatic islets has implications for islet cell function", Proc. Natl Acad. Sci. U.S., Vol. 103: 2334-2339, (2006)]. Human islets do not show obvious subdivisions, but 90% of α-cells are in direct contact with β-cells, and β-cells intermingled freely with other endocrine cells throughout the islet. β, α, and δ-cells had equivalent and random access to blood vessels within the islet, ruling out the possibility that the different endocrine cells are organized in layers around blood vessels. These results support a model in which there is no set order of islet perfusion and in which any given cell type can influence other cell types, including its own cell type [G. da Silva Xavier et al., "Per-arnt-sim (PAS) domain-containing protein kinase is downregulated in human islets in type 2 diabetes and regulates glucagon secretion", Diabetologia, Vol. 54: 819-827, (2011)].

Diabetes as an Autoimmune Disease

Diabetes mellitus is a group of metabolic diseases characterized by hyperglycemia. Chronic hyperglycemia is associated with long-term damage, dysfunction, and potential failure of organs, including the eyes, kidneys, nerves, heart and blood vessels. The ideal therapeutic agent for treating diabetes has yet to be developed.

Type 1 Diabetes Mellitus (T1D)

In type 1 diabetes mellitus, β cells are destroyed by an autoimmune process and largely replaced by α-cells. [Unger R. H. et al., "Paracrinology of islets and the paracrinopathy of diabetes", Proc. Natl Acad. Sci., U.S., Vol. 107(37): 16009-16012, (2010)]. These α-cells lack the tonic restraint normally provided by the high local concentrations of insulin from juxtaposed β-cells, resulting in inappropriate hyperglucagoneria [Raskin P. et al. Glucagon and diabetes. The Medical Clinics of North America 62, 713 (1978)]; [Habener J. F. et al., "Alpha cells some of age", Trends in Endocrinology & Metabolism: TEM Vol. 24, 153-163 (2013)]; [Unger R. H. et al., "Glucagonocentric restructuring of diabetes: a pathophysiologic and therapeutic makeover", J. Clinical Investig. Vol. 122(1): 4-12, (2012)]; [Vuguin P. M. et al. "Novel insight into glucagon receptor action: lessons from knockout and transgenic mouse models", Diabetes, Obesity & Metabolism, Vol. 13(1), 144-150, (2011)], which drives surges of hyperglycemia which increases glucagon secretion [Unger R. H. et al., "Glucagonocentric restructuring of diabetes: a pathophysiologic and therapeutic makeover", J. Clinical Investig. Vol. 122(1): 4-12, (2012)]. Supernormal insulin levels are needed to match the insulin that neighboring β-cells give to α-cells in normal islets. This results in lifelong hyperinsulinemia, which exposes the subject to frequent incidences of hypoglycemia, which increases such sequelae as accumulation of low density lipoprotein (LDL) in the walls of blood vessels, causing the blockages of atherosclerosis, and coronary artery disease.

Four Pathological Characteristics of T1D are Blood Glucose Levels, Hemoglobin A1C, Glucagon and C-Peptide The immune dysfunction in T1 D is complicated, with effects both in pancreatic islets and outside the pancreas. Different components of the immune system [e.g., CD4+, CD8+ T cells, T regulatory cells (Tregs), B cells, dendritic cells (DCs), monocyte/macrophages (Mo/Mφs). natural killer T cells (NKTs)] are all envisioned to actively contribute to auto-immune responses in T1 D, thus complicating potential efforts to develop effective and successful treatments or a cure that will work across individuals with the disease. Several clinical trials [Bach J. F., "Anti-CD3 antibodies for type 1 diabetes: beyond expectations", Lancet., Vol. 378: 459-460, (2011)]; [Wherrett D. K. et al., "Antigen-based therapy with glutamic acid decarboxylase (GAD) vaccine in patients with recent-onset type 1 diabetes: a randomized double-blind trial", Lancet., Vol. 378: 319-327, (2011)] highlight the obstacles in developing a therapy and finding a cure for T1 D, and point to the need for an approach that produces comprehensive immune modulation at both the local pancreatic and systematic levels rather than targeting the pancreatic effects of one or a few components of the immune system.

Possible triggers for autoimmunity in T1 D include, without limitation, genetic, epigenetic, physical, social, and environmental factors, which may act independently or jointly to initiate or potentiate the development of autoimmunity. T1 D-related dysfunction in the immune system has been traced to dysfunctions in multiple cell types and targets including T cells, B cells, regulatory T cells (Tregs), monocytes/macrophages, dendritic cells (DCs), natural killer (NK) cells, and natural killer T (NKT) cells [Lehuen A. et al., "Immune cell crosstalk in type I diabetes", Nat Rev Immunol. Vol. 10: 501-513, (2010)]. Due to the polyclonal nature of T1 D-related autoimmune responses and the global challenges of immune regulation in T1 D patients, therapies and trials that only target one or a few components of the autoimmune response are likely to fail just as recent trials involving anti-CD3 Ab for T cells, anti-CD19 Ab for B cells, and GAD 65 vaccination have failed [Bach J. F., "Anti CD-3 antibodies for type 1 diabetes: beyond expectations", Lancet, Vol. 378: 459-460, (2011)]; [Mathieu C. et al., "Arresting type I diabetes after diagnosis: GAD is not enough", Lancet, Vol. 378: 291-292, (2011)].

While stem cell therapy has been explored as a means of replacing destroyed pancreatic islet β-cells, this approach does little in the absence of reducing the underlying autoimmune response.

Attempts to address the underlying autoimmunity in T1D have been unsuccessful [Zhao Y. et al., "Human cord blood stem cells and the journey to a cure for type 1 diabetes", Autoimmun Rev., Vol. 10: 103-107, (2010)] due to the polyclonal nature of the autoimmune response and the global challenges of immune regulation in T1 D patients [Zhao Y. et al., "Human cord blood stem cells and the journey to a cure for type 1 diabetes", Autoimmun Rev., Vol. 10: 103-107, (2010)]; [Abdi R. et al., "Immunomodulation by mesenchymal stem cells: a potential therapeutic strategy for type 1 diabetes", Diabetes, Vol. 57: 1759-1767, (2008)]; [Aguayo-Mazzucato C. et al., "Stem cell therapy for type I diabetes", Nat Rev Endocrinol., Vol. 6: 139-148, (2010)]; [Uccelli A. et al., "Mesenchymal stem cells in health and disease", Nat Rev Immunol., Vol. 8: 726-736, (2008)]; [Zhao Y. et al., "Immune regulation of T lymphocyte by a newly characterized human umbilical cord blood stem cell", Immunol Lett., Vol. 108: 78-87, (2007)]. Combinations of individual approaches have been proposed to address these challenges [Aguayo-Mazzucato C et al., "Stem cell therapy for type I diabetes mellitus", Nat Rev Endocrinol, Vol. 6: 139-148, (2010)]; [Zhao Y. et al., "Human cord blood stem cell-modulated regulatory T lymphocytes reverse the autoimmune-caused type 1 diabetes in nonobese diabetic (NOD) mice", PLoS ONE, Vol. 4: e4226, (2009)]; [Zhao Y. et al., "Reversal of type 1 diabetes via islet β-cell regeneration following immune modulation by cord blood-derived multipotent stem cells", BMC Med. Vol. 10(3), 1-11, (2012)], but adherence to these approaches is still complicated and often very costly.

Type 2 Diabetes

Type 2 diabetes (T2D) is a hyperglycemic disorder in which β-cells are present, thus distinguishing it from type 1 diabetes. Although numerous factors contribute to the development of T2D, the central defects are inadequate insulin secretion (insulin deficiency) and/or diminished tissue responses to insulin (insulin resistance) at one or more points in the complex pathways of hormone action [Triplitt C. L., "Examining the mechanisms of glucose regulation", Am. J. Manag. Care, Vol. 18 (1 Suppl) S4-S10, (2012)]. Insulin deficiency and insulin resistance frequently coexist, though the contribution to hyperglycemia can vary widely along the spectrum of T2D.

There is evidence that the etiology of T2D includes an autoimmune component that initiates inflammation affecting pancreatic islet β-cells, which provides new insight into the mechanism and potential treatment of insulin resistance through immune modulation. Some clinical studies showed increasing levels of IL-17 production in T2D patients [Jagannathan-Bogdan M. et al., "Elevated proinflammatory cytokine production by a skewed T cell compartment requires monocytes and promotes inflammation in type 2 diabetes", J Immunol, Vol. 186: 1162-1172, (2011)] and obese patients [Sumarac-Dumanovic M. et al., "Increased activity of interleukin-23/intereukin-17 proinflammatory axis in obese women", Int J Obes (Lond), Vol. 33: 151-156, (2009)]. Other studies show that the level of $T_{H1}$-associated cytokine IL-12 is increased in T2D subjects [Wu H. P. et al., "High interleukin-12 production from stimulated peripheral blood mononuclear cells of type 2 diabetes patients", Cytokine, Vol. 51: 298-304, (2010)].

Platelet-Like Cells and Human Pancreatic β Cell-Related Markers

We are interested in exploring whether a platelet-rich fraction from cord blood comprising platelet-like cells can be used to reprogram peripheral blood cells, and whether the reprogrammed cells may differentiate to supplement the existing/depleted population of β cells in pancreatic islets of diabetic subjects.

To explore whether platelet like cells may contribute to the regeneration of islet β cells, we examined human islet β cell-specific markers including insulin and C-peptide productions, transcription factors (MAFA, PDX1, NKX6.1, NEUROD1, and NGN3), KATP channel proteins (Sur1 and Kir6.2) and glucokinase (GCK) by RT-PCR. Platelet-like cells from cord blood were isolated as described above and analyzed by real-time PCR and Western blot.

Figure 5:
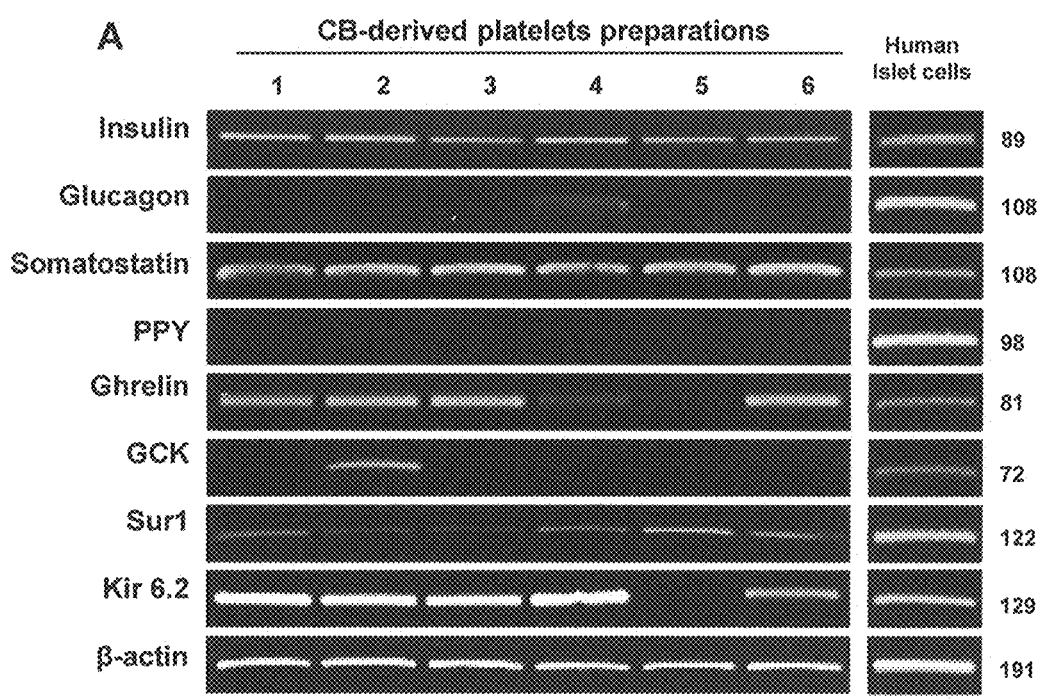
Figure 5:
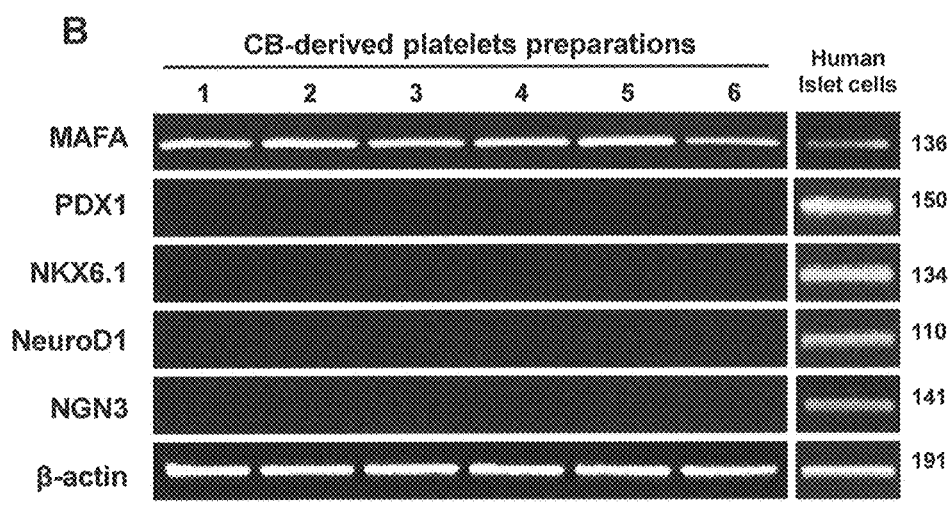
Figure 5:
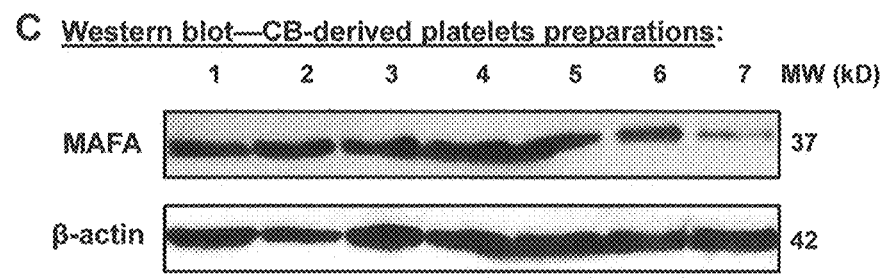
Figure 5:
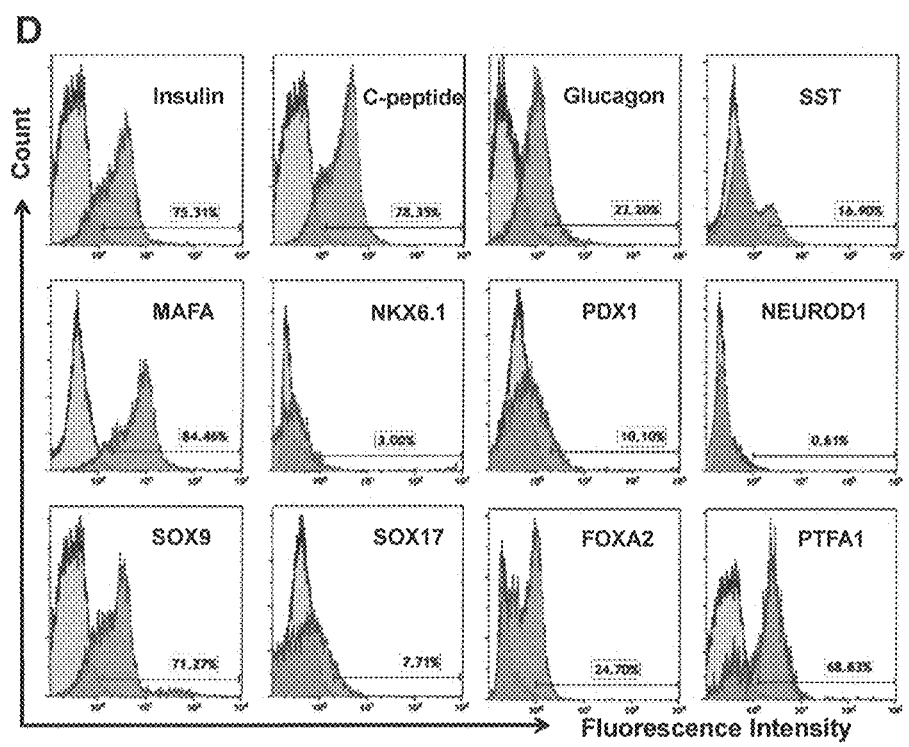
Figure 5:
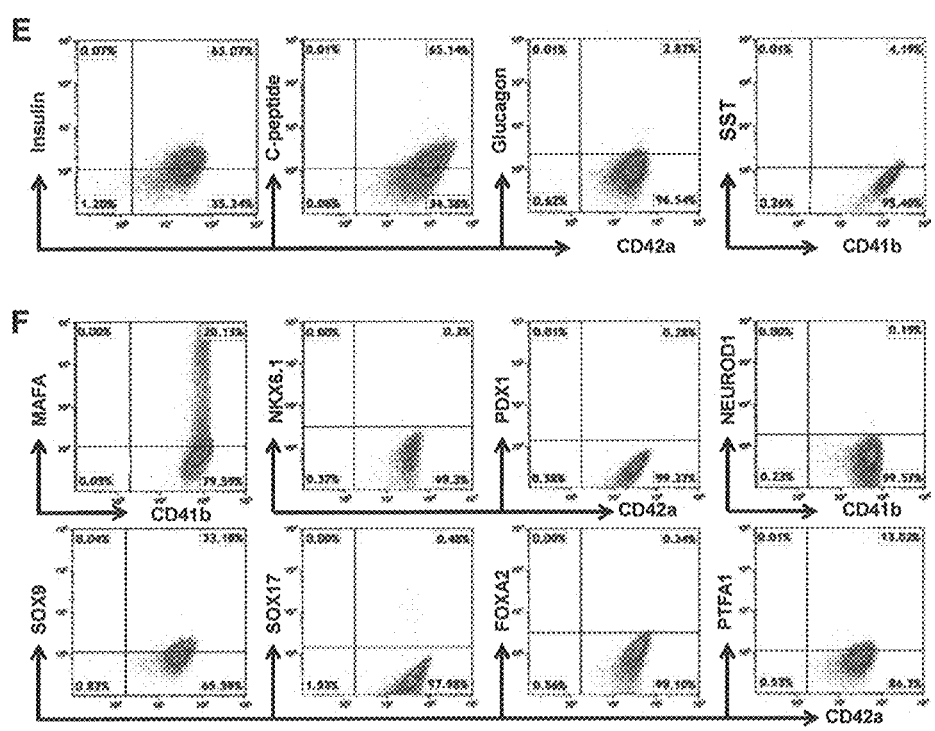
Figure 5:
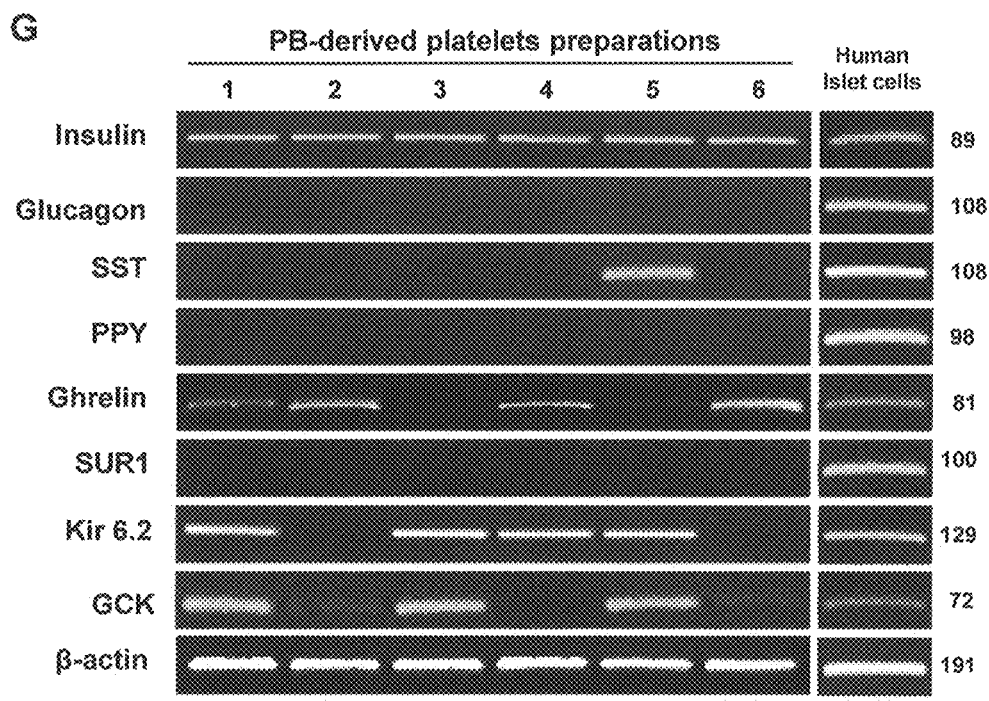
Figure 5:
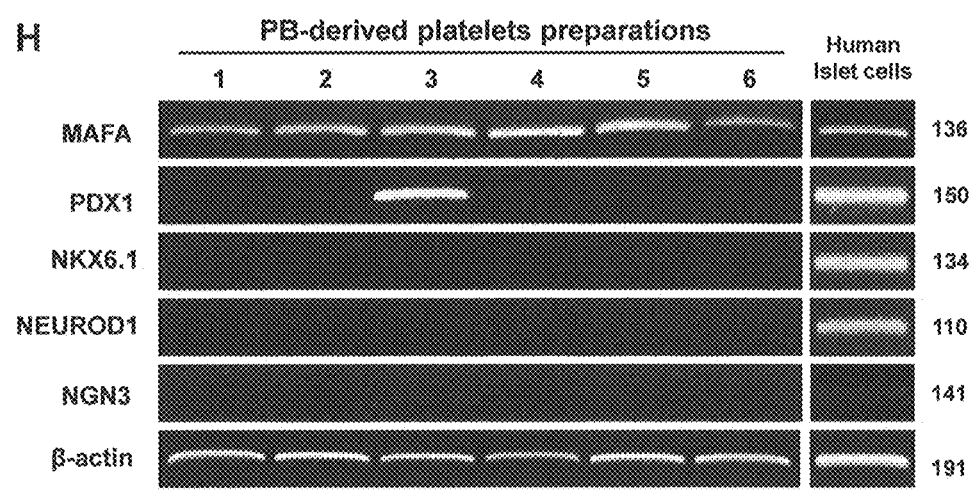
Figure 5:
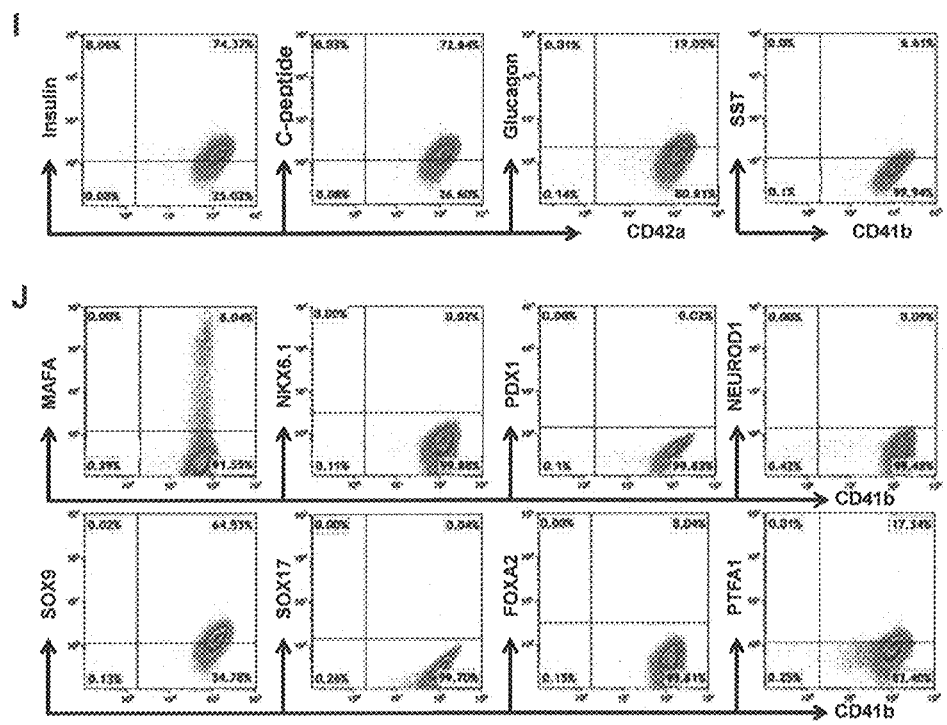

Real time PCR data revealed the expression of insulin, MAFA, and Sur1 mRNAs in CB-derived platelets (n=6). Kir 6.2 mRNA was displayed in most samples (5/6), while few samples (1/6) were positive for GSK (FIGS. 5A and B). In the same samples, there was no or very weak expression of PDX1, NKX6.1, NEUROD1, and NGN3 (FIG. 5B). CB-derived platelet like cells displayed the pancreatic islet δ cell-released hormone somatostatin and ε cell marker Ghrelin mRNAs, with very weak or no expression of glucagon and PPY mRNAs (FIG. 5A). RT-PCR of human islet cells was performed simultaneously with RT-PCR of CB-platelet like cells as a positive control (FIGS. 5 A and B, right panels). Values to the right of each panel indicate the quantified intensity of the human islet cell band in relative intensity units.

Western blotting further demonstrated the expression of the mature beta cell marker MAFA at protein levels (FIG. 5O). Numbers to the right of each blot represent the average quantified amount of protein identified in relative intensity units.

Using freshly isolated human pancreatic islet cells as positive controls (FIG. 5D), flow cytometry confirmed expression of pancreatic cell markers in profiles of cord blood derived platelet like cells, such as CD42+Insulin+ (63.07%) CD42+C– peptide+ (65.14%), CD41+MAFA+ (20.12%), CD42+PDX1+ (0.28%), CD42+NKX6.1+(0.3%), and CD42+Glucagon 1+(2.82%) (FIGS. 5E and 5F). Additionally, flow cytometry revealed low expression of normal β-cell development-related transcription factors such as CD42+PTFA1+ (13.02%), CD42+FoxA2+ (0.34%), and CD42+Sox17+ (0.48%) (FIG. 5F).

Additional studies in adult human peripheral blood-derived platelet like cells demonstrated the expressions of similar markers and patterns as those in the cord blood-derived platelet like cells (FIG. 5G-J). In contrast to the cord blood derived samples, the GSK mRNA of peripheral blood derived samples was displayed in most samples (5/6). Few samples (1/6) were positive for SST, with no expression of Sur1 (FIG. 5G).

Confocal microscopy of cord blood derived- and peripheral blood derived-samples confirmed that there were no typical insulin granules formations in the cytoplasm, as dense granules and a granules of platelets (FIG. 5K). As shown in FIG. 5K, fields of view of many platelets were immunostained for insulin (blue), dense granule marker ADP (red), and alpha-granule marker vWF (green). The fluorescence images show no granule formation. Scale bar represents a length of 5 microns. Individual platelets are approximately 2 microns in length. The white dashed box in the upper panels indicates the zoomed in region seen in the middle panels (See FIG. 5K). The orange dashed boxed shows a field of view after probing with isotype matched control IgGs, with an exposure time equal to the experimental groups. The data depicted in FIG. 5K is representative of platelet like cells obtained from six separate experiments. These data showed that the expression of islet β-cell-associated markers in human platelets, resulted in the higher potential to promote the differentiation and regeneration of islet β cells.

Previous work identified a novel cell population from adult human blood, designated peripheral blood insulin-producing cells (PB-IPC). In vitro and in vivo experiments demonstrated that PBIPC could reduce hyperglycemia and migrate into pancreatic islets after transplantation into the diabetic mice (Zhao Y, et al., A unique human blood-derived cell population displays high potential for producing insulin (Biochem Biophys Res Commun 2007, 360: 205-211).

The described data indicates that the platelet-rich fraction from cord blood comprising cord blood platelet-like cells can be contacted with PB-IPCs, which can then be prompted to differentiate into functional islet cell-like cells. Furthermore, the described data indicates that adult mononuclear cells contacted with the platelet-rich fraction from cord blood comprising cord blood platelet-like cells can generate PB-IPCs.

Example 6. Mitochondria Released by Platelets Improve Function and Survival of Human Pancreatic Islets Freshly-isolated human pancreatic islets were purchased from Lonza (San Francisco, Calif.). Pancreatic islets were dissociated into single cells with 0.25% trypsin/EDTA for 5 min at room temperature. Pancreatic islet cells ($1\times10^5$ cells/mil) were seeded in the top inserts of a transwell culture system with 0.4 μm pore size (EMD Millipore, Billerica, Mass.). Pancreatic islets were co-cultured with MitoTracker Deep Red-labeled platelet like cells, which were placed in the bottom chamber of the transwell culture system. The islet cells were collected at different time points for kinetic flow cytometry at 1, 2, 4, 6, 20, 24 hr. After 7 days, the treated and untreated islet cells were collected to examine cell viability and viable cell number by using a TC20 automated cell counter (Bio-Rad, Hercules, Calif.).

Mitochondria were isolated from platelet like cells using the Oproteome Mitochondria Isolation kit (Qiagen, Hidden, Germany). Whole pancreatic islet cells were seeded in the top chamber of a transwell (0.4 μm pore size) at 125 islet equivalents (IEQ) per well, and treated at 37° C., in 8% C02 with the isolated mitochondria derived from platelet like cells (250 μg/ml, bottom well), which were seeded in the bottom chamber of the transwell. Pancreatic islets cultured only in pancreatic islet medium (Lonza) served as control. After 7 days of culturing the islets, the mitochondrion-treated and untreated islets were collected respectively for functional studies, such as flow cytometry, cell viability, and insulin/C-peptide release.

Dissociated pancreatic islet cells were pre-treated with 20 μg/ml anti-CD29 and/or 20 μg/ml anti-TLR4 Abs respectively, at 37° C. for 30 min. MitoTracker Green-labeled mitochondria (125 mg/ml) isolated from platelets were then added. Islet cells co-cultured with mitochondria in the absence of blocking Abs served as control. After 5 hr, the mitochondrion-treated and untreated islets cells were washed and fixed and permeabilized by using PerFix-nc (no centrifuge assay) kit (Beckman Coulter), and followed by an intra-cellular staining with islet f-cell marker insulin for flow cytometry.

Flow cytometry showed that platelet like cells could release a basal level of mitochondria (FIG. 6A). As shown in FIG. 6A, flow cytometry revealed that gated mitochondria (as determined by forward scatter and side scatter) obtained from platelet like cells, as described above, were positive for the MitoTracker fluorescent stain.

Platelet like cells were stimulated with various platelet aggregators, such as adenine di-phosphate (ADP), arachidonic acid (ARA), and thrombin prior to isolating the mitochondria. the amount of released MitoTracker stained mitochondria was quantified in arbitrary fluorescence intensity units. The data in FIG. 6B show that the level of released mitochondria as measured by fluorescence intensity was increased by agonists adenosine diphosphate (ADP) and arachidonic acid (ARA), but decreased by treatment with thrombin (FIG. 6B).

Islets and platelet like cells were co-cultured in a transwell system. As shown in FIG. 6C, human pancreatic islet cells were cultured in the upper chamber of the transwell, and the platelet like cells were deposited in the lower chamber. Using the transwell co-culture system (FIG. 6C), the pancreatic islet cells were harvested after co-culturing for 1, 2, 4, 6, 20 or 24 hours, and the kinetics of mitochondrial binding to the islets determined by flow cytometry.

As shown in FIG. 6D, flow cytometry data showed that the MitoTracker-labeled mitochondria released from the platelet-like cells in the lower chamber can pass through the transwells to be taken up by pancreatic islet cells in the top chamber. The "count" y-axis represents the quantified islet cells, while the fluorescence intensity (x-axis) represents a quantified amount of fluorescently stained mitochondria. The percentage of islet cells that took up stained mitochondria increased from 37.21% at 1 hr to 55.26% at 2 hr to 58.03% at 4 hr, to, 69.22% at 6 hr to 97.42% at 20 hr, and to 95.65% at 24 hr.

Next, the molecular mechanisms leading to the migration of mitochondria to islet β3 cells were explored. Flow cytometry revealed that platelet like cell-derived mitochondria strongly express adhesion molecule and chemokine receptors such as fibronectin, CXC chemokine receptor 2 (CXCR2), CXCR4, and chemokine C—C motif receptor 7 (CCR7), but are negative for CD62L (FIG. 6E; the vertical axis represents the quantified amount of respective adhesion molecule/receptor, while the horizontal axis represents fluorescence intensity of MitoTracker stain).

By flow cytometry, human pancreatic islet β cells were shown to express the fibronectin ligand CD29 (integrin β1), Toll-like receptor 4 (TLR4), and TLR6 (FIG. 6F; the vertical axis represents the quantified amount of respective receptor, while islet beta cells were identified by expression of insulin quantified on the horizontal axis). There were low or negative expression levels of type II transmembrane glycoprotein CD38, thrombospondin receptor CD36, C—C motif chemokine ligand 2 (CCL2), C—C motif chemokine receptor CCR4, and CCR6 (FIG. 6F).

To determine what molecules are involved in the interaction between mitochondria and islet β cells, platelet-derived mitochondria were co-cultured with pancreatic islets in the presence of blocking antibodies to CD29 and/or TLR4. As shown in FIG. 6G, the data showed that the uptake of MitoTracker-labeled mitochondria by islet 3 cells was markedly reduced by blocking with CD29 and/or TLR4 Abs, which indicates that CD29 and TLR4 contribute to the adhesion and uptake of mitochondria by human islet β cells.

To determine the biological effects of platelet like cell-derived mitochondria on islet β cells, trypsin/EDTA-dissociated single pancreatic islet β cells were co-cultured with platelets in transwells as shown in FIG. 6C. The results showed that both cell viability and viable cell numbers were substantially increased after co-culture for 7 days, compared to control islet cells (FIGS. 6H and I). Mitochondria-treated islets had more than a 40% increase in cell viability when compared to untreated control islets (FIG. 6H). The total number of viable cells increased from about $2.4 \times 10^4$ cells/mL to about $4.5 \times 10^4$ cells/mL (FIG. 6I).

Whole pancreatic islets (as opposed to trypsinzed, dissociated cells) were co-cultured with isolated mitochondria in transwells as shown schematically in FIG. 6J. The data showed that islet cell viability increased by a statistically significant amount in the presence of mitochondria for 7 days (FIG. 6K). Quantification of average islet size indicated that the pancreatic islets were enlarged by a statistically significant amount after treatment with mitochondria (P=0.026, FIG. 6L).

C-peptide release of islet β cells was also investigated. Freshly-isolated human pancreatic islets (Lonza, San Francisco, Calif.) at 125 IEQ per well (top insert) were treated with platelet-derived mitochondria (250 μg/ml, bottom well) in 12-well tissue culture-treated plates with transwell inserts at 37° C., in 8% $CO_2$. Untreated pancreatic islets cultured in pancreatic islet medium (Lonza) served as control. After 7 days, the mitochondria-treated and untreated pancreatic islets were respectively collected into 2 ml conical tubes and washed twice with Kreb's buffer (137 mM NaCl, 4.7 mM KCl, 1.2 mM KH2PO4, 2.5 mM $CaCl_2$, 1.2 mM $MgCl_2$, 25 mM $NaHCO_3$, 0.1% BSA), and then incubated with 1 ml Kreb's buffer for 30 min in the absence of glucose, at 37° C. condition. After removing the Kreb's buffer, pancreatic islets were incubated with different concentration of glucose (5.5 and 16.7 mM) and/or 10 μM tolbudamide (Sigma) in 300 μl Kreb's buffer/well for 1 h, at 37° C. condition. The supernatants were collected from each group after incubation. The C-peptide level of each group was examined respectively using the Quantikine ELISA kit (R & D Systems, Minneapolis, Minn.) following the manufacturer's protocol.

Flow cytometry showed that the percentage of C-peptide+ Ki67+islet β cells was substantially enriched after treatment with platelet-derived mitochondria for 7 days in transwells (FIG. 6M). About 23.38%±3.13 of control human islets in medium alone were positive for C-peptide and Ki67, while 44.35%±8.15 of mitochondria-treated human islets were positive for C-peptide and Ki67.

Functional analysis substantiated that the mitochondria-treated pancreatic islet β3 cells significantly improved C-peptide release in response to different insulin secretagogues, such as high glucose (16.7 mM) and tolbutamide. Mitochondria treatment appeared to correct the functional defects of control islet group in the absence of mitochondria treatment (FIG. 6N). Tolbutamide, which is supposed to stimulate the secretion of insulin by islet cells, had no effect on control islet cells in the presence of 5.5 mM glucose. In contrast, tolbutamide significantly increased insulin secretion in mitochondria-treated islet cells, compared to controls (FIG. 6N, right panel). Without being limited by theory, these data indicate that pancreatic islet β-cell function is improved after the treatment with platelet-derived mitochondria.

Additional immunohistochemistry studies of diabetic patient pancreatic tissue showed the presence of platelets in pancreatic islets in the form of singlets or clusters (FIG. 6O). Insulin stained islet cells (red) and stained platelet like cells (green) are found in proximity to one another, with individual and clustered platelets. Without being limited by theory, mitochondria release from local platelets in diabetic patients may lead to the improvement of islet β-cell function.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for functionally reprogramming pancreatic islet cells comprising:
   (a) isolating a population of pancreatic islet cells from a subject;
   (b) isolating a platelet rich fraction comprising platelet-like cells from a Ficoll-Paque gradient fraction from umbilical cord blood wherein the platelet-like cells comprise a population of cells positive for Sur1 and one or more of OCT3/4, NANOG, NKX6.1, MAFA, Kir6.2, PD-L1, CD270, Galectin 9, TGF-β1, AIRE, CCR3, CXCR4, and CCL2 and negative for one or more of CXCL10, CCR4, CCR5, CCR7, CXCR1, CXCR2, CXCR3, CD62L, and CXCL1; and
   (c) contacting the population of pancreatic islet cells of step (a) with the platelet rich fraction of step (b) in vitro, wherein the contacting of step (c) comprises uptake of the mitochondria by the pancreatic islet cells, and wherein the contacting is effective to reprogram the pancreatic islet cells to increase one or more of cell viability, viable cell number, cell size, and C-peptide release as compared to a control pancreatic islet cell not contacted with the platelet rich fraction of step (b).

2. The method according to claim 1, wherein the platelet rich fraction comprising platelet-like cells comprises one or more of whole cells, mitochondria, microparticles, exosomes, lysed cells, and alpha granules.

3. The method according to claim 2, wherein the whole cells comprise one or more of hematopoietic stem cells, hematopoietic progenitor cells, common lymphoid progenitors, common myeloid progenitors, megakaryocyte-erythrocyte progenitors; granulocyte-monocyte progenitors, megakaryocyte lineage-committed progenitors, megakaryocytes, and platelet-like cells.

4. The method according to claim 1, wherein the platelet-like cells comprise a population of cells positive for OCT3/4, NANOG, NKX6.1, MAFA, Sur1, Kir6.2, PD-L1, CD270, Galectin 9, TGF-β1, AIRE, CCR3, CXCR4, and CCL2 and negative for CXCL10, CCR4, CCR5, CCR7, CXCR1, CXCR2, CXCR3, CD62L, and CXCL1.

5. A pharmaceutical composition comprising a cell product containing a therapeutic amount of a pancreatic islet cell population that has been functionally reprogrammed to have one or more of increased cell viability, viable cell number, cell size, and C-peptide release by contact with a platelet rich fraction comprising platelet-like cells from a Ficoll-Paque gradient fraction from umbilical cord blood of a donor and expanded and redifferentiated in vitro, wherein the platelet-rich fraction comprises a population of cells positive for Sur1 and one or more of OCT3/4, NANOG, NKX6.1, MAFA, Kir6.2, PD-L1, CD270, Galectin 9, TGF-β1, AIRE, CCR3, CXCR4, and CCL2; and negative for CXCL10, CCR4, CCR5, CCR7, CXCR1, CXCR2, CXCR3, CD62L, and CXCL1.

6. The pharmaceutical composition according to claim 5, wherein the cell product is produced by a process comprising:
   (a) isolating a population of pancreatic islet cells from a donor;
   (b) isolating a platelet rich fraction comprising platelet-like cells from a Ficoll-Paque gradient fraction from umbilical cord blood of the donor, wherein the platelet-like cells comprise a population of cells positive for Sur1 and one or more of OCT3/4, NANOG, NKX6.1, MAFA, Kir6.2, PD-L1, CD270, Galectin 9, TGF-β1, AIRE, CCR3, CXCR4, and CCL2 and negative for one or more of CXCL10, CCR4, CCR5, CCR7, CXCR1, CXCR2, CXCR3, CD62L, and CXCL1;
   (c) contacting the population of pancreatic islet cells of step (a) with the platelet rich fraction of step (b) in vitro, wherein the contacting is effective to reprogram the pancreatic islet cells to increase one or more of cell viability, viable cell number, cell size, and C-peptide release as compared to a control pancreatic islet cell not contacted with the platelet rich fraction of step (b);
   (d) expanding the reprogrammed pancreatic islet cells of step (c) in vitro under culture conditions effective to generate a cell product containing a therapeutically effective amount of a pancreatic islet cell population; and
   (e) formulating the cell product with a pharmaceutically acceptable carrier to form the pharmaceutical composition.

7. The pharmaceutical composition according to claim 5, wherein platelet-like cells comprise a population of cells positive for OCT3/4, NANOG, NKX6.1, MAFA, Sur1, Kir6.2, PD-L1, CD270, Galectin 9, TGF-β1, AIRE, CCR3, CXCR4, and CCL2 and negative for CXCL10, CCR4, CCR5, CCR7, CXCR1, CXCR2, CXCR3, CD62L, and CXCL1.

8. The method according to claim 1, wherein the subject is a human subject.

9. The method according to claim 1, wherein the mitochondria are effective to exert an immune modulatory activity on T cells.

10. The method according to claim 1, wherein the mitochondria are effective to increase percentage of CD4+PD1+ T cells.

11. The method according to claim 1, wherein the contacting of the population of pancreatic islet cells by the mitochondria is effective to improve function and survival of the population of pancreatic islet cells.

12. The method according to claim 1, wherein the contacting of the population of pancreatic islet cells by the mitochondria is effective to improve function of the population of pancreatic islet beta cells.

13. The pharmaceutical composition according to claim 5, wherein the platelet rich fraction comprising platelet-like cells comprises one or more of whole cells, mitochondria, microparticles, exosomes, lysed cells, and alpha granules.

14. The pharmaceutical composition according to claim 5, wherein the mitochondria are effective to exert an immune modulatory activity on T cells.

15. The pharmaceutical composition according to claim 5, wherein the mitochondria are effective to increase percentage of CD4+PD1+ T cells.

16. The pharmaceutical composition according to claim 5, wherein the contacting of the population of pancreatic islet cells by the mitochondria is effective to improve function and survival of the population of pancreatic islet cells.

17. The pharmaceutical composition according to claim 5, wherein the contacting of the population of pancreatic islet cells by the mitochondria is effective to improve function of the population of pancreatic islet beta cells.

18. An isolated pancreatic islet cell comprising platelet-like cell mitochondria, wherein the platelet-like cell mitochondria adhere to and are taken up by the isolated pancreatic islet cell.

19. The pancreatic islet cell according to claim 18, wherein the mitochondria are positive for one or more of OCT3/4, NANOG, NKX6.1, MAFA, Sur1, PD-L1, CD270, Galectin 9, TGF-β1, AIRE, CCR3, CXCR4, and CCL2 and negative for one or more of CXCL10, CCR4, CCR5, CCR7, CXCR1, CXCR2, CXCR3, CD62L, and CXCL1.

20. The pancreatic islet cell according to claim 19, wherein the mitochondria are positive for OCT3/4, NANOG, NKX6.1, MAFA, Sur1, Kir6.2, PD-L1, CD270, Galectin 9, TGF-β1, AIRE, CCR3, CXCR4, and CCL2 and negative for CXCL10, CCR4, CCR5, CCR7, CXCR1, CXCR2, CXCR3, CD62L, and CXCL1.

* * * * *